US012653982B2

(12) United States Patent
Maurer et al.

(10) Patent No.:  US 12,653,982 B2
(45) Date of Patent:      Jun. 16, 2026

(54) RESPIRATORY PRESSURE TREATMENT SYSTEM

(71) Applicant: RESMED PTY LTD, Bella Vista (AU)

(72) Inventors: Dimitri Marco Maurer, Gosford (AU); Jeremy William Workman, Blue Mountains (AU)

(73) Assignee: ResMed Pty Ltd, Bella Vista (AU)

( * ) Notice:   Subject to any disclaimer, the term of this patent is extended or adjusted under 35 U.S.C. 154(b) by 1141 days.

(21) Appl. No.:   17/280,700

(22) PCT Filed:   Sep. 26, 2019

(86) PCT No.:   PCT/IB2019/058184
§ 371 (c)(1),
(2) Date:   Mar. 26, 2021

(87) PCT Pub. No.:   WO2020/065581
PCT Pub. Date: Apr. 2, 2020

(65)   Prior Publication Data
US 2021/0379322 A1      Dec. 9, 2021

Related U.S. Application Data

(60) Provisional application No. 62/750,715, filed on Oct. 25, 2018, provisional application No. 62/737,719, filed on Sep. 27, 2018.

(51) Int. Cl.
*A61M 16/00*      (2006.01)
*A61M 16/08*      (2006.01)
*A61M 16/16*      (2006.01)

(52) U.S. Cl.
CPC ........ *A61M 16/16* (2013.01); *A61M 16/0816* (2013.01); *A61M 16/0066* (2013.01); *A61M 2205/3331* (2013.01); *A61M 2205/3368* (2013.01); *A61M 2209/086* (2013.01)

(58) Field of Classification Search
CPC ............ A61M 16/16; A61M 2209/086; A61M 16/183; A61M 16/186; A61M 16/0066;
(Continued)

(56)   References Cited

U.S. PATENT DOCUMENTS

| | | | |
|---|---|---|---|
| 4,028,444 A | | 6/1977 | Brown et al. |
| 4,344,646 A | * | 8/1982 | Michel ................ E05B 65/5276 |
| | | | 292/87 |

(Continued)

FOREIGN PATENT DOCUMENTS

| | | |
|---|---|---|
| CA | 2 424 662 A1 | 8/2002 |
| CN | 1930421 A | 3/2007 |

(Continued)

OTHER PUBLICATIONS

Extended European Search Report Mailed Aug. 29, 2022 in European Application No. 19865301.6, 7 pages.
(Continued)

*Primary Examiner* — Brandy S Lee
*Assistant Examiner* — Sarah B Lederer
(74) *Attorney, Agent, or Firm* — Nixon & Vanderhye P.C.

(57)   ABSTRACT

An apparatus for humidifying a flow of breathable gas includes a water reservoir including a chamber structured to hold a volume of water, a water reservoir dock structured and arranged to receive the water reservoir in an operative position, and a latch movable between (1) a locked position to releasably lock the water reservoir to the water reservoir dock in the operative position, and (2) an unlocked position to allow insertion of the water reservoir into the water reservoir dock and removal of the water reservoir from the water reservoir dock.

3 Claims, 89 Drawing Sheets

(58) Field of Classification Search

CPC ......... Y10T 292/1051; Y10T 292/0911; Y10T 292/1043; Y10T 292/178; Y10S 292/11; Y10S 292/38; Y10S 292/63

See application file for complete search history.

(56) References Cited

U.S. PATENT DOCUMENTS

| | | | |
|---|---|---|---|
| 4,782,832 A | 11/1988 | Trimble et al. | |
| 4,944,310 A | 7/1990 | Sullivan | |
| 5,259,370 A | 11/1993 | Howe | |
| 5,797,389 A * | 8/1998 | Ryder ................... | A61M 16/12 128/200.21 |
| 5,932,148 A | 8/1999 | Hansell, Jr. et al. | |
| 6,003,204 A | 12/1999 | Roach et al. | |
| 6,256,454 B1 | 7/2001 | Dykes | |
| 6,532,959 B1 | 3/2003 | Berthon-Jones | |
| 6,581,594 B1 | 6/2003 | Drew et al. | |
| 6,588,734 B2 | 7/2003 | Redner et al. | |
| 6,718,974 B1 | 4/2004 | Moberg | |
| 6,935,337 B2 | 8/2005 | Virr et al. | |
| 7,096,864 B1 | 8/2006 | Mayer et al. | |
| 7,111,624 B2 | 9/2006 | Thudor et al. | |
| 7,413,173 B2 | 8/2008 | DiMatteo et al. | |
| 7,673,855 B2 | 3/2010 | Anderson et al. | |
| 7,677,246 B2 | 3/2010 | Kepler et al. | |
| 7,766,310 B2 | 8/2010 | Wolff et al. | |
| 7,866,944 B2 | 1/2011 | Kenyon et al. | |
| 8,240,306 B2 | 8/2012 | Cortez, Jr. et al. | |
| 8,316,848 B2 | 11/2012 | Kwok et al. | |
| 8,333,195 B2 | 12/2012 | Cortez, Jr. et al. | |
| 8,356,593 B2 | 1/2013 | Cortez, Jr. et al. | |
| 8,550,072 B2 | 10/2013 | Thudor et al. | |
| 8,636,479 B2 | 1/2014 | Kenyon et al. | |
| 8,638,014 B2 | 1/2014 | Sears et al. | |
| 8,677,993 B2 | 3/2014 | Cortez, Jr. et al. | |
| 8,733,349 B2 | 5/2014 | Bath et al. | |
| 8,739,780 B2 | 6/2014 | Tang et al. | |
| 8,905,384 B2 | 12/2014 | Rodrigs et al. | |
| 9,038,629 B2 | 5/2015 | Smith et al. | |
| 9,106,061 B1 | 8/2015 | Shotey et al. | |
| 9,227,035 B2 | 1/2016 | Crumblin et al. | |
| 9,328,962 B2 | 5/2016 | Lee et al. | |
| 9,707,370 B2 | 7/2017 | Smith et al. | |
| 10,238,829 B2 | 3/2019 | Kat | |
| 10,252,019 B2 | 4/2019 | Potharaju et al. | |
| 10,252,837 B2 | 4/2019 | Miller et al. | |
| 10,293,125 B2 | 5/2019 | Jeha et al. | |
| 10,317,098 B2 | 6/2019 | Bayer et al. | |
| 10,342,950 B2 | 7/2019 | Bath et al. | |
| 10,864,343 B2 | 12/2020 | Bath et al. | |
| 11,344,694 B2 | 5/2022 | Workman et al. | |
| 11,529,491 B2 | 12/2022 | Workman et al. | |
| 2003/0116989 A1 | 6/2003 | Guanzon et al. | |
| 2007/0132117 A1 | 6/2007 | Pujol | |
| 2007/0193580 A1 | 8/2007 | Feldhahn | |
| 2008/0251071 A1 | 10/2008 | Armitstead et al. | |
| 2008/0302361 A1 | 12/2008 | Snow et al. | |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2011/0155132 A1 | 6/2011 | Virr | |
| 2012/0298099 A1 * | 11/2012 | Lalonde .............. | A61M 16/021 128/200.16 |
| 2013/0174843 A1 | 7/2013 | Smith et al. | |
| 2014/0137861 A1 | 5/2014 | Feldhahn et al. | |
| 2014/0174442 A1 | 6/2014 | Cortez, Jr. et al. | |
| 2014/0246021 A1 | 9/2014 | Buechi et al. | |
| 2014/0264975 A1 * | 9/2014 | Bath ................. | A61M 16/0683 261/141 |
| 2014/0290655 A1 | 10/2014 | Snow et al. | |
| 2015/0027204 A1 * | 1/2015 | Stoks .................... | G01K 13/02 73/31.05 |
| 2015/0040897 A1 * | 2/2015 | Buechi .............. | A61M 16/0003 128/203.26 |
| 2015/0151074 A1 | 6/2015 | Hermez | |

| | | | |
|---|---|---|---|
| 2015/0258300 A1 | 9/2015 | Lin et al. | |
| 2015/0359989 A1 | 12/2015 | Potharaju et al. | |
| 2016/0008560 A1 | 1/2016 | Kwok | |
| 2016/0022954 A1 | 1/2016 | Bath et al. | |
| 2016/0228671 A1 | 8/2016 | Jackson et al. | |
| 2016/0310691 A1 | 10/2016 | Bath | |
| 2017/0121067 A1 | 5/2017 | Miller et al. | |
| 2017/0151411 A1 | 6/2017 | Osborne et al. | |
| 2017/0173293 A1 | 6/2017 | Osborne et al. | |
| 2017/0252531 A1 | 9/2017 | Hensman et al. | |
| 2017/0259019 A1 | 9/2017 | Cariola et al. | |
| 2017/0348505 A1 | 12/2017 | Doo et al. | |
| 2017/0361053 A1 | 12/2017 | Dimatteo et al. | |
| 2018/0071480 A1 | 3/2018 | Tang et al. | |
| 2018/0127911 A1 | 5/2018 | Chen et al. | |
| 2018/0177967 A1 | 6/2018 | Miller et al. | |
| 2018/0185606 A1 | 7/2018 | Van Schalkwyk et al. | |
| 2018/0185607 A1 | 7/2018 | Holley et al. | |
| 2018/0214660 A1 | 8/2018 | Stoks et al. | |
| 2018/0333556 A1 | 11/2018 | Ormrod et al. | |
| 2019/0038865 A1 | 2/2019 | Smith et al. | |
| 2019/0117931 A1 | 4/2019 | Virr et al. | |
| 2019/0209802 A1 | 7/2019 | Virr et al. | |
| 2019/0298964 A1 | 10/2019 | Bayer et al. | |
| 2019/0321580 A1 | 10/2019 | Kirchberger et al. | |
| 2020/0101258 A1 | 4/2020 | DiMatteo et al. | |
| 2020/0155876 A1 | 5/2020 | Appareti et al. | |
| 2020/0330720 A1 | 10/2020 | Formica et al. | |
| 2021/0379322 A1 | 12/2021 | Maurer | |
| 2022/0096784 A1 | 3/2022 | Workman et al. | |
| 2022/0226597 A1 | 7/2022 | Workman et al. | |

FOREIGN PATENT DOCUMENTS

| | | | |
|---|---|---|---|
| CN | 1936442 A | 3/2007 |
| CN | 101220988 B | 9/2010 |
| CN | 201768243 U | 3/2011 |
| CN | 204193230 U | 3/2015 |
| CN | 204293650 U | 4/2015 |
| CN | 204671683 U | 9/2015 |
| CN | 105727404 A | 7/2016 |
| CN | 208927355 U | 6/2019 |
| EP | 3 406 289 A1 | 11/2018 |
| EP | 2 178 590 B1 | 4/2021 |
| GB | 2321668 A | 8/1998 |
| JP | 3464916 B2 | 11/2003 |
| JP | 4489478 B2 | 6/2010 |
| WO | WO 98/004310 A1 | 2/1998 |
| WO | WO 98/034665 A1 | 8/1998 |
| WO | WO 2000/078381 A1 | 12/2000 |
| WO | WO 02/066106 A1 | 8/2002 |
| WO | WO 2004/073778 A1 | 9/2004 |
| WO | WO 2004/112873 A1 | 12/2004 |
| WO | WO 2005/063328 A1 | 7/2005 |
| WO | WO 2006/074513 A1 | 7/2006 |
| WO | WO 2006/130903 A1 | 12/2006 |
| WO | WO 2007/019625 A1 | 2/2007 |
| WO | WO 2007/019626 A1 | 2/2007 |
| WO | WO 2009/052560 A1 | 4/2009 |
| WO | WO 2009/127192 A1 | 10/2009 |
| WO | WO 2010/135785 A1 | 12/2010 |
| WO | WO 2012/171072 A1 | 12/2012 |
| WO | WO 2013/020167 A1 | 2/2013 |
| WO | WO 2014/138804 A1 | 9/2014 |
| WO | WO 2015/089582 | 6/2015 |
| WO | WO 2015/089582 A1 | 6/2015 |
| WO | WO 2018/094452 A1 | 5/2018 |
| WO | WO 2019/216774 A1 | 11/2019 |
| WO | WO 2020/212902 A1 | 12/2020 |

OTHER PUBLICATIONS

Notification concerning Transmittal of International Preliminary Report on Patentability mailed Apr. 8, 2021 in International Application No. PCT/IB2019/058184, 10 pages.

U.S. Appl. No. 63/011,052, filed Apr. 16, 2020, for "Acoustic Detection in Respiratory Treatment Apparatus," 204 pages.

(56) References Cited

OTHER PUBLICATIONS

"*Respiratory Physiology*", by John B. West, Lippincott Williams & Wilkins, $9^{th}$ edition published 2012 (8 pages).
International Search Report Mailed Feb. 11, 2020 in International Application No. PCT/IB2019/058184, 11 pages.
Written Opinion of the International Searching Authority mailed Feb. 11, 2020 in International Application No. PCT/IB2019/058184, 8 pages.
Notification of the First Office Action mailed Feb. 23, 2024 in Chinese Application No. 201980070669.9, with English translation, 31 pages.

* cited by examiner

Nasal cavity

Oral cavity

Larynx

Vocal folds

Oesophagus

Trachea

Bronchus

Lung

Heart

Diaphragm

Alveolar sacs

4500

5202

5116

5125

5123

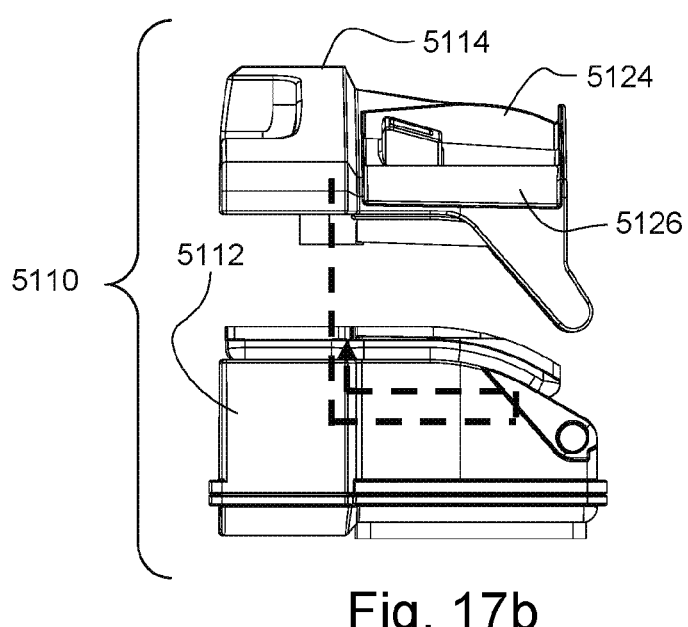
Fig. 17b
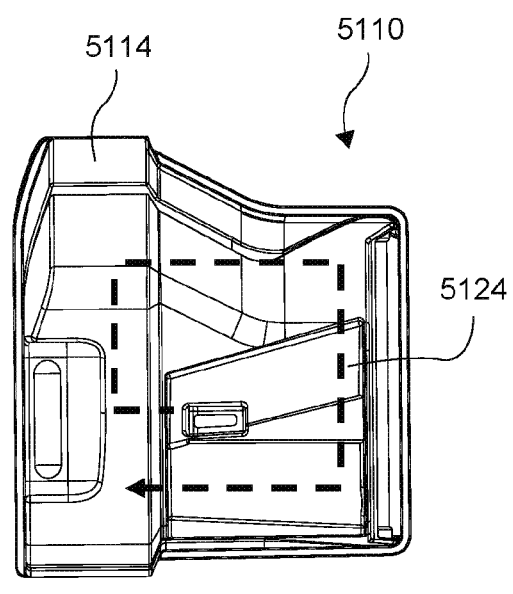
Fig. 17c
Fig. 17a

5114

5116

5112

External
Pressures/Forces

Internal
Pressures/Forces

5139

5112

5112

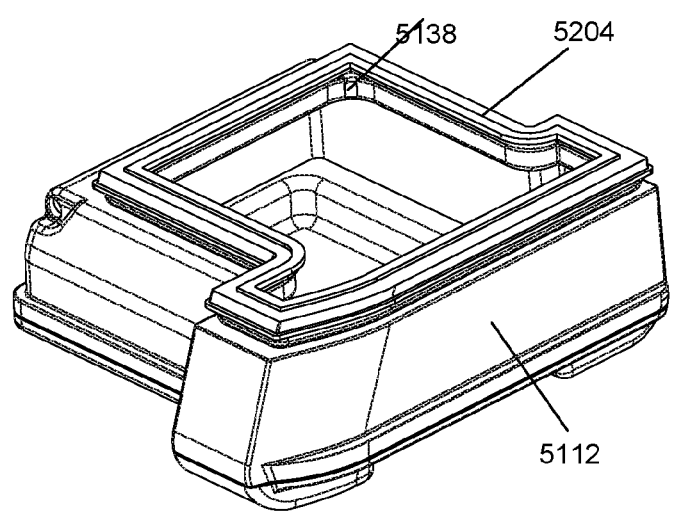
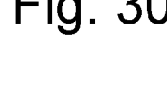
Fig. 30
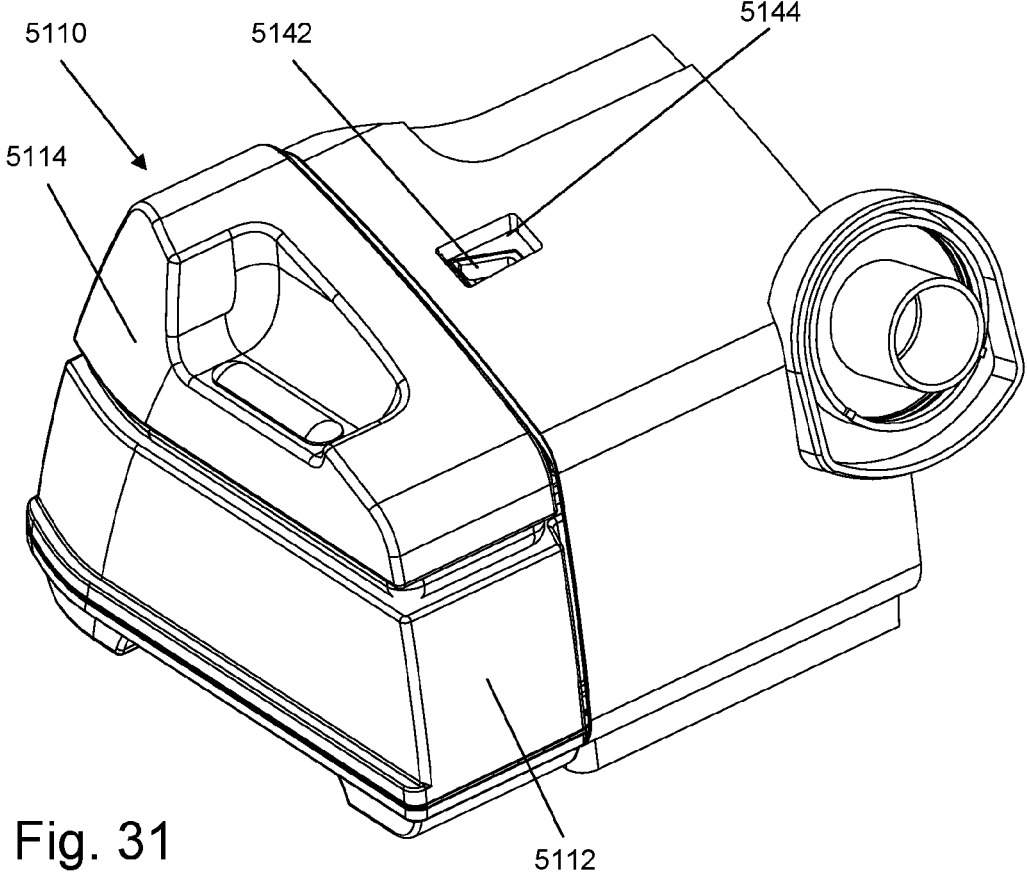
Fig. 31

5110
5118
5124
5122
5125
5127
5182
5126

5118   5124
5110
5125
5184
5182
5127
5122   5126

5202

5194

5196

5204

5195

5194

5198

5204

5202

5194

5197

5196

5198

5194

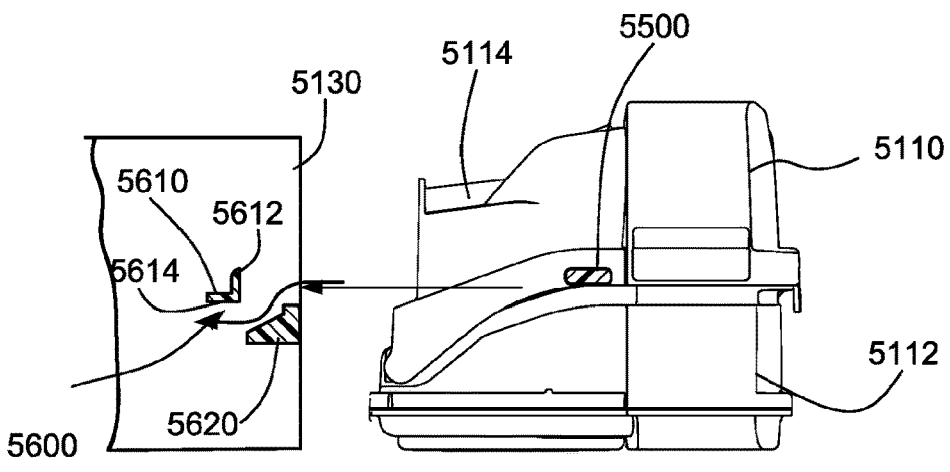
Fig. 67a
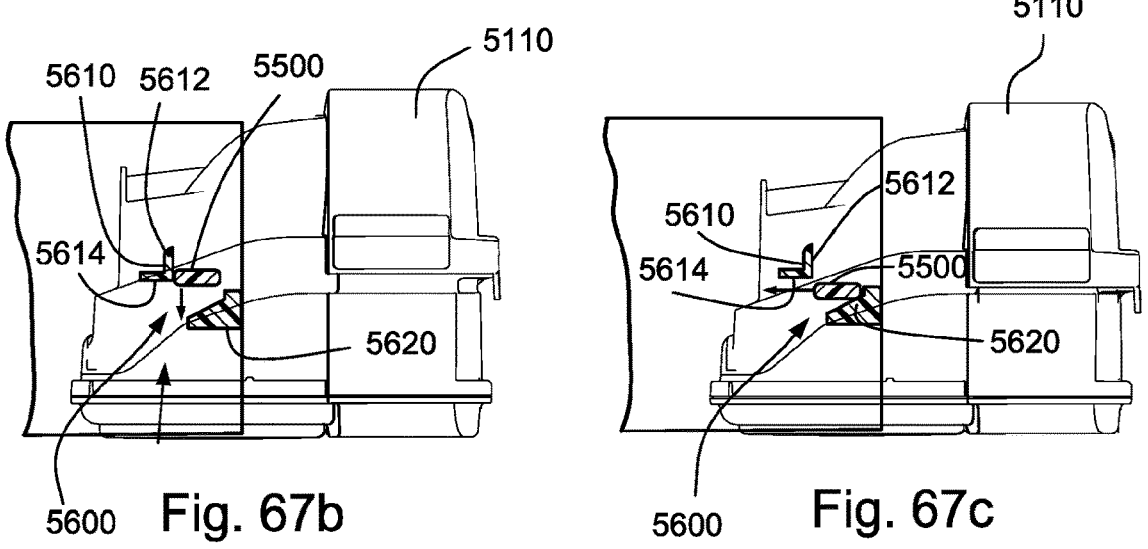
Fig. 67b
Fig. 67c
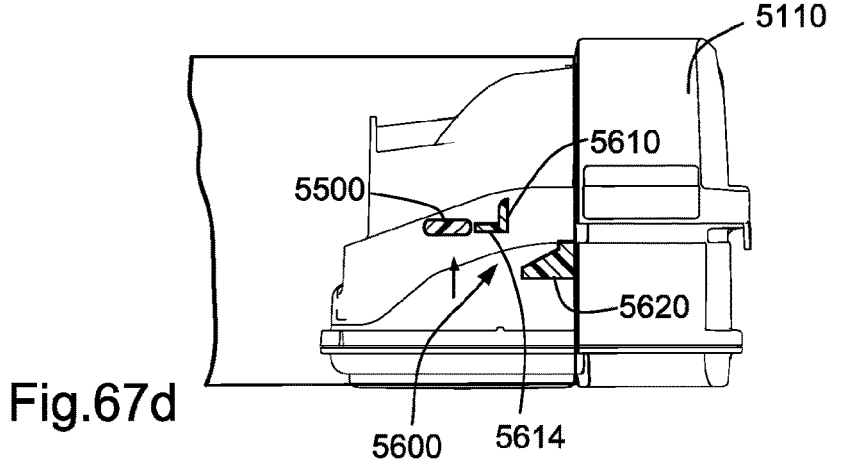
Fig.67d

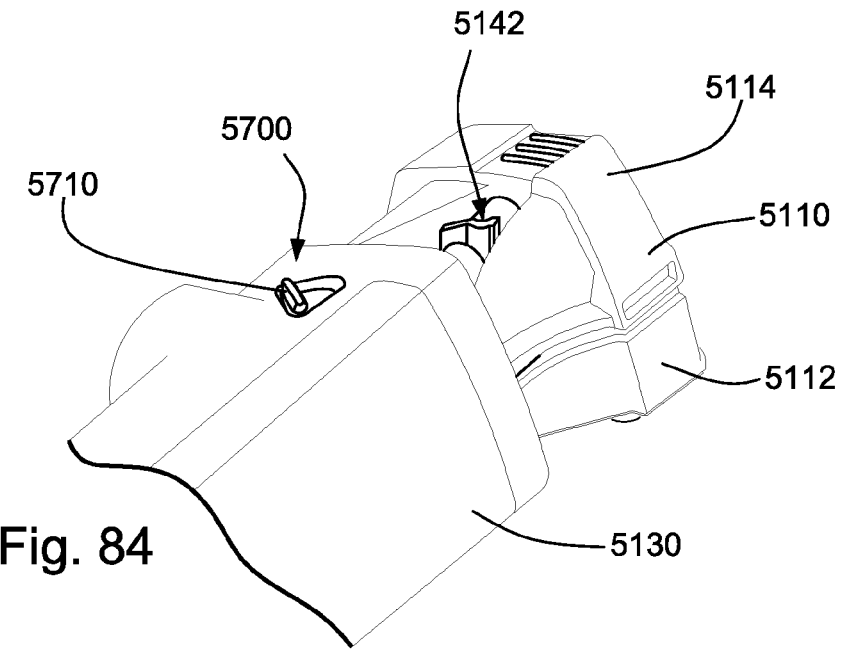
Fig. 84
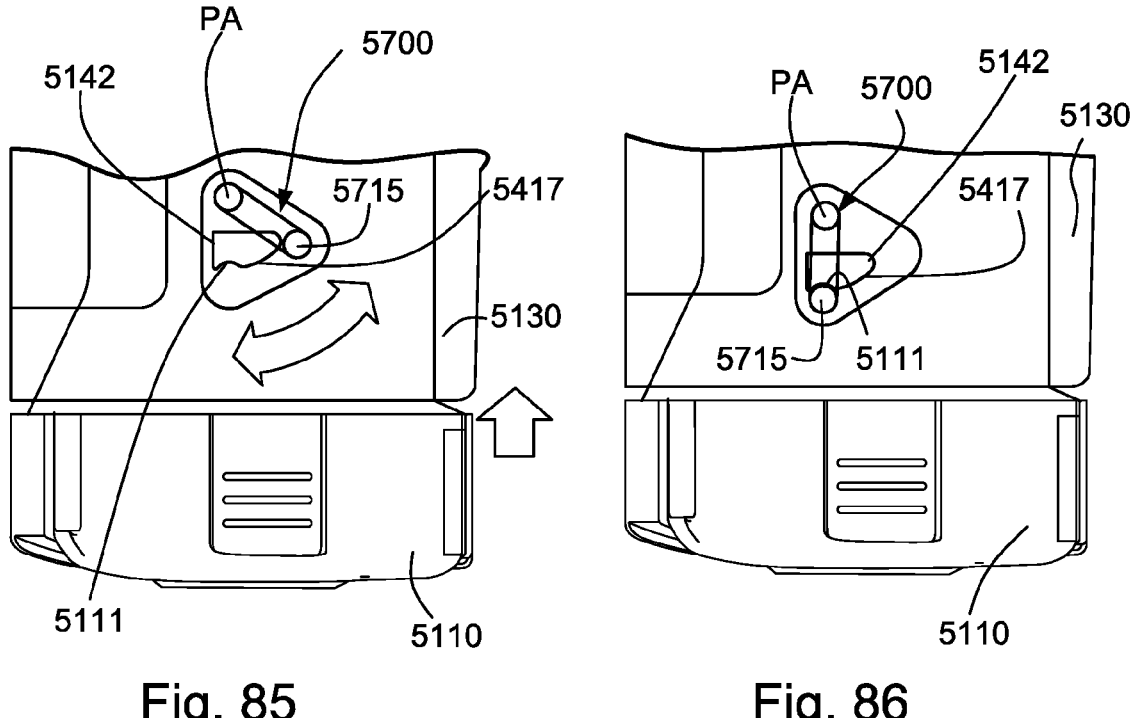
Fig. 85                    Fig. 86

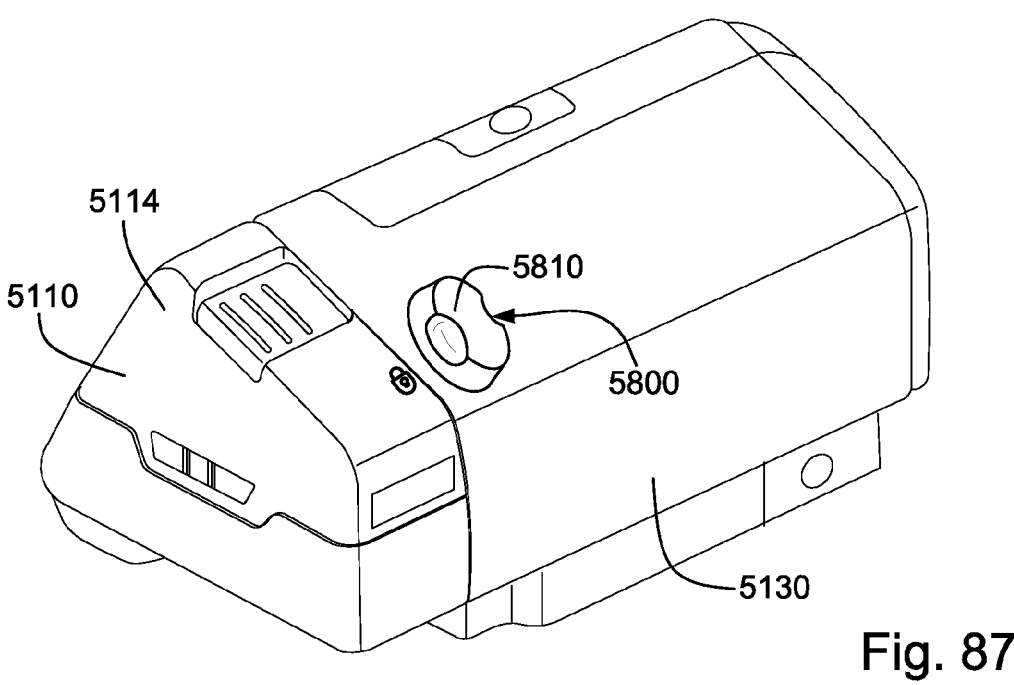
Fig. 87
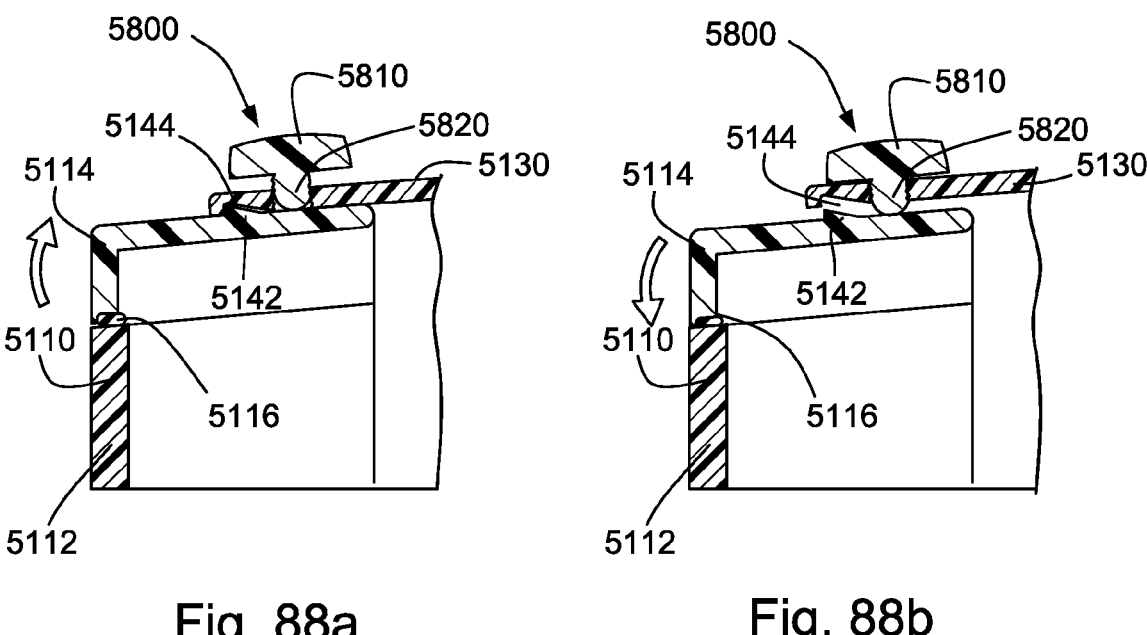
Fig. 88a                    Fig. 88b

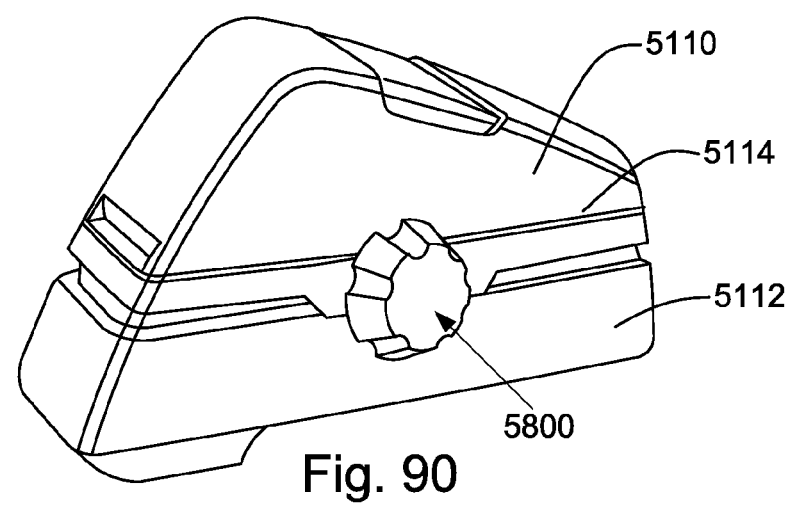
Fig. 90
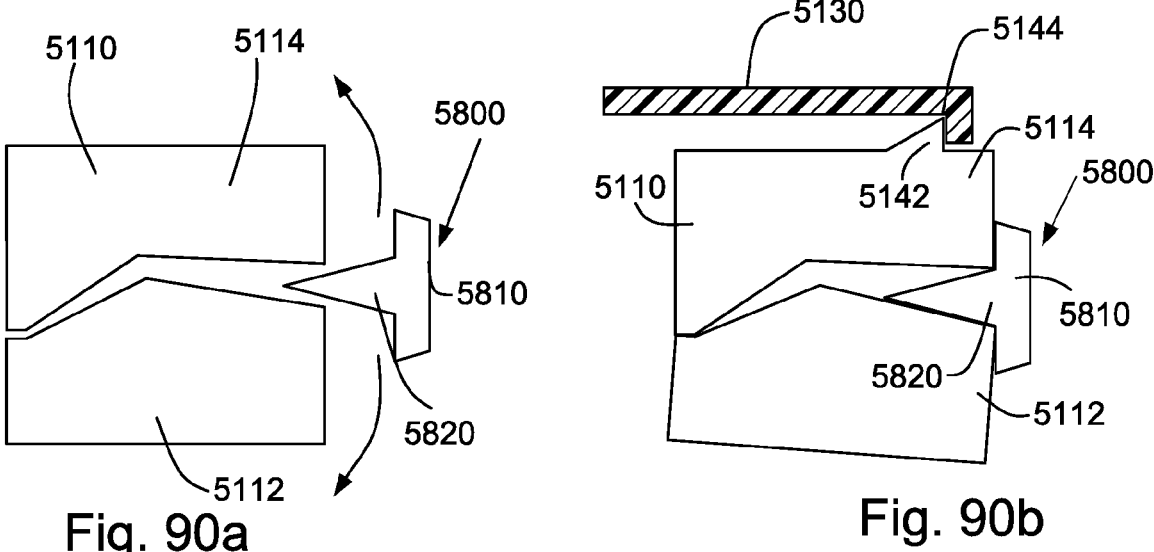
Fig. 90a
Fig. 90b
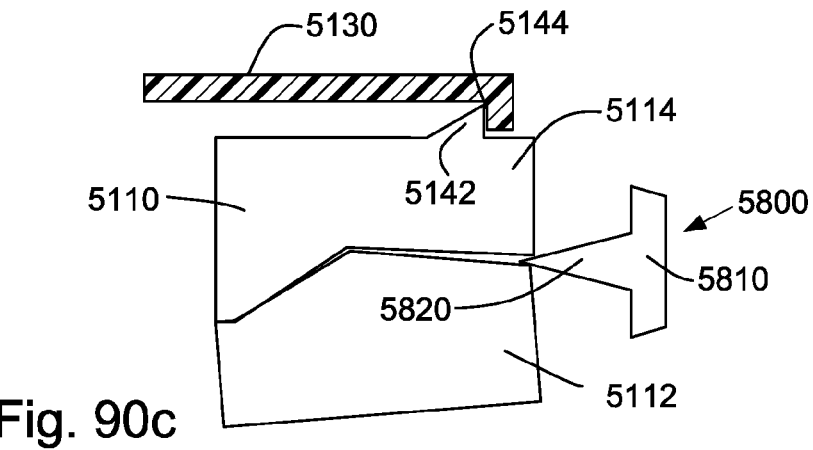
Fig. 90c

RESPIRATORY PRESSURE TREATMENT SYSTEM

CROSS-REFERENCE TO RELATED APPLICATIONS

This application is the U.S. national phase of International Application No. PCT/IB2019/058184 filed Sep. 26, 2019 which designated the U.S. and claims priority to U.S. Provisional Application Nos. 62/737,719, filed Sep. 27, 2018, and 62/750,715, filed Oct. 25, 2018, the entire contents of each of which are hereby incorporated by reference.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

2 BACKGROUND OF THE TECHNOLOGY

2.1 Field of the Technology

The present technology relates to one or more of the detection, diagnosis, treatment, prevention and amelioration of respiratory-related disorders. In particular, the present technology relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See *"Respiratory Physiology"*, by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Treatment of OSA by nasal CPAP therapy may be voluntary, and hence patients may elect not to comply with therapy if they find devices used to provide such therapy one or more of uncomfortable, difficult to use, expensive or aesthetically unappealing.

Non-invasive ventilation (NIV) provides ventilatory support to a patient through the upper airways to assist the patient in taking a full breath and assist to maintain adequate oxygen levels in the body by doing some or all of the work of breathing. The ventilatory support is provided via a patient interface. NIV has been used to treat CSR, OHS, COPD, MD and Chest Wall disorders.

Invasive ventilation (IV) provides ventilatory support to patients that are no longer able to effectively breathe themselves and may be provided using a tracheostomy tube.

2.2.3 Diagnosis and Treatment Systems

These therapies may be provided by a treatment system or device. Systems and devices may also be used to diagnose a condition without treating it.

A treatment system may comprise a Respiratory Pressure Therapy Device (RPT device), an air circuit, a humidifier, a patient interface, and data management.

2.2.3.1 Patient Interface

A patient interface may be used to interface respiratory equipment to its user, for example by providing a flow of air. The flow of air may be provided via a mask to the nose, the mouth or the nose and the mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH2O. For other forms of therapy, such as the delivery of oxygen, the patient interface may not include a seal sufficient to facilitate delivery to the airways of a supply of gas at a positive pressure of about 10 cmH2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, mask designed as part of personal protection equipment (e.g. filter masks), SCUBA masks, or for the administration of anaesthetics may be tolerable for their original application, but nevertheless be undesirably uncomfortable to be worn for extended periods of time, e.g. several hours This discomfort may lead to a reduction in patient compliance with therapy. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of nasal CPAP during sleep form a distinct field.

2.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, including one or more of comfort, noise, ease of use, efficacy, size, weight, manufacturability, cost, and reliability.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity, temperature (or both) of the flow of air in relation to ambient air when required, typically where the patient may be asleep or resting (e.g. at a hospital). As a result, a medical humidifier is preferably small for bedside placement, and it is preferably configured to only humidify, heat or humidify and heat the flow of air delivered to the patient without humidifying, heating or humidifying and heating the patient's surroundings. Room-based systems (e.g. a sauna, an air conditioner, an evaporative cooler), for example, may also humidify air that is breathed in by the patient, however they would also humidify, heat or humidify and heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to an apparatus for use in treating a respiratory disorder comprising a housing, a pressure generator within the housing and configured to supply a flow of air, a device outlet fluidly coupled to the pressure generator and configured to be coupled to an air circuit to deliver the flow of air to a patient interface for treating a respiratory disorder, and a wireless data communication interface integrated with the housing, the wireless data communication interface configured to connect to another device or a network.

One aspect of the present technology relates to an apparatus for humidifying a flow of breathable gas, comprising a heater plate, a chamber in fluid communication with the flow of breathable gas and a reservoir comprising a conductive portion in thermal engagement with the heater plate, the apparatus configured so that varying a first pressure of the flow of breathable gas in the chamber varies a level of thermal engagement between the conductive portion and the heater plate.

In one form, the reservoir further comprises an inlet and an outlet.

In one form, the thermal engagement is in a first direction that is substantially normal to a surface of the conductive portion.

In one form, the apparatus is further configured to vary a magnitude of a force between the conductive portion and the heater plate in the first direction as the first pressure is varied.

In one form, the chamber is part of the reservoir.

In one form, the chamber further comprises a variable portion.

In one form, the apparatus further comprises a dock configured to receive the reservoir, and the dock comprises the heater plate.

In one form, the dock further comprises a cavity having a top portion and a bottom portion, the bottom portion having the heater plate located thereon, the cavity configured to retain at least a portion of the reservoir therein.

In one form, the variable portion is compressed to enable insertion of the reservoir into the cavity of the dock.

In one form, the top portion of the cavity is moveable between an open and closed configuration to facilitate insertion of the reservoir into the cavity.

In one form, the variable portion is configured to adjust in size as the first pressure is varied to vary the level of thermal engagement between the heater plate and the conductive portion.

In one form, the reservoir further includes a base and a lid, the base structured to hold a volume of liquid and including the conducting portion.

In one form, the base and lid are pivotally coupled together.

In one form, the variable portion forms a seal between the base and lid.

In one form, the reservoir further includes a latch to secure the base and lid together.

In one form, the reservoir further comprises at least one handle to facilitate coupling of the reservoir to the dock.

In one form, the reservoir further includes a retaining clip adapted to engage with a recess on the dock to retain the reservoir in the cavity of the dock.

In one form, the reservoir is structured to prevent refilling of the reservoir when the reservoir is coupled to the dock.

In one form, at least a portion of the reservoir is prevented from being opened when the reservoir is coupled to the dock.

In one form, the reservoir includes a re-filling cap.

In one form, the apparatus further comprises an overfill protection element configured to prevent filling the reservoir above a predetermined maximum volume of water.

In one form, the overfill protection element comprises at least one orifice formed in a wall of the reservoir, the at least one orifice defines an egress path of water when the predetermined maximum volume of water is exceeded.

In one form, the overfill protection element comprises a sloped profile in the side profile of a wall of the reservoir, the sloped profile defines an egress path of water when the predetermined maximum volume of water is exceeded.

One aspect of the present technology relates to a method for varying thermal contact between a heater plate and a reservoir in a humidification system for humidifying a flow of breathable gas, the method comprising varying a pressure of the flow of breathable gas in the reservoir that is in fluid communication with the flow of breathable gas to vary a force between the heater plate and the reservoir.

Another aspect of the present technology relates to an apparatus for humidifying a flow of breathable gas, comprising a heater plate and a reservoir comprising an inlet to receive the flow of breathable gas, an outlet and a conductive portion in thermal contact with the heater plate, and wherein the apparatus is configured so that varying a pressure of the flow of breathable gas in the reservoir varies a force between the heater plate and the conductive portion in a direction of thermal contact.

In one form, the apparatus further comprises a dock connectable with the reservoir.

In one form, the dock is configured to constrain the reservoir from opening in the direction of thermal contact.

Another aspect of the present technology relates to a reservoir configured to contain a volume of liquid for humidifying a pressurised flow of breathable air, comprising a base portion comprising a conductive portion, a lid portion comprising an inlet and an outlet and a seal portion wherein the base portion and the lid portion are pivotably engaged and configurable in an open configuration and a closed configuration while pivotably engaged, and the seal sealingly engages the base portion and the lid portion when the reservoir is in the closed configuration.

In one form, the seal portion comprises an outlet tube, and a baffle, the baffle being configured to connect to the inlet tube.

Another aspect of the present technology relates to an apparatus for humidifying a flow of breathable gas, comprising a heater plate and a reservoir comprising an inlet, an outlet, a variable portion and a conductive portion in thermal contact with the heater plate, wherein the apparatus is configured so that varying a height of the variable portion varies a level of thermal engagement between the conductive portion and the heater plate.

In one form, the apparatus is configured so that the thermal engagement is in a first direction that is substantially normal to a surface of the conductive portion.

Another aspect of the present technology relates to a method of varying a level of thermal engagement in a humidifier apparatus, the method comprising (i) thermally engaging a heater plate with a conductive portion of a reservoir and (ii) varying a height of a variable portion of the reservoir to vary a level of thermal engagement between the conductive portion and the heater plate.

A reservoir to hold a predetermined maximum volume of water, comprising a base portion including an overfill protection element, wherein the reservoir is configured to be convertible between an open configuration and a closed configuration and the overfill protection element prevents filling the reservoir above the maximum volume of water when the reservoir is in the open configuration.

In one form, the seal portion is configured to sealingly engage the lid portion and the base portion when the reservoir is in the closed configuration.

In one form, the overfill protection element is configured so that excess water above the maximum volume of water will spill out via the overfill protection element when a maximum water capacity is exceeded and the base portion is in its normal, working orientation.

In one form, the overfill protection element is at least one orifice that defines an egress path of water when the maximum water capacity of the base portion is exceeded when the humidifier reservoir is in an open configuration.

In one form, the overfill protection element is a sloped profile in the side profile of the base portion that defines an egress path of water when the maximum water capacity of the base portion is exceeded when the humidifier reservoir is in an open configuration.

Another aspect of the present technology relates a method of preventing overfilling in a humidifier reservoir, the method comprising (i) incorporating an overfill protection element in a base portion of the humidifier reservoir and (ii) configuring the overfill protection element so that excess water above a predetermined maximum volume of water will spill out via the overfill protection element when a maximum water capacity is exceeded and the base portion is in its normal, working orientation.

In one form, the overfill protection element includes at least one orifice.

In one form, the overfill protection element includes a sloped profile.

Another aspect of the present technology relates to a reservoir configured to hold a predetermined maximum volume of water, comprising a plurality of walls forming a cavity structured to hold the predetermined maximum volume of water, an inlet tube configured to deliver a supply of breathable gas into the cavity, the inlet tube having an inlet interior end and an inlet exterior end and an outlet tube configured to deliver a humidified supply of breathable gas from the cavity, the outlet tube having an outlet interior end and an outlet exterior end, wherein the inlet interior end and the outlet interior end are located within the cavity and the inlet exterior end and the outlet exterior end are located in one of the plurality of walls of the cavity, a first axis defined by the inlet interior end and the inlet exterior end and a second axis defined by the outlet interior end and the outlet exterior end, wherein when the reservoir is tilted approximately 90° to normal working orientation the first axis is on a first angle such that the inlet interior end and the inlet exterior end are positioned at different heights, such that the predetermined maximum volume of water is below at least one of the inlet interior end or the inlet exterior end to prevent spillback of water through the inlet tube.

In one form, the reservoir is further configured so that when the reservoir is tilted approximately 90° to normal working orientation the second axis is on a second angle such that the outlet interior end and the outlet exterior end are positioned at different heights, such that the predetermined maximum volume of water is below at least one of the outlet interior end or the outlet exterior end to prevent spillback of water through the outlet tube.

In another aspect of the present technology, a swing latch may be utilized to secure a tub lid to a tub base.

In another aspect of the present technology, a swing latch may be utilized to secure a tub to a dock.

In examples, (a) a locking end may include one or more downward extending retention protrusions, (b) a dock locking recess in the upper surface of the dock may be shaped to receive the corresponding protrusion(s), (c) the swing latch may be biased to a closed position in which the retention protrusion is in a lowered position in which it can engage in the dock locking recess, (d) the front face may be tapered to allow the swing latch to raise without manual intervention when the tapered front face engages the dock wall, (e) to release the tub, the button end may be depressed again to raise the retention protrusion disengaging it from the dock locking recess and allowing the tub to slide out, and/or (f) a variety of spring configurations may be suitable to bias the locking end to the closed position.

In other forms of the present technology, the humidifier tub (or reservoir) may be engageable with the reservoir dock of the pap device. These forms may share various features, structures, and characteristics of the tubs previously described above such that repeat description of like features is unnecessary.

In another aspect, an inlet formed separately from the humidifier tub lid and subsequently attached to the top of the lid.

In another aspect, the retention protrusions for engaging the dock locking recesses in the humidifier dock are situated on a swingable latch.

In another aspect, a tongue and key are utilized in the engagement between the tub and humidifier dock.

In another aspect, a flat face that engages an exterior face of the humidifier dock adjacent the locking recess.

In another aspect, a drop on lid utilizes opposing clips to retain the humidifier lid on the humidifier base.

In another aspect, a camming slide lock is utilized to draw the humidifier tub into the fully seated position and lock the tub there.

In another aspect, a camming slide lock is combined with a latch and utilized to draw the tub into the fully seated position and lock the tub there.

In another aspect, a rotating lever is deployed through the roof of the dock to engage a tub retention feature formed on the tub lid which when rotated draws the tub into the fully seated position.

In another aspect, a release knob is deployed through the roof of the dock to engage the tub lid, preventing the lid from returning to the undepressed state until the release knob is rotated.

In another aspect, a release knob, or rotary wedge, is deployed on the tub itself to move the tub between the depressed and undepressed states.

In another aspect, a locking latch on the roof of the dock engages the tub lid to hold the tub in the fully seated position.

In another aspect, the pivotable locking latch is formed on the tub lid and engages a catch on the dock roof.

Another aspect of the present technology relates to an apparatus for use in treating a respiratory disorder including a housing, a pneumatic block comprising an air path therein, a pressure generator located in the pneumatic block and configured to supply a flow of air, a device outlet fluidly coupled to the pressure generator and configured to be coupled to an air circuit to deliver the flow of air to a patient interface for treating a respiratory disorder, and a chassis configured to locate the housing, the pneumatic block and the device outlet, the chassis comprising a dock for receiving a muffler or a humidifier reservoir.

Another aspect of the present technology relates to a CPAP system including a humidifier, a patient interface, and an air delivery tube to deliver humidified air to the patient interface. In an example, the humidifier is integrated with an RPT device structured to produce a flow of air at positive pressure.

Another aspect of the present technology relates to a water reservoir for an apparatus for humidifying a flow of breathable gas.

Another aspect of the present technology relates to a water reservoir dock for an apparatus for humidifying a flow of breathable gas.

Another aspect of the present technology relates to an apparatus for humidifying a flow of breathable gas including a water reservoir including a chamber structured to hold a volume of water and a water reservoir dock structured and arranged to receive the water reservoir in an operative position.

Another aspect of the present technology relates to an apparatus for humidifying a flow of breathable gas including a water reservoir including a chamber structured to hold a volume of water, a water reservoir dock structured and arranged to receive the water reservoir in an operative position, and an air delivery tube configured to pass the flow of breathable gas that has been humidified in the water reservoir to a patient interface.

Another aspect of the present technology relates to an apparatus for humidifying a flow of breathable gas including a water reservoir including a chamber structured to hold a volume of water, a water reservoir dock structured and arranged to receive the water reservoir in an operative position, and a latch movable between (1) a locked position to releasably lock the water reservoir to the water reservoir dock in the operative position, and (2) an unlocked position to allow insertion of the water reservoir into the water reservoir dock and removal of the water reservoir from the water reservoir dock.

In an example, the latch is pivotably movable between the locked position and the unlocked position. In an example, the latch is provided to a lid of the water reservoir and movable to engage the water reservoir dock in the locked position. In an example, the latch is slidably movable between the locked position and the unlocked position.

Another aspect of the present technology relates to a water reservoir for an apparatus for humidifying a flow of breathable gas including a base, a lid connected to the base, the lid and the base forming a chamber structured to hold a volume of water, an inlet tube arranged to provide an inlet for receiving a flow of breathable gas into the chamber, and an outlet tube arranged to provide an outlet for delivering a flow of humidified breathable gas from the chamber. The outlet tube comprises a one-piece construction with the lid. The inlet tube comprises a separate and distinct structure from the lid and subsequently attached to a top of the lid. The inlet tube includes an inlet portion including inlet end and an outlet portion including outlet end, and, when the inlet tube is attached to the lid, the inlet end is arranged outside the chamber and the outlet end is arranged inside the chamber.

In an example, the inlet portion extends transverse to the outlet portion. In an example, the top of the lid includes an inlet seat configured to receive the inlet portion of the inlet tube. In an example, the top of the lid includes an opening configured to receive the outlet portion of the inlet tube therethrough.

Another aspect of the present technology relates to an apparatus for humidifying a flow of breathable gas including a water reservoir including a chamber structured to hold a volume of water, a water reservoir dock structured and arranged to receive the water reservoir in an operative position, and a pivotable latch pivotably movable between (1) a locked position to releasably lock the water reservoir to the water reservoir dock in the operative position, and (2) an unlocked position to allow insertion of the water reservoir into the water reservoir dock and removal of the water reservoir from the water reservoir dock. The pivotable latch is provided to a lid of the water reservoir and movable to engage the water reservoir dock in the locked position.

In an example, the pivotable latch includes one or more retention protrusions adapted to engage within respective locking recesses provided to the water reservoir or the water reservoir dock in the locked position. In an example, each of the retention protrusions includes a taper along its front face. In an example, the pivotable latch is biased to the locked position. In an example, the pivotable latch is biased to the unlocked position.

Another aspect of the present technology relates to an apparatus for humidifying a flow of breathable gas including: a water reservoir including a chamber structured to hold a volume of water, the water reservoir including an inlet tube arranged to provide an inlet for receiving a flow of breathable gas into the chamber, and an outlet tube arranged to provide an outlet for delivering a flow of humidified breathable gas from the chamber; a water reservoir dock structured and arranged to receive the water reservoir in an operative position; and a pivotable latch pivotably movable between (1) a locked position to releasably lock the water reservoir to the water reservoir dock in the operative position, and (2) an unlocked position to allow insertion of the water reservoir into the water reservoir dock and removal of the water reservoir from the water reservoir dock. The pivotable latch is provided to the water reservoir dock and movable to engage the water reservoir in the locked position.

In an example, the pivotable latch includes one or more retention protrusions adapted to engage within respective locking recesses provided to the water reservoir or the water reservoir dock in the locked position.

Another aspect of the present technology relates to an apparatus for humidifying a flow of breathable gas including a water reservoir including a chamber structured to hold a volume of water, a water reservoir dock structured and arranged to receive the water reservoir in an operative position, and a tongue and key arrangement structured and arranged to guide the water reservoir into the operative position, the tongue and key arrangement forming a keyway extending in a horizontal direction and in a vertical direction.

In an example, the tongue and key arrangement includes a tongue on each side of the water reservoir, and top and bottom key rails on each side of the water reservoir dock forming the keyway configured to receive a respective tongue.

Another aspect of the present technology relates to a water reservoir for an apparatus for humidifying a flow of breathable gas including a base and a lid connected to the base. The base and the lid form a chamber structured to hold a volume of water. The lid includes a first clip on one side of the lid and a second clip on an opposing side of the lid, and each of the first clip and the second clip is structured and arranged to releasably interlock with a respective protrusion provided to opposing sides of the base with a snap-fit.

Another aspect of the present technology relates to an apparatus for humidifying a flow of breathable gas including a water reservoir including a chamber structured to hold a volume of water and a water reservoir dock structured and arranged to receive the water reservoir in an operative position. The water reservoir includes one or more retention protrusions adapted to engage within respective locking recesses provided to the water reservoir dock in the operative position. Each of the retention protrusions includes a flat face configured and arranged to engage an exterior face of the water reservoir dock adjacent respective locking recesses during insertion of the water reservoir.

Another aspect of the present technology relates to an apparatus for humidifying a flow of breathable gas including a water reservoir including a chamber structured to hold a volume of water, a water reservoir dock structured and arranged to receive the water reservoir in an operative position, and a slidable lock slidably movable between (1) a locked position to releasably lock the water reservoir to the water reservoir dock in the operative position, and (2) an unlocked position to allow insertion of the water reservoir into the water reservoir dock and removal of the water reservoir from the water reservoir dock.

In an example, the slidable lock is configured to interact with a ramp or cam surface during movement into the locked position.

Another aspect of the present technology relates to an apparatus for humidifying a flow of breathable gas including a compressible water reservoir including a chamber structured to hold a volume of water, and a water reservoir dock structured and arranged to receive the compressible water reservoir in an operative position. The compressible water reservoir includes a rotary wedge configured and arranged to expand and collapse the compressible water reservoir to lock and release the compressible water reservoir to the water reservoir dock.

Of course, portions of the aspects may form sub-aspects of the present technology. Also, various ones of the sub-aspects, aspects or both may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1a shows a system including a patient 1000 wearing a patient interface 3000, in the form of a nasal pillows, receives a supply of air at positive pressure from an RPT device 4000. Air from the RPT device is humidified in a humidifier 5000, and passes along an air circuit 4170 to the patient 1000. A bed partner 1100 is also shown.

4.2 Respiratory System and Facial Anatomy

Figure 1A:
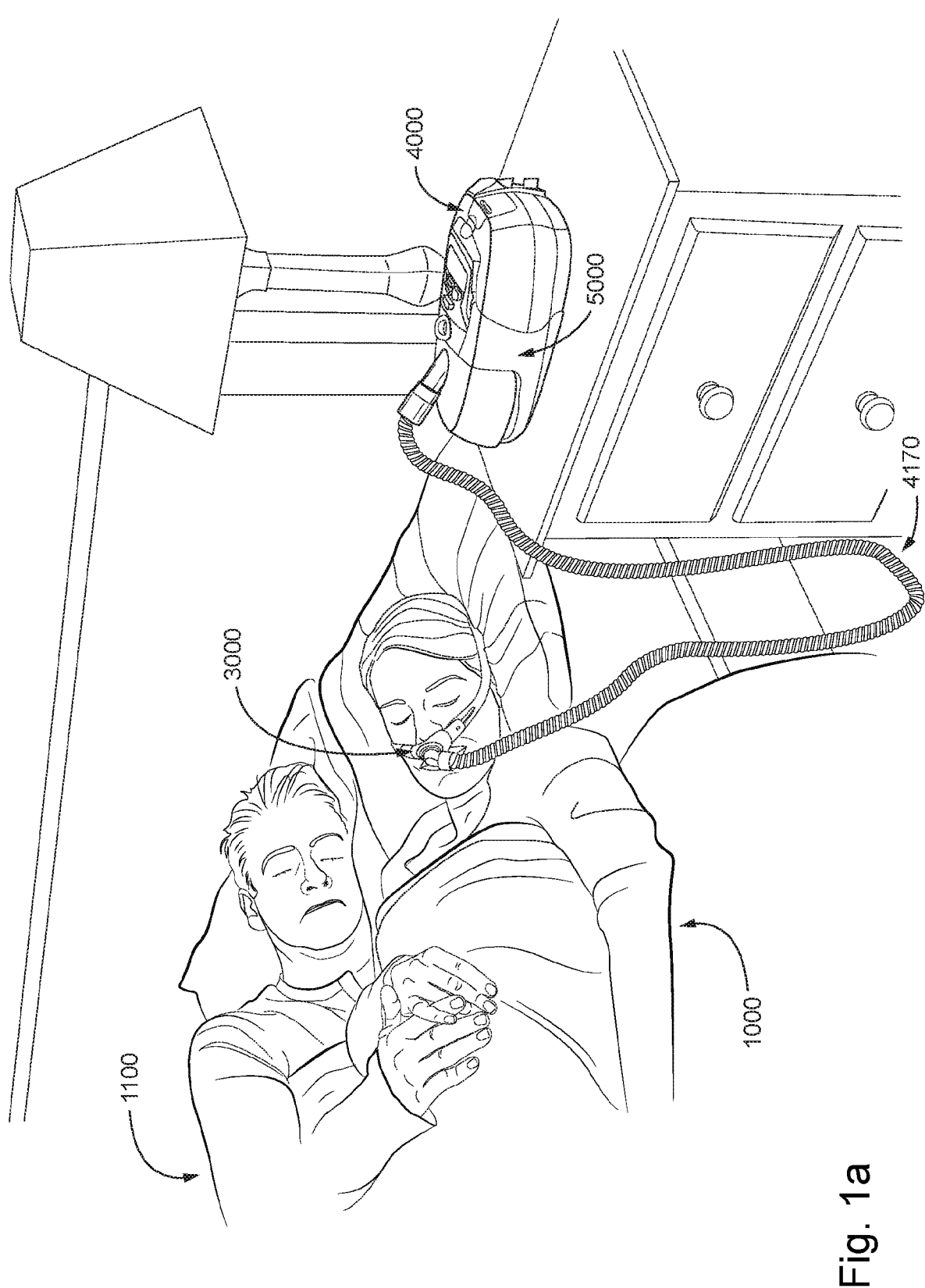
FIG. 1b shows a system including a patient 1000 wearing a patient interface 3000, in the form of a nasal mask, receives a supply of air at positive pressure from an RPT device 4000. Air from the RPT device is humidified in a humidifier 5000, and passes along an air circuit 4170 to the patient 1000.
FIG. 1c shows a system including a patient 1000 wearing a patient interface 3000, in the form of a full-face mask, receives a supply of air at positive pressure from an RPT device 4000. Air from the RPT device is humidified in a humidifier 5000, and passes along an air circuit 4170 to the patient 1000.
Figure 1B:
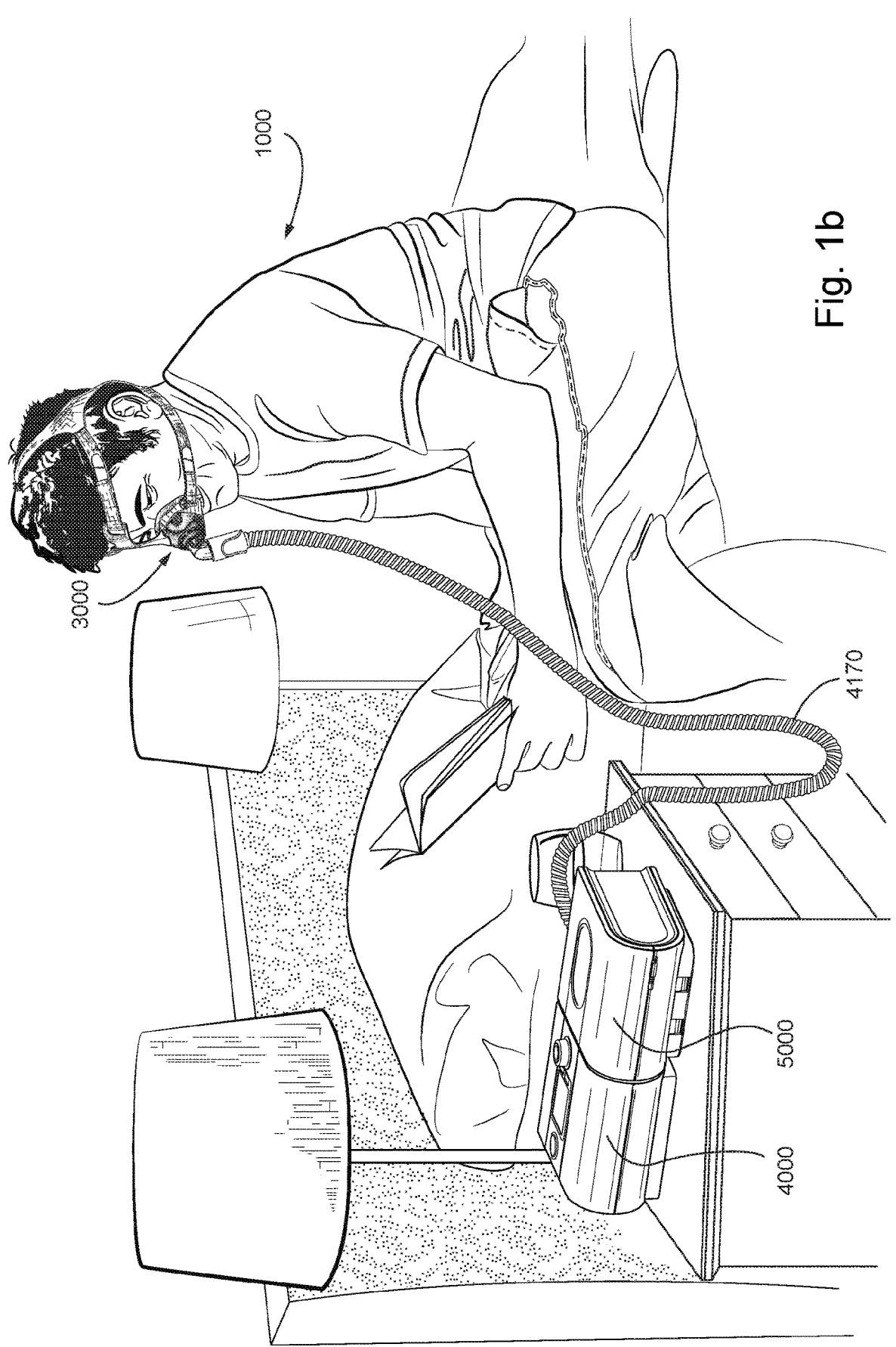
Figure 1C:
Figure 2A:
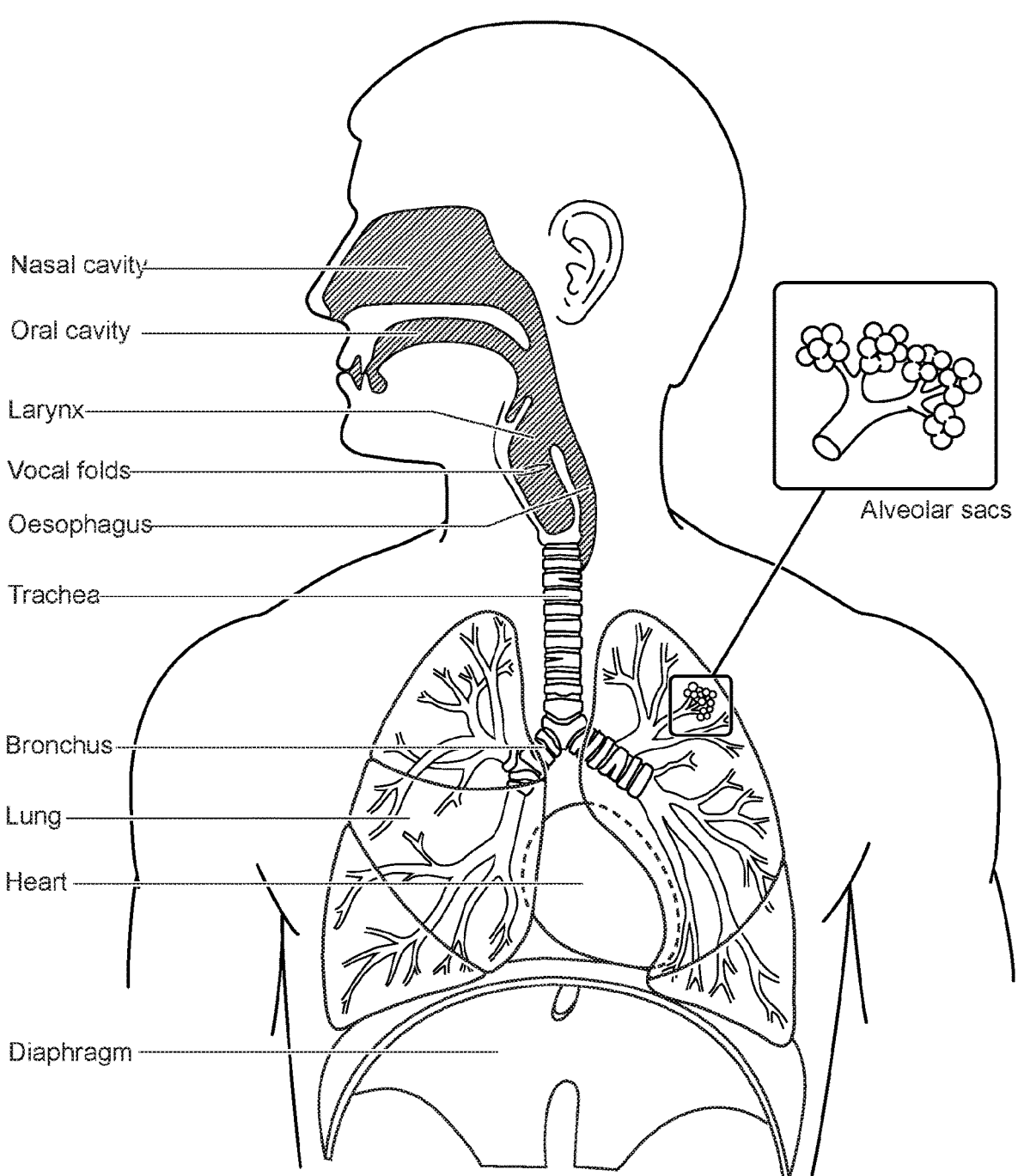

FIG. 2a shows an overview of a human respiratory system including the nasal and oral cavities, the larynx, vocal folds, oesophagus, trachea, bronchus, lung, alveolar sacs, heart and diaphragm.

4.3 Patient Interface

Figure 3A:
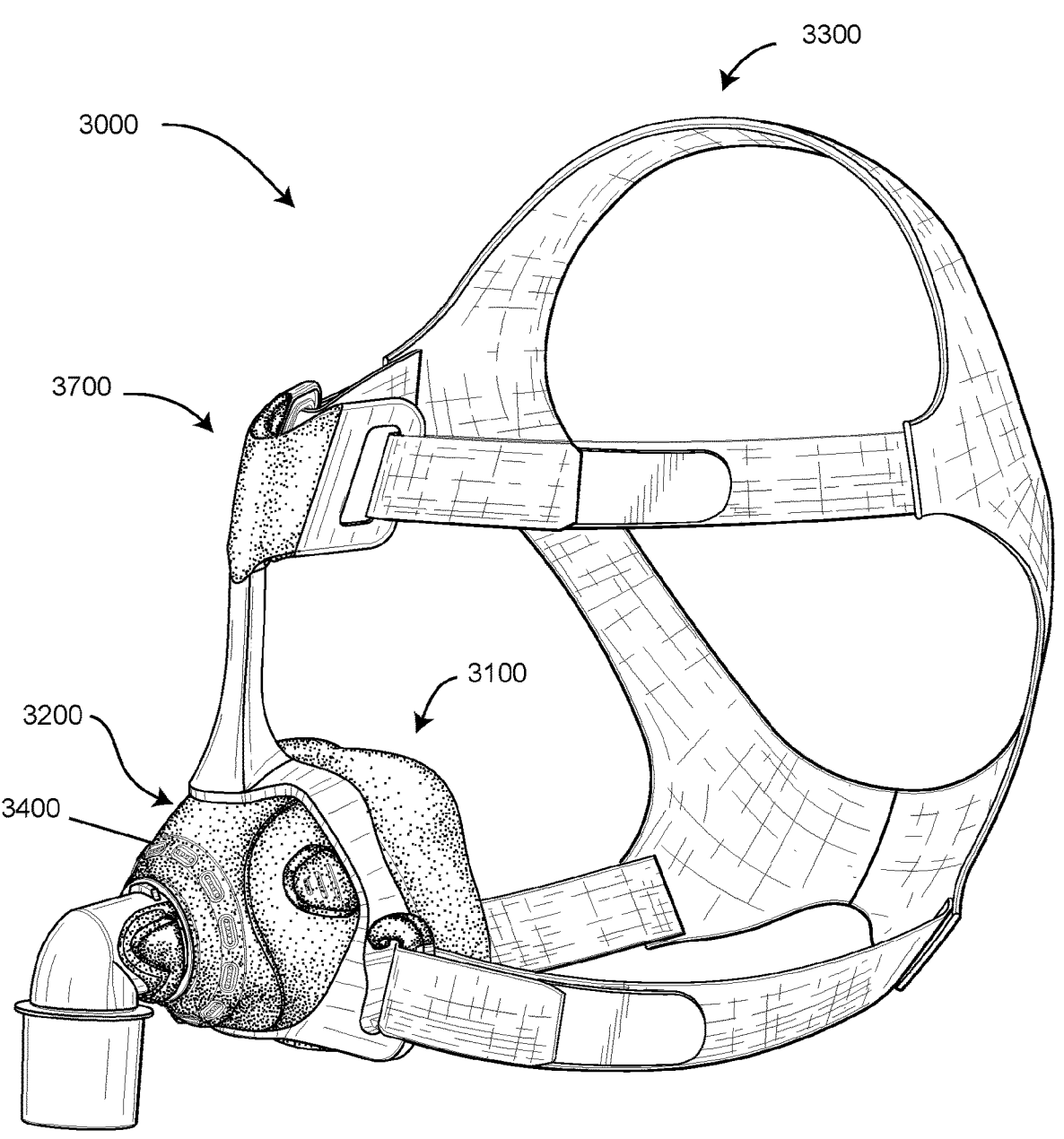

FIG. 3a shows a patient interface in the form of a nasal mask in accordance with one form of the present technology.

4.4 Breathing Waveforms

Figure 4:
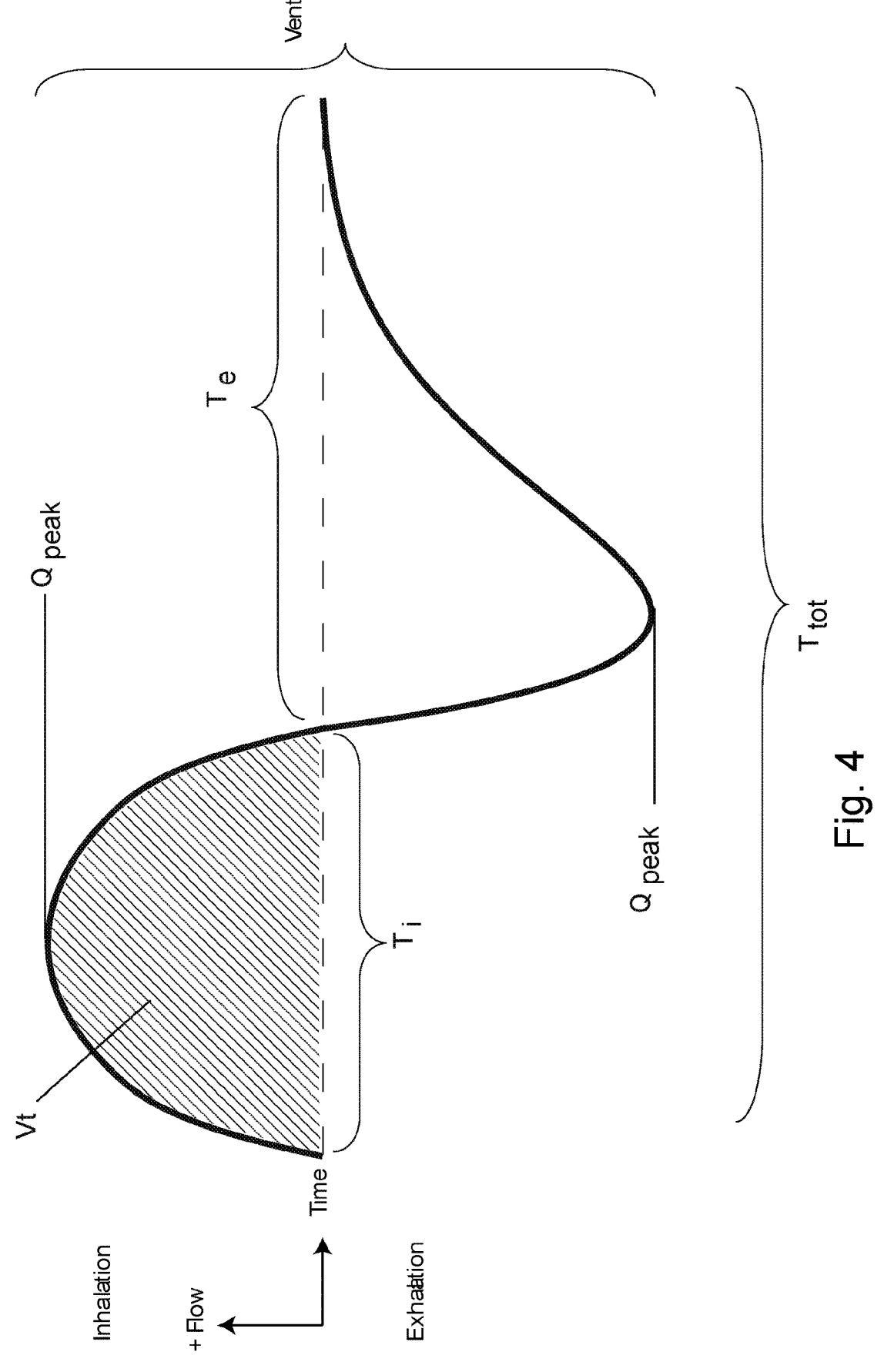

FIG. 4 shows a model typical breath waveform of a person while sleeping.

4.5 RPT Device and Humidifier

Figure 5A:
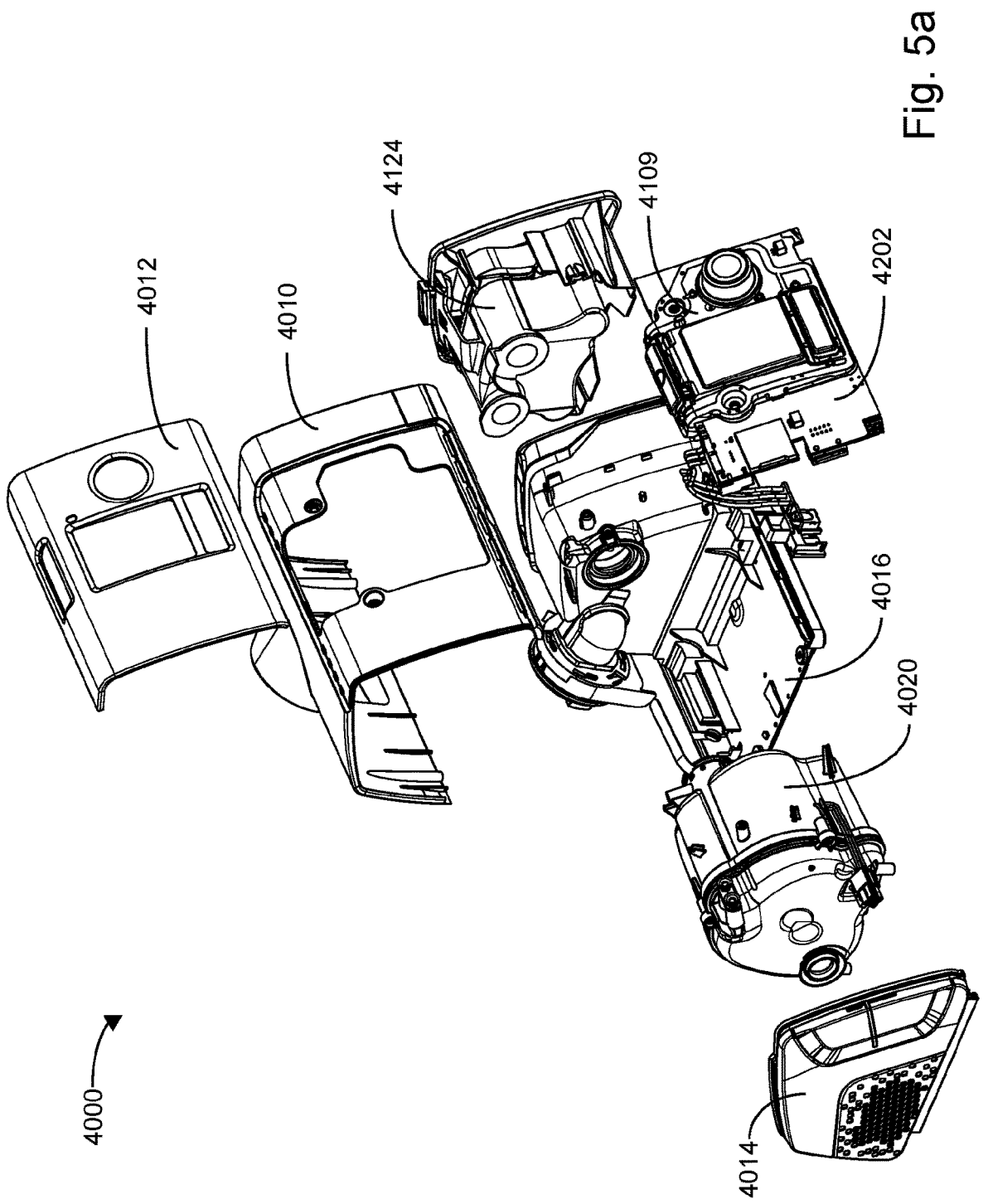

FIG. 5a shows an exploded perspective view of an RPT device 4000 in accordance with one form of the present technology.

Figure 5B:
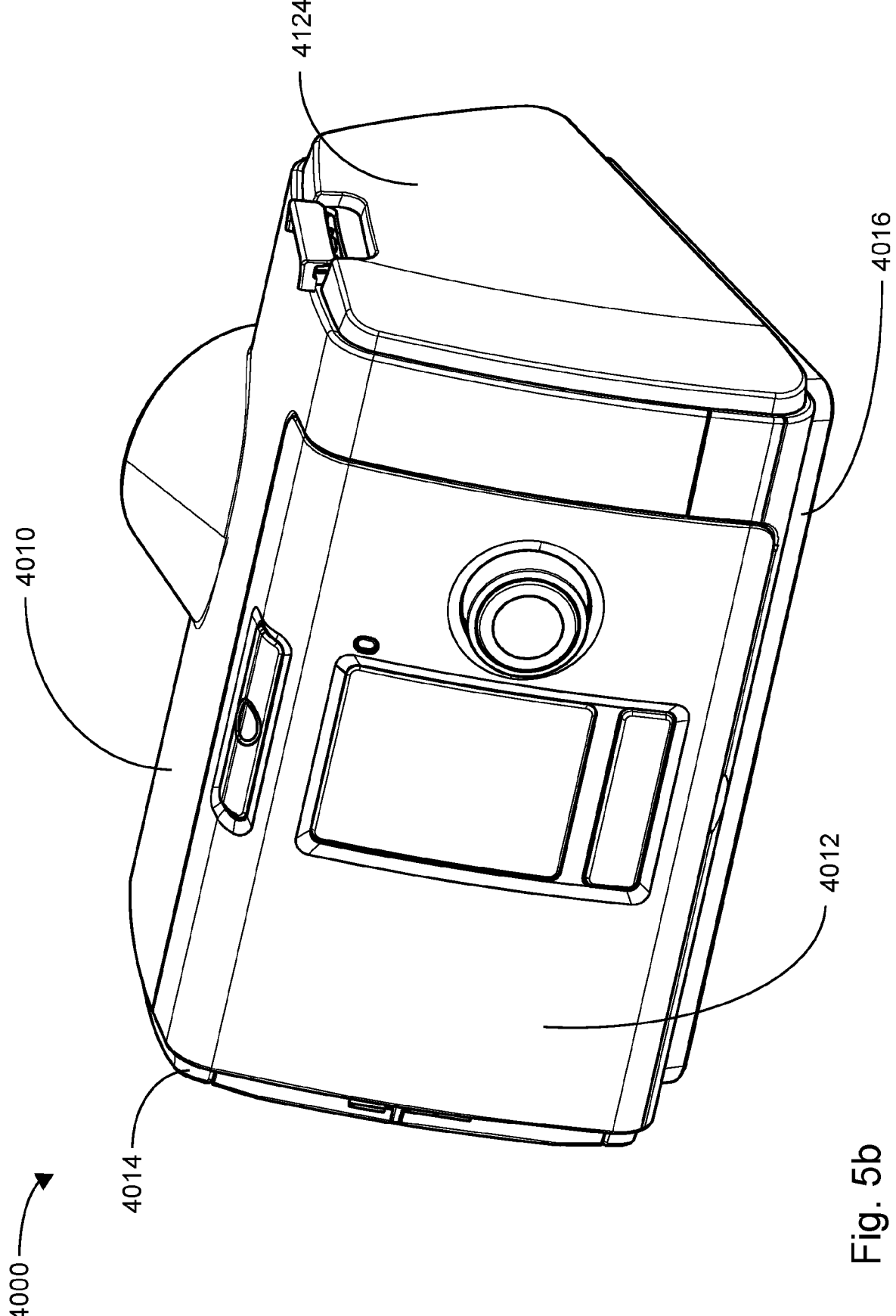

FIG. 5b shows a perspective view of an RPT device 4000 comprising an outlet muffler 4124 in accordance with one form of the present technology.

Figure 5C:
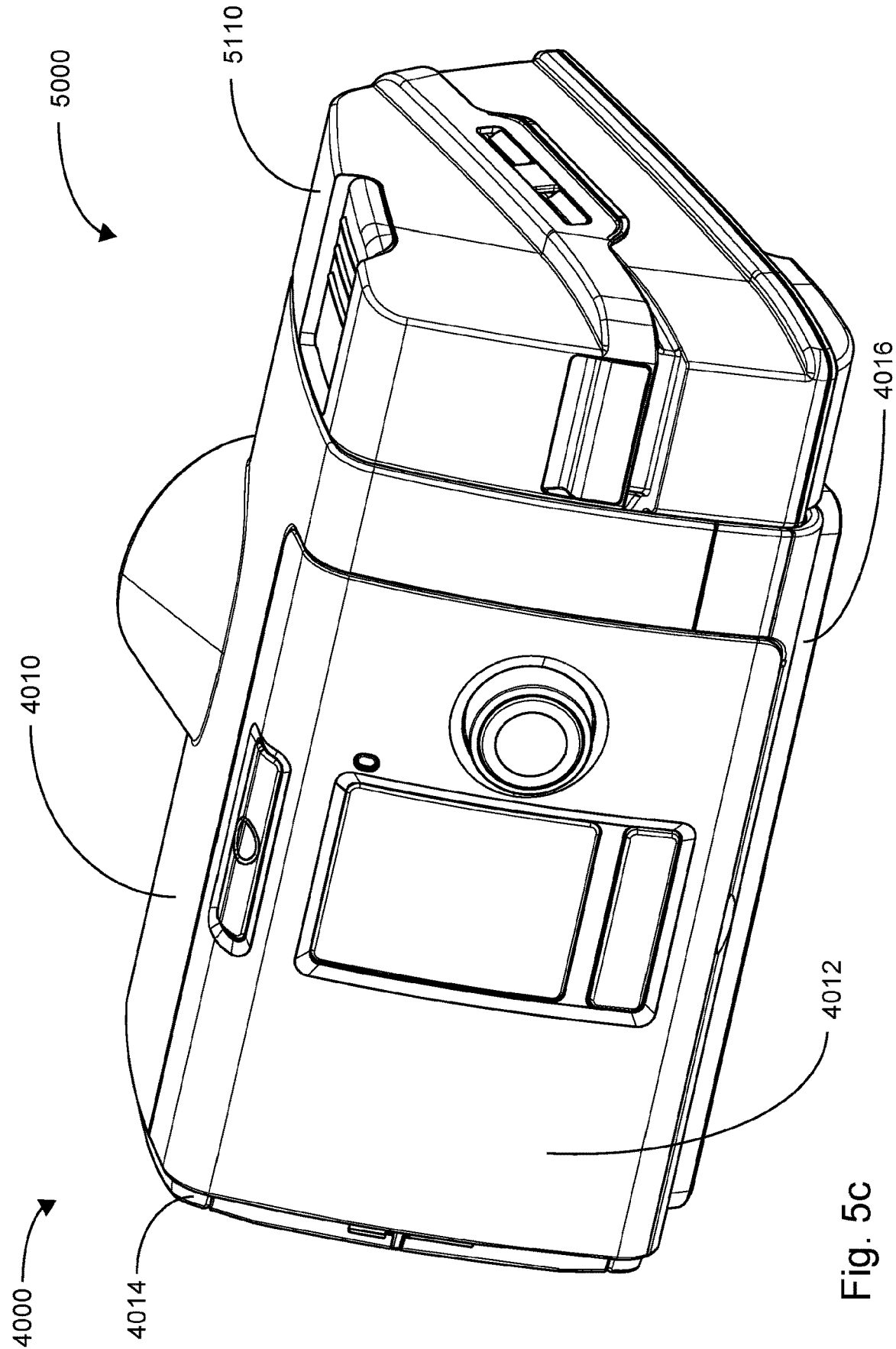

FIG. 5c shows a perspective view of an RPT device 4000 with an integrated humidifier 5000 comprising a water reservoir 5110 in accordance with one form of the present technology.

Figure 5D:
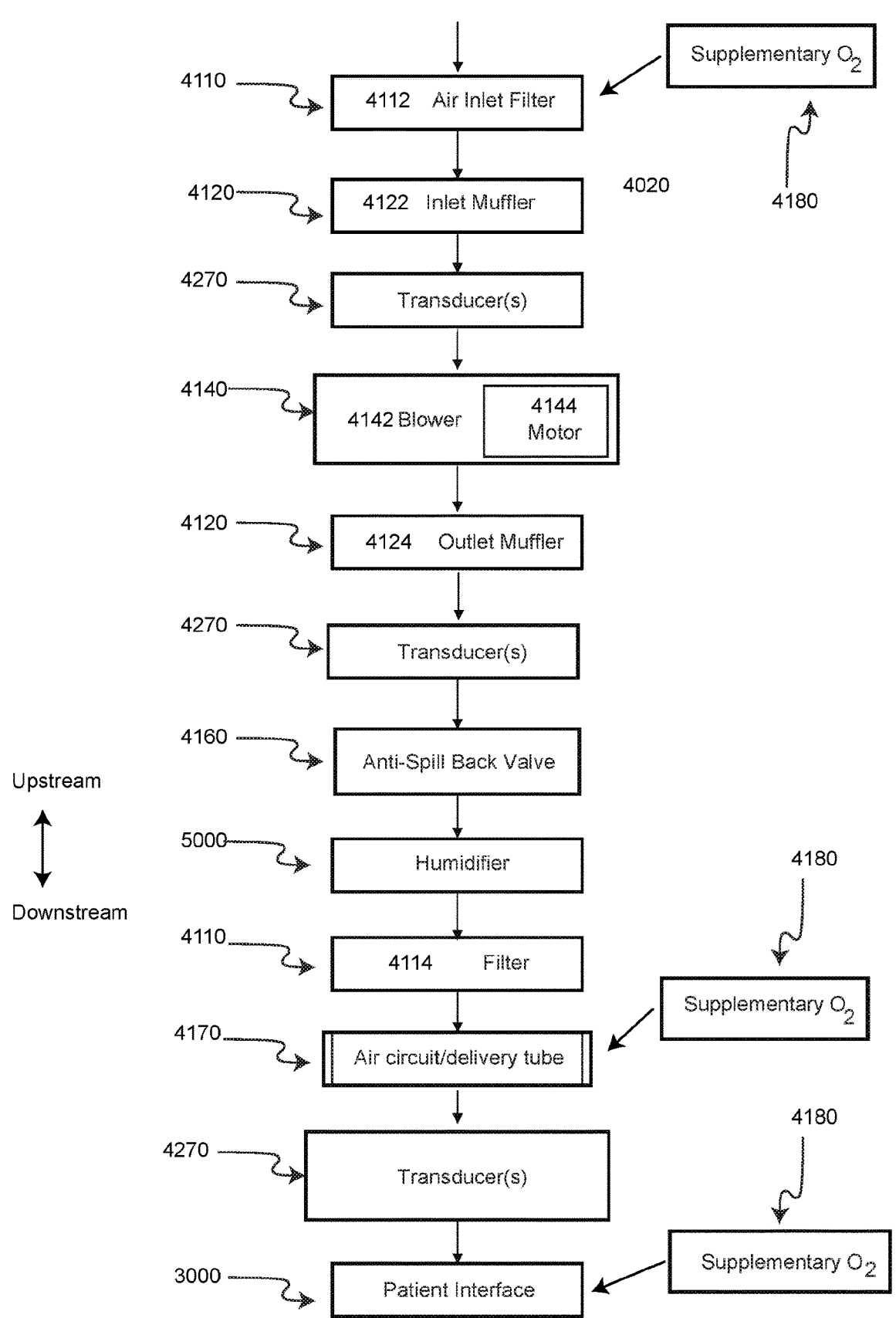

FIG. 5d shows a schematic diagram of the pneumatic path of an RPT device in accordance with one form of the present technology. The directions of upstream and downstream are indicated.

Figure 5E:
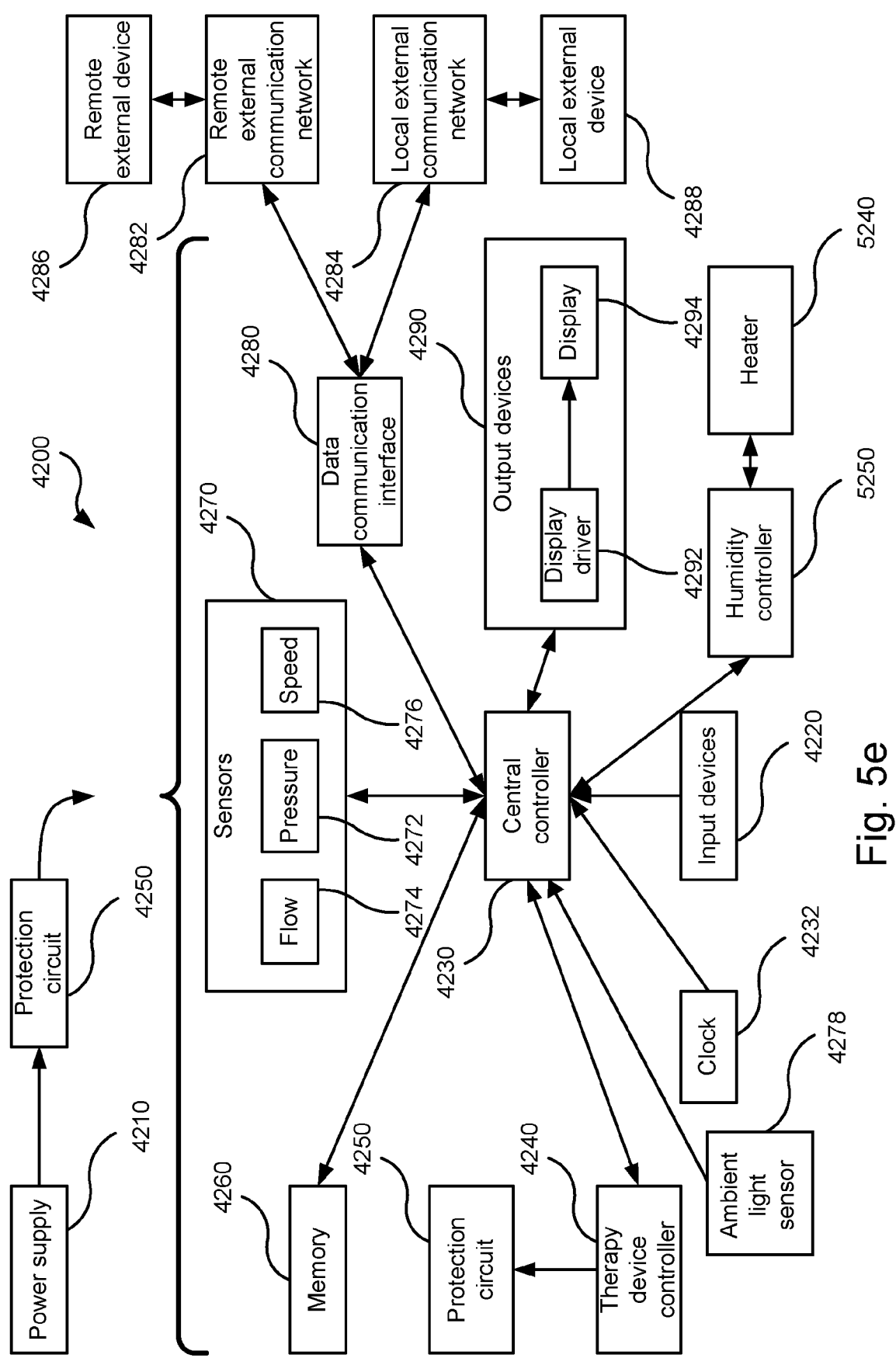

FIG. 5e shows a schematic diagram of the electrical components of an RPT device in accordance with one aspect of the present technology.

Figure 5F:
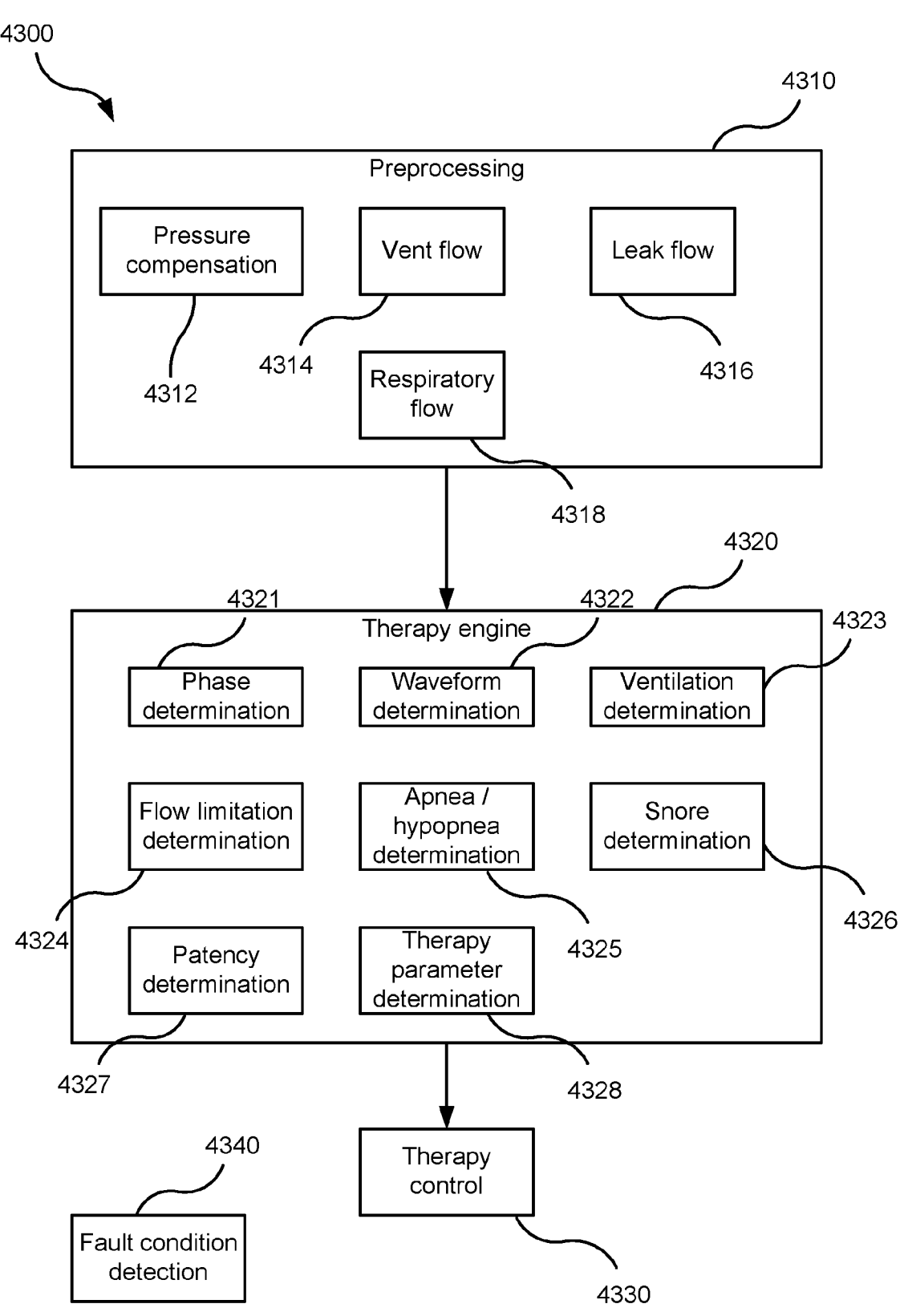

FIG. 5f shows a schematic diagram of the algorithms implemented in a PAP device in accordance with an aspect of the present technology. In this figure, arrows with solid lines indicate an actual flow of information, for example via an electronic signal.

Figure 5G:
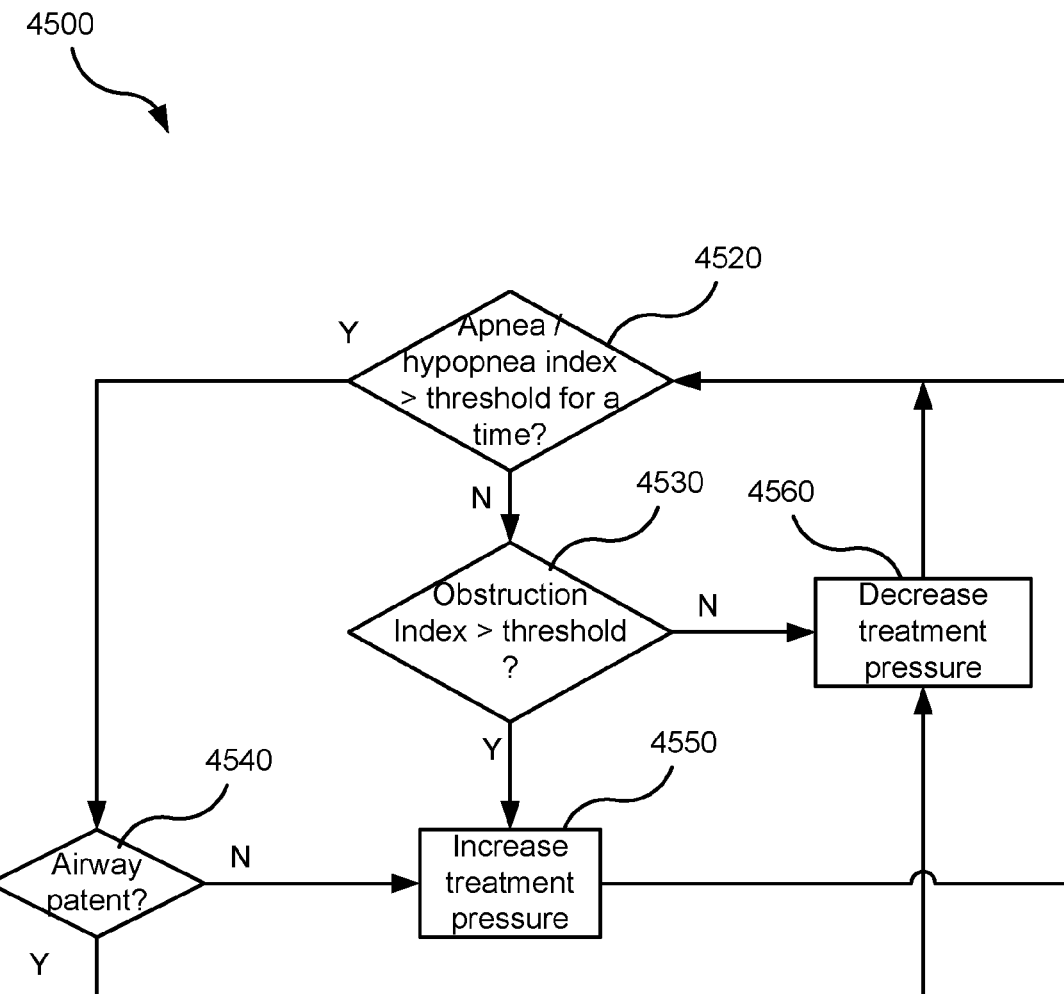

FIG. 5g is a flow chart illustrating a method carried out by the therapy engine of FIG. 5f in accordance with one aspect of the present technology.

Figures 5H, 5I:
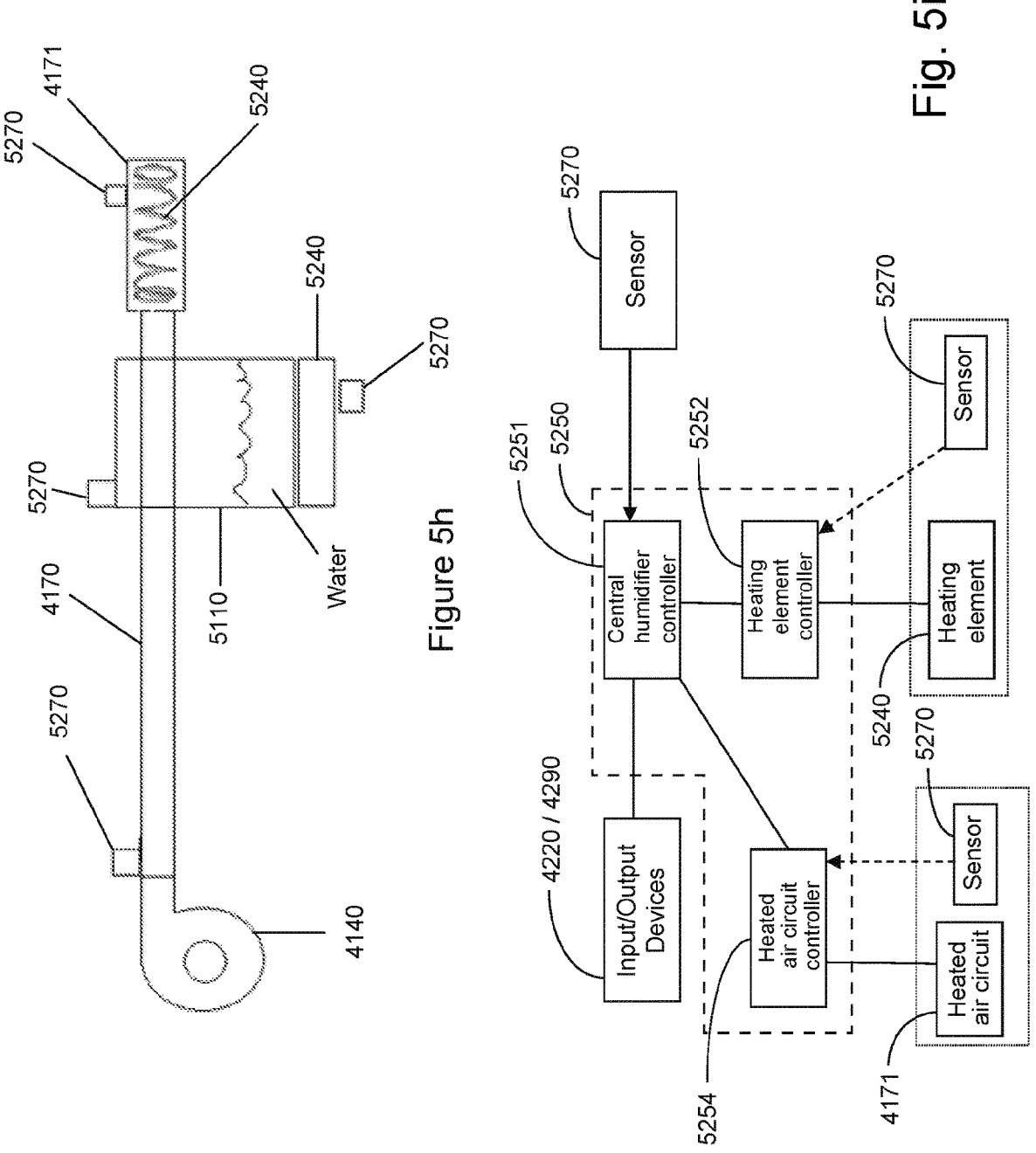

FIG. 5h shows a simplified representation of a humidifier connected to a blower and a patient conduit.

FIG. 5i shows a schematic of a humidifier.

Figure 6A:
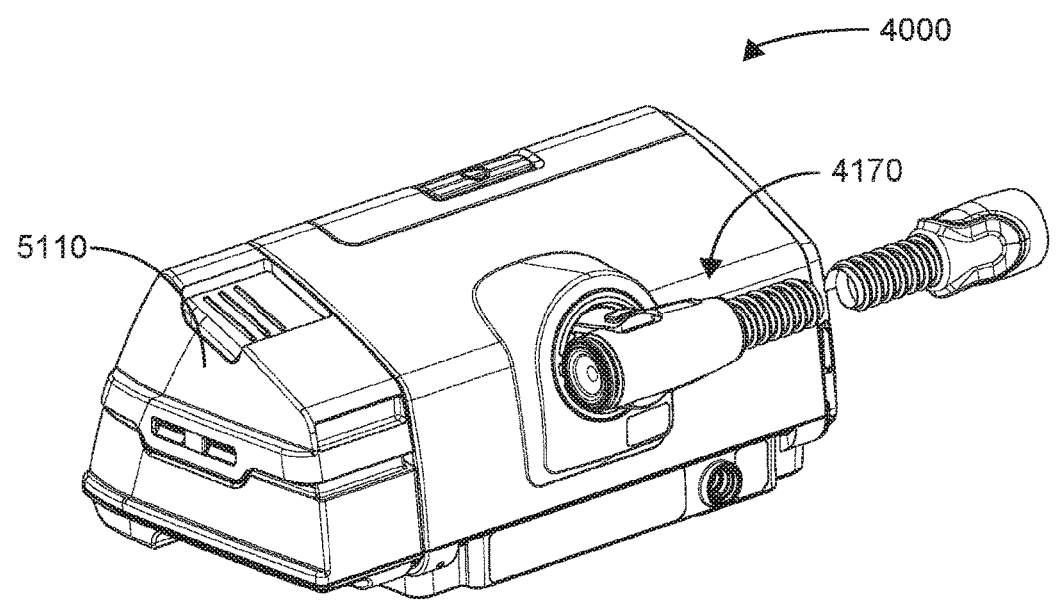

FIG. 6a shows a rear perspective view of an RPT device 4000 in accordance with one form of the present technology, showing an air circuit 4170 engaged with the RPT device 4000.

Figure 6B:
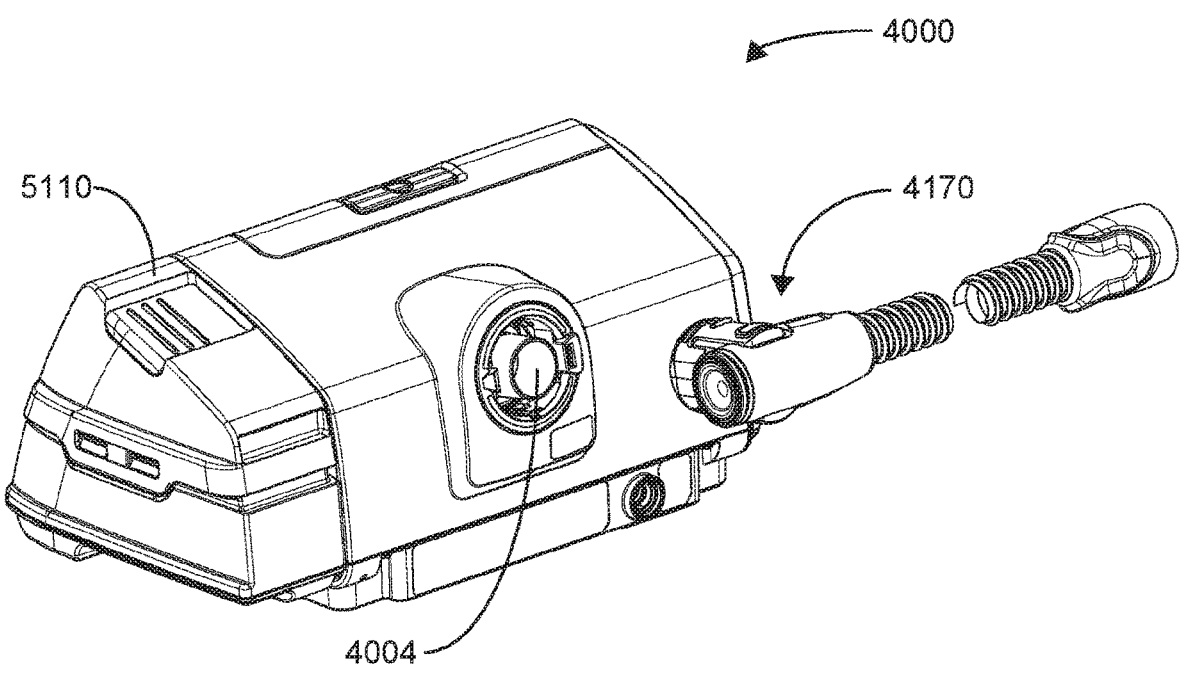

FIG. 6b shows a rear perspective view of an RPT device 4000 in accordance with one form of the present technology, showing an air circuit 4170 in exploded view.

Figure 6C:
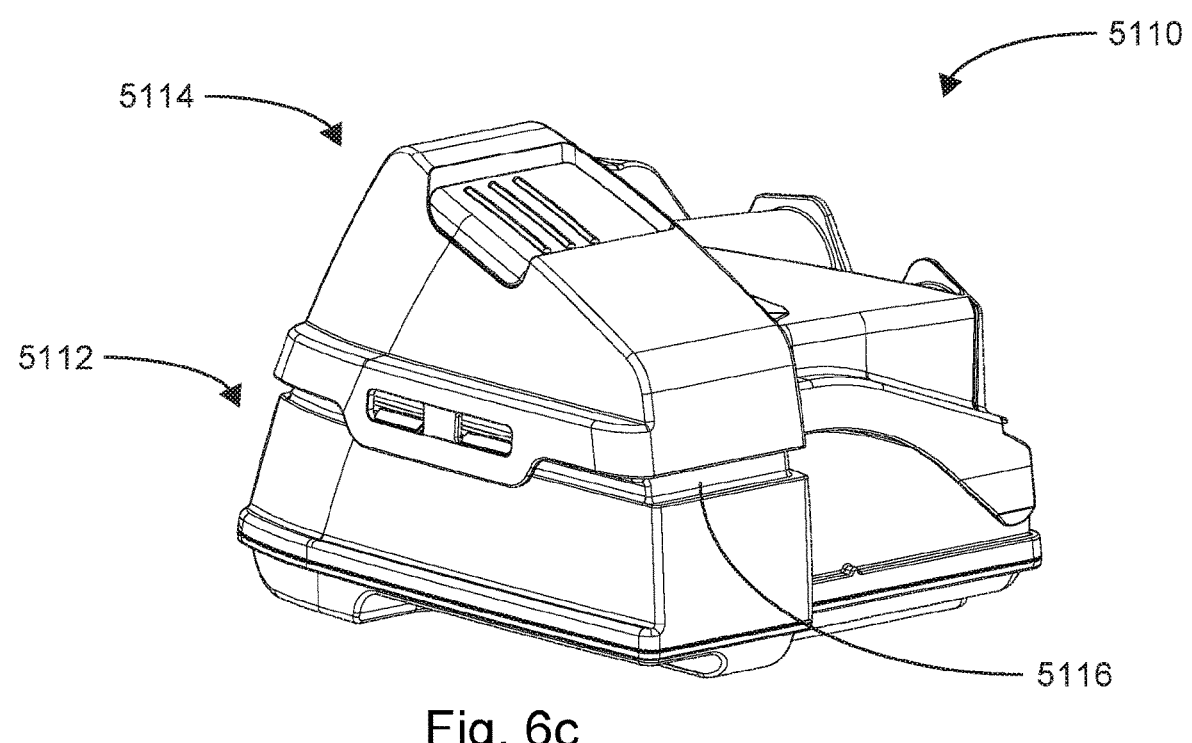

FIG. 6c shows a perspective view of a water reservoir 5110 in accordance with one form of the present technology.

Figure 6D:
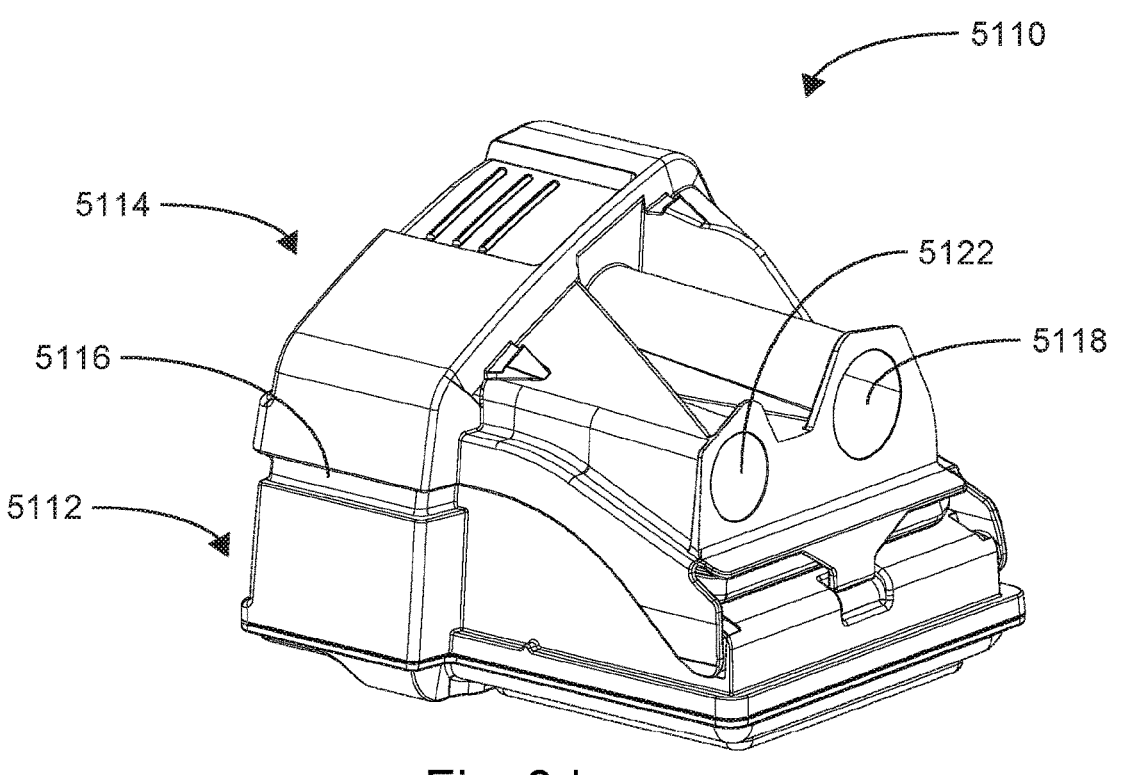

FIG. 6d shows another perspective view of a water reservoir 5110 in accordance with one form of the present technology.

Figure 6E:
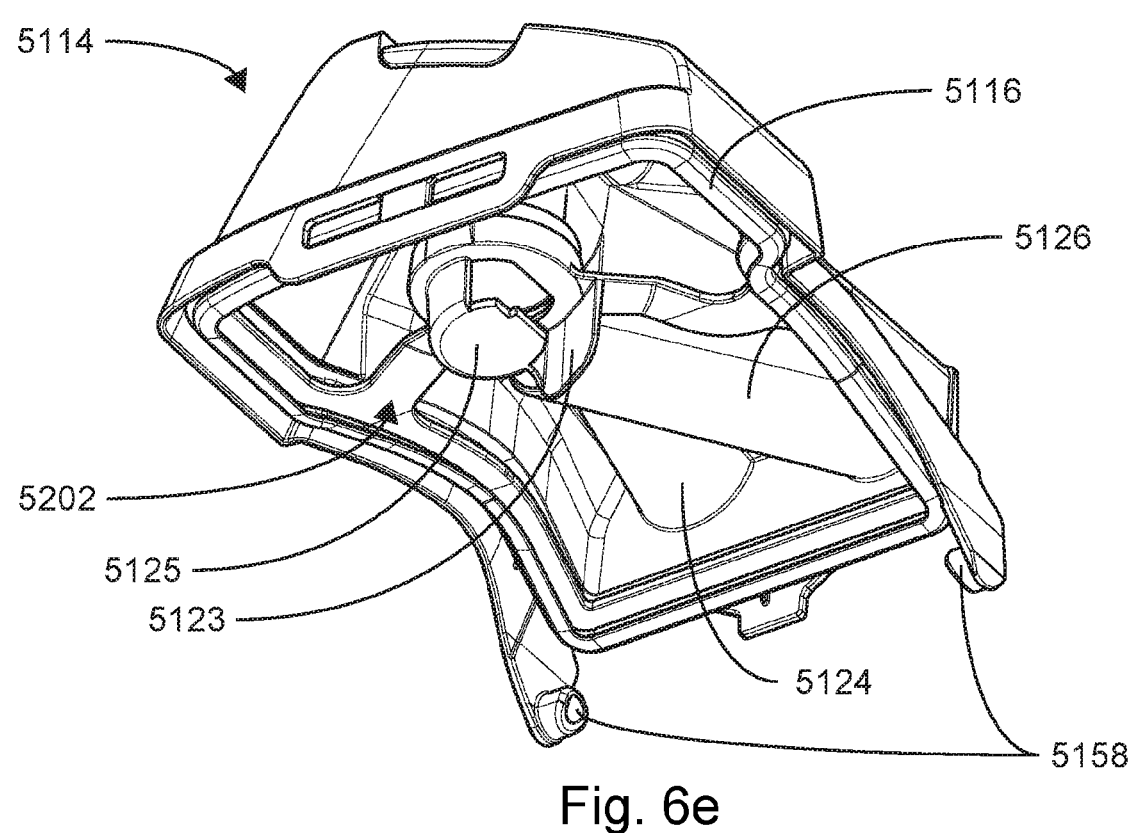

FIG. 6e shows a perspective view of a water reservoir lid 5114 and an intermediate portion 5202 in accordance with one form of the present technology.

Figure 6F:
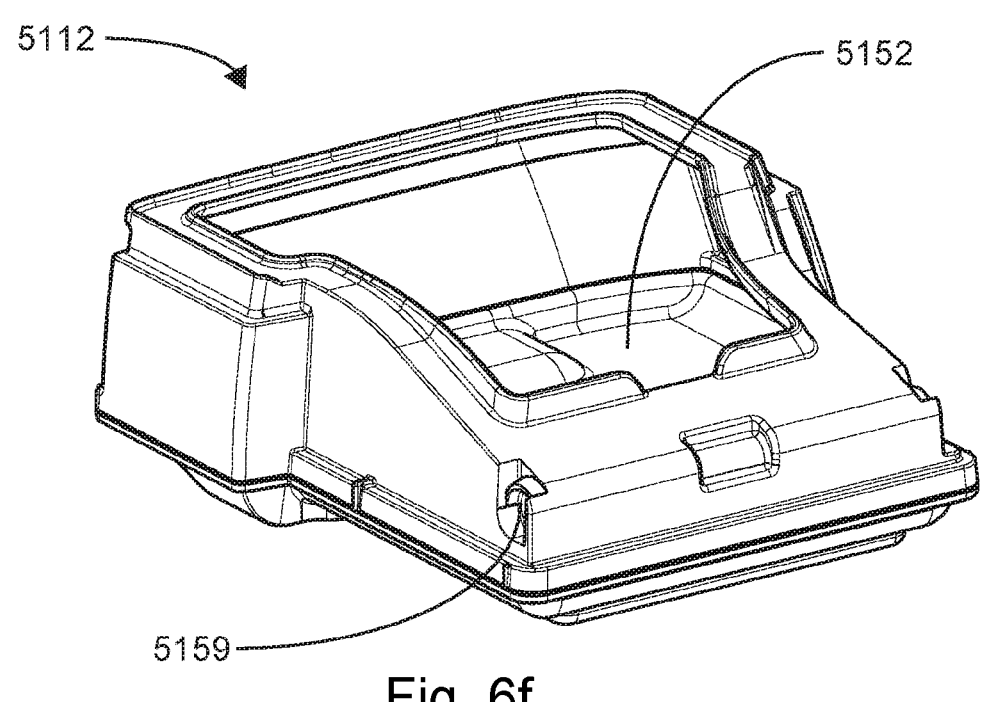

FIG. 6f shows a perspective view of a water reservoir base 5112 in accordance with one form of the present technology.

Figure 6G:
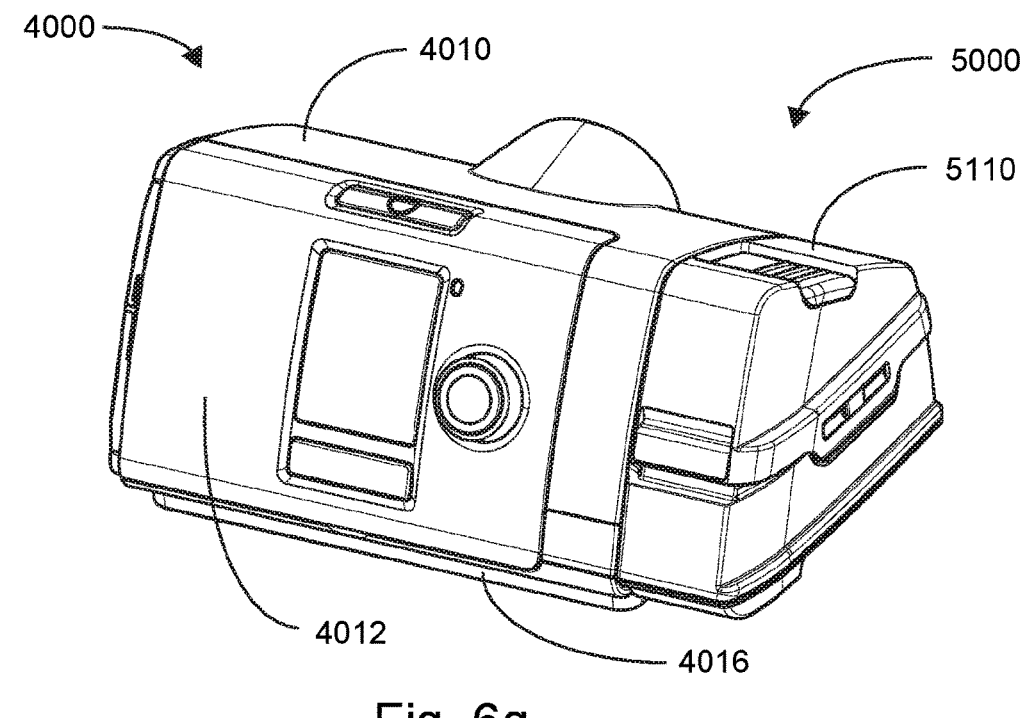

FIG. 6g shows a perspective view of an RPT device 4000 comprising an integrated humidifier 5000 and a water reservoir 5110 in accordance with one form of the present technology.

Figure 6H:
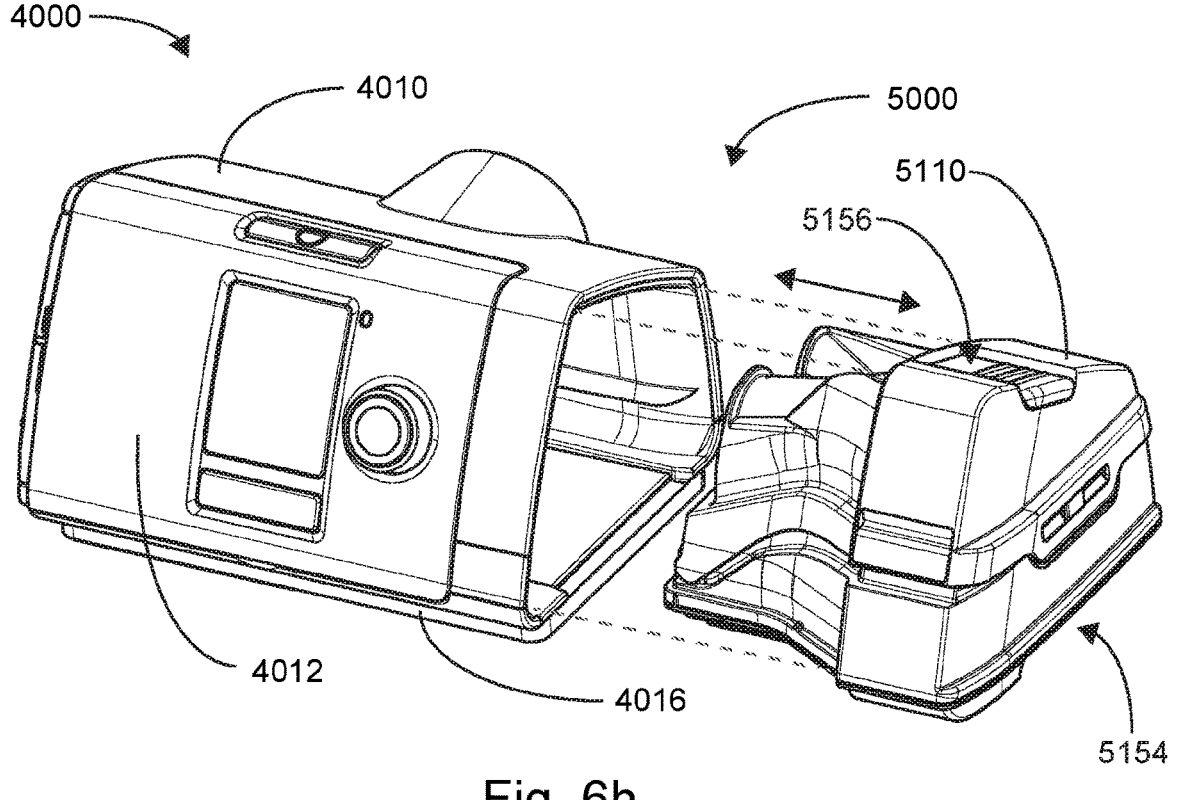

FIG. 6*h* shows a perspective view of an RPT device 4000 comprising an integrated humidifier 5000 in accordance with one form of the present technology, showing the water reservoir 5110 in exploded view.

Figure 6I:
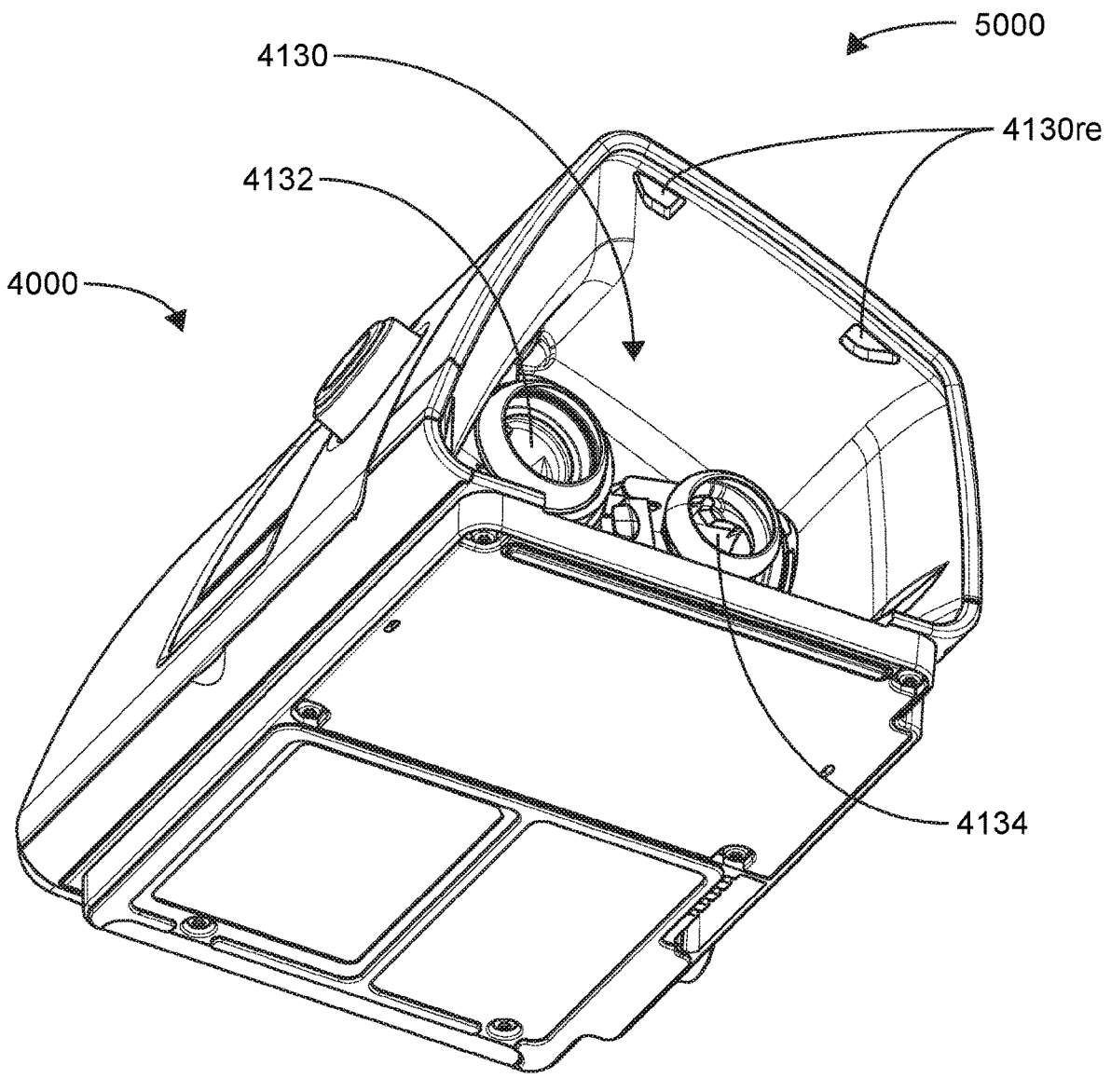

FIG. 6*i* shows a perspective view of an RPT device 4000 comprising an integrated humidifier 5000 in accordance with one form of the present technology, not showing the water reservoir 5110.

Figure 6J:
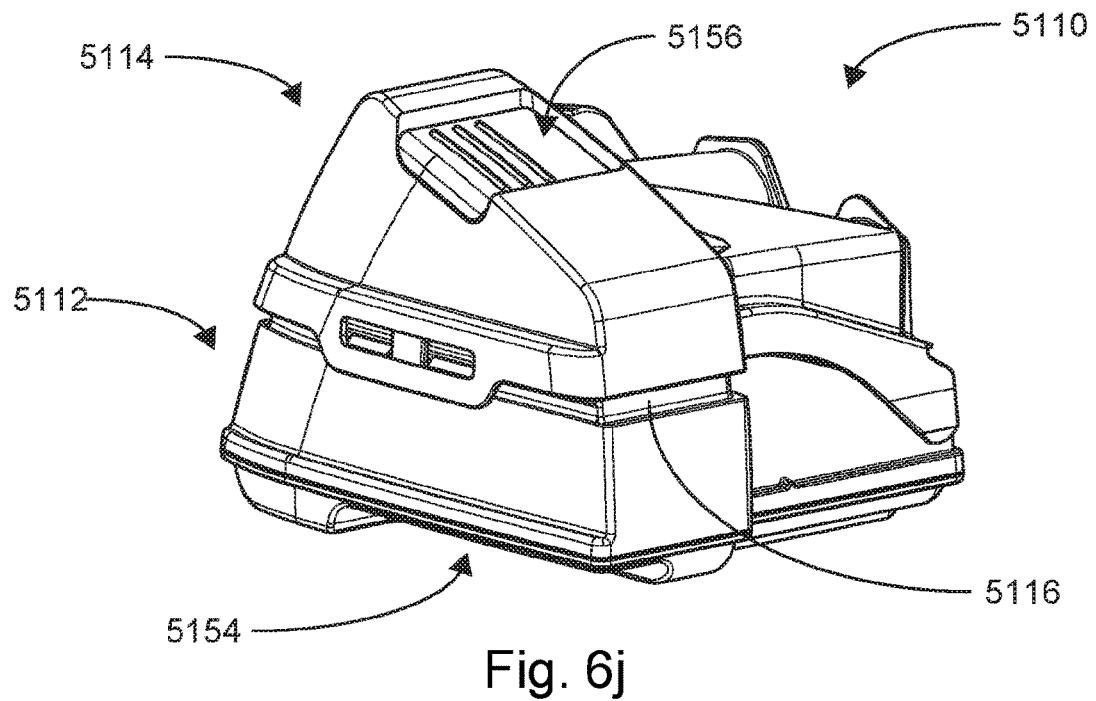

FIG. 6*j* shows a perspective view of a water reservoir 5110 in accordance with one form of the present technology, showing the water reservoir 5110 in a closed configuration.

Figure 6K:
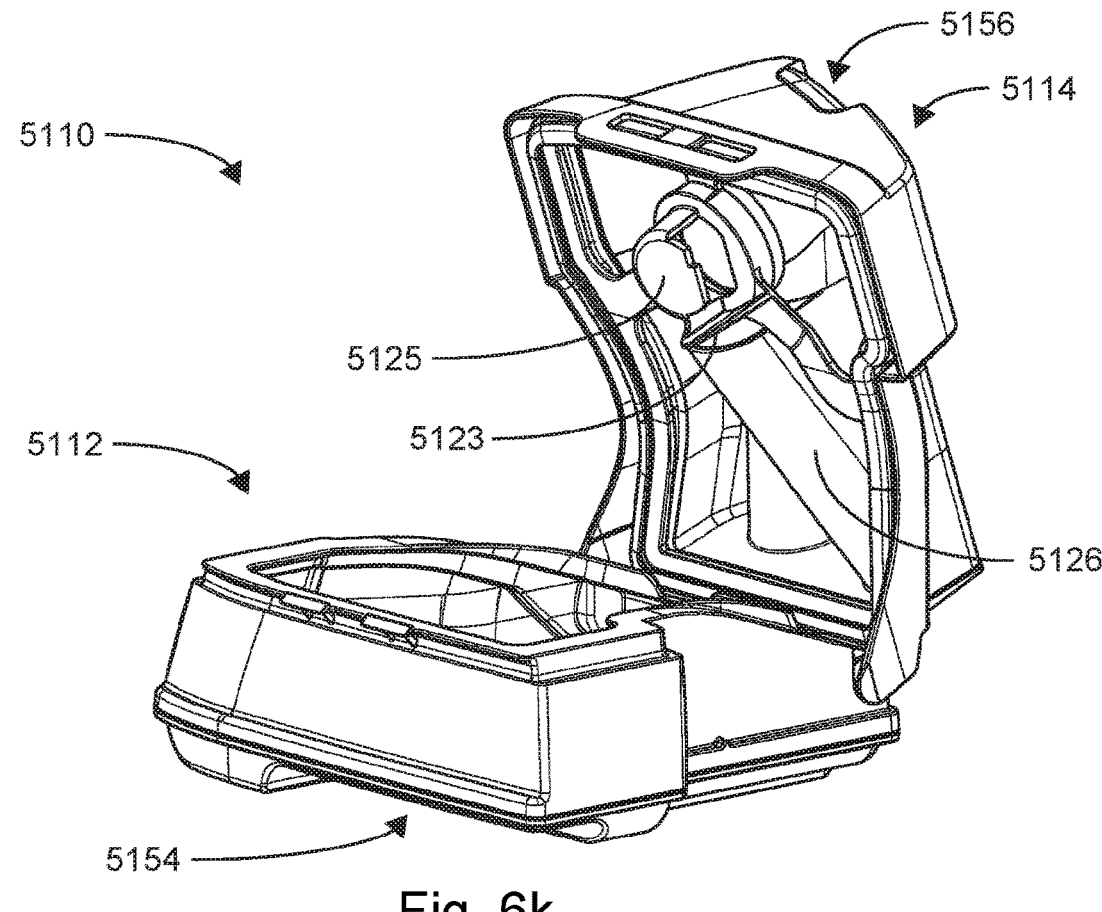
Figure 6I:
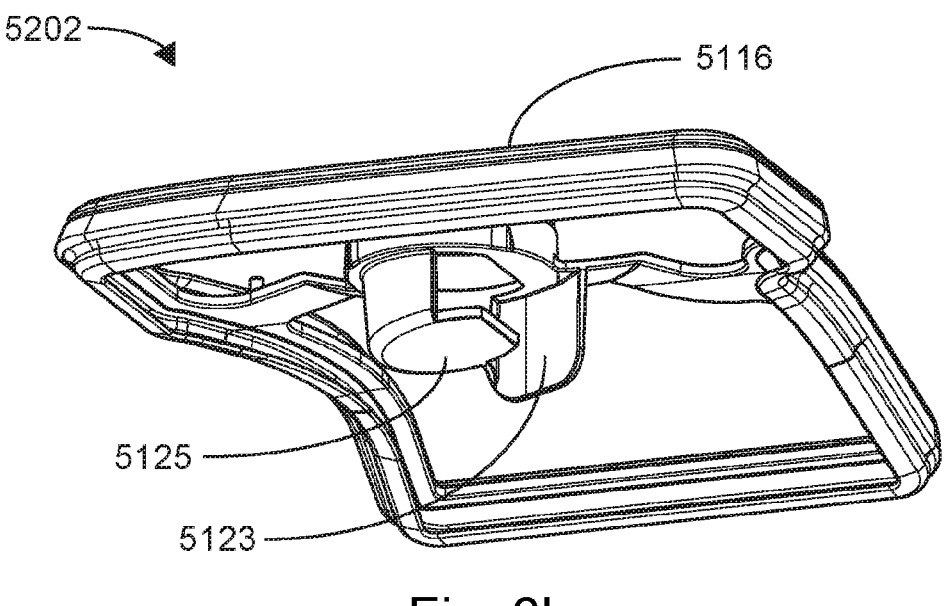

FIG. 6*k* shows a perspective view of a water reservoir 5110 in accordance with one form of the present technology, showing the water reservoir 5110 in an open configuration.

FIG. 6*l* shows a perspective view of an intermediate portion 5202 in accordance with one form of the present technology.

Figure 7:
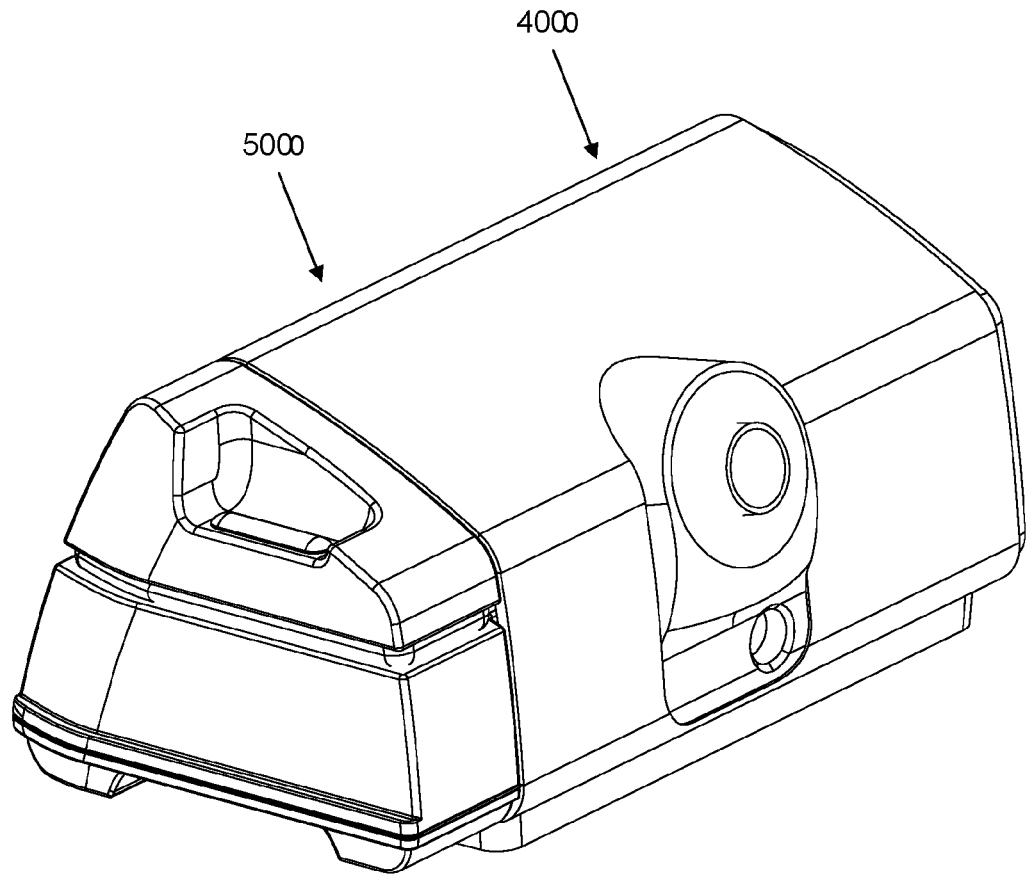

FIG. 7 shows an example of the present technology, showing a PAP device 4000 and an integrated humidifier 5000.

Figure 8:
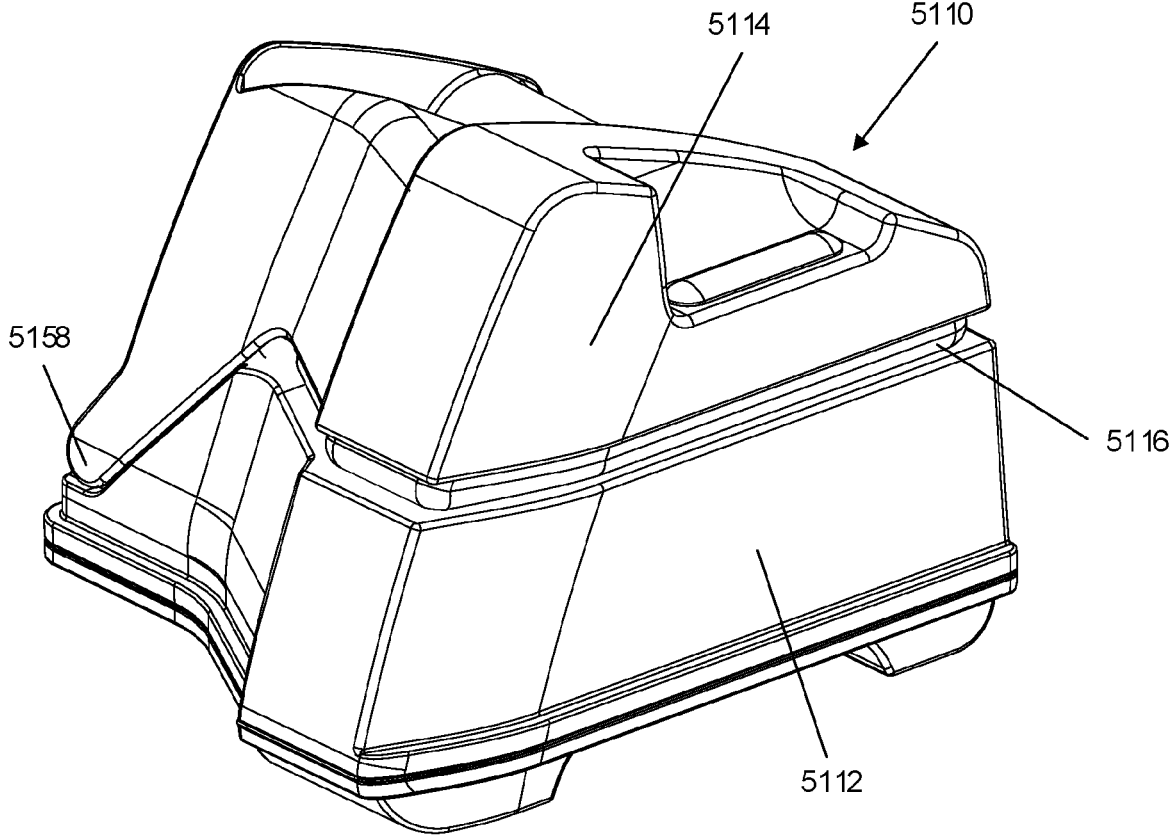
Figure 9:
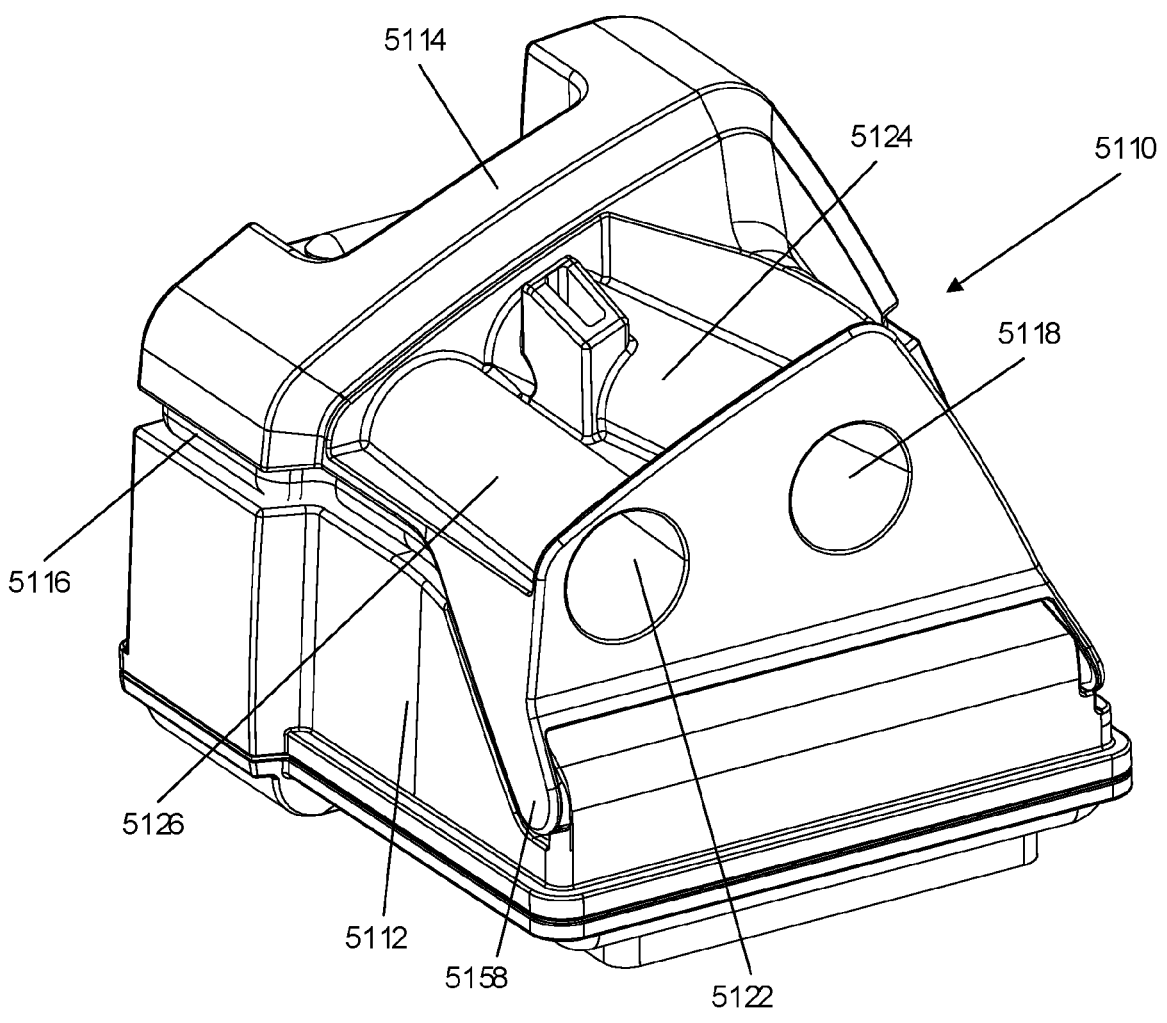
Figure 10:
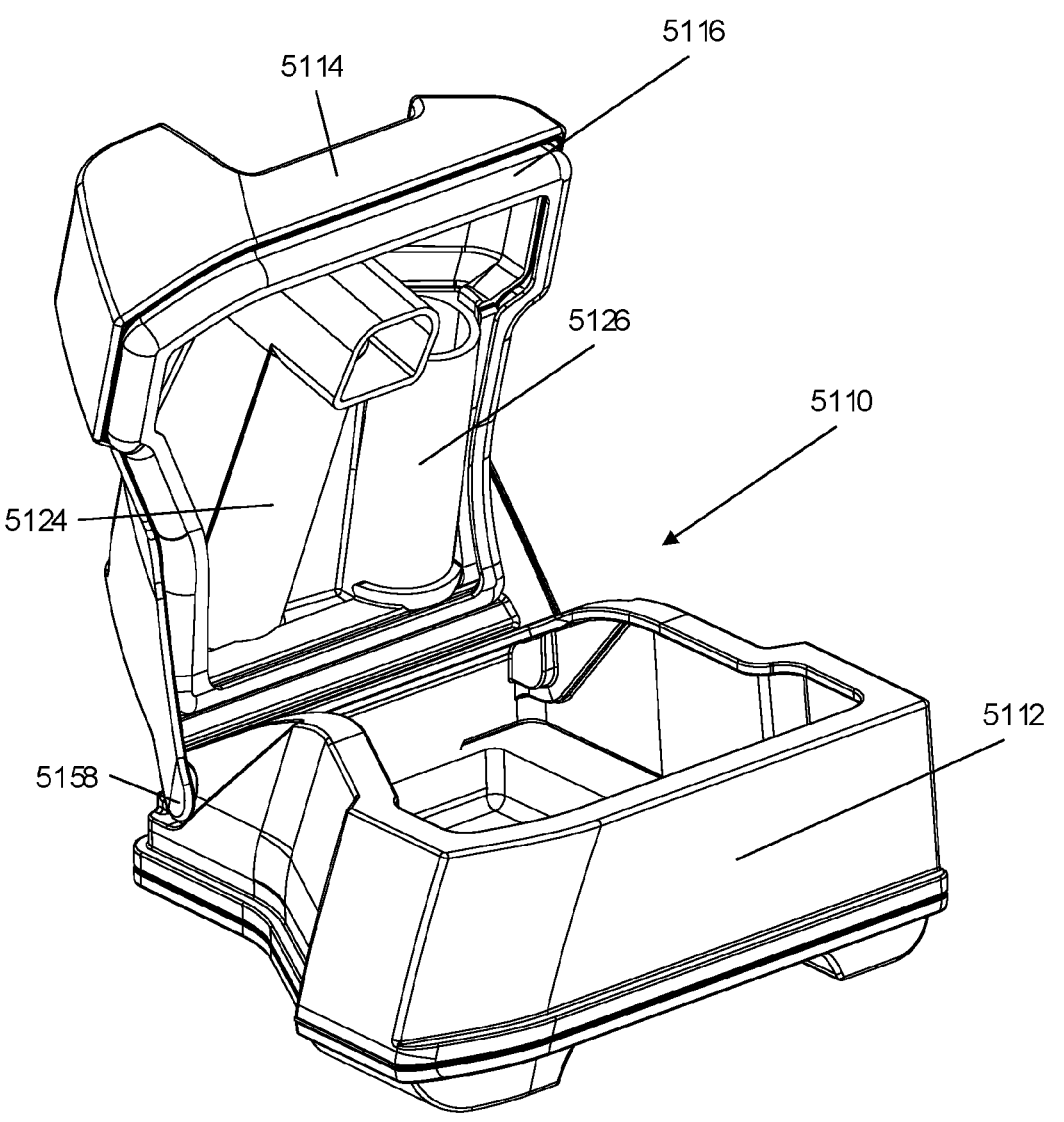
Figure 11:
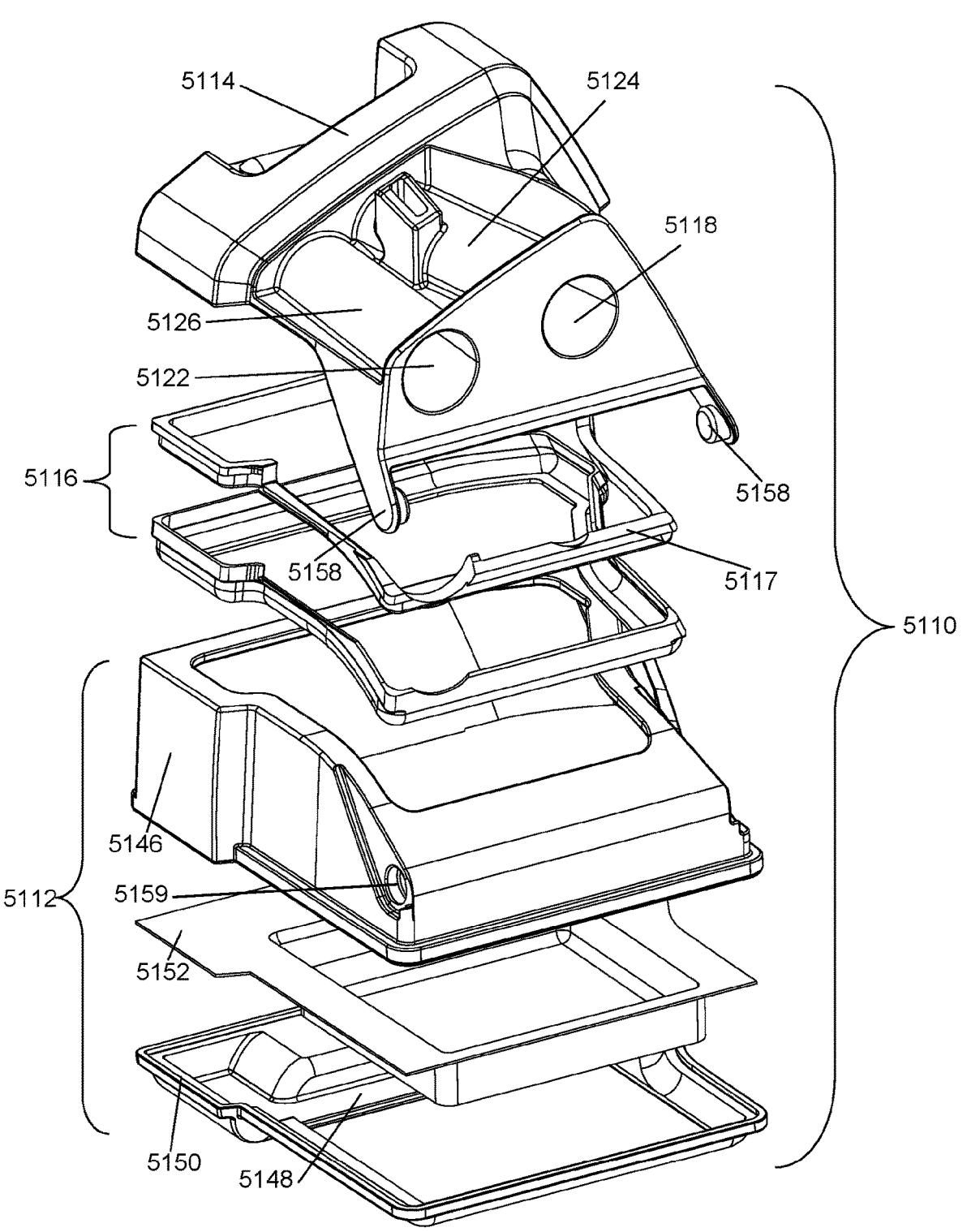

FIGS. 8-11 show various views of a humidifier reservoir 5110 in accordance with one aspect of present technology, wherein FIGS. 8-9 show the humidifier reservoir 5110 in a 'closed' configuration, FIG. 10 shows the humidifier reservoir 5110 in an 'open' configuration, and FIG. 11 is an exploded view of the humidifier reservoir 5110.

FIGS. 12-15 show the humidifier 5000 from various perspectives, demonstrating the engagement of the humidifier reservoir 5110 with the reservoir dock 5130 and/or engagement of the humidifier 5000 with the air circuit 4170.

FIGS. 16*a*-18*c* show a time-lapse chart of an exemplary flow path of gas as it enters the humidifier reservoir 5110 through the inlet 5118 and exits through the outlet 5122 after traversing through the inside of the humidifier reservoir 5110.

Figure 19:
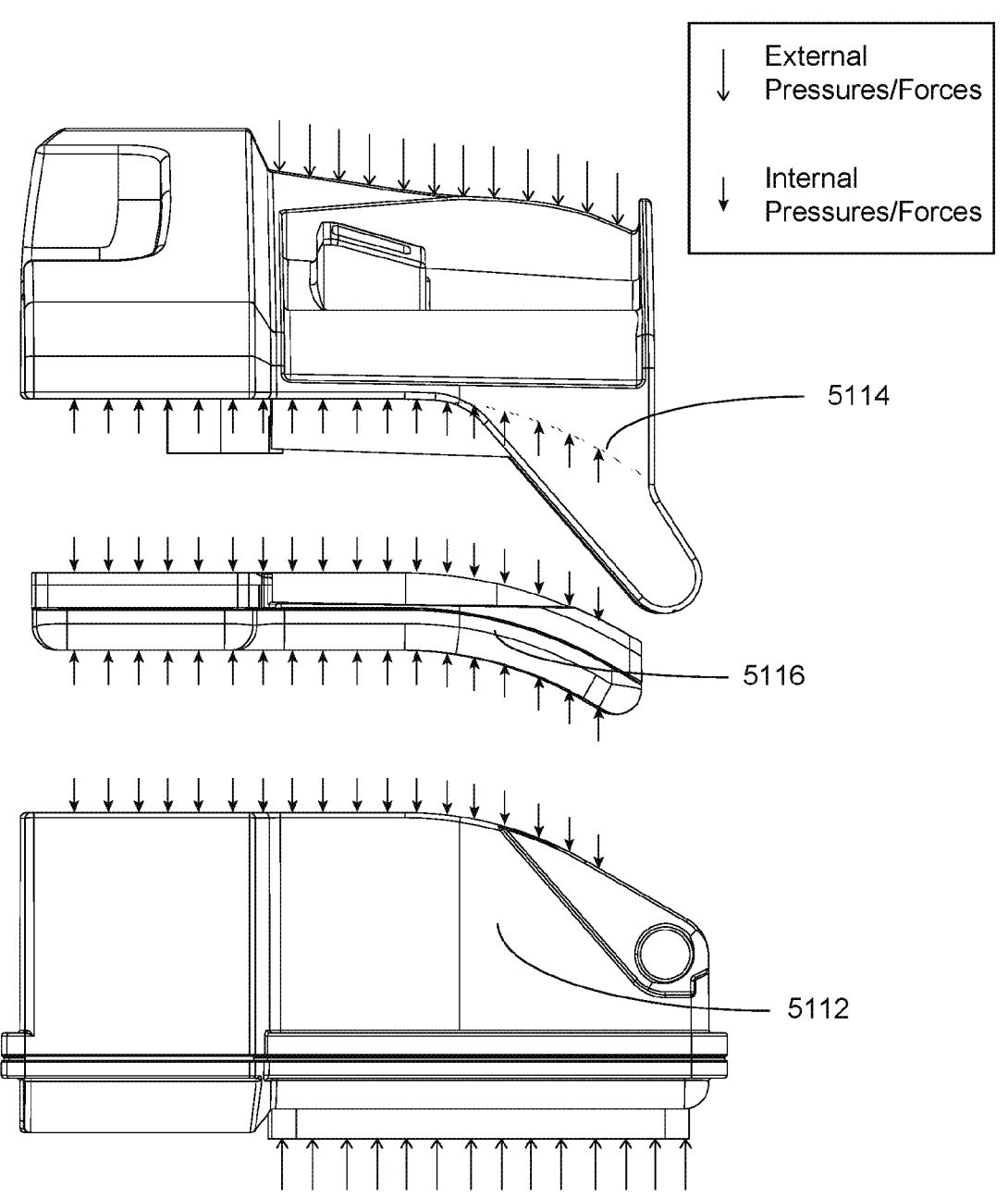
Figure 20:
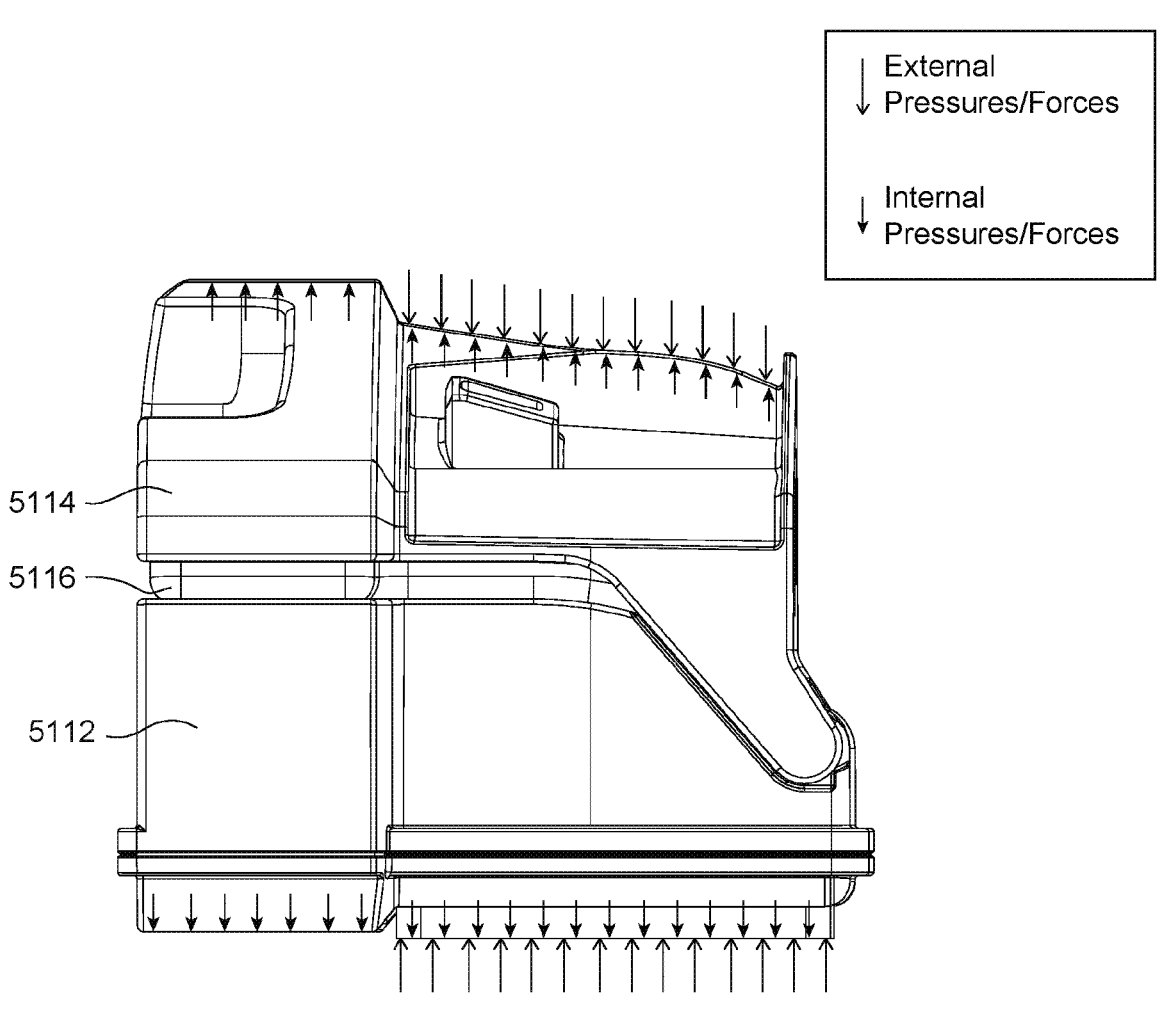

FIGS. 19-20 show exemplary distributions of pressure/ force in the humidifier reservoir 5110 in various configurations.

FIGS. 21-28 show varying configurations of the reservoir lid 5114, in particular variations in configurations of the inlet tube 5124 and the outlet tube 5126 according to aspects of the present technology.

Figure 29A:
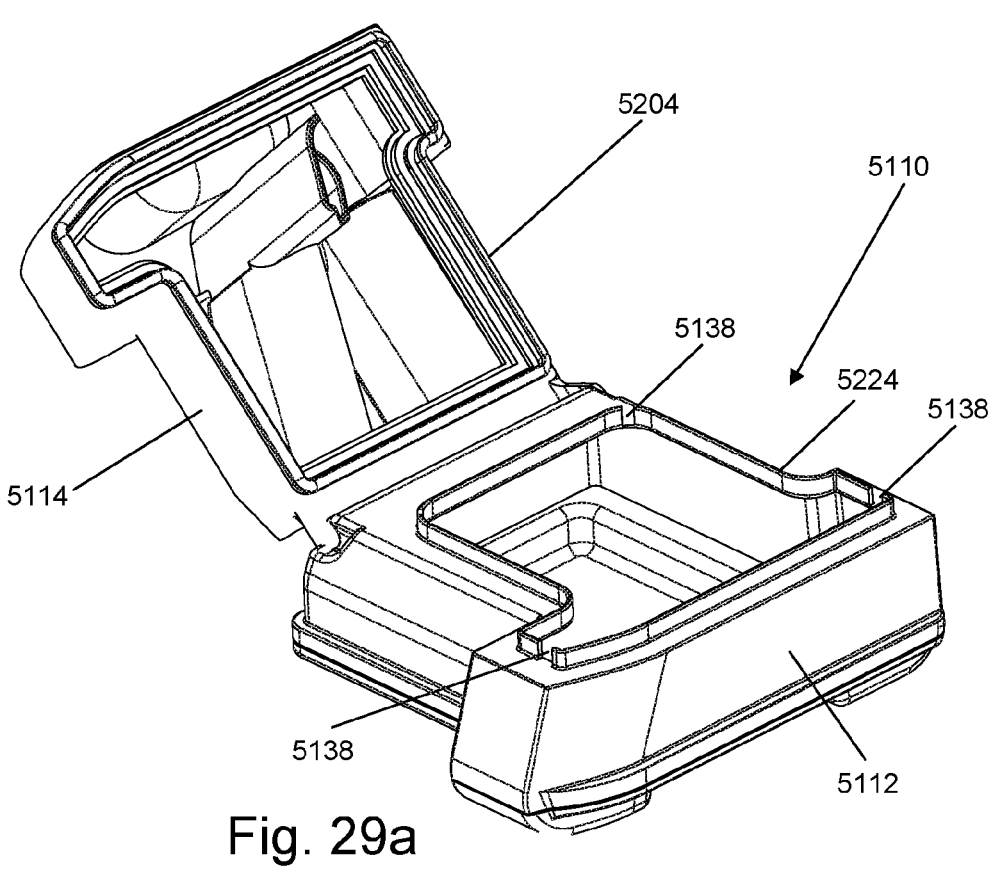
Figure 29B:
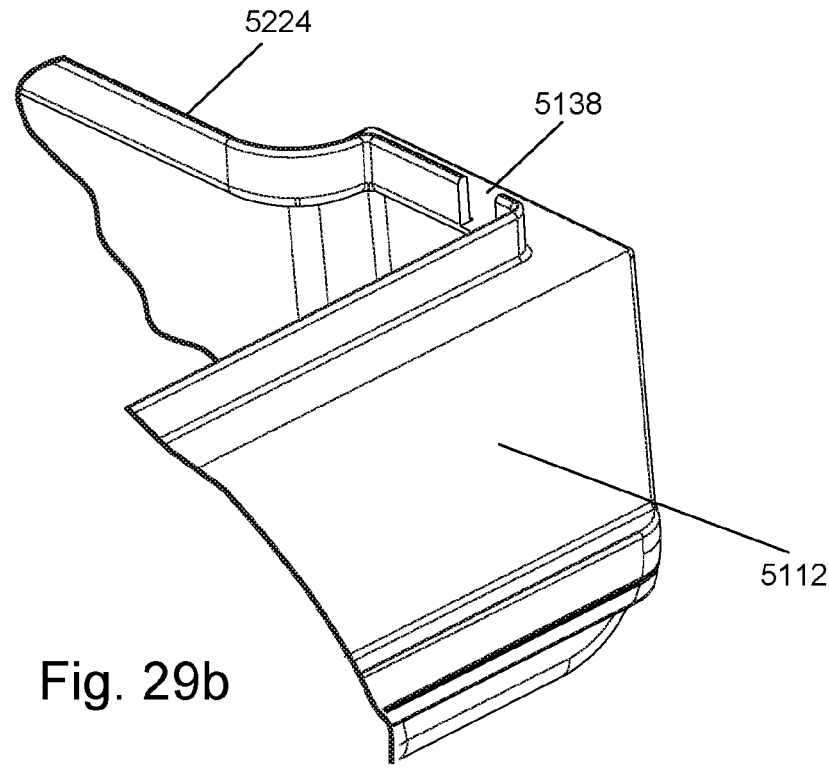

FIGS. 29*a*, 29*b* and 30 show the humidifier reservoir 5110 and in particular they aim to show the orifice 5138.

Figure 29C:
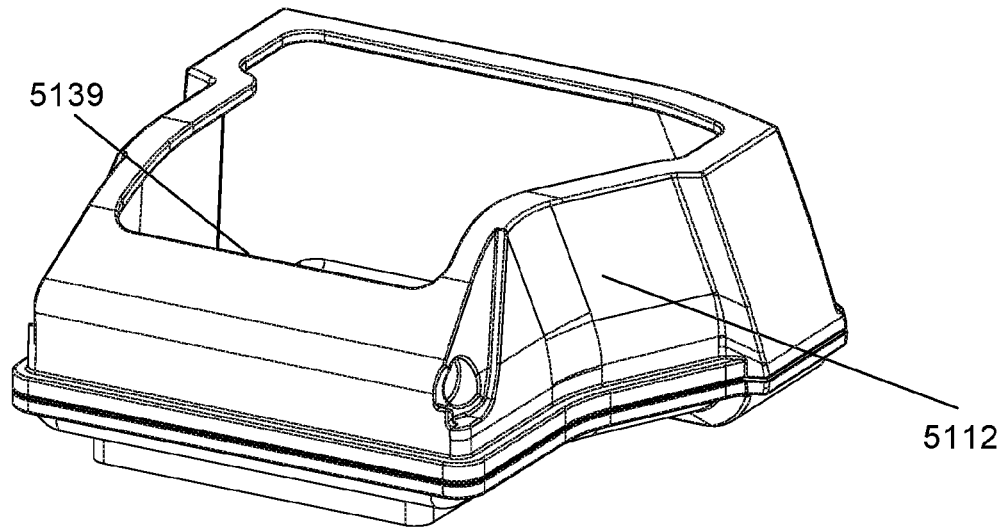
Figure 29D:
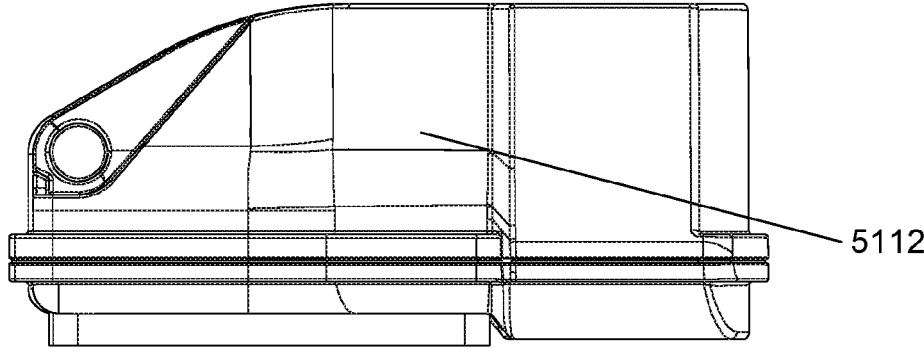

FIGS. 29*c* and 29*d* show the humidifier base 5112 and in particular they aim to show the sloped profile 5139.

Figure 32:
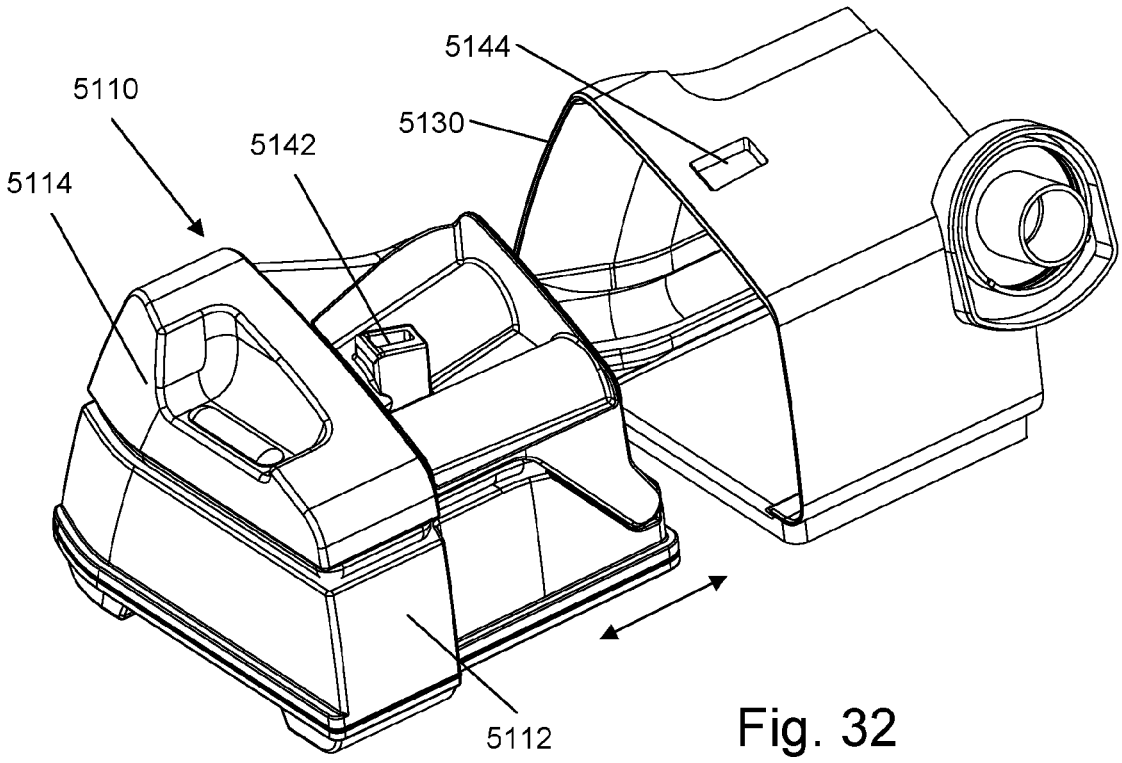

FIGS. 31-32 show the humidifier dock 5130 and the humidifier reservoir 5110, and in particular show the interaction between the lid retention protrusion 5142 and the dock locking recess 5144 according to one aspect of the present technology.

Figure 33:
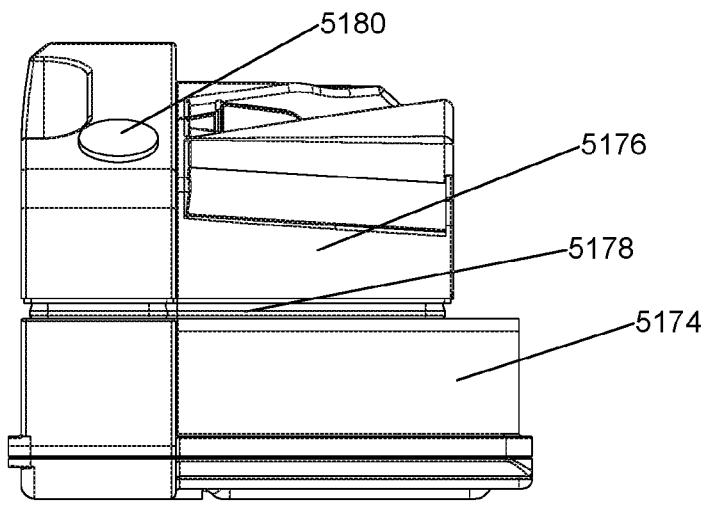

FIG. 33 shows the humidifier reservoir 5110 according to another example of the current technology, wherein it is configured with a re-filling cap 5180 and a base, top and variable portion may be affixed together.

FIGS. 34-37 shows other representations of a humidifier reservoir 5110 according to an aspect of the present technology, with particular regard to the arrangement of the inlet tube 5124 and the outlet tube 5126.

Figure 38:
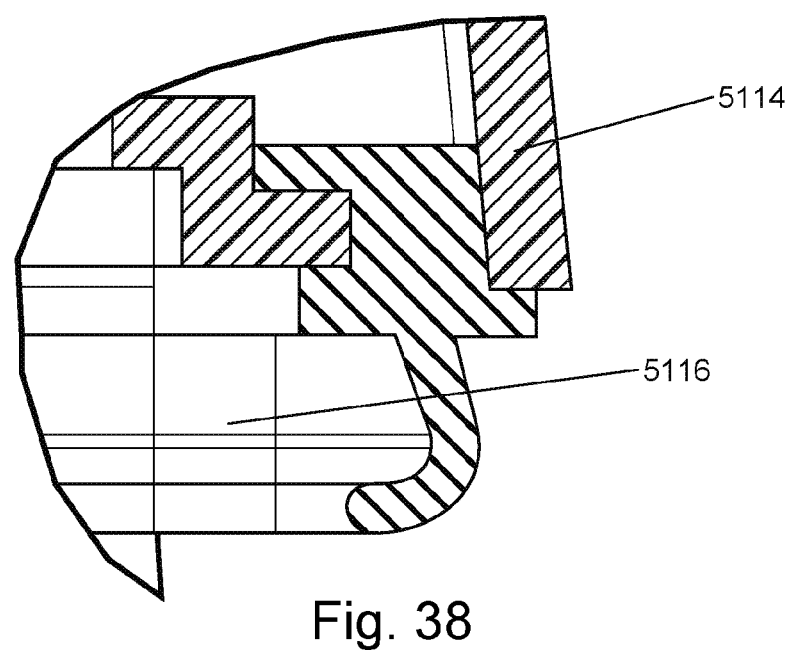

FIG. 38 shows a cross-sectional view of a reservoir lid 5114 and a variable portion in the form of a variable portion 5116 according to an aspect of the present technology.

Figure 39:
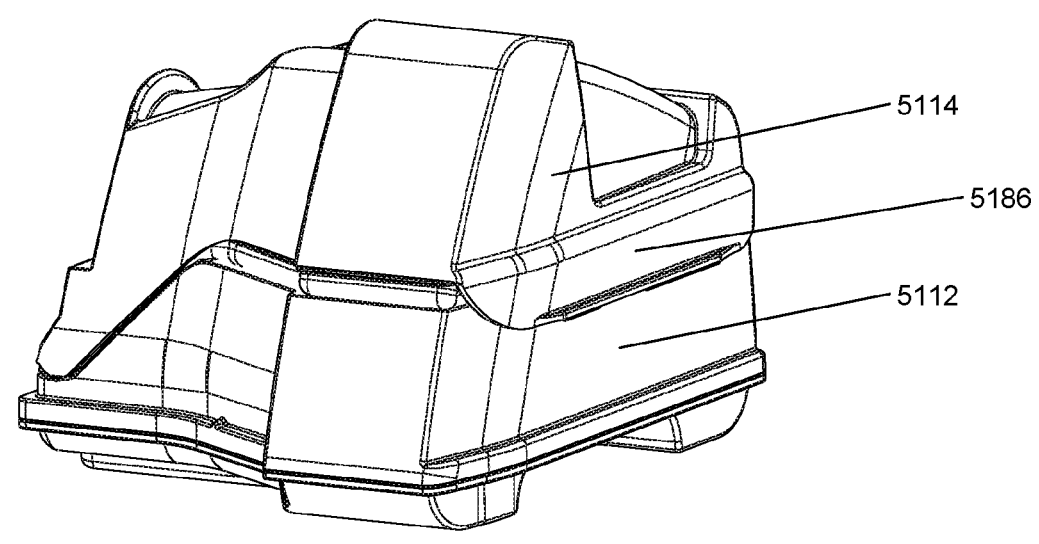

FIG. 39 shows an example of the humidifier reservoir 5110 according to another example of the current technology, wherein it is configured with a latch 5186.

Figures 40A, 40B:
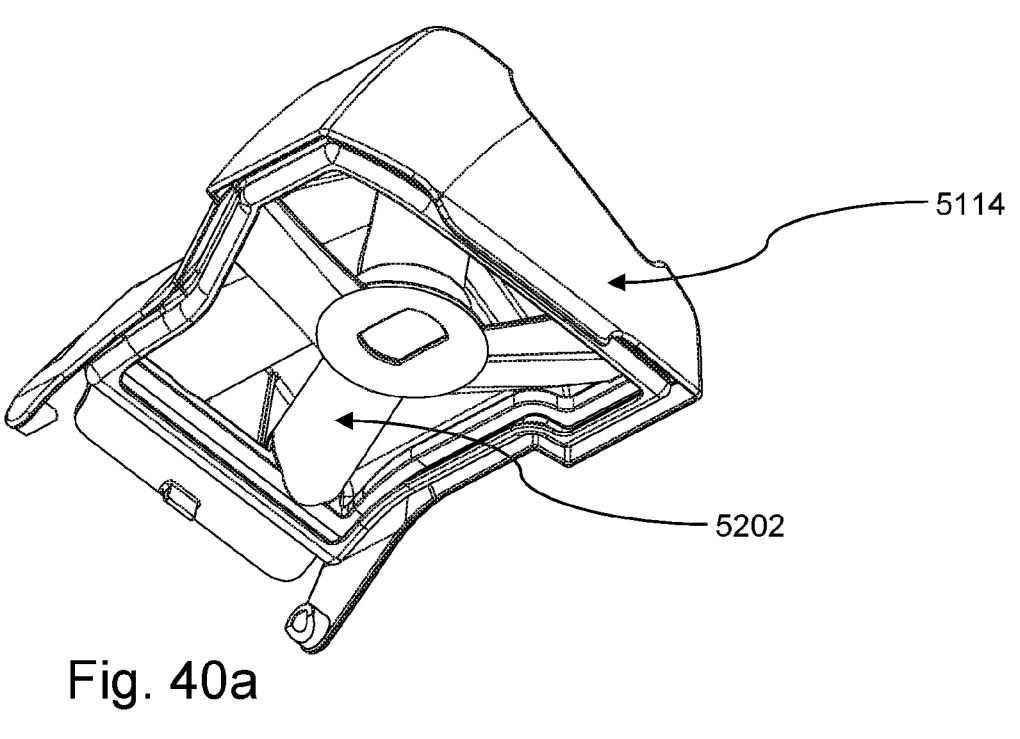
Figure 41:
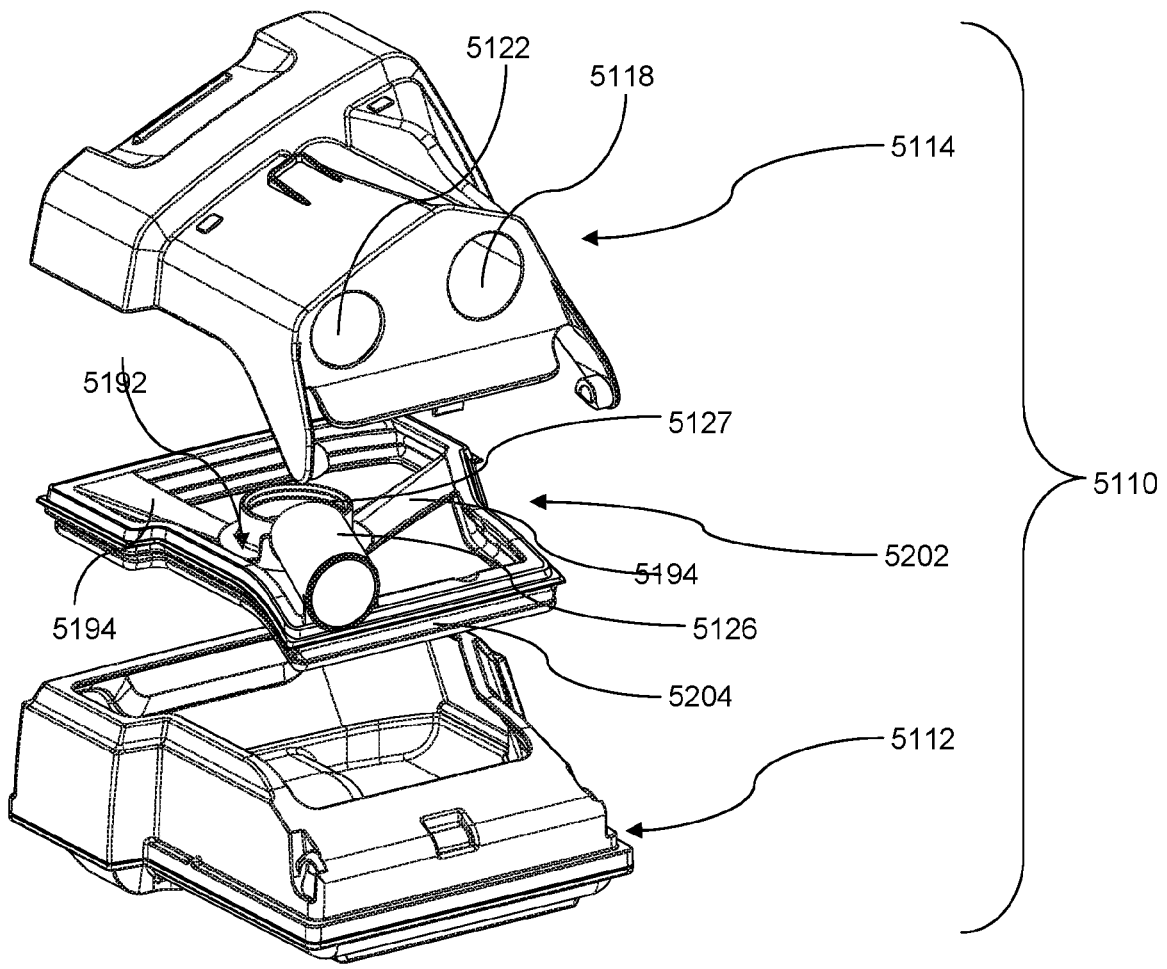

FIGS. 40*a*-41 show a portion of the humidifier reservoir 5110 according to another example of the current technology. In this configuration, the reservoir 5110 comprises a reservoir lid 5114 including an inlet tube 5124, an intermediate portion 5202 which comprises an outlet tube 5126 and a base portion 5112 (as seen in an exploded view shown in FIG. 41).

Figure 42A:
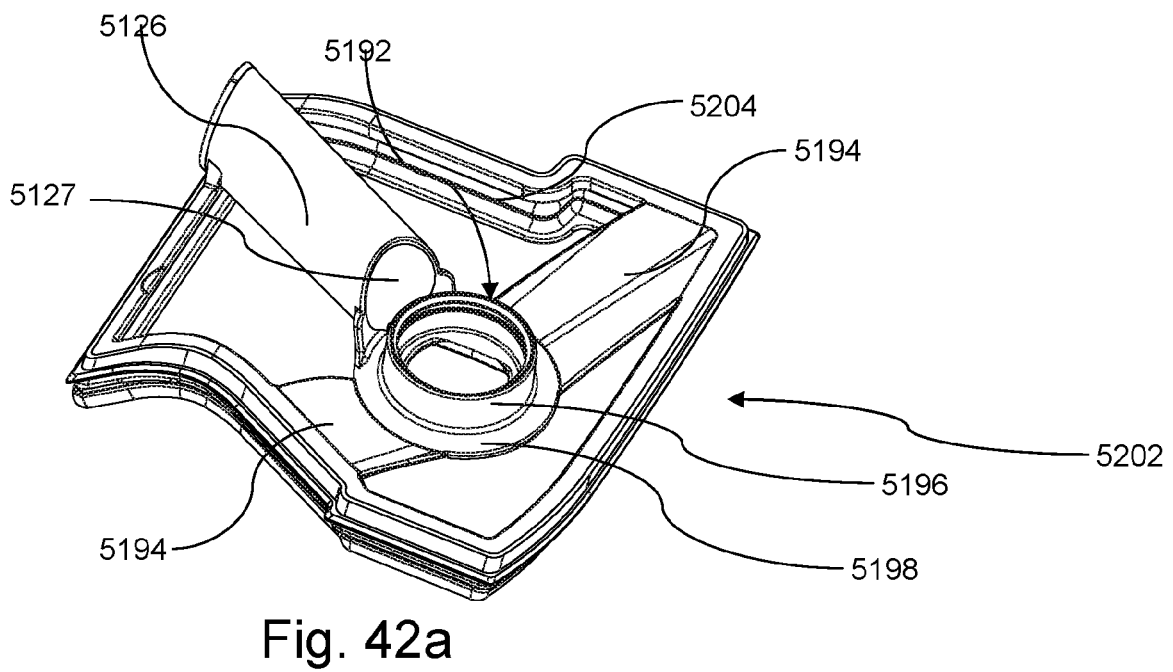
Figure 42B:
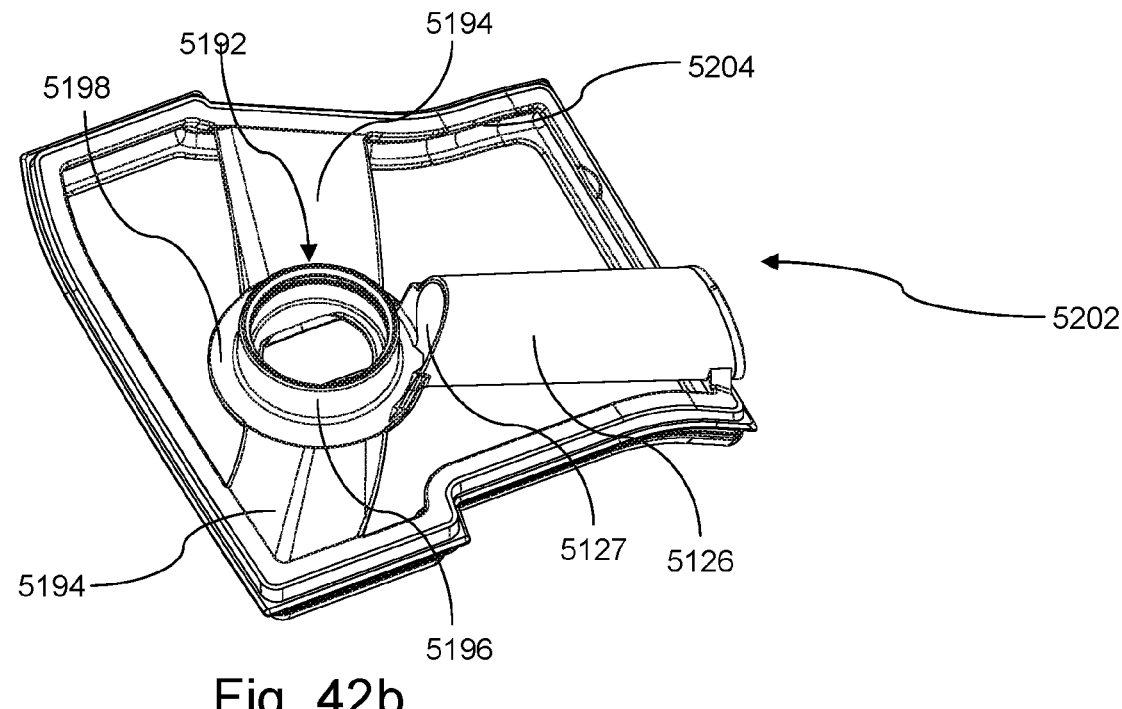

FIGS. 42*a*-42*b* show the intermediate portion 5202 of the reservoir 5110 from various angles. In particular they aim to show the baffle 5192, the outlet tube 5126 and the support spokes 5194.

Figure 43:
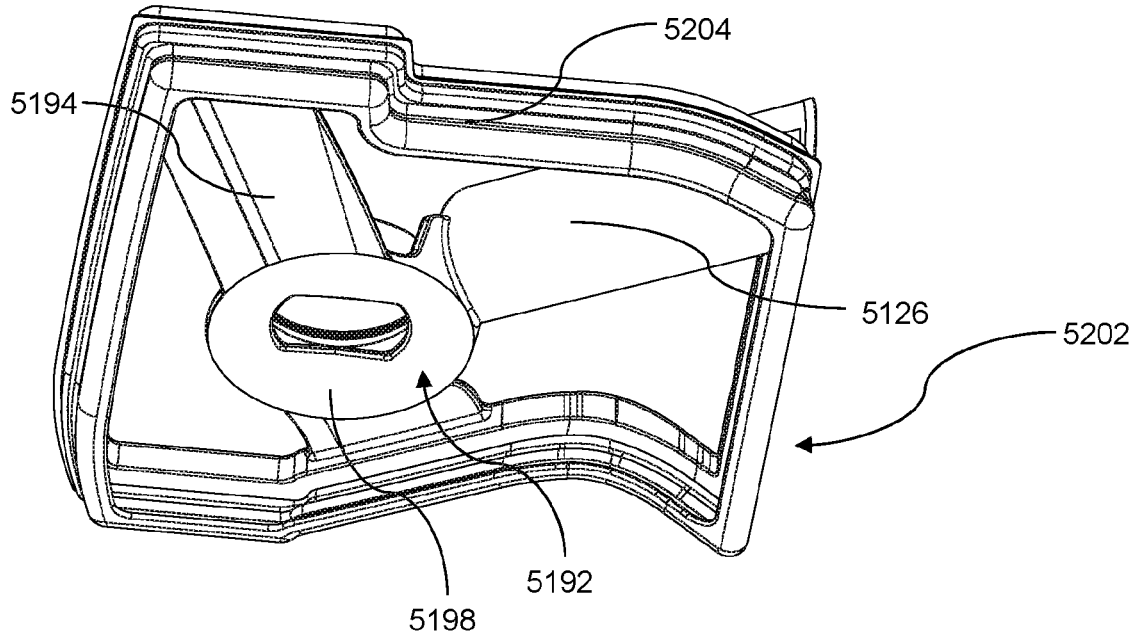

FIG. 43 shows a perspective bottom view of the intermediate portion 5202 of the reservoir 5110.

Figure 44A:
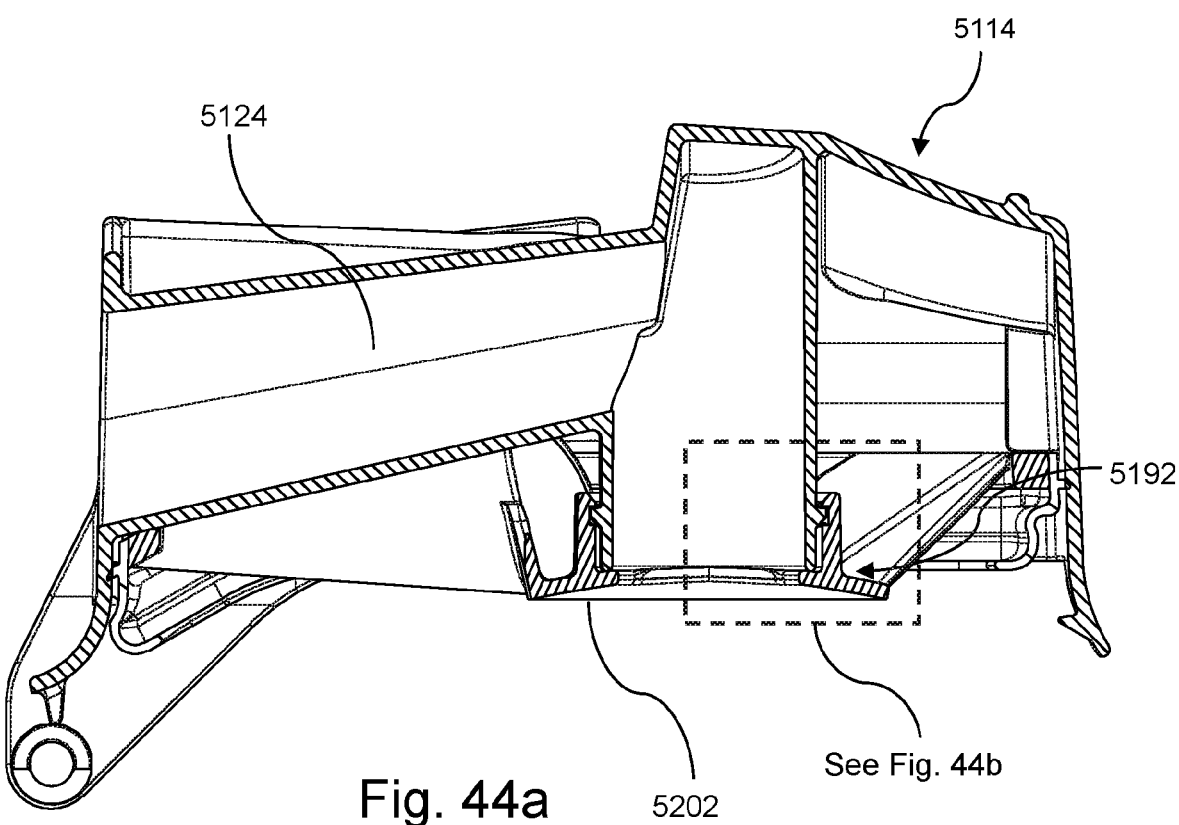
Figure 44B:
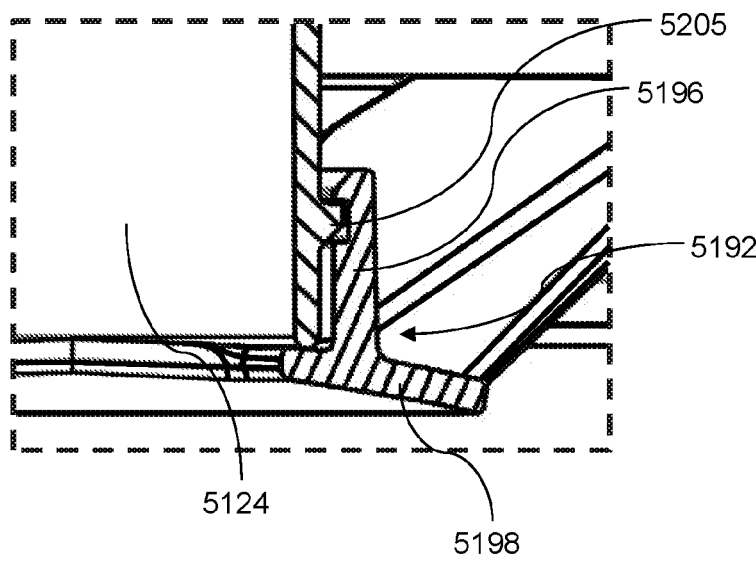

FIGS. 44*a*-44*b* show a cross section of the reservoir lid 5114 and the intermediate portion 5202 connected together. FIG. 44*b* shows the cross section of the baffle 5192 in further detail, in particular the arrangement of the vertical portion of the inlet tube 5124, the locating portion 5196 of the baffle 5192 and the deflector portion 5198 of the baffle 5192.

Figure 45:
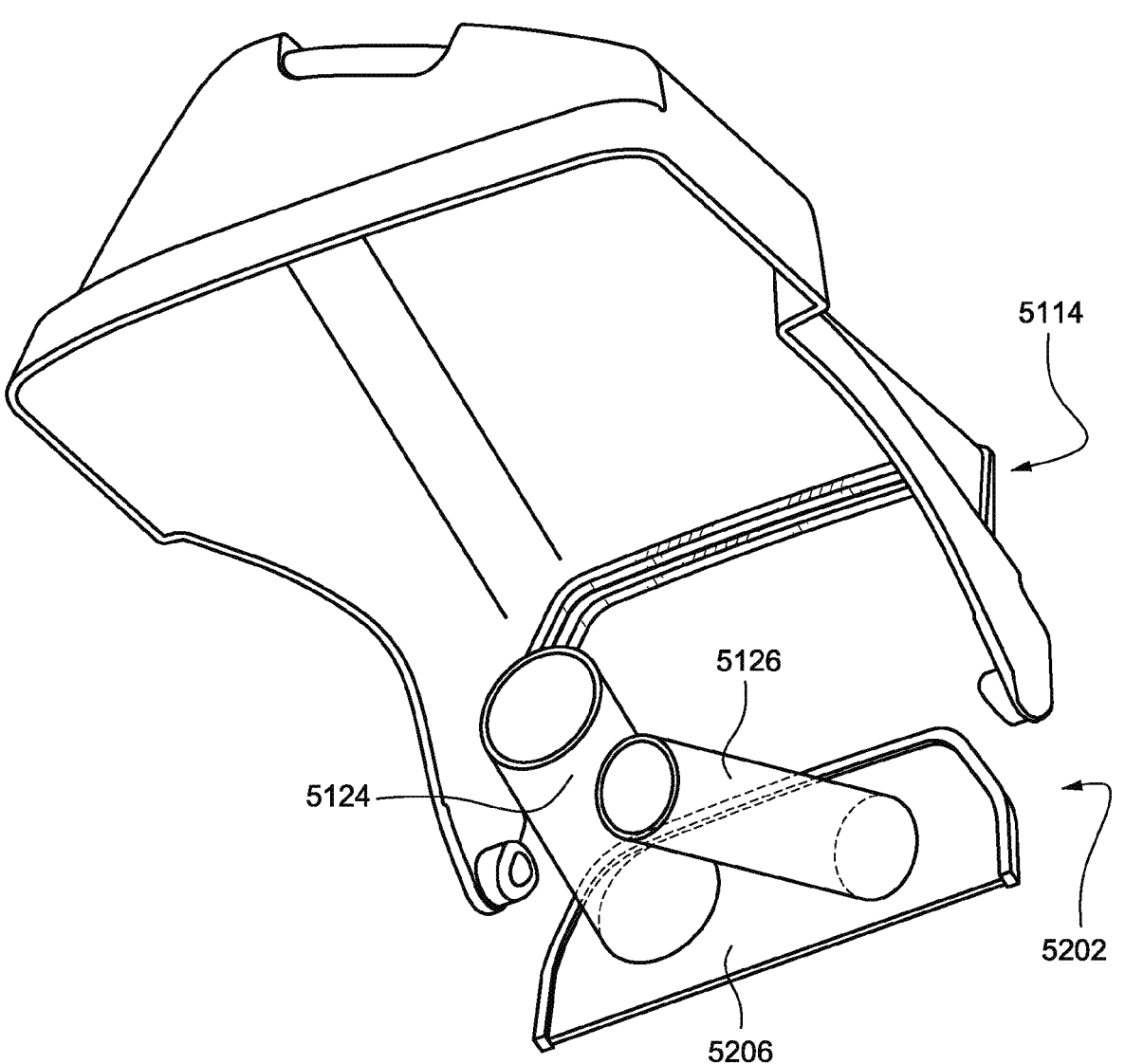

FIG. 45 shows an upper portion of the humidifier reservoir 5110 according to another example of the current technology. In this configuration, the reservoir 5110 comprises a reservoir lid portion 5114, a base portion (not shown), and an intermediate portion 5202 that comprises an outlet tube 5126, an inlet tube 5124 as well as a wall portion 5206.

Figure 46A:
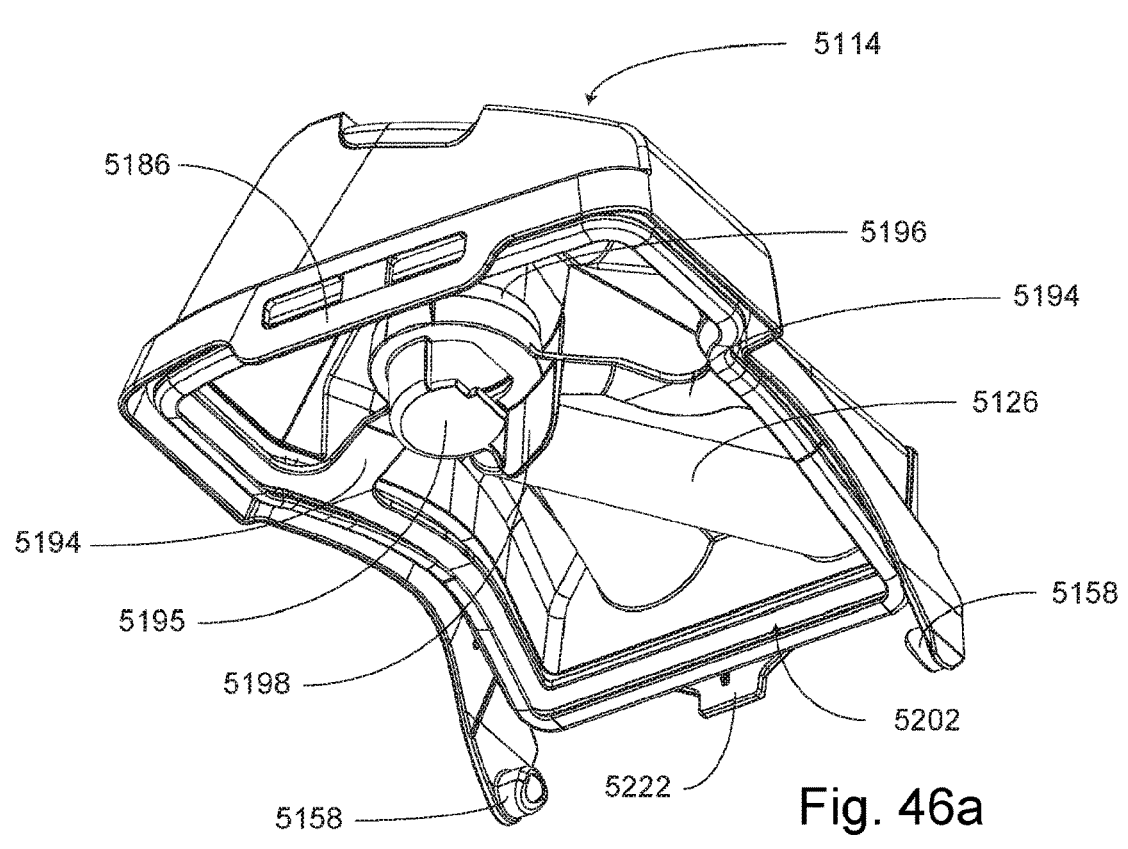
Figure 46B:
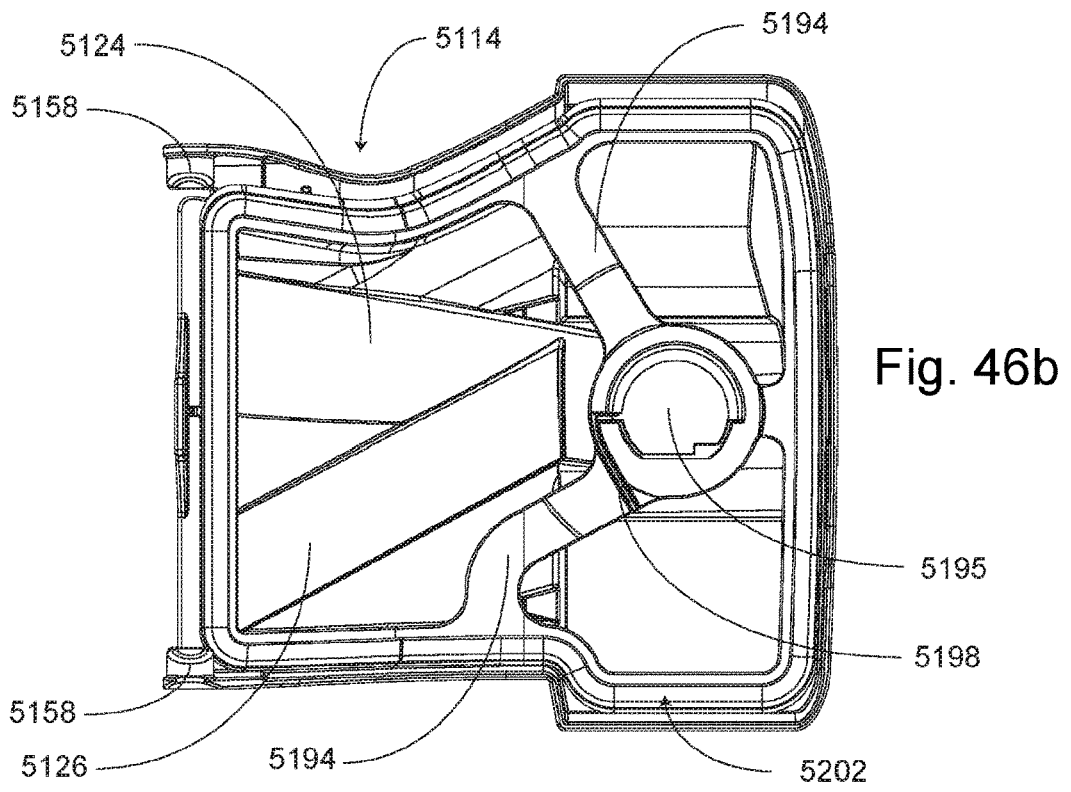

FIGS. 46*a*-46*b* show a portion of the humidifier reservoir 5110 according to another example of the current technology. FIGS. 46*a*-46*b* show the reservoir lid 5114 connected to the intermediate portion 5202, and in particular they aim to show the inlet tube 5124, the outlet tube 5126, the deflector portion 5198 and the flow director 5195.

Figure 47A:
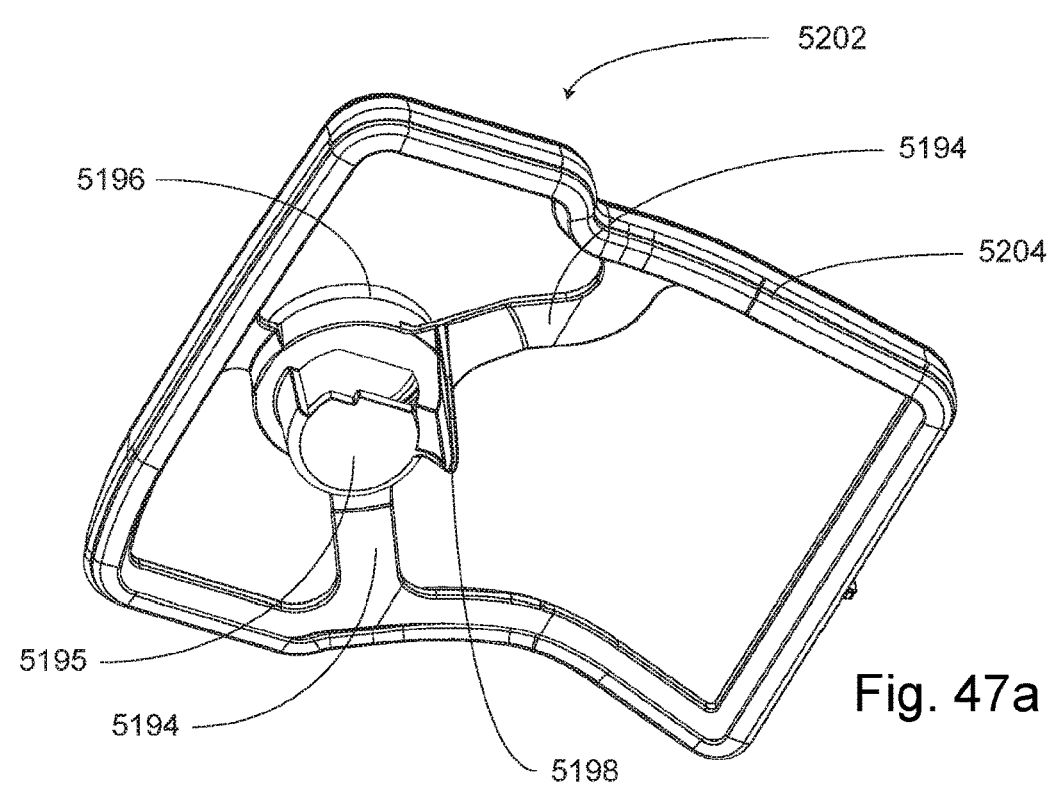
Figure 47B:
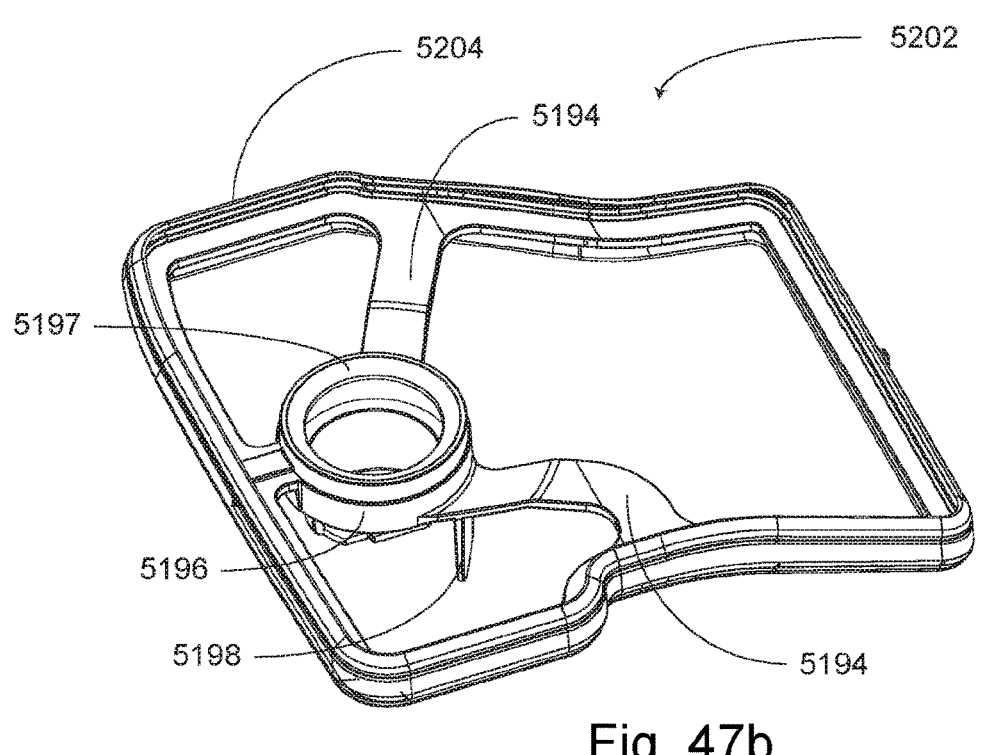

FIGS. 47*a*-47*b* show the intermediate portion 5202 according to another example of the current technology, and in particular they aim to show the deflector portion 5198, the flow director 5195, the locating portion 5196 and the seal 5204.

Figure 48:
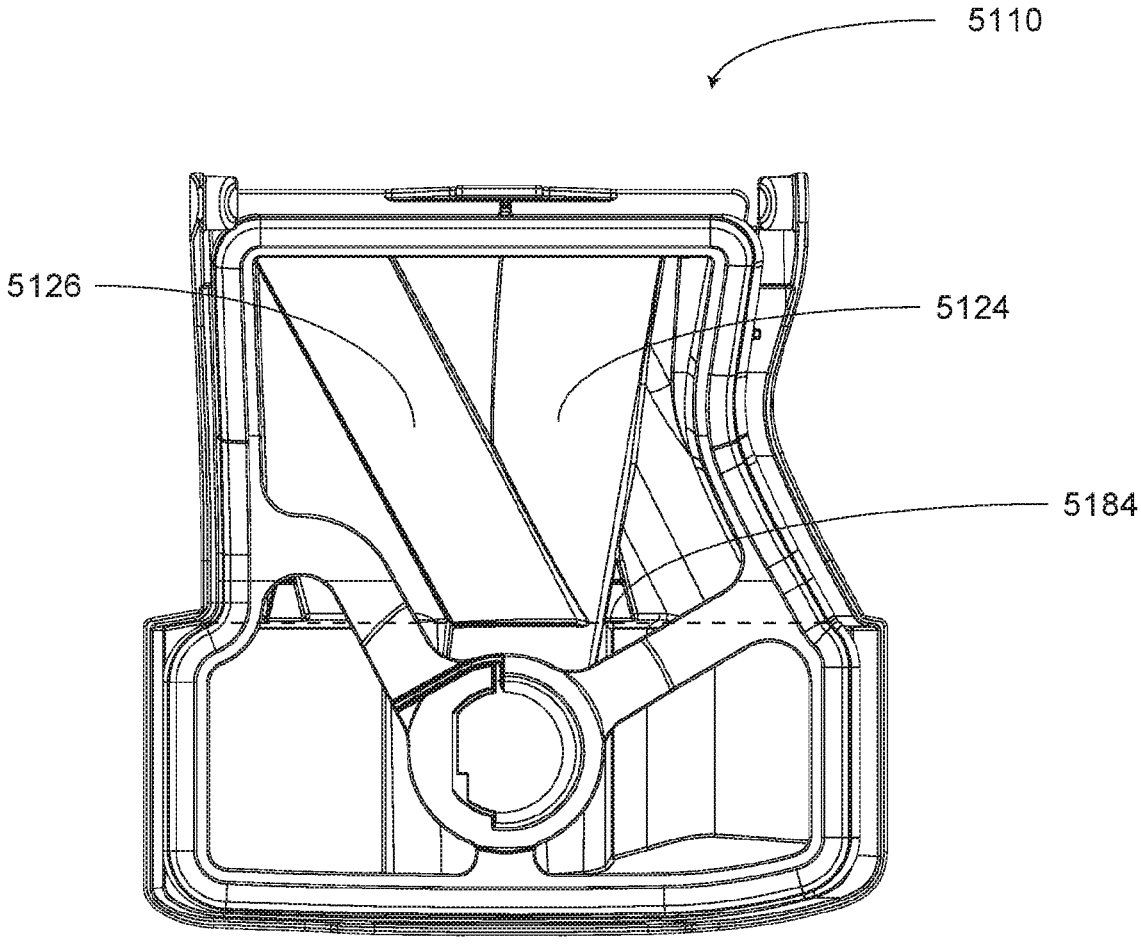
Figure 49A:
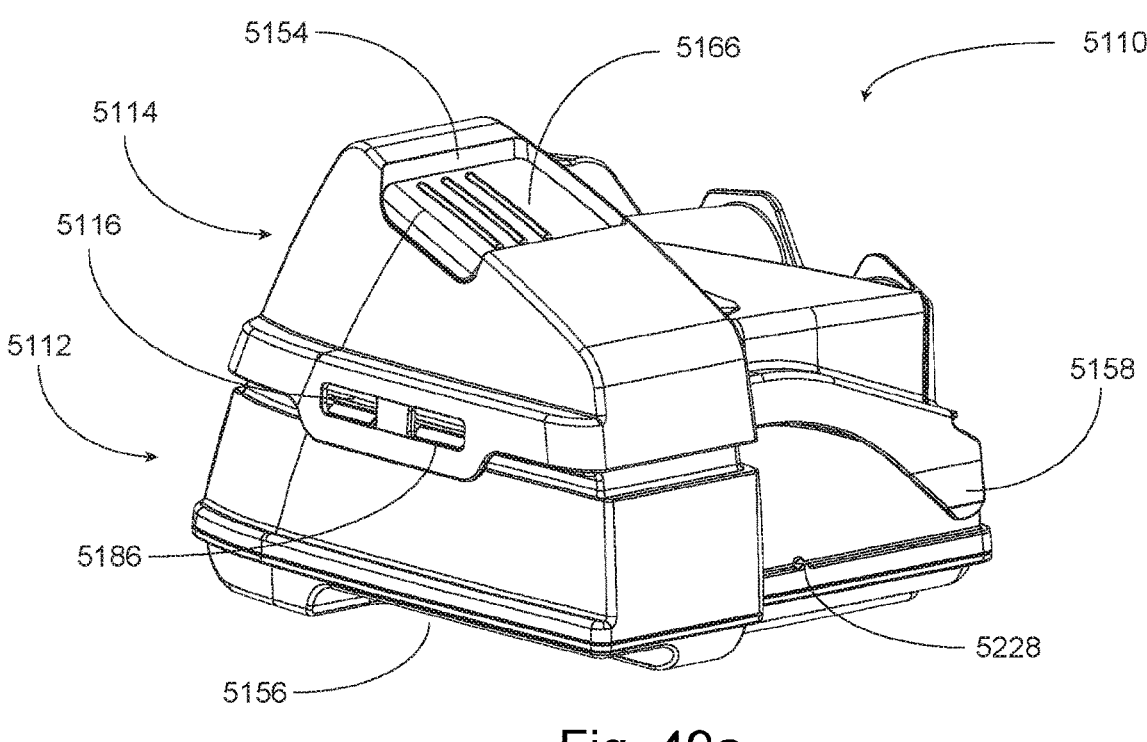
Figure 49B:
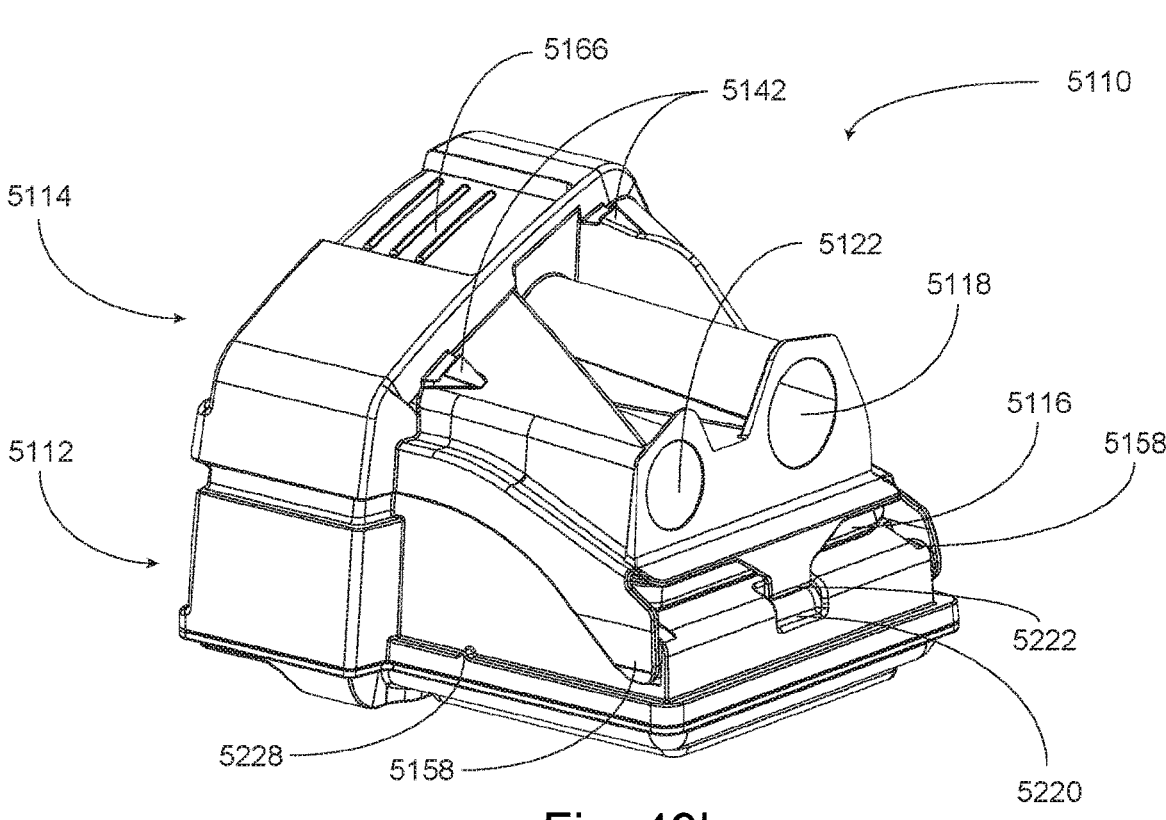

FIG. 48 shows a portion of the humidifier reservoir 5110 according to another example of the current technology. In particular, FIG. 48 shows a water level 5184 at which the air locks would be formed to prevent further ingress of liquid into the reservoir 5110 when the predetermined maximum volume of liquid is in the reservoir 5110.

Figure 50A:
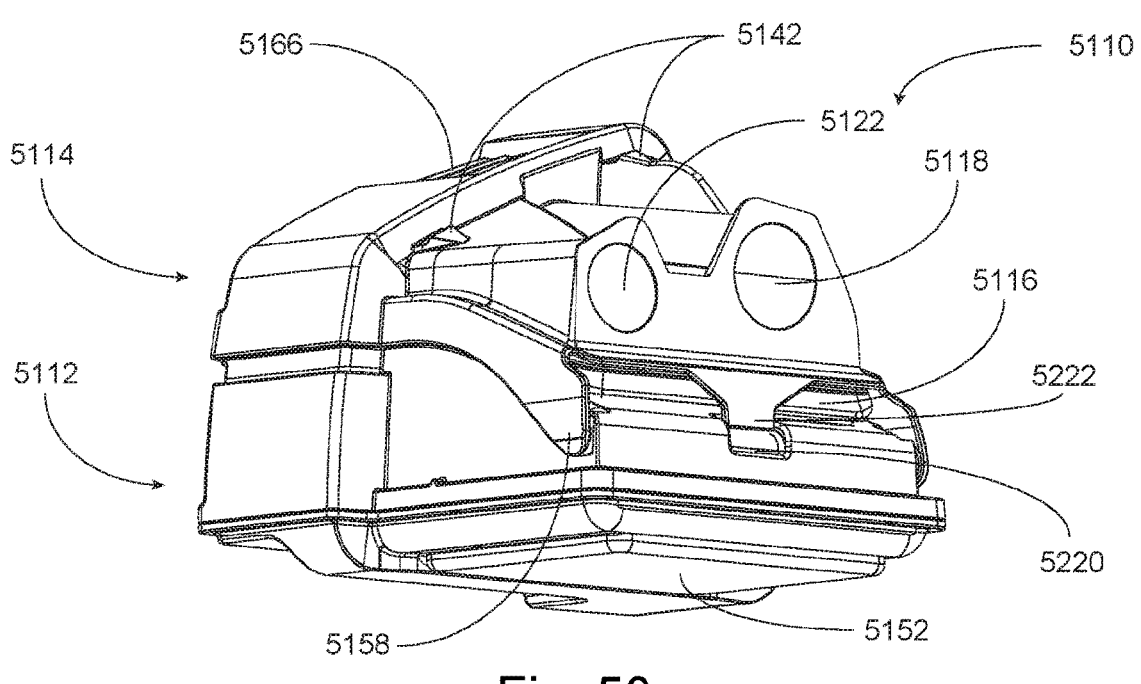
Figure 50B:
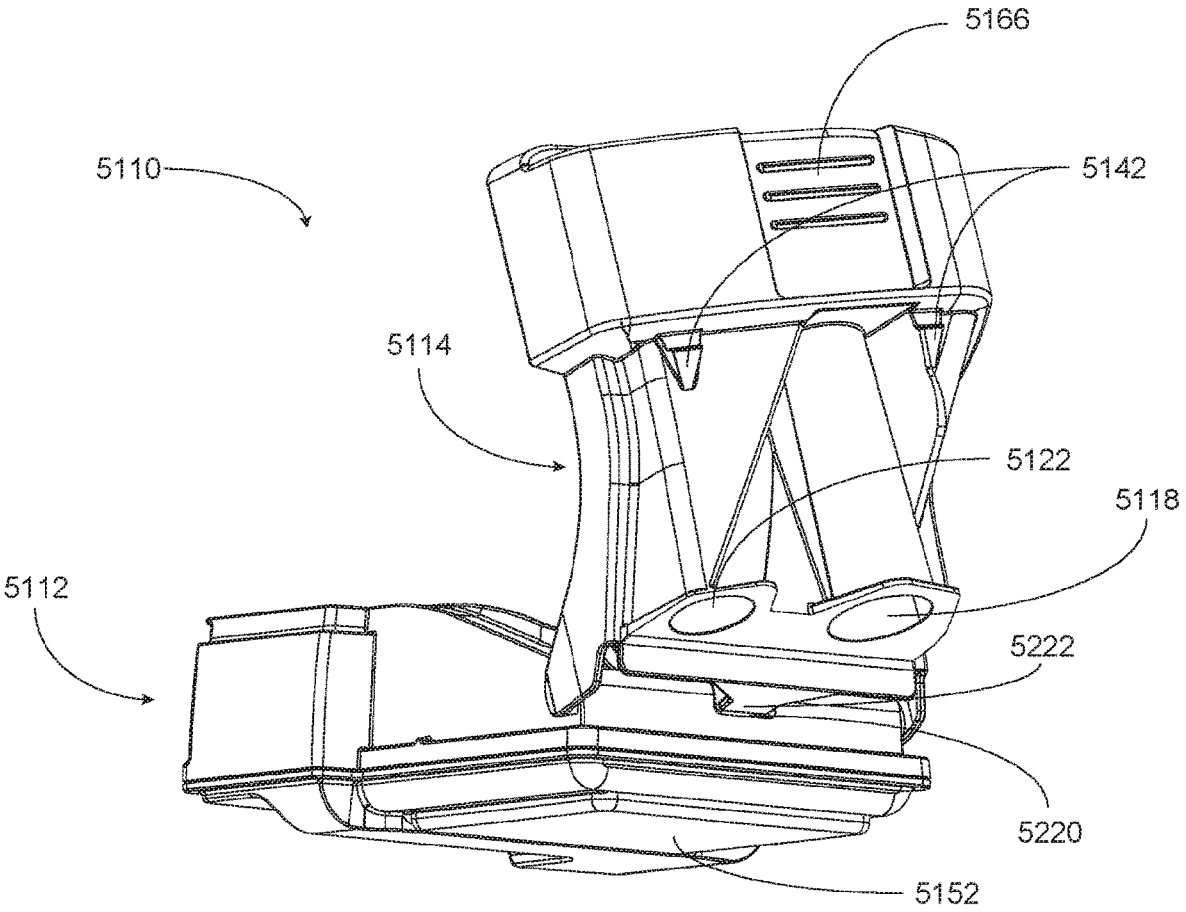

FIGS. 49*a*-50*b* show various views of a humidifier reservoir 5110 in accordance with one aspect of present technology, wherein FIGS. 49*a*-50*a* show the humidifier reservoir 5110 in a 'closed' configuration, FIG. 50*b* shows the humidifier reservoir 5110 in an 'open' configuration.

Figures 51A, 51B:
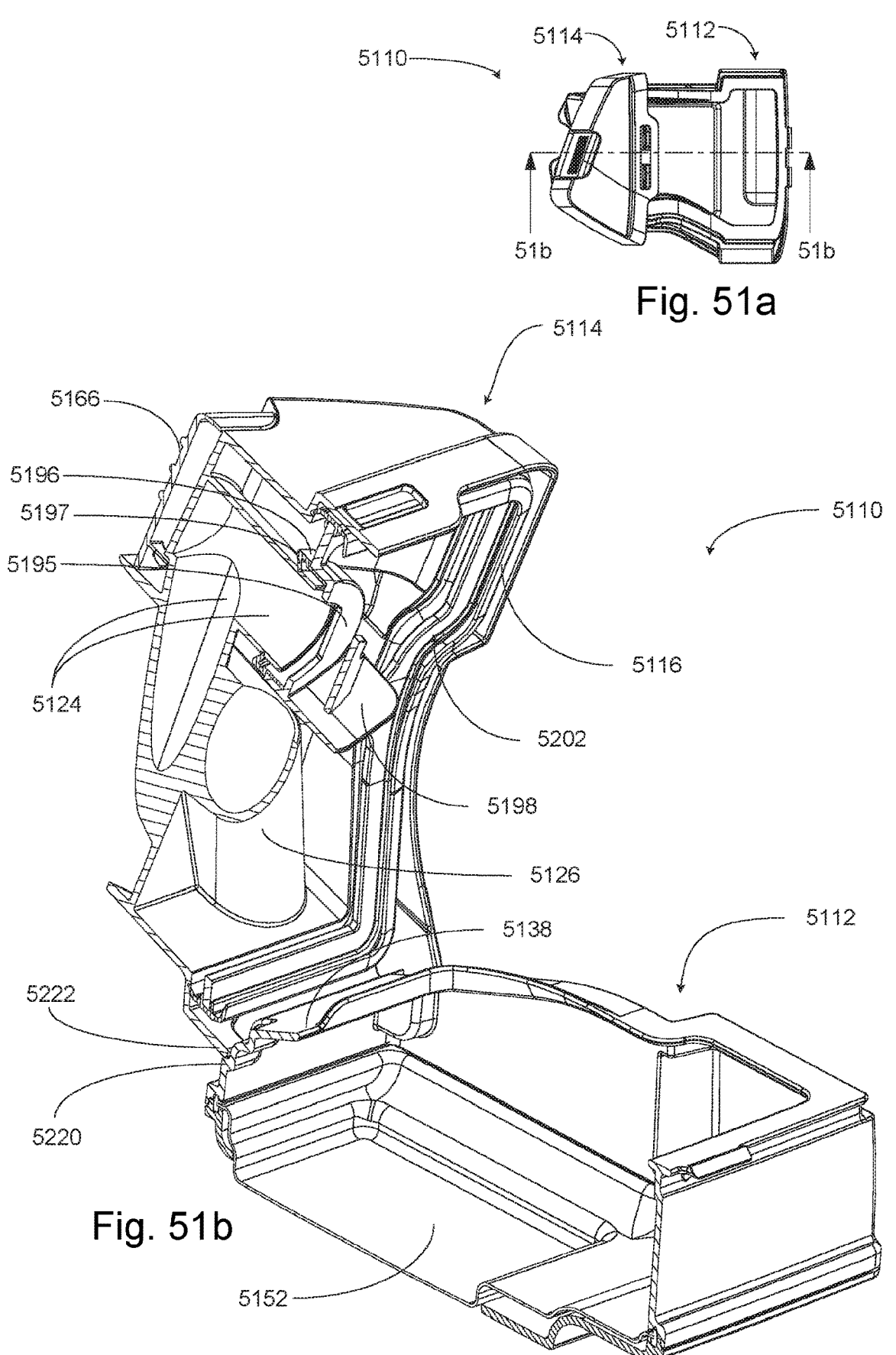

FIGS. 51*a*-51*b* show various views of a humidifier reservoir 5110 in accordance with one aspect of present technology. FIG. 51*a* shows a plan view of the humidifier reservoir 5110 in an 'open configuration', indicating a cross section to be shown in FIG. 51*b*, and FIG. 51*b* shows the reservoir 5110 with the cross section taken through line 51*b*-51*b* of FIG. 51*a* visible.

Figure 52:
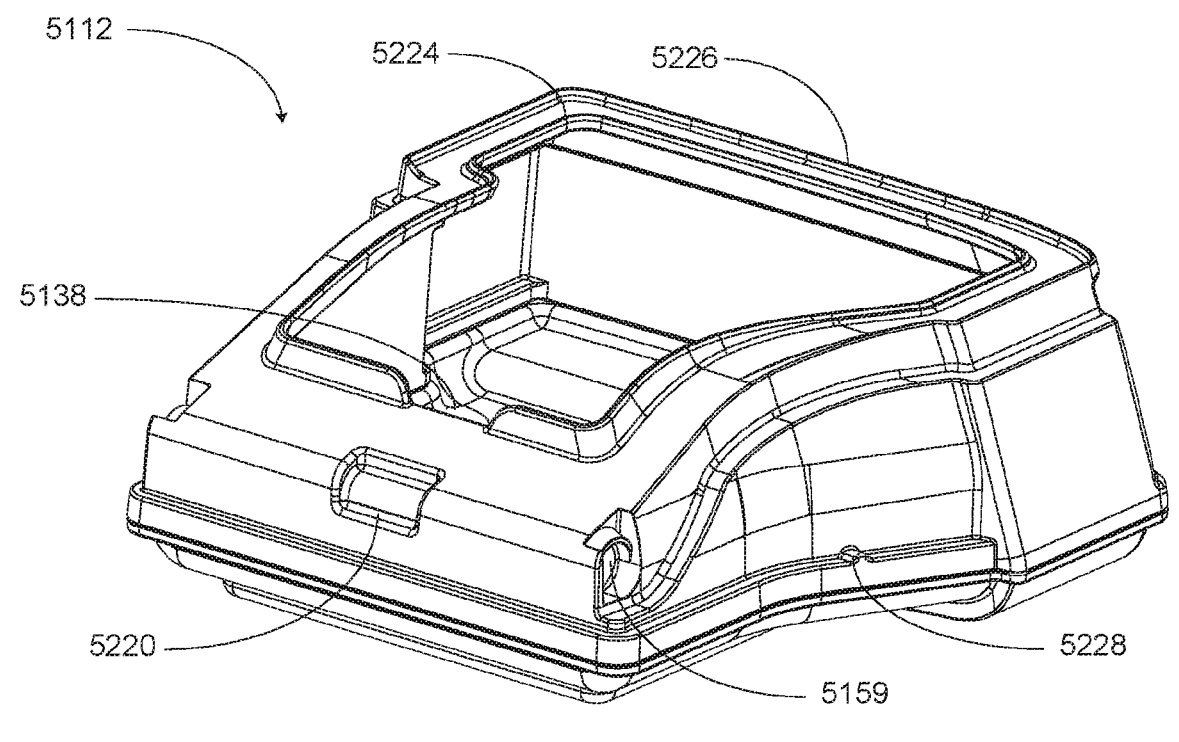
Figure 53:
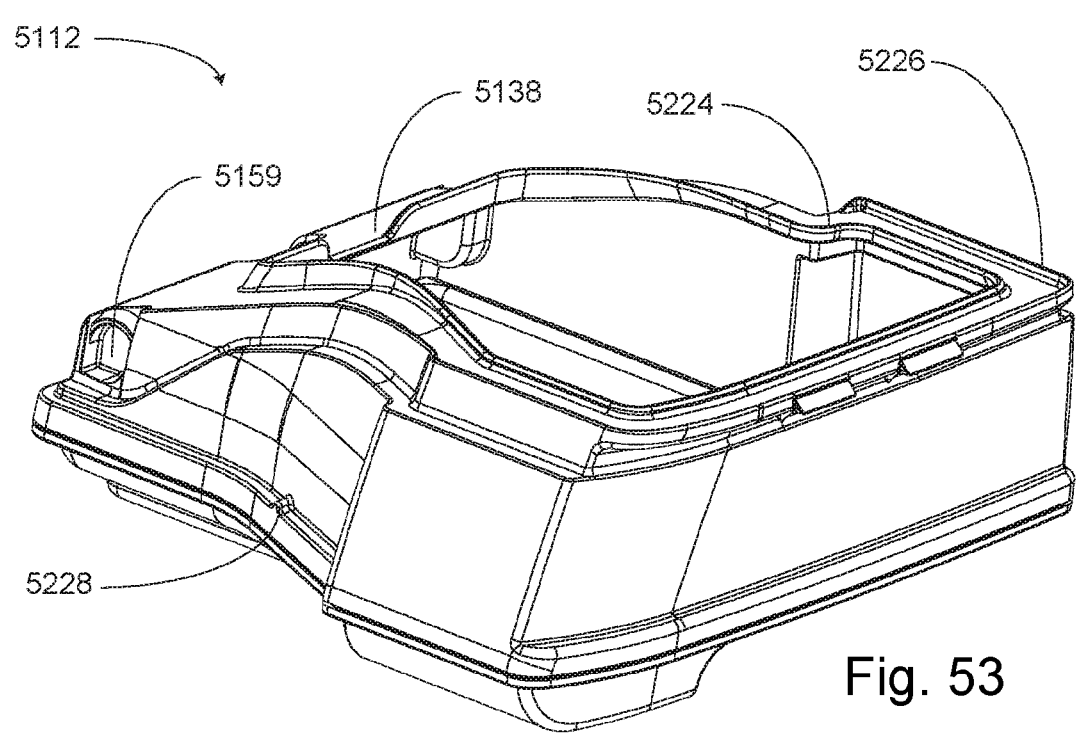

FIGS. 52-53 show various views of a reservoir base 5114 in accordance with one aspect of present technology.

Figure 54:
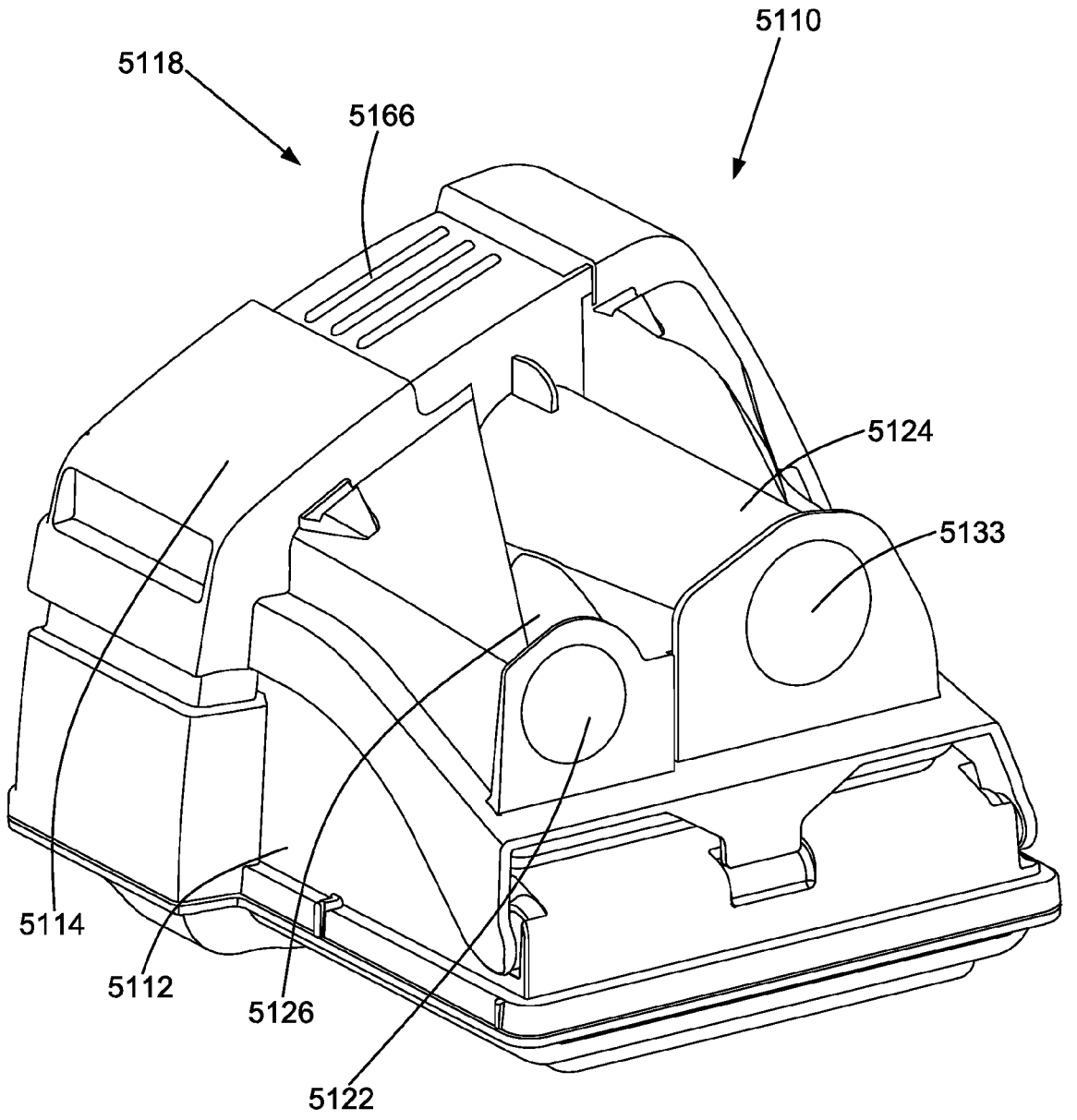

FIG. 54 shows a perspective view of a humidifier tub including a separately formed inlet according to an example of the present technology.

Figure 55:
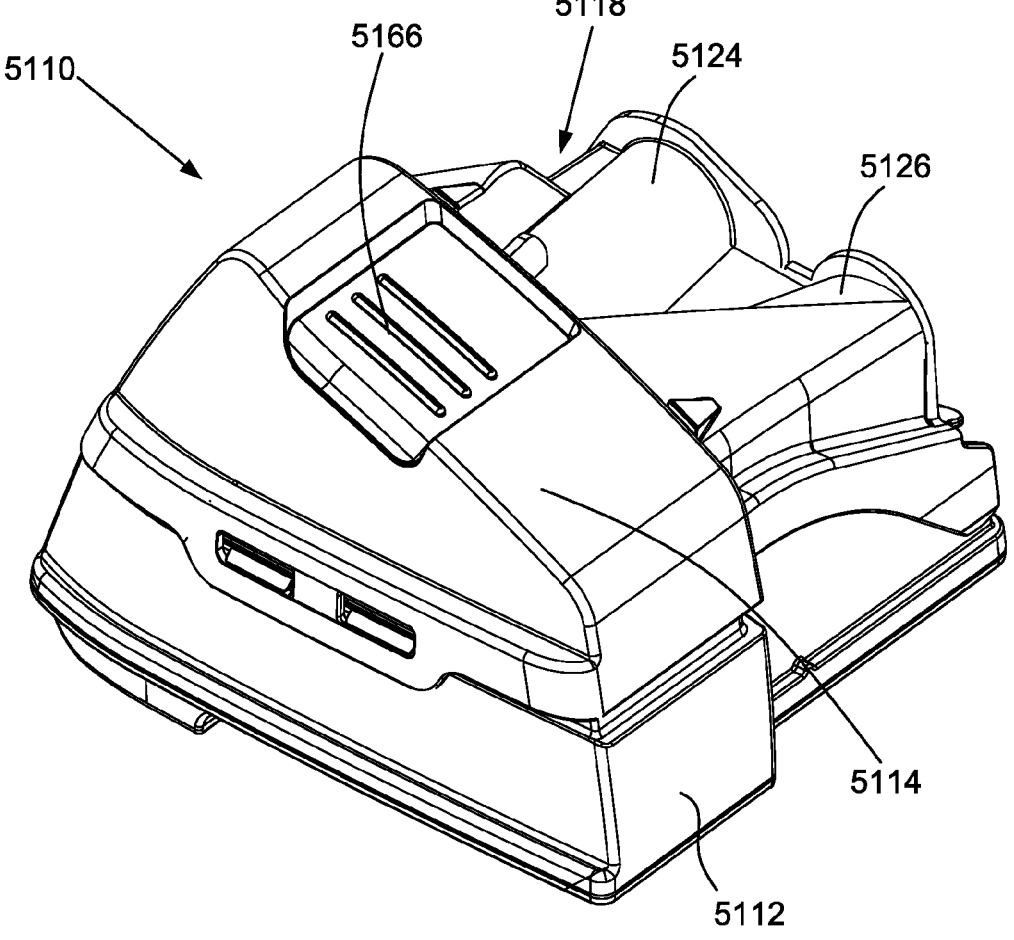

FIG. 55 shows another perspective view of the humidifier tub of FIG. 54.

Figure 56:
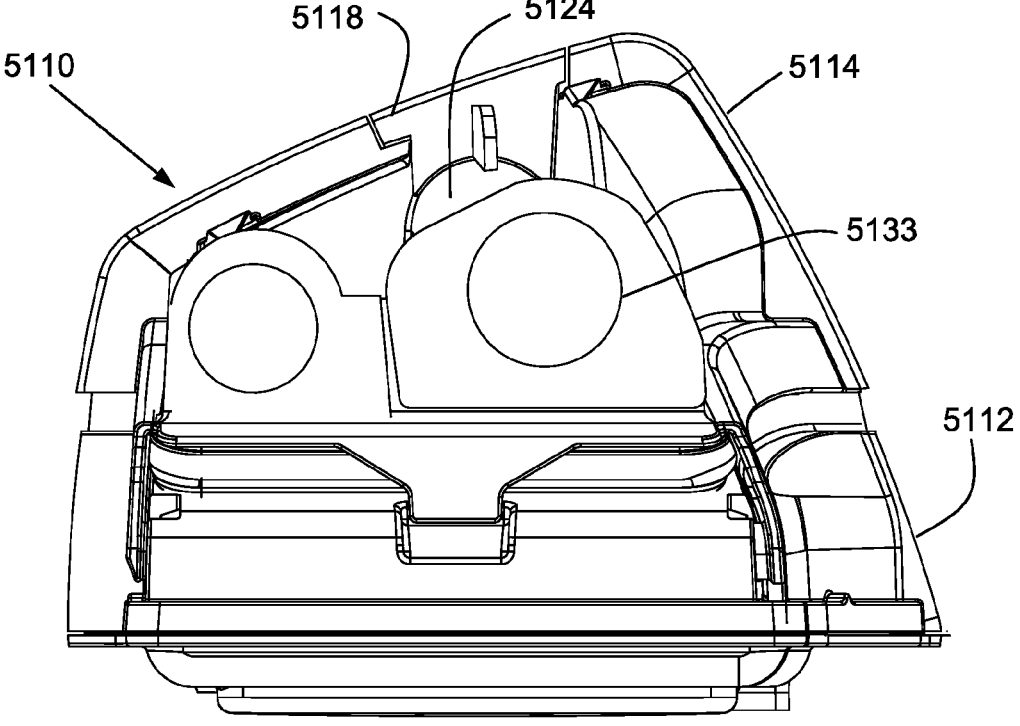

FIG. 56 shows a front view of the humidifier tub of FIG. 54.

Figure 57:
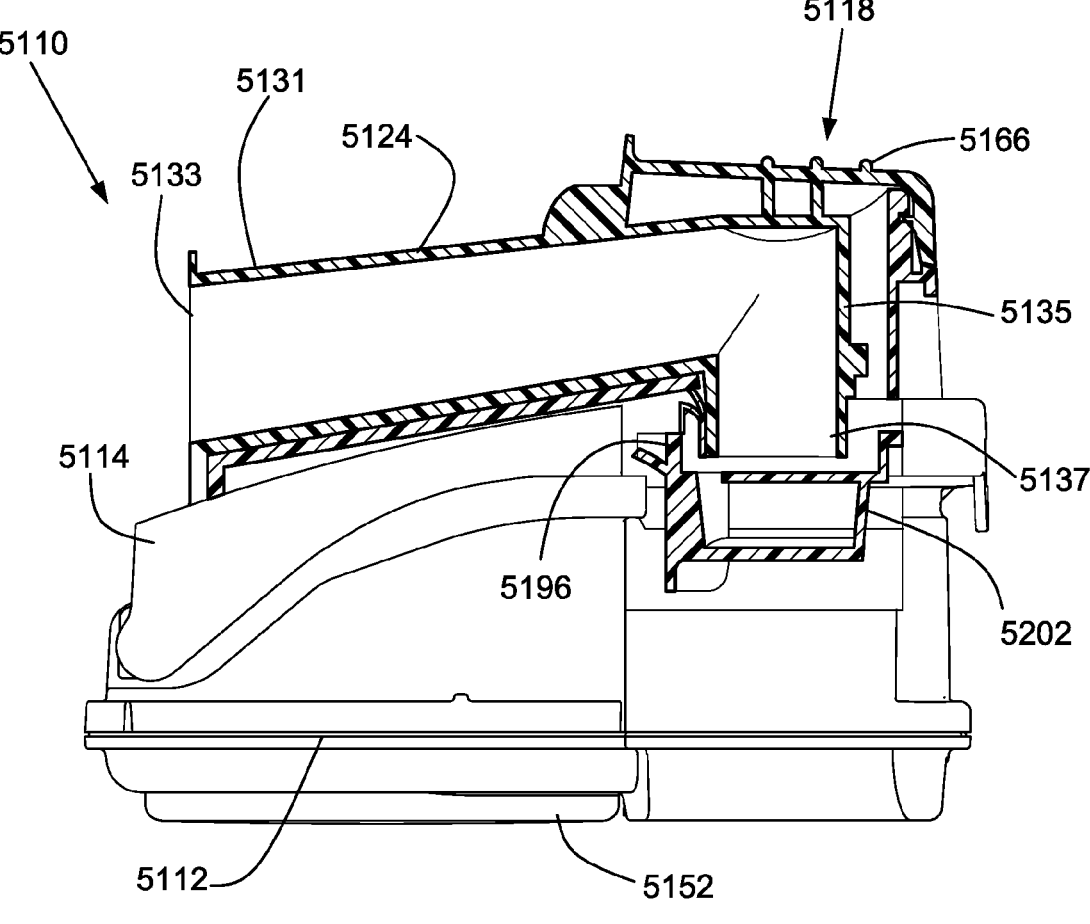

FIG. 57 shows a partial cross-sectional view of the humidifier tub of FIG. 54.

Figure 58:
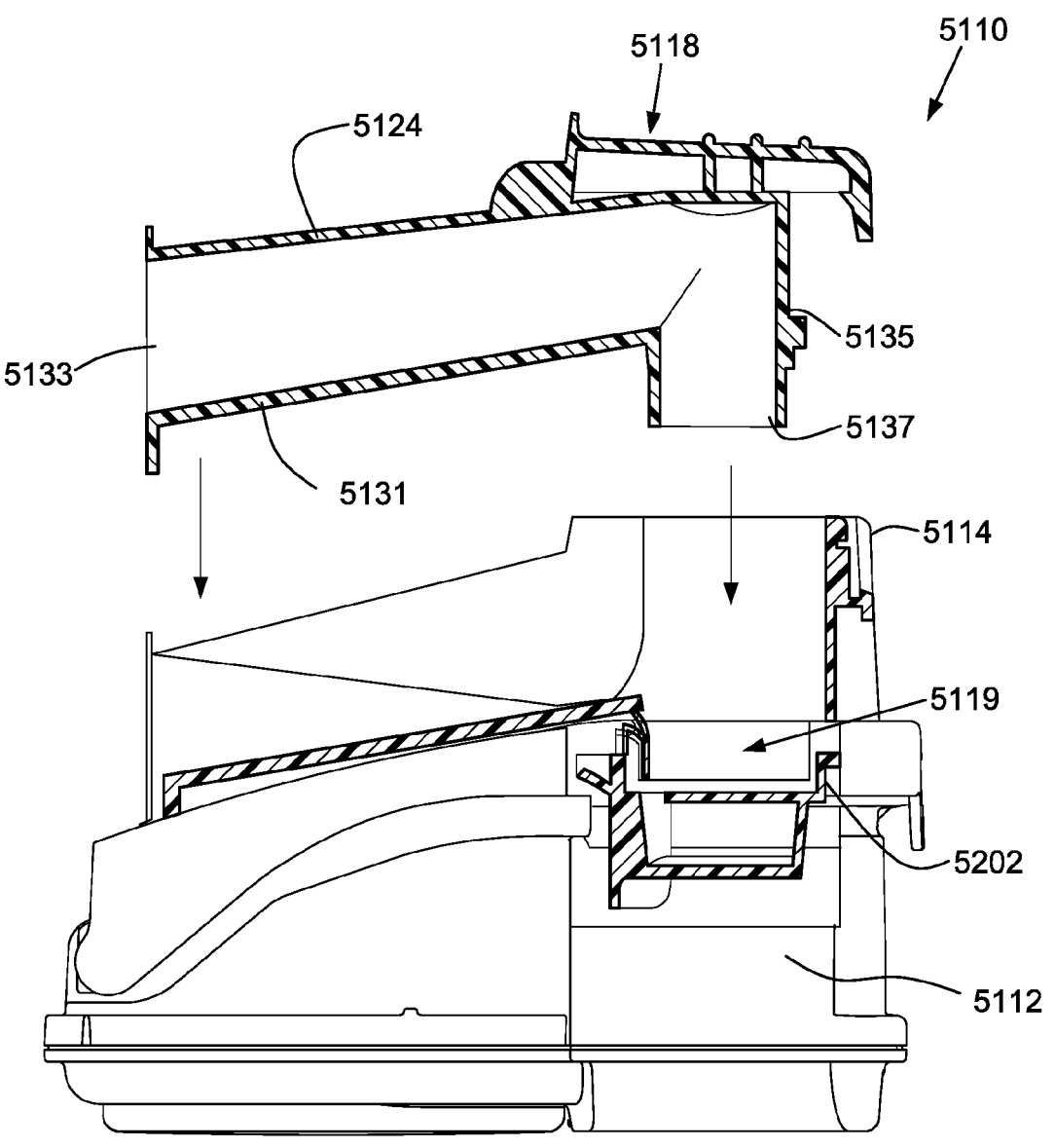

FIG. 58 shows an exploded view of the partial cross-sectional view of FIG. 57.

Figure 59:
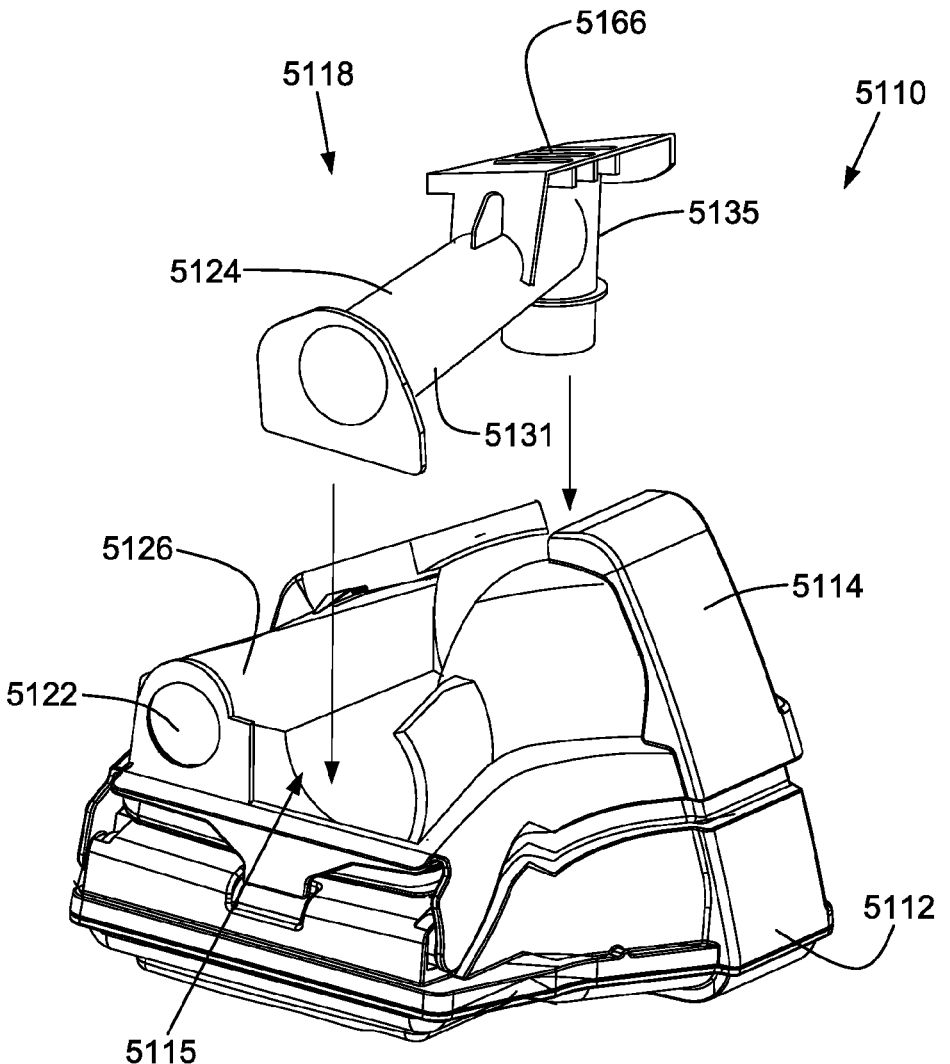

FIG. 59 shows an exploded view of the humidifier tub of FIG. 54.

Figure 60:
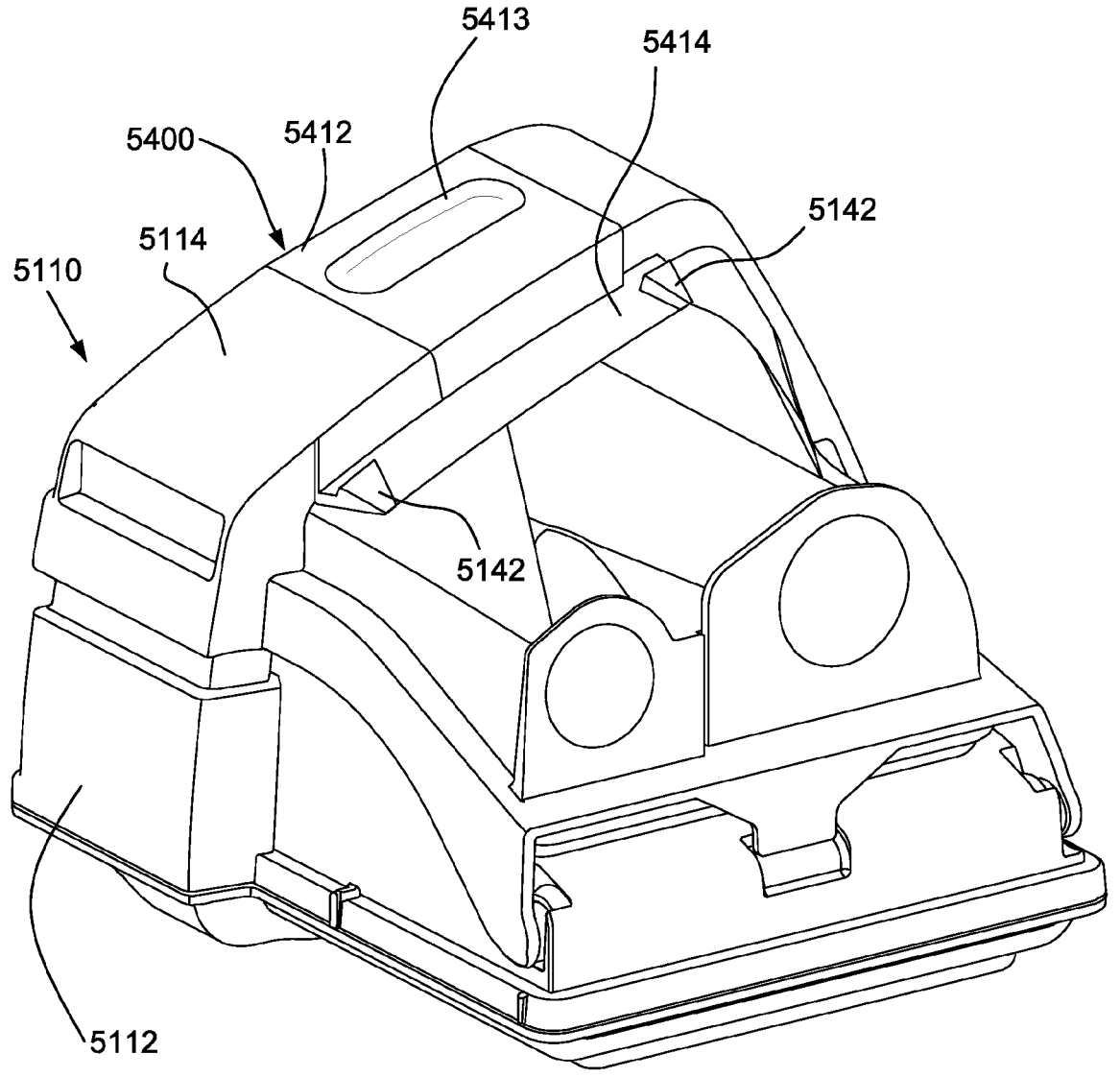

FIG. 60 shows a perspective view of a humidifier tub including a retention mechanism according to an example of the present technology.

Figure 61A:
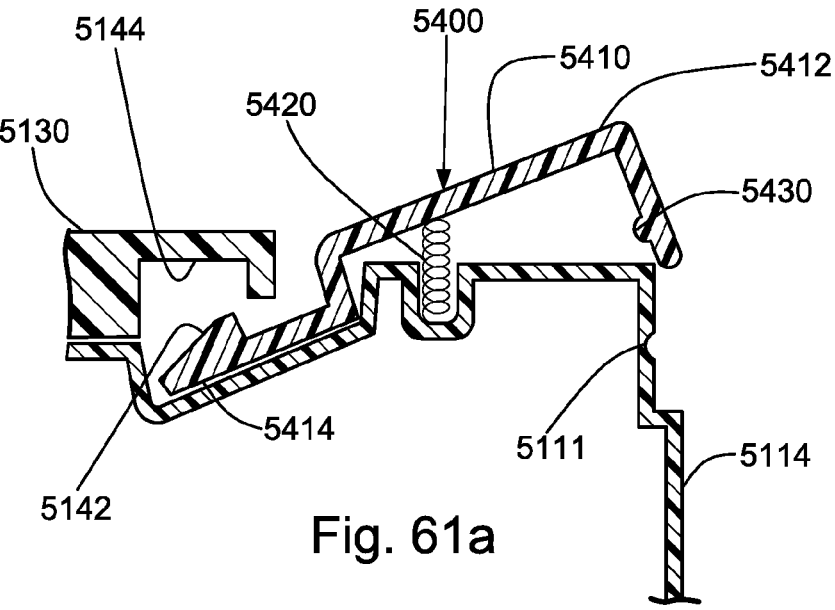

FIG. 61*a* shows a partial cross-sectional view of the retention mechanism of the humidifier tub of FIG. 60 in an unlocked position according to an example of the present technology.

Figure 61B:
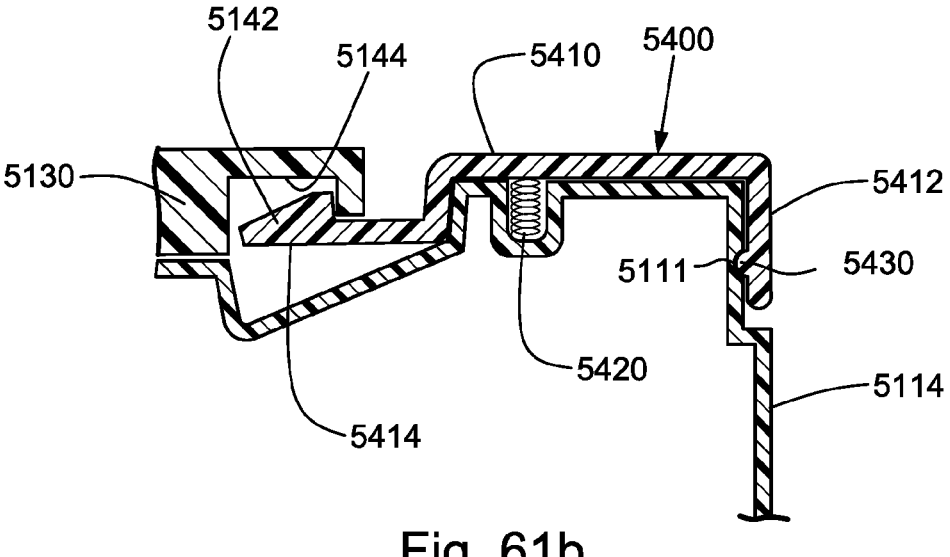

FIG. 61*b* shows a partial cross-sectional view of the retention mechanism of the humidifier tub of FIG. 60 in a locked position according to an example of the present technology.

Figure 62:
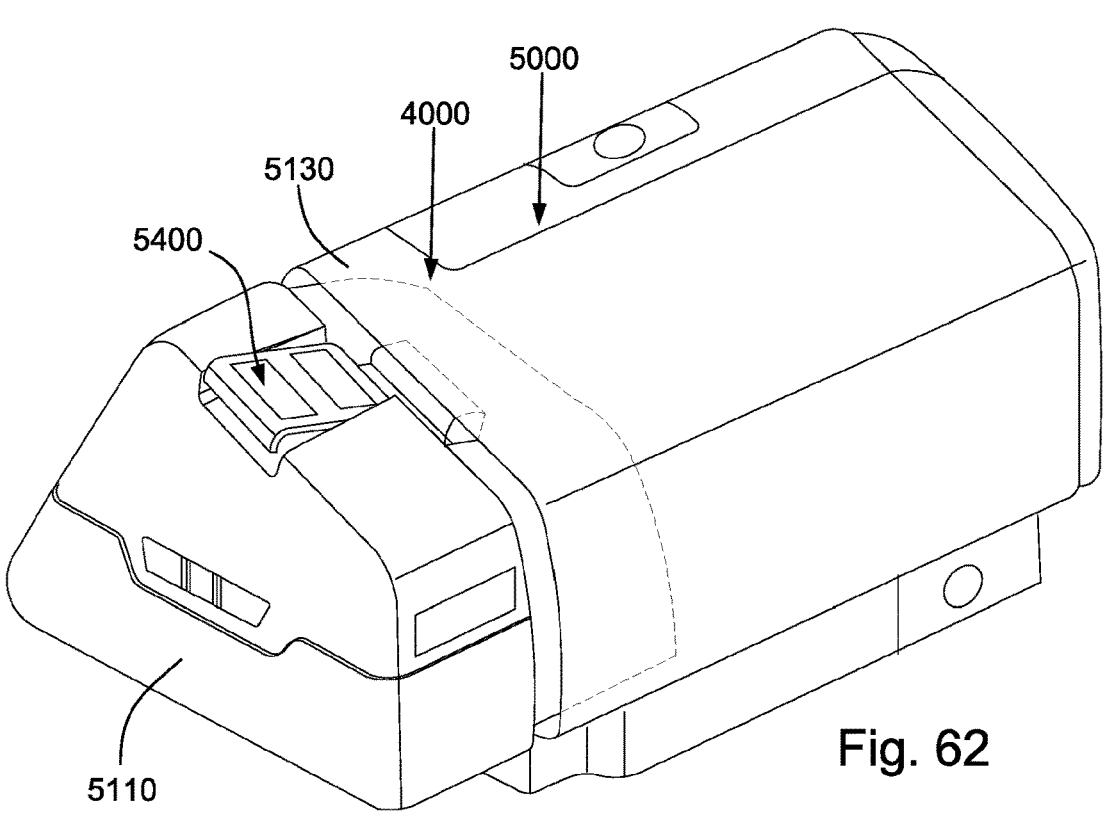

FIG. 62 shows a perspective view of an RPT device and humidifier including a humidifier tub according to an example of the present technology.

Figure 63:
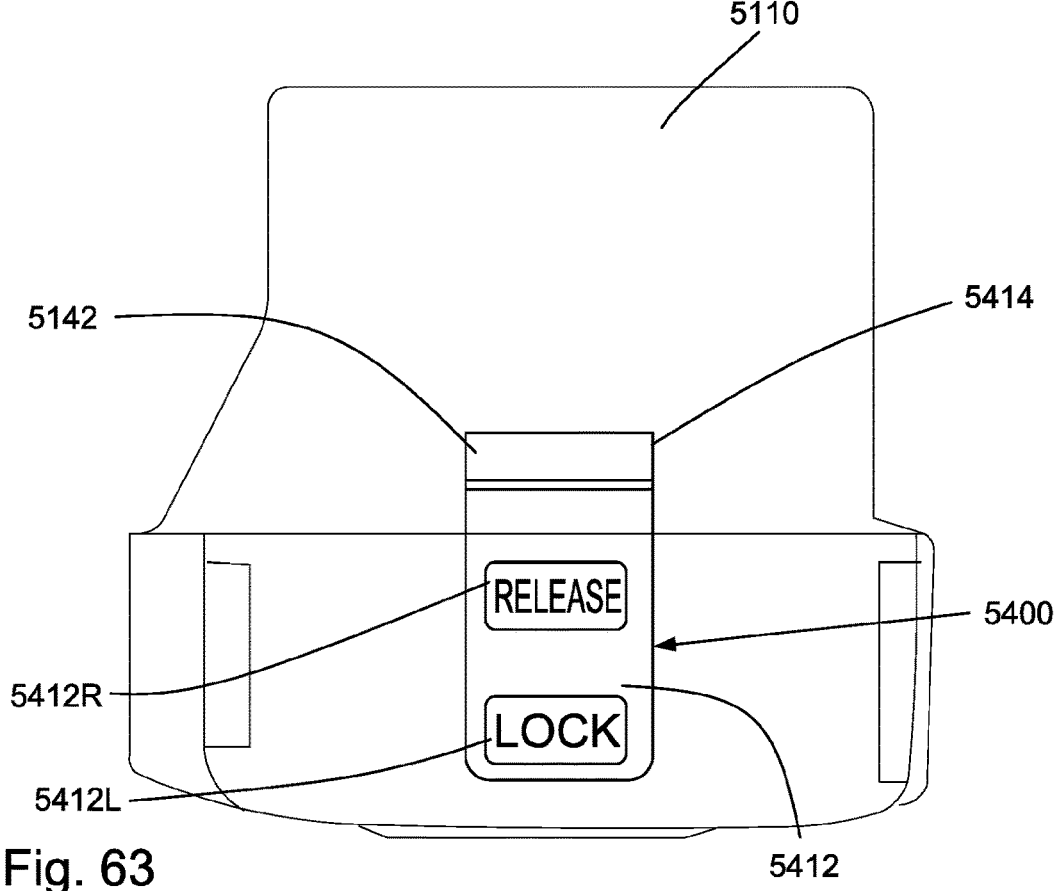

FIG. 63 shows a top view of the humidifier tub of FIG. 62.

Figure 64:
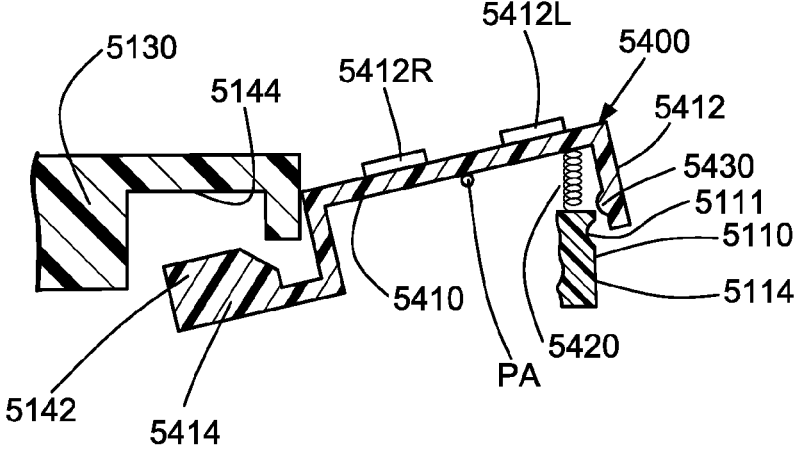

FIG. 64 shows a partial cross-sectional view of a retention mechanism of the humidifier tub of FIG. 63 in an unlocked position according to an example of the present technology.

Figure 65:
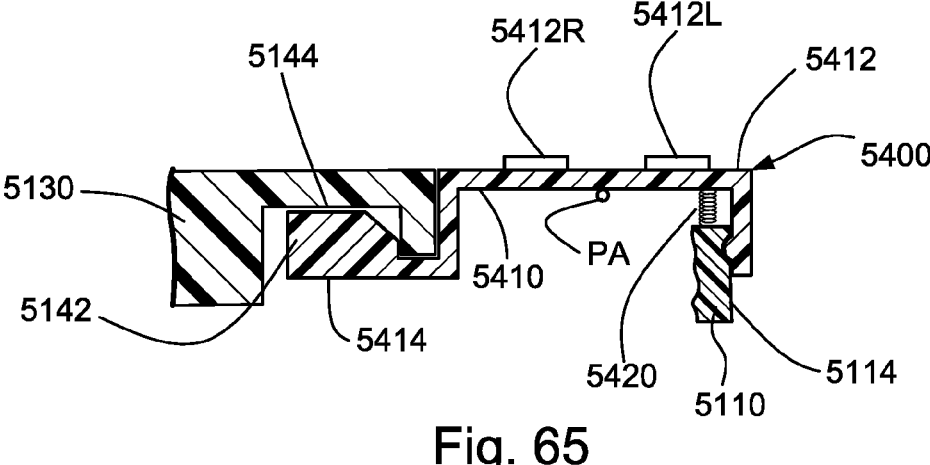

FIG. 65 shows a partial cross-sectional view of a retention mechanism of the humidifier tub of FIG. 63 in a locked position according to an example of the present technology.

Figure 66:
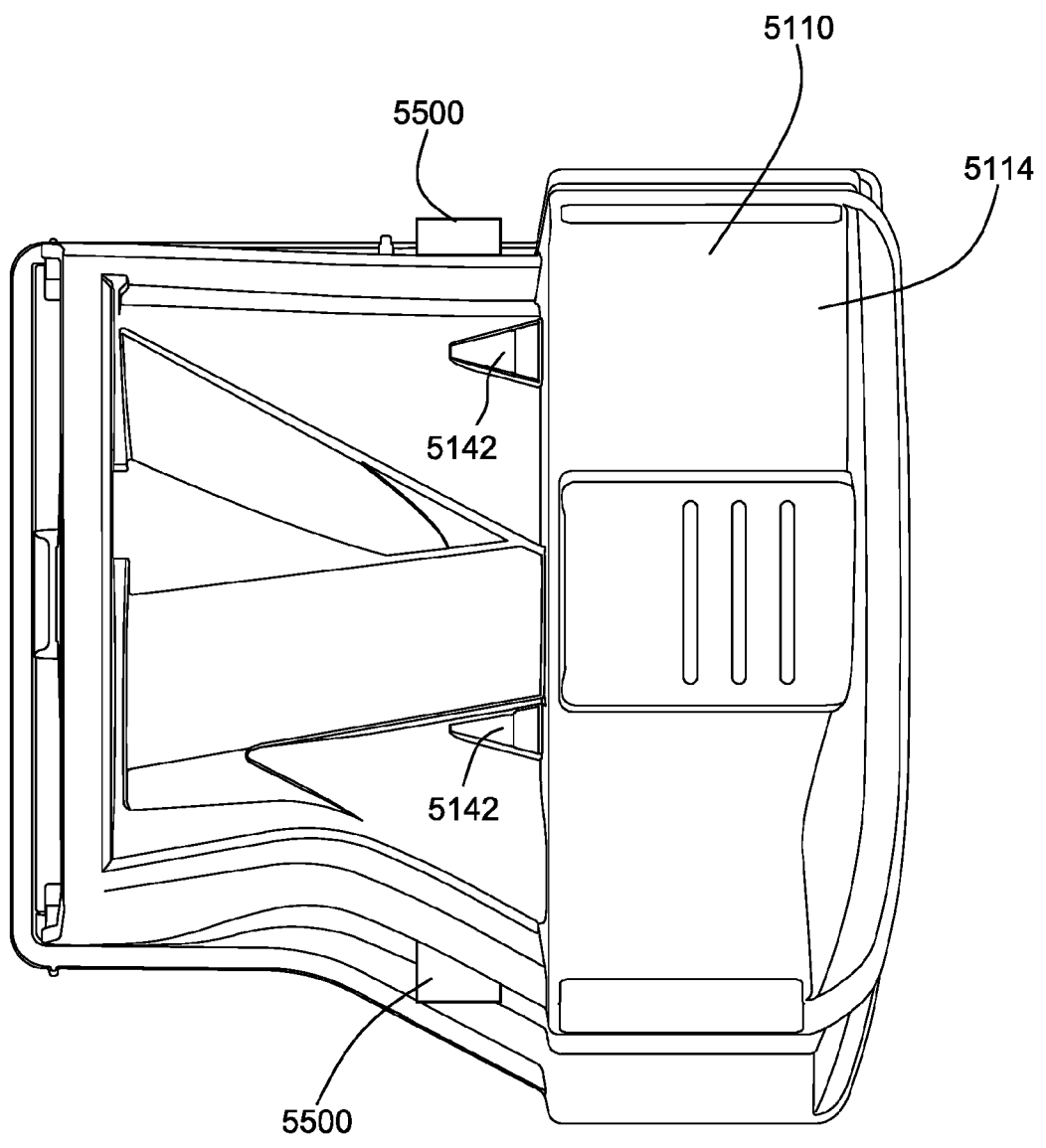

FIG. 66 shows a top view of a humidifier tub including a retention mechanism according to an example of the present technology.

FIG. 67*a* shows a partial cross-sectional view of the retention mechanism of the humidifier tub of FIG. 66.

FIG. 67*b* shows a partial cross-sectional view of engagement of the tub with the dock into an operative position.

FIG. 67*c* shows a partial cross-sectional view of further engagement of the tub with the dock into an operative position.

FIG. 67*d* shows a partial cross-sectional view of further engagement of the tub with the dock into an operative position.

Figures 68, 69:
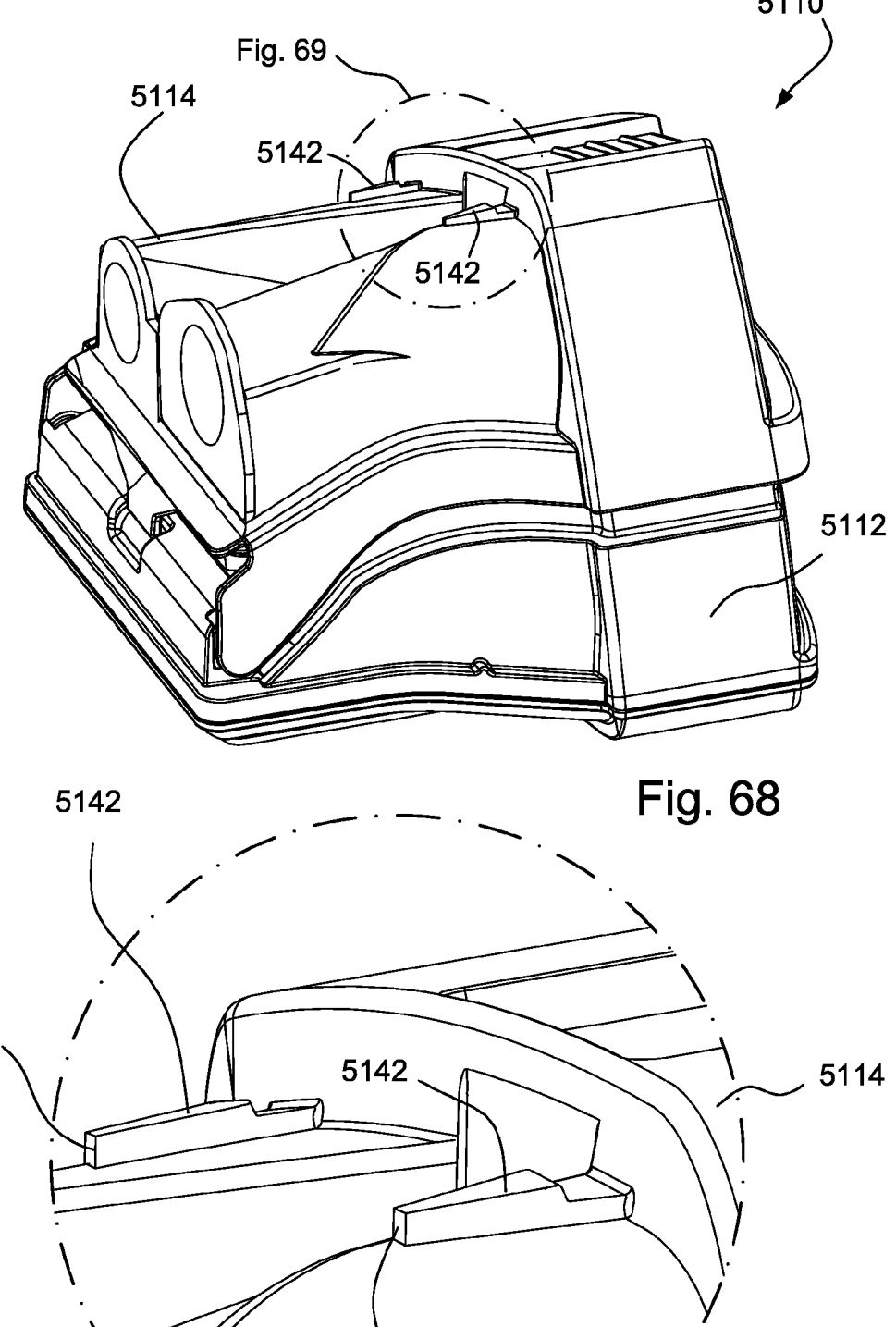

FIG. 68 shows a perspective view of a humidifier tub including a retention mechanism according to an example of the present technology.

FIG. 69 shows an enlarged view of the humidifier tub of FIG. 68.

Figure 70:
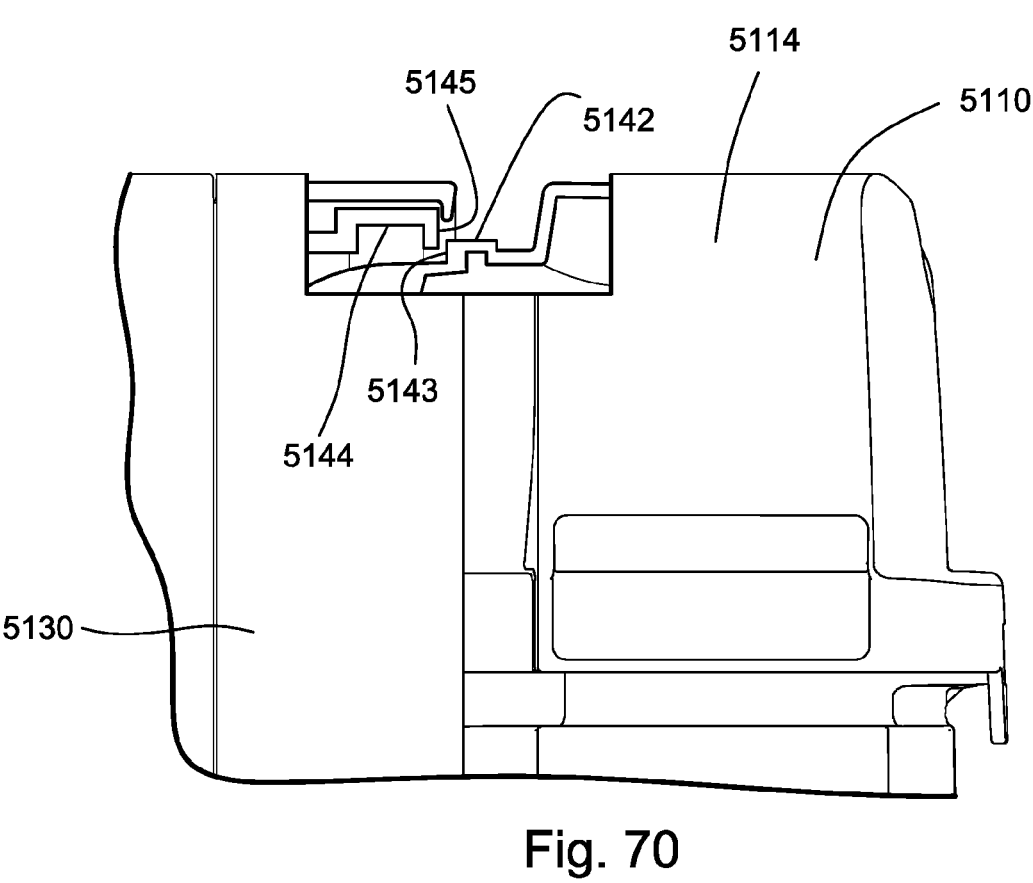

FIG. 70 shows a partial cross-sectional view of an RPT device and humidifier with the humidifier tub of FIG. 68 in a state of partial engagement according to an example of the present technology.

Figure 71:
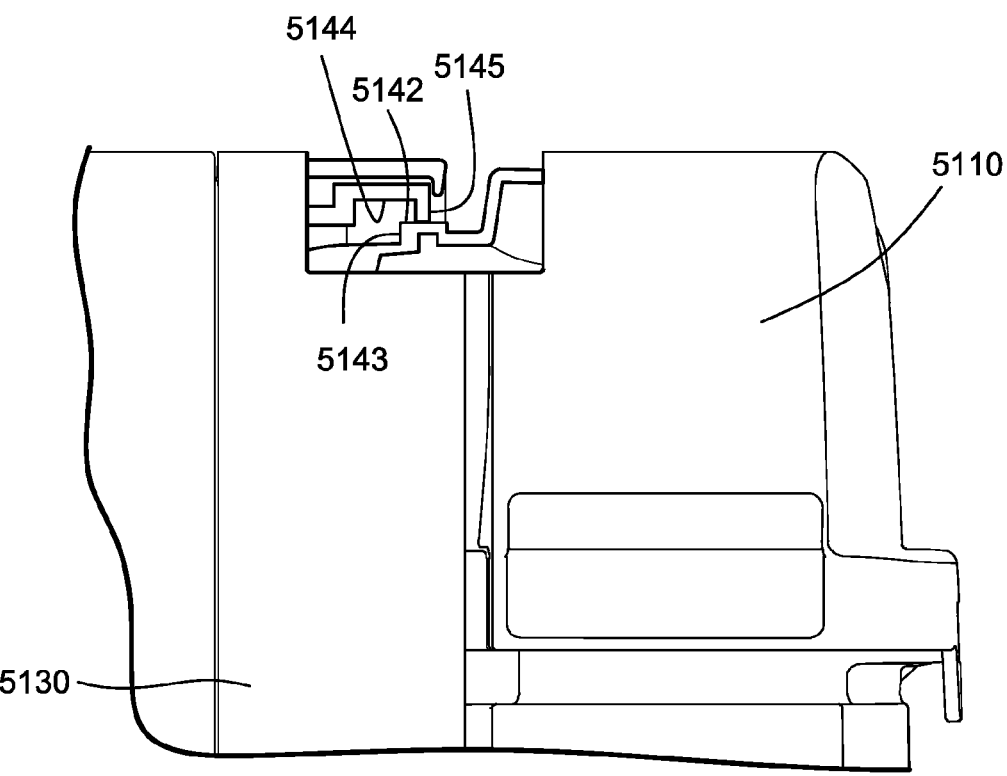

FIG. 71 shows a partial cross-sectional view of an RPT device and humidifier with the humidifier tub of FIG. 68 in another state of partial engagement according to an example of the present technology.

Figure 72:
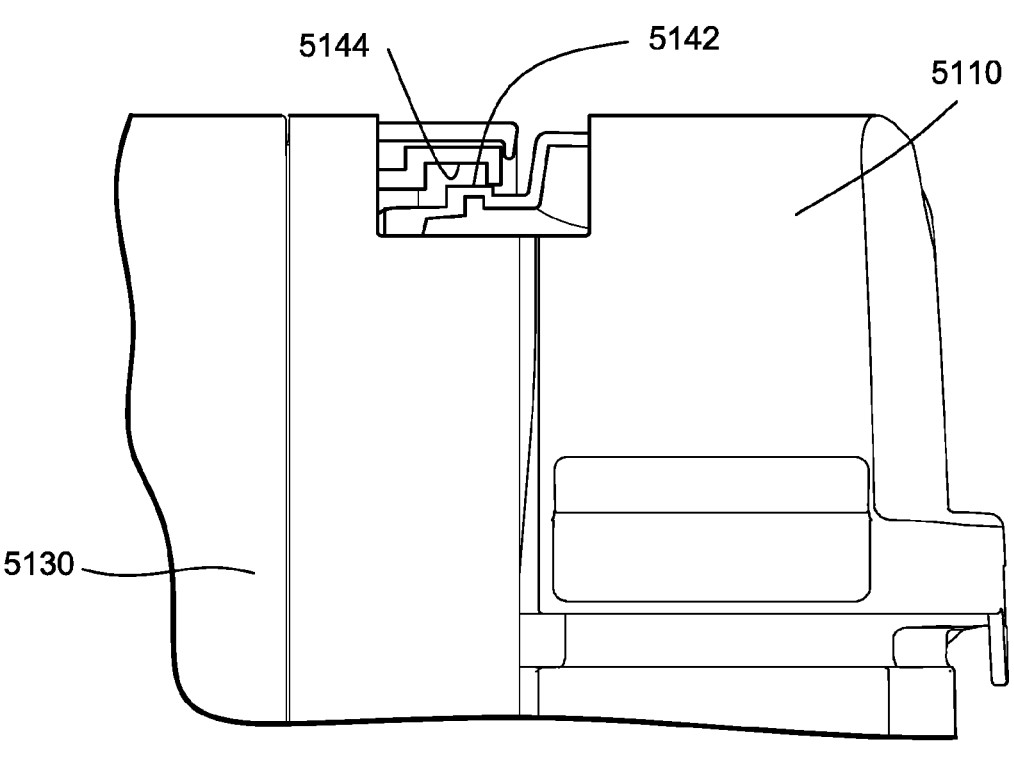

FIG. 72 shows a partial cross-sectional view of an RPT device and humidifier with the humidifier tub of FIG. 68 in another state of partial engagement according to an example of the present technology.

Figure 73:
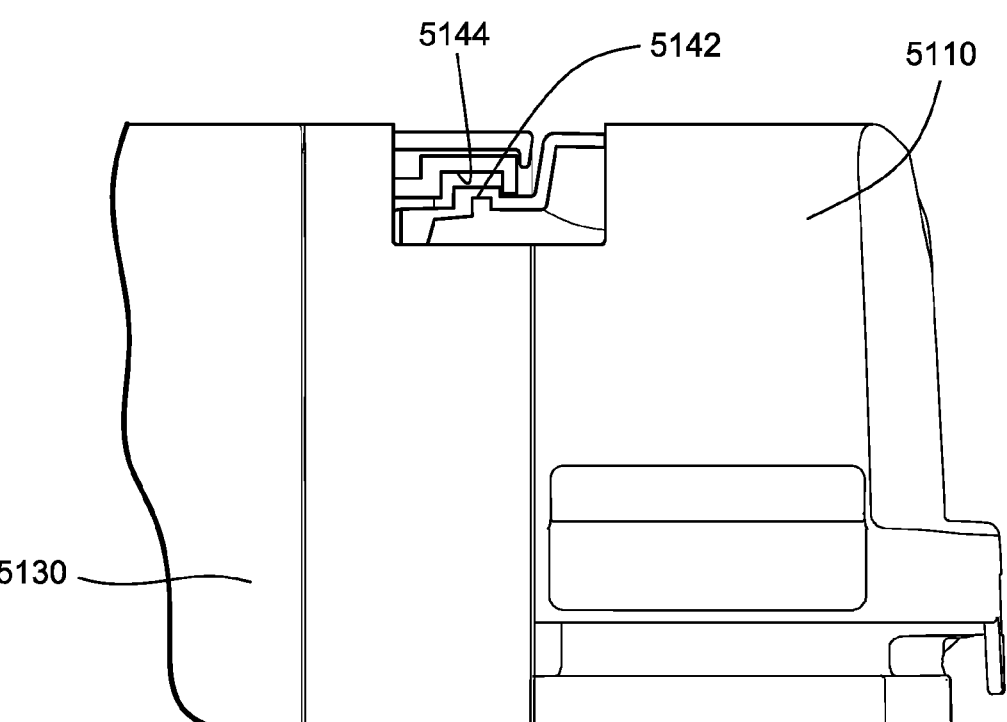

FIG. 73 shows a partial cross-sectional view of an RPT device and humidifier with the humidifier tub of FIG. 68 in a state of engagement according to an example of the present technology.

Figure 74:
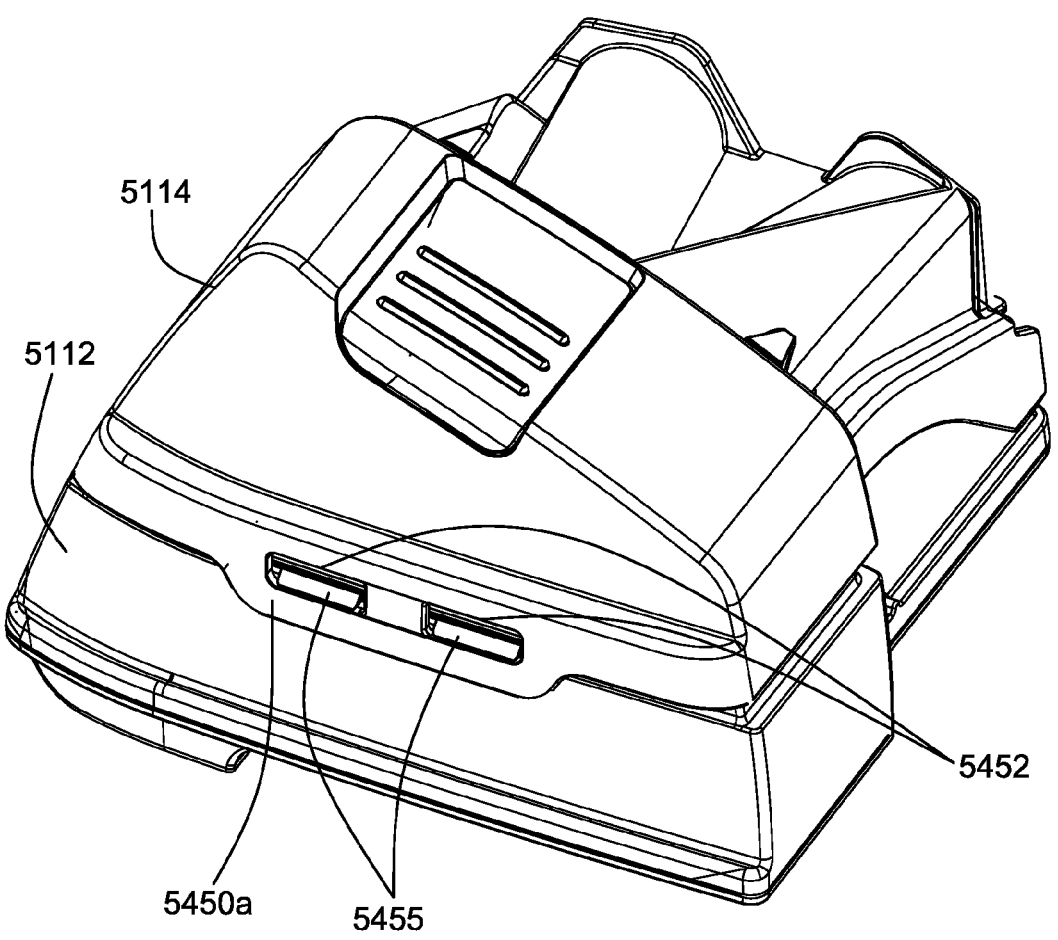

FIG. 74 shows a perspective view of a humidifier tub including a lid with opposing clips according to an example of the present technology.

Figure 75:
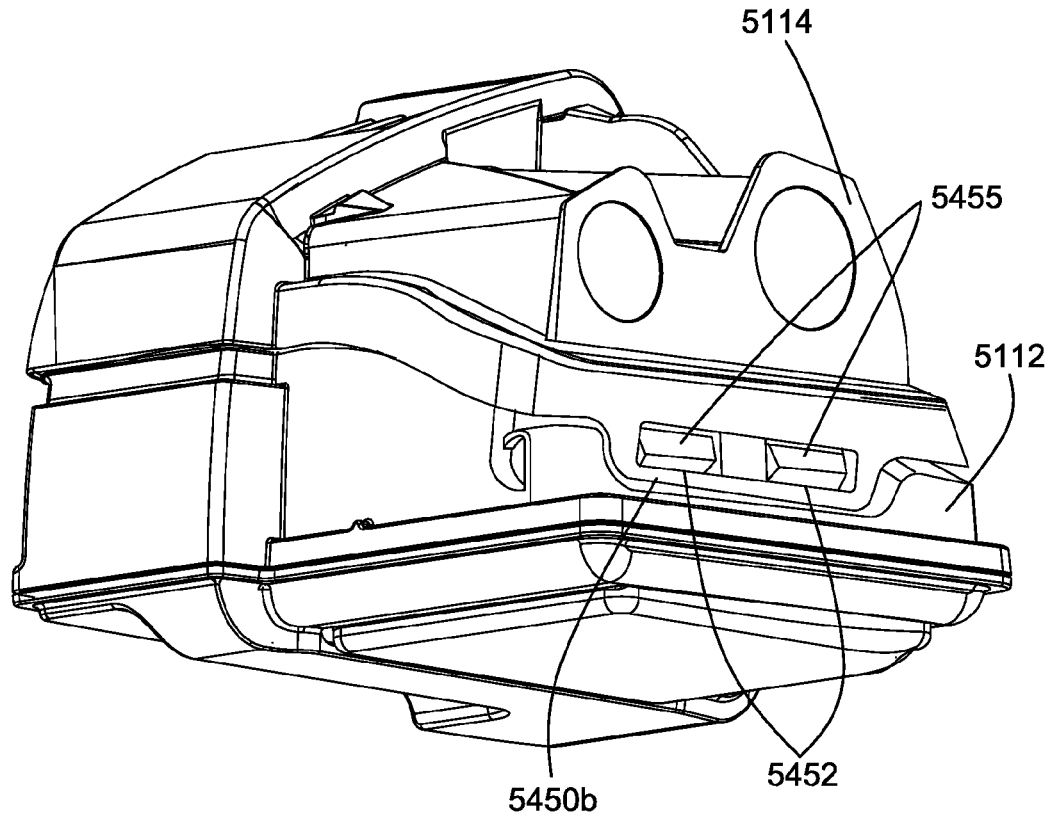

FIG. 75 shows another perspective view of the humidifier tub of FIG. 74.

Figure 76:
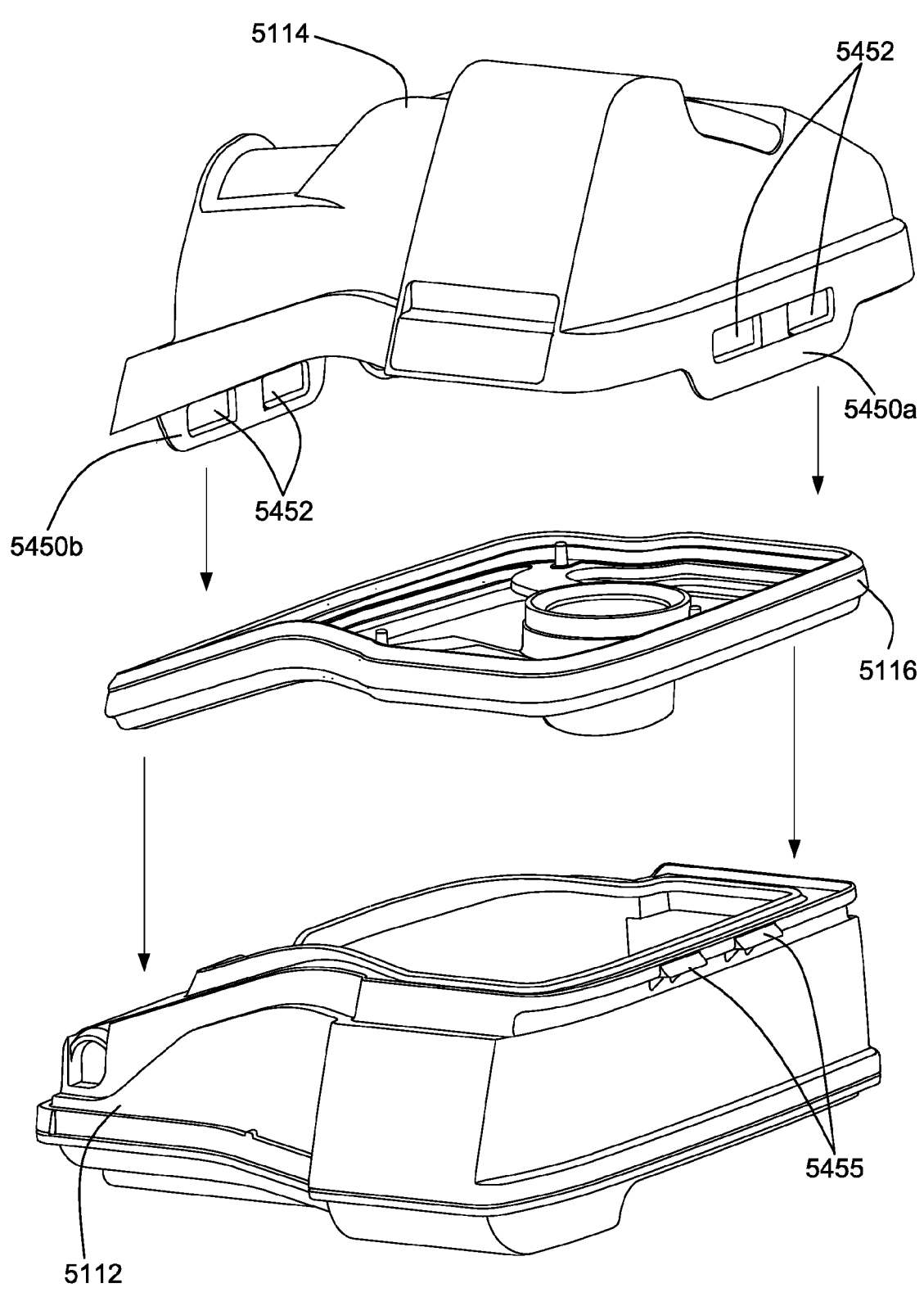

FIG. 76 shows an exploded view of the humidifier tub of FIG. 74.

Figure 77:
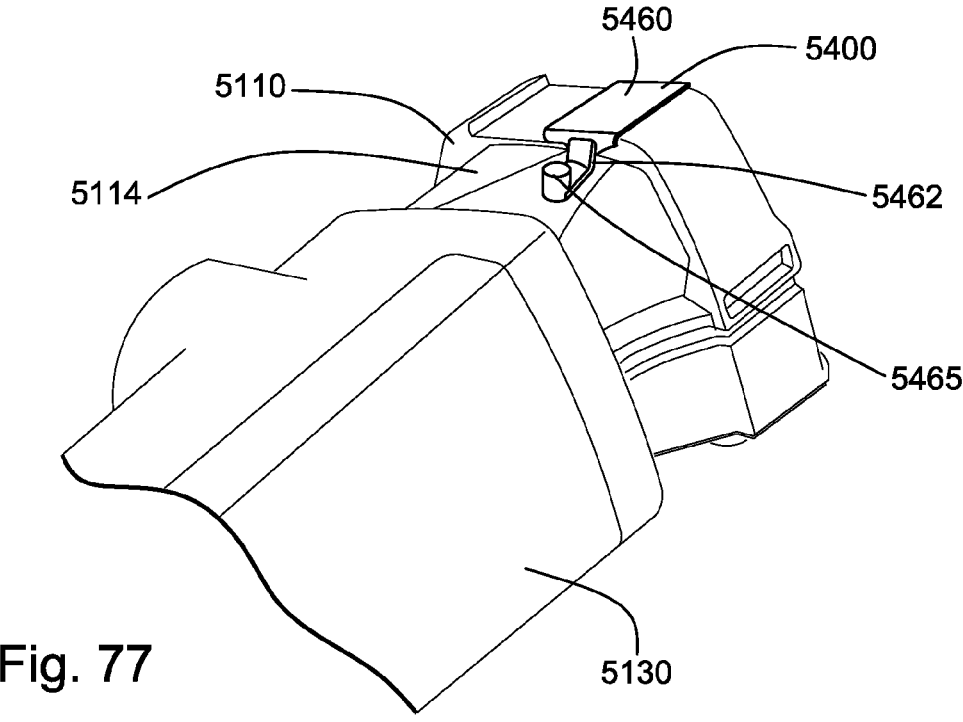

FIG. 77 shows a front perspective view of an RPT device and humidifier including a humidifier tub in a state of partial engagement according to an example of the present technology.

Figure 78:
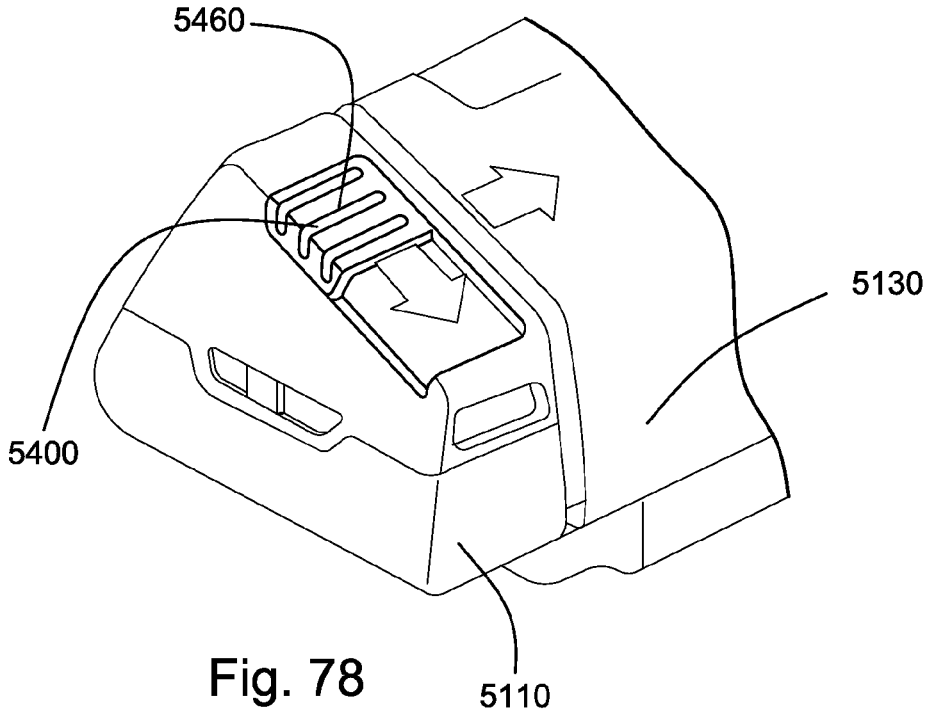

FIG. 78 shows a rear perspective view of an RPT device and humidifier with the humidifier tub of FIG. 77 in a state of partial engagement according to an example of the present technology.

Figure 79A:
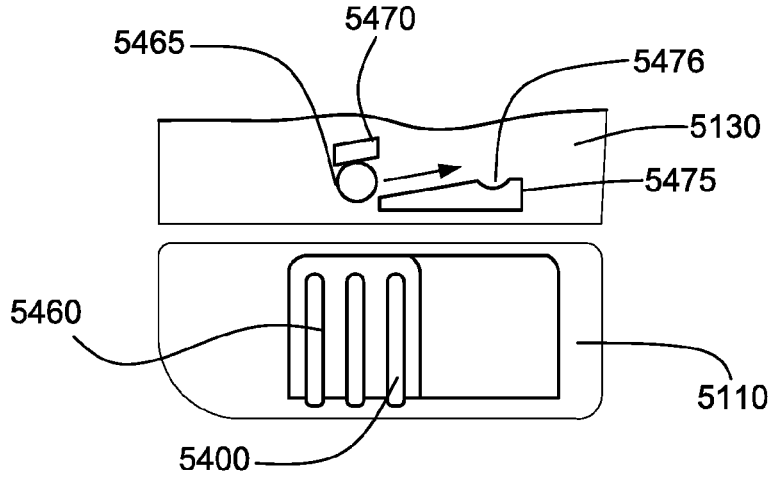

FIG. 79*a* shows a top view of an RPT device and humidifier with the humidifier tub of FIG. 77 in a state of partial engagement with a retention mechanism in an unlocked position according to an example of the present technology.

Figure 79B:
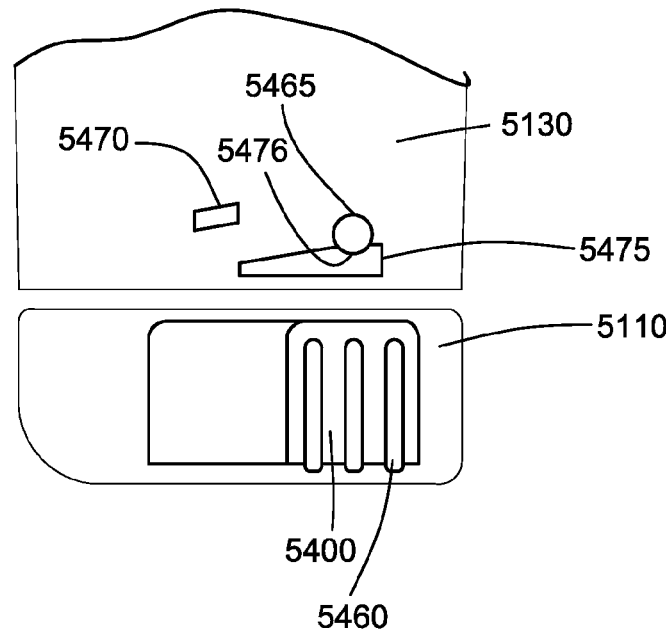

FIG. 79*b* shows a top view of an RPT device and humidifier with the humidifier tub of FIG. 77 in a state of engagement with a retention mechanism in a locked position according to an example of the present technology.

Figures 80, 81A, 81B, 82A, 82B, 83:
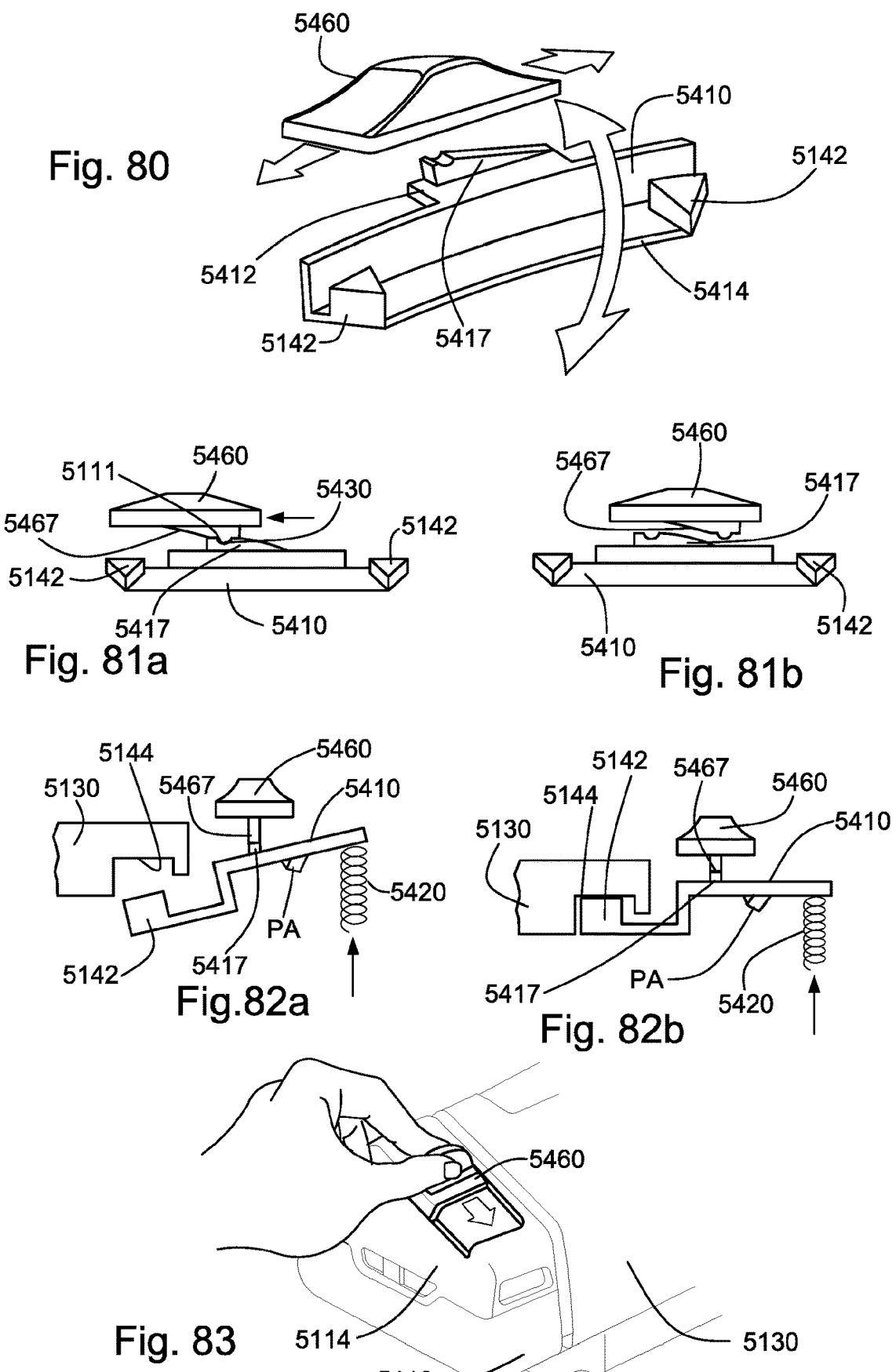

FIG. 80 shows an exploded view of a retention mechanism for a humidifier tub according to an example of the present technology.

FIG. 81*a* shows a front view of the retention mechanism of FIG. 80 in an unlocked position.

FIG. 81*b* shows a front view of the retention mechanism of FIG. 80 in a locked position.

FIG. 82*a* shows a side view of the retention mechanism of FIG. 80 in an unlocked position.

FIG. 82*b* shows a side view of the retention mechanism of FIG. 80 in a locked position.

FIG. 83 shows a rear perspective view of an RPT device and humidifier including a humidifier tub with the retention mechanism of FIG. 80 according to an example of the present technology.

FIG. 84 shows a front perspective view of an RPT device and humidifier including a humidifier tub in a state of partial engagement according to an example of the present technology.

FIG. 85 shows a top view of an RPT device and humidifier with the humidifier tub of FIG. 84 in a state of partial engagement according to an example of the present technology.

FIG. 86 shows a top view of an RPT device and humidifier with the humidifier tub of FIG. 84 in a state of engagement according to an example of the present technology.

FIG. 87 shows a rear perspective view of an RPT device and humidifier including retention mechanism for a humidifier tub according to an example of the present technology.

FIG. 88*a* shows a partial cross-sectional view of the retention mechanism of FIG. 87 in a locked position according to an example of the present technology.

FIG. 88*b* shows a partial cross-sectional view of the retention mechanism of FIG. 87 in an unlocked position according to an example of the present technology.

Figures 89A, 89B, 89C, 89D:
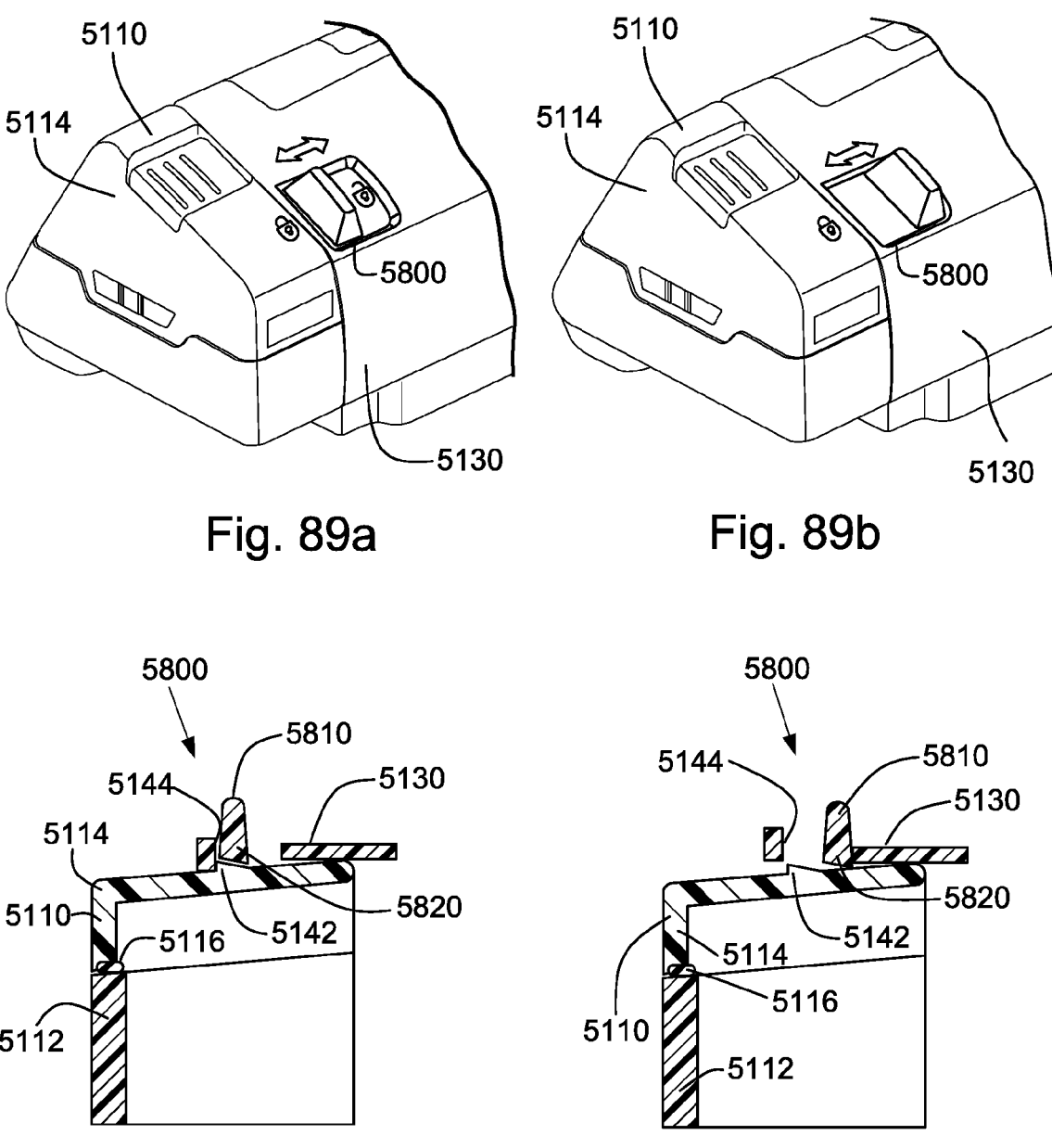

FIG. 89*a* shows a rear perspective view of an RPT device and humidifier including a retention mechanism for a humidifier tub according to an example of the present technology, the retention mechanism being shown in a locked position according to an example of the present technology.

FIG. 89*b* shows a partial perspective view of the retention mechanism of FIG. 89*a* in an unlocked position according to an example of the present technology.

FIG. 89*c* shows a partial cross-sectional view of the retention mechanism of FIG. 89*a* in a locked position according to an example of the present technology.

FIG. 89*d* shows a partial cross-sectional view of the retention mechanism of FIG. 89*a* in an unlocked position according to an example of the present technology.

FIG. 90 shows a perspective view of a portion of a humidifier tub including a retention mechanism according to an example of the present technology.

FIG. 90*a* shows a cross-sectional view of the tub and retention mechanism of FIG. 90.

FIG. 90*b* shows a partial cross-sectional view of the tub and retention mechanism of FIG. 90 with the retention mechanism in a locked position according to an example of the present technology.

FIG. 90*c* shows a partial cross-sectional view of the tub and retention mechanism of FIG. 90 with the retention mechanism in an unlocked position according to an example of the present technology.

Figure 91:
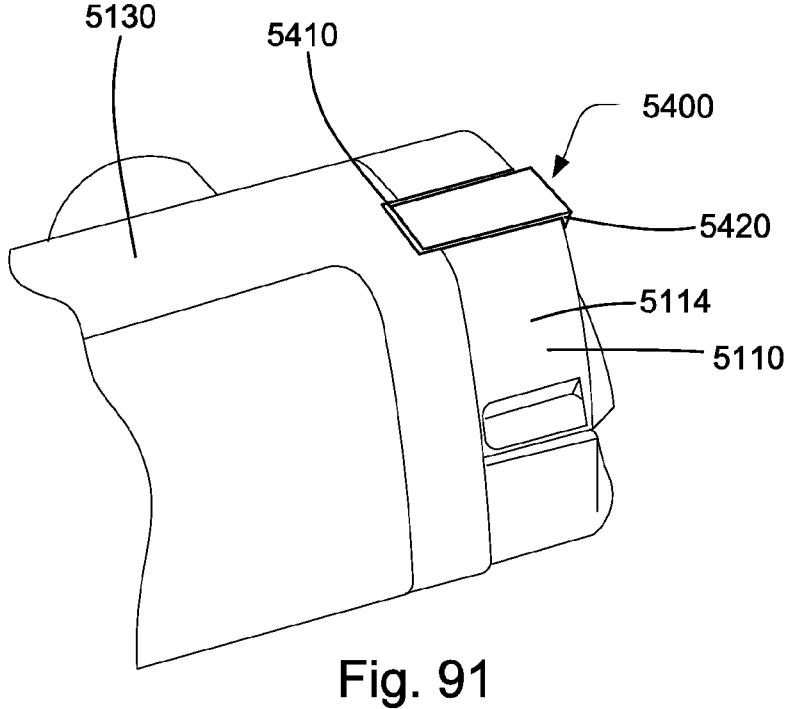

FIG. 91 shows a front perspective view of an RPT device and humidifier including a retention mechanism for a humidifier tub in a locked position according to an example of the present technology.

Figure 92:
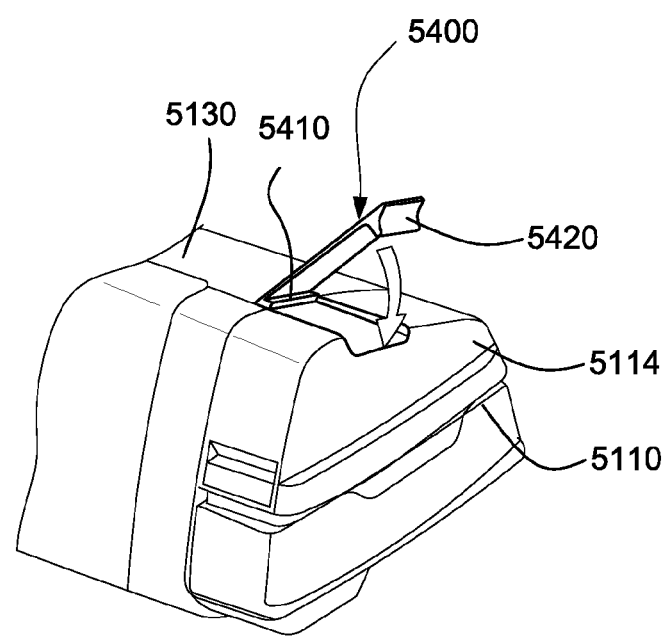

FIG. 92 shows another perspective view of an RPT device and humidifier including the retention mechanism for a humidifier tub of FIG. 91 in an unlocked position.

Figure 93A:
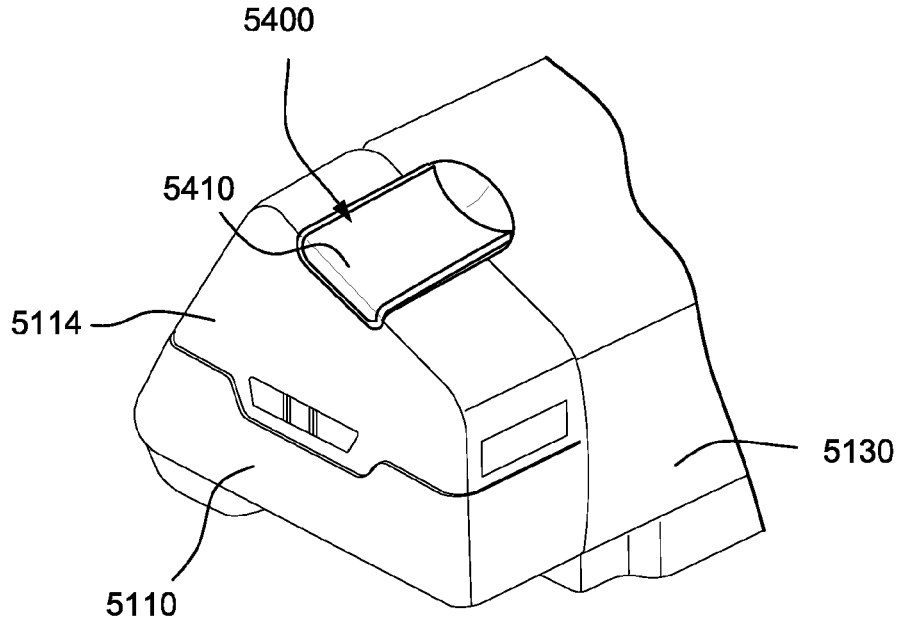

FIG. 93*a* shows a rear perspective view of an RPT device and humidifier including a retention mechanism for a humidifier tub in a locked position according to an example of the present technology.

Figure 93B:
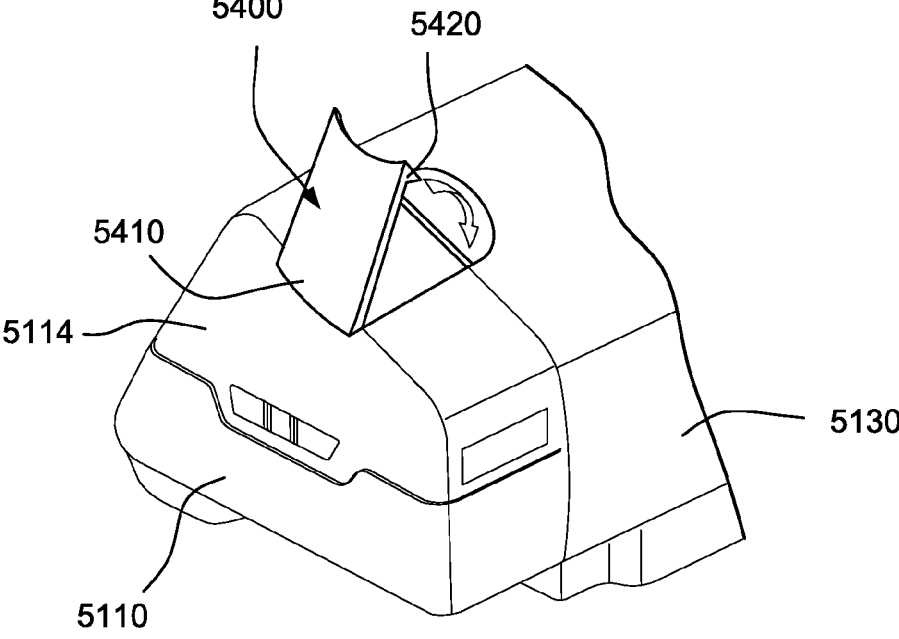

FIG. 93*b* shows another perspective view of an RPT device and humidifier including the retention mechanism for a humidifier tub of FIG. 93*a* in an unlocked position.

Figure 94:
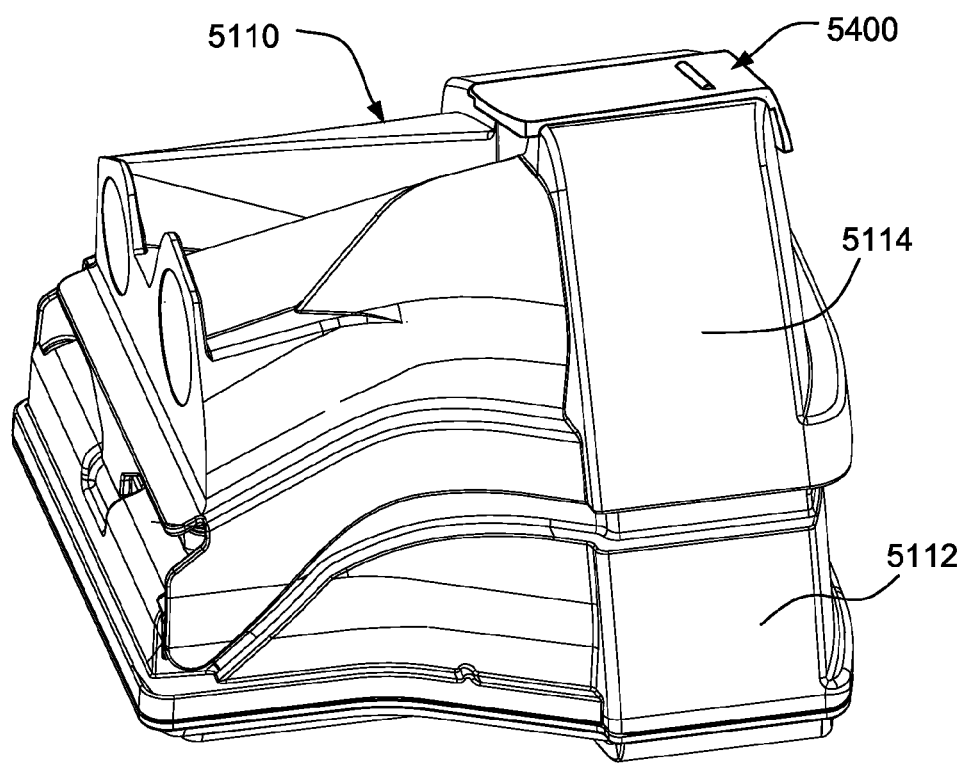

FIG. 94 shows a perspective view of a humidifier tub including a retention mechanism according to an example of the present technology.

Figure 95:
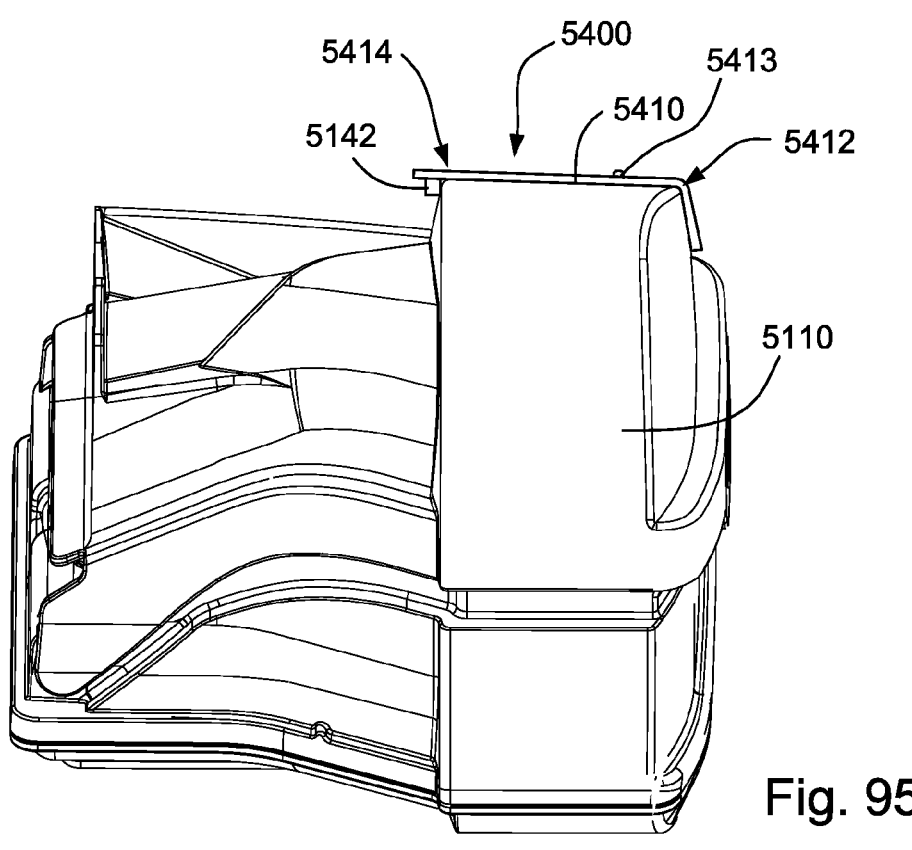

FIG. 95 is a side view of the humidifier tub of FIG. 94.

Figure 96:
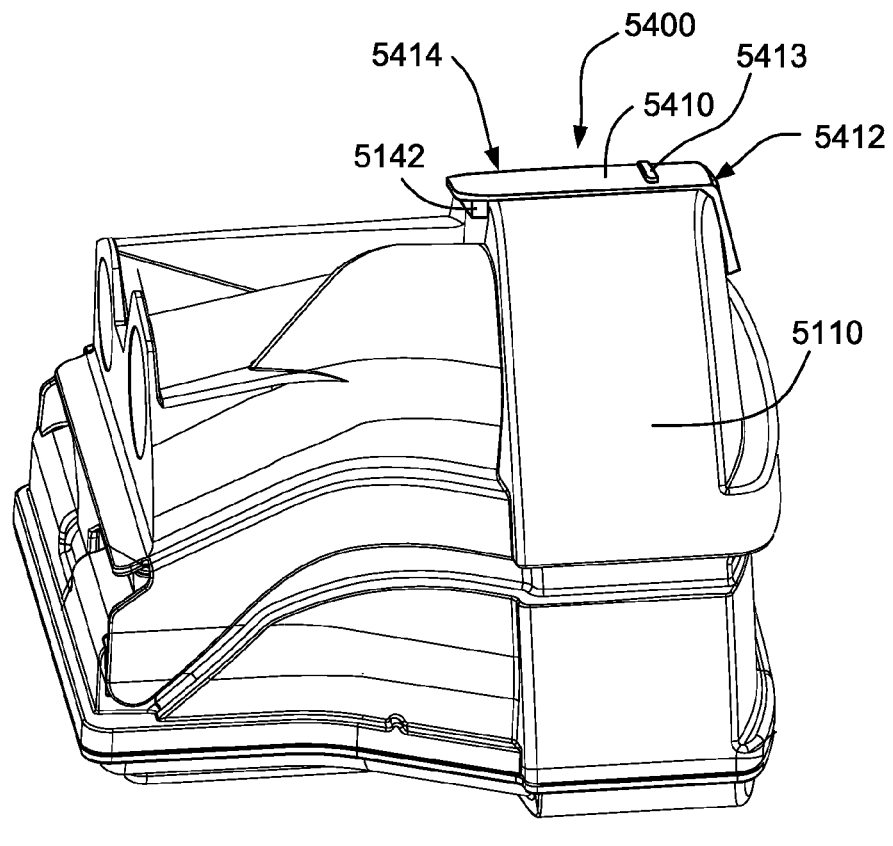

FIG. 96 is an enlarged perspective view of the humidifier tub of FIG. 94.

Figures 97A, 97B, 97C:
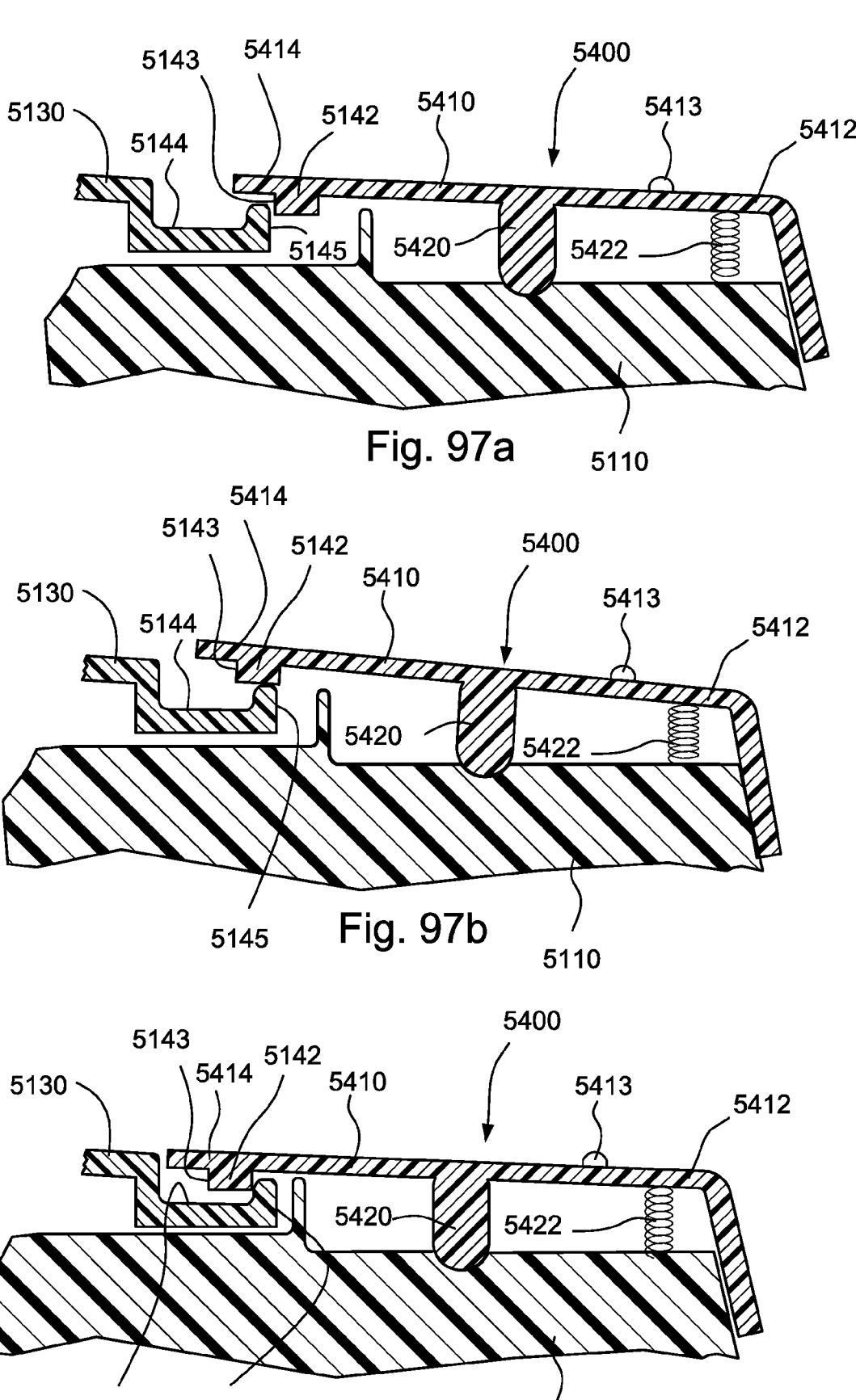

FIG. 97*a* is a partial cross-sectional view showing the humidifier tub of FIG. 94 in a state of engagement with the RPT device and humidifier, the retention mechanism in a locked position according to an example of the present technology.

FIG. 97*b* is a partial cross-sectional view showing the humidifier tub of FIG. 94 in a state of engagement with the RPT device and humidifier, the retention mechanism in an unlocked position according to an example of the present technology.

FIG. 97*c* is a partial cross-sectional view showing the humidifier tub of FIG. 94 engaged with the RPT device and humidifier, the retention mechanism in a locked position according to an example of the present technology.

Figure 98:
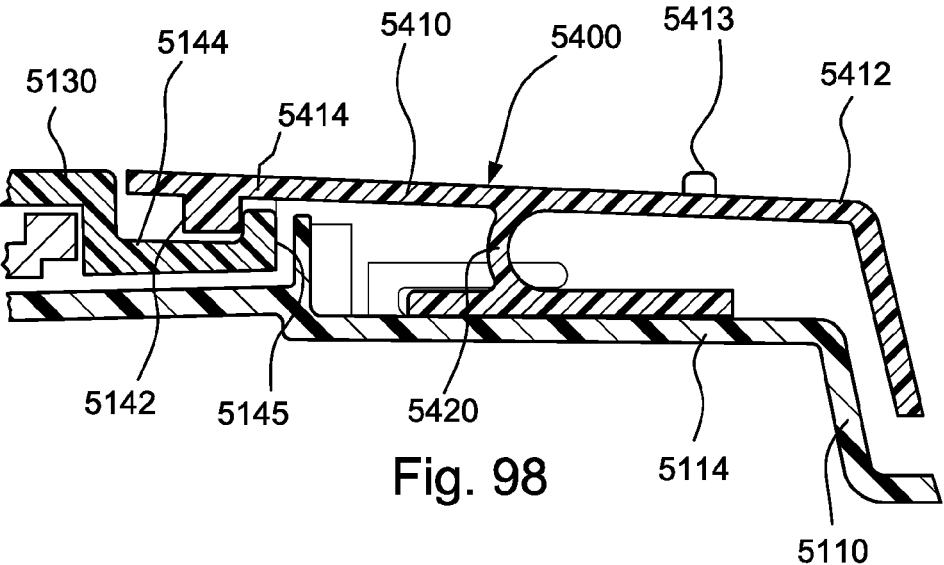

FIG. 98 is a partial cross-sectional view showing a humidifier tub engaged with a RPT device and humidifier, the humidifier tub including a retention mechanism in a locked position according to an example of the present technology.

Figure 99:
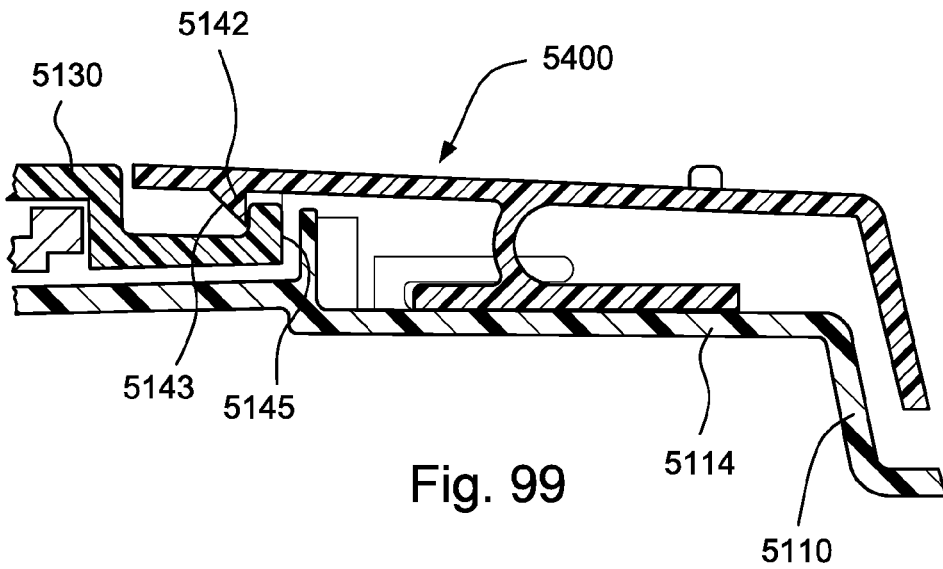

FIG. 99 is a partial cross-sectional view showing a humidifier tub engaged with a RPT device and humidifier, the humidifier tub including a retention mechanism in a locked position according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

5.1 Therapy

In one form, the present technology comprises a method for treating a respiratory disorder comprising the step of applying positive pressure to the entrance of the airways of a patient 1000.

In certain embodiments of the present technology, a supply of air at positive pressure is provided to the nasal passages of the patient via one or both nares.

In certain embodiments of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised respiratory gas, such as air, to the patient 1000 via an air circuit 4170 to a patient interface 3000.

5.3 Patient Interface 3000

A non-invasive patient interface 3000 in accordance with one aspect of the present technology comprises the following functional aspects: a seal-forming structure 3100, a plenum chamber 3200, a vent 3400, a positioning and stabilising structure 3300 and one form of connection port 3600 for connection to air circuit 4170. The patient interface 3000 may optionally include a forehead support structure 3700 that couples with the stabilising structure 3300. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.4 RPT Device 4000

An exploded view of an RPT device 4000 in accordance with one aspect of the present technology is shown in FIG. 5*a*. An RPT device 4000 may comprise mechanical and pneumatic components, electrical components and be configured to execute one or more algorithms. The RPT device may include one or more panel(s) such as a front panel 4012 and a side panel 4014. The RPT device 4000 may also comprise an outlet muffler 4124 as shown in FIGS. 5*a* and 5*b*. The outlet muffler 4124 may be removable and replaced with a water reservoir 5110 (see FIG. 5*c*). In such forms, the RPT device 4000 may be considered to include an integrated humidifier 5000. Thus, the RPT device 4000 may be used with or without humidification depending upon whether the water reservoir 5110 or the outlet muffler 4124 respectively is attached. Preferably the RPT device 4000 comprises a chassis 4016 that supports one or more internal components of the RPT device 4000. In one form the RPT device 4000 comprises a pressure generator 4140, which may be housed in a pneumatic block 4020 coupled to the chassis 4016.

The pneumatic path of the RPT device 4000 (e.g. shown in FIG. 5*d*) may comprise an inlet air filter 4112, an inlet muffler 4122, a pressure generator 4140 capable of supplying air at positive pressure (preferably a blower 4142) and an outlet muffler 4124 (or a water reservoir 5110 if humidification is required). One or more transducers 4270, such as pressure sensors 4272 and flow sensors 4274 may be included in the pneumatic path. The pneumatic path may also include anti-spill back valve 4160 to prevent water from the humidifier 5000 spilling back to the electrical components of the RPT device 4000.

The RPT device 4000 may comprise one or more electrical components which may be mounted on a single Printed Circuit Board Assembly (PCBA) such as the main PCBA 4202. In an alternative form, the RPT device 4000 may include more than one PCBAs.

An RPT device may comprise one or more of the following components in an integral unit. In an alternative form, one or more of the following components may be located as respective separate units. For example, the RPT device may comprise one or more of an air filter, side panel, muffler, pressure generator, pneumatic block, chassis, transducer (flow transducer, pressure transducer, motor speed transducer), light sensor, anti-spillback valve, air circuit, air circuit connector, oxygen delivery port, power supply, central controller, therapy device controller, protection circuit, data connection interface, memory, output devices (e.g., display, alarms, etc.) and a user interface panel(s), such as those described in PCT Application No. PCT/AU2014/050426 (WO 2015/089582), which is incorporated herein by reference in its entirety.

5.5 Humidifier 5000

5.5.1 Humidifier Overview

In one form of the present technology there is provided a humidifier 5000 to change the absolute humidity of air or gas for delivery to a patient relative to ambient air. Typically, the humidifier 5000 is used to increase the absolute humidity and increase the temperature of the flow of air (relative to ambient air) before delivery to the patient's airways. In one form, the humidifier 5000 may be a discrete unit that is connectable to an RPT device 4000. In another form, the humidifier 5000 may be integrated with the RPT device 4000, for example as shown in FIG. 5c and as described in further detail below.

A humidifier 5000 may comprise a water reservoir 5110, heating element 5240 and one or more transducers. The humidifier 5000 may be configured to receive a flow of air from a RPT device 4000 and deliver a flow of humidified air to a patient interface 3000 for example via an air circuit 4170.

5.5.2 Humidifier Components
5.5.2.1 Water Reservoir 5110

According to one arrangement, the humidifier 5000 may comprise a water reservoir 5110 configured to hold, or retain, a volume of liquid (e.g. water) to be used for humidification of the flow of air. FIGS. 6c-6d show one form of a water reservoir 5110, which comprises a reservoir base 5112, a reservoir lid 5114, and an intermediate portion 5202 including a compliant portion 5116. The water reservoir 5110 is configured to hold a predetermined maximum volume of water in order to provide adequate humidification for at least the duration of respiratory therapy, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

The reservoir 5110 may also be configured to discourage egress of liquid therefrom, such as when the reservoir 5110 is displaced or rotated from its normal, working orientation, such as through any apertures or in between its sub-components. As the flow of air to be humidified by the humidifier 5000 is typically pressurised, the reservoir 5110 may also be configured to prevent losses in pneumatic pressure through leak or flow impedance.

The water reservoir 5110 may comprise an inlet 5118 for receiving the flow of air into the reservoir 5110, and an outlet 5122 for delivering a flow of air from the reservoir 5110. The reservoir 5110 may include a reservoir inlet tube 5124 and a reservoir outlet tube 5126 (e.g., see FIG. 6e). In one configuration, the inlet 5118 and reservoir inlet tube 5124 are integrally formed as one inlet component and the outlet 5122 and the reservoir outlet tube 5126 are integrally formed as one outlet component.

FIGS. 8-11 show one form of a water reservoir 5110, which comprises a reservoir base 5112, a reservoir lid 5114, and a variable portion 5116. The reservoir 5110 is configured to hold a given, maximum volume of liquid (e.g. water), typically several hundred millilitres, e.g. 300 millilitres (ml), 325 ml, 350 ml or 400 ml, although it is to be understood that other volumes of liquid may be utilised such as 100 ml, 200 ml, 250 ml, 500 ml or more or less. In one form, the reservoir 5110, may comprise a cavity formed by a plurality of walls to hold the given, maximum volume of liquid as shown in FIGS. 10-11.

5.5.2.2 Water Reservoir Dock 5130

Figure 12:
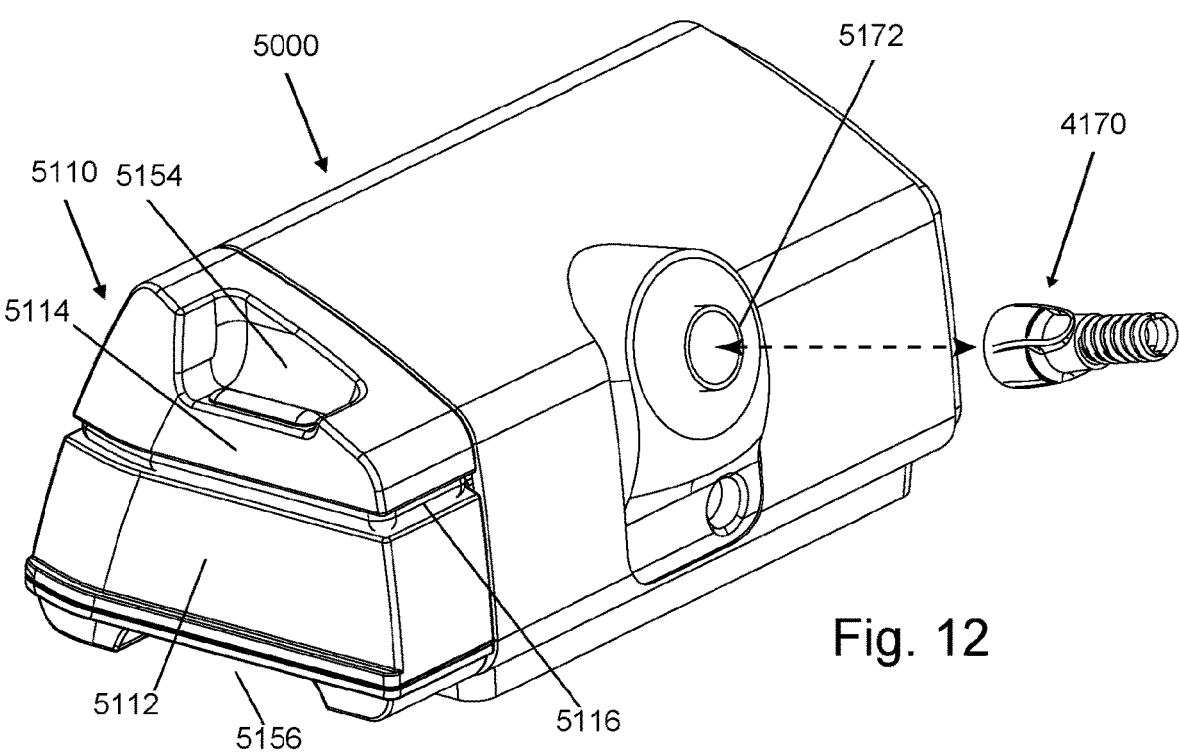
Figure 13:
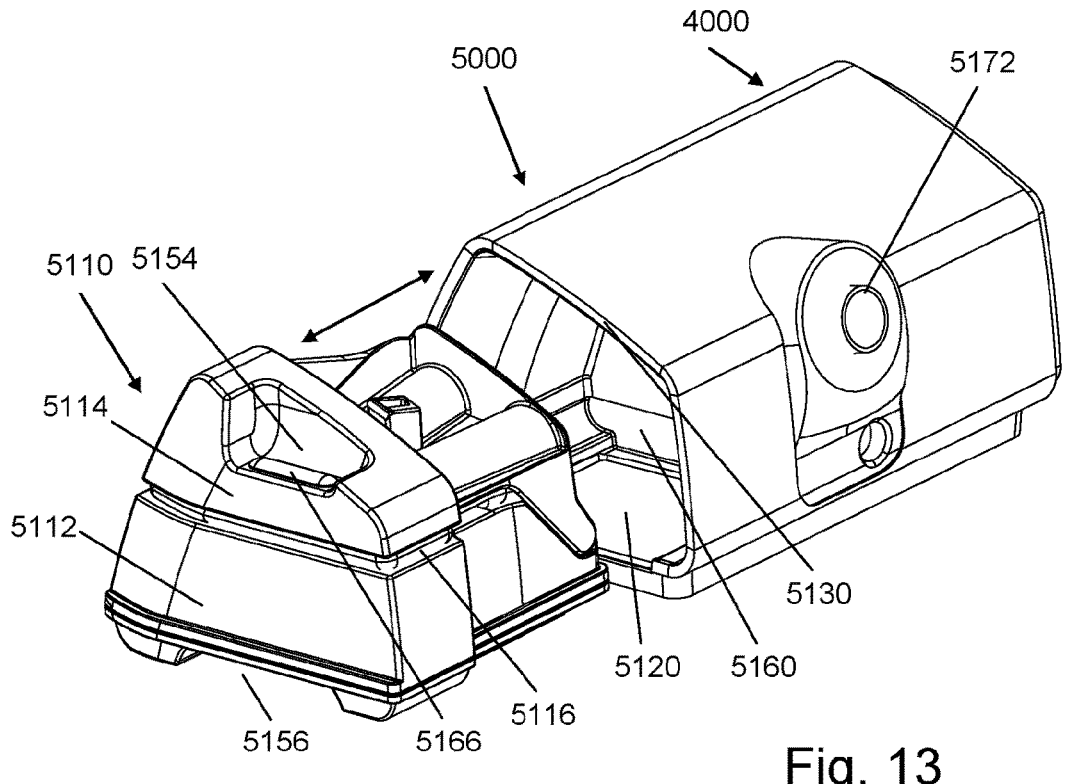

A humidifier 5000 may comprise a water reservoir dock 5130 to receive a water reservoir 5110. As shown in FIG. 13, the water reservoir dock 5130 may form a cavity 5160 to receive the water reservoir 5110. In one form, the water reservoir dock 5130 may be integrated with the humidifier 5000 as shown in FIGS. 12-15. The water reservoir dock 5130 may also connect the water reservoir 5110 to the pneumatic path. In this arrangement, the reservoir dock 5130 comprises a dock gas outlet 5168 to output a flow of breathable gases to a water reservoir 5110, a dock gas inlet 5170 to receive the flow of breathable gases that has been humidified in the water reservoir 5110, and a humidifier outlet 5172 to transfer the flow of humidified breathable gases to the air circuit 4170. The cavity 5160 may include a top portion configured to cover at least a portion of the lid of the reservoir 5110 and a bottom portion including the heater plate 5120.

It should be understood that the reservoir dock 5130 may be provided separately to a humidifier 5000 in an alternate arrangement. In such an arrangement, additional interfaces may be used to connect the reservoir dock 5130 to the humidifier 5000.

In another arrangement, a water reservoir dock 5130 may comprise an opening in a substantially horizontal plane, so that the water reservoir 5110 may be inserted from above or below the water reservoir dock 5130.

5.5.2.3 Water Reservoir Lid 5114

In one form, the water reservoir lid 5114 is pivotably connected to the base 5112 (e.g. by hinges 5158 as shown in FIG. 6e) to allow the reservoir 5110 to be converted between an open configuration and a closed configuration (see FIGS.

6*j* and 6*k*). When the water reservoir 5110 is in its closed configuration, the compliant portion 5116 is put into sealing engagement between the base 5112 and the lid 5114 to seal the base 5112 and the lid 5114. The hinges 5158 may couple to complementary hinge recess portions 5159 (shown in FIG. 6*f*) located in the reservoir base 5112. In one form, the lid 5114 may be constructed from a bio-compatible material, such as a plastic or thermoplastic polymer, for example, acrylonitrile butadiene styrene (ABS) or polycarbonate material. The pivotable connection may further allow the water reservoir lid 5114 and the base 5112 to be compressed towards each other in comparison to their normal operating configuration, for example for insertion of the reservoir 5110 into the dock 4130 as will be described in further detail below.

Another aspect of the present technology relates to the operation of the pivoting action in the lid 5114 in relation to the base 5112. As the lid 5114 rotates about the hinges 5158, a range of rotation may be defined as shown in FIG. 50*a* and FIG. 50*b*. In one form, two ends of the range of rotation may be defined by closure of the lid 5114 with respect to the base 5112, where one of the two ends may be a fully open position defined by a rotation guide 5220, which may interfere with a rotation stop 5222 at the fully open position.

According to another aspect, the lid 5114 may be config- ured so that when a user attempts to open the lid 5114 further than the rotation stop 5222 and the rotation guide 5220, the lid 5114 would disconnect from the base 5112. As shown in FIG. 50*b* and FIG. 51*b*, at the fully open position the rotation guide 5220 may be in contact with the rotation stop 5222. In this form, attempts to further open the lid 5114 with respect to the base 5112 would cause the rotation stop 5222 to act as a pivot of a cantilever, and cause the lid 5114 to separate from the base 5112 at the hinges 5158, whereby damage to the reservoir 5110, for example from application of exces- sive force thereto, may be avoided. In one form, the hinges 5158 may be configured to allow disconnection more easily at one orientation of the lid 5114 with respect to the base 5112 (e.g. then the reservoir 5110 is in the fully open position) than at another orientation. This may be achieved by, for example, introduction of a taper to the hinges 5158 on the lid 5114 as shown in FIGS. 46*a* and 46*b*.

The water reservoir lid 5114 may comprise the inlet 5118, the reservoir inlet tube 5124, the outlet 5122 and the reservoir outlet tube 5126 in one form as shown in FIG. 6*e*. The reservoir 5110 may further comprise flow elements, such as a baffle (e.g. inlet cap 5125 shown in FIG. 6*e* and FIG. 6*k* and/or a plate 5123 as shown in FIG. 6*e* and FIG. 6*k*), configured to increase the length of the tortuous flow path and/or to prevent ingress of water into the inlet tube 5124 and/or the outlet tube 5126. In one example, the water reservoir lid 5114 may further comprise one or more baffles configured to direct the air through a tortuous path in the water reservoir 5110. In one form, the baffle may be coupled to an end of the reservoir inlet tube 5124 as an inlet cap 5125 (as shown in FIG. 6*e* and FIG. 6*k*), and in another form, the baffle may be arranged as a plate 5123 (as shown in FIGS. 6*e* and 6*k*).

FIGS. 74 to 76 depict another example in which a pivotally coupled lid 5114 is replaced with a drop on lid 5144 that utilizes opposing clips 5450*a*, 5450*b* to retain the lid 5144 on the base 5112. In this example, a first clip 5450*a* is provided on one side of the lid 5144 and a second clip 5450*b* is provided on an opposing side of the lid 5144. Each of the clips 5450*a*, 5450*b* includes at least one slot 5452, e.g., a pair of slots as shown in FIGS. 74 to 76. Opposing sides of the base 5112 include at least one retaining protrusion 5455, e.g., a pair of retaining protrusion as shown in FIGS. 74 to 76, adapted to releasably interlock with respec- tive clips 5450*a*, 5450*b*. As shown in FIGS. 74 and 75, the slots 5452 of each clip 5450*a*, 5450*b* are structured and arranged to receive respective retaining protrusions 5455, e.g., with a snap-fit, to releasably retain the lid 5114 to the base 5112.

FIGS. 94 to 99 depict an example of the present technol- ogy in which a swing latch 5400 is utilized to releasably lock the tub 5110 in an operative position.

In this example, the swing latch 5400 is provided to the humidifier tub 5110 (or reservoir) engageable with the reservoir dock 5130 of the integrated PAP device and humidifier described above. The following examples may share various features, structures, and characteristics of the tubs previously described above such that repeat description of like features is unnecessary.

As illustrated, the latch 5400 includes a locking lever 5410 and a support member 5420 that is pivotally connected to the lid 5114 to allow the latch 5400 to pivot relative to the lid 5114 about a pivot point.

The locking lever 5410 includes a button end 5412 at one end of the locking lever 5410 and a locking end 5414 at the other end of the locking lever 5410. The locking end 5114 includes one or more downwardly extending retention pro- trusions 5142, and the button end 5412 includes a finger grip 5413, e.g., elongated rib, to assist the patient in manipulating the latch 5400. The latch 5400 may be biased to a locked or closed position by any suitable spring configuration. For example, in FIGS. 97*a* to 97*c*, a spring 5422 is arranged along the button end 5412 to bias the latch 5400 to the locked or closed position. In an alternative example, as shown in FIG. 98, the support member 5420 comprises a flexible configuration configured to support the locking lever 5410 on the lid 5114 and resiliently bias the latch 5400 to the locked or closed position.

FIGS. 97*a* to 97*b* show engagement of the tub 5110 with the dock 5130. As illustrated, a dock locking recess 5144 in the upper surface of the dock 5130 may be shaped to receive the corresponding protrusion(s) 5142. During insertion of the tub 5110, the latch 5400 is biased to the locked or closed position so that the flat or square front face 5143 of the protrusion(s) 5142 is configured and arranged to engage an exterior face 5145 of the dock 5130 adjacent the locking recess 5144 (see FIG. 97*a*), i.e., catching mechanism imple- mented to require force application for assembly and disas- sembly. This engagement prohibits full insertion of the tub 5110 into the dock 5130 until a user manually depresses the button end 5412 of the latch 5400 to pivot the locking end 5114 and raise the retention protrusions 5142 thereof upwardly above the exterior face 5145 of the dock 5130 into the unlocked position (see FIG. 97*b*), thereby allowing the protrusions 5142 and hence the tub 5110 to pass further into the dock 5130. Once the tub 5110 reaches an operative position, the protrusions 5142 pass beyond the exterior face 5145 and the button end 5412 of the latch 5400 can be manually released, thereby allowing the locking end 5114 and retention protrusions 5142 thereof to resiliently return to the locked position in which the retention protrusions 5142 lower or drop down into engagement with respective dock locking recesses 5144 (see FIG. 97*c*). In an alternative example, as shown in FIG. 99, the front face 5143 of the protrusion 5142 could be tapered to allow the swing latch 5400 to raise without manual intervention when the tapered front face 5143 engages the exterior face 5145 of the dock 5130. To release the tub 5110 from the dock 5130, the button end 5412 may be depressed again to raise the retention protrusion 5142 disengaging it from the dock locking recess 5144 and allowing the tub 5110 to slide out from the dock 5130.

5.5.2.4 Compliant/Variable Portion 5116

In one form, when the water reservoir 5110 is in use, the compliant portion 5116 may act as a seal between the reservoir base 5112 and the reservoir lid 5114. The compliant portion 5116 may be provided as part of the reservoir lid 5114 or as part of the reservoir base 5112, or independently of both, for example as part of an intermediate portion 5202 (see FIG. 61). The compliant portion 5116 may be engaged with the reservoir lid 5114 or the reservoir base 5112 by any number of means including, and not limited to, ultrasonic welding, friction fitting, gluing or by using an intermediate component.

The compliant portion 5116 preferably includes a sufficiently resilient construction so as to be able to resist forces and/or pressures generated in the reservoir 5110, such as those generated by the user, the reservoir dock 5130 and/or the flow of air flowing through the reservoir 5110. The compliant portion 5116 is also preferably compliant to be to able couple to the lid 5114 and/or the base 5112, and conform to its shape to form a seal. In one form, a rigid portion of the intermediate portion may be constructed from a nylon material of approximately 2 mm thickness (such as 1 mm, 1.5 mm, 2.5 mm or 3 mm), and a silicone material may be used to overmould onto the rigid portion to form the compliant portion 5116.

In some arrangements, the compliant portion 5116 may couple to the lid 5114 and/or the base 5112, and the base 5112 and/or the lid 5114 may be formed as two separate parts that are able to be assembled with the compliant portion 5116 coupled therebetween.

In an alternative arrangement, the compliant portion 5116 may be located within a wall of the reservoir base 5112 and/or a wall of the reservoir lid 5114, for example integrally by overmoulding or as a separate component connected as a sub-assembly. In such an arrangement the compliant portion would not be located between the reservoir base 5112 and the reservoir lid 5114 but within the reservoir base 5112 and/or the reservoir lid 5114. There may be more than one compliant portion 5116 or the compliant portion may be formed in multiple parts to provide more compliance in movement of the reservoir 5110.

In one form, when the water reservoir 5110 is in use, the variable portion 5116 may act as a seal between the reservoir base 5112 and the reservoir lid 5114. The variable portion 5116 may also perform other functions, such as to improve thermal contact between the reservoir 5110 and the heater plate 5120, as will be described in further detail below.

The variable portion 5116 may be provided as part of the reservoir lid 5114 or as part of the reservoir base 5112, or independently of both. The variable portion 5116 may be engaged with the reservoir lid 5114 or the reservoir base 5112 by any number of means including, and not limited to, ultrasonic welding, friction fitting, gluing or by using an intermediate component. The variable portion 5116 may comprise a carrier 5117 (as shown in FIG. 11).

The variable portion 5116 is preferably constructed sufficiently resiliently so as to be able to resist compressive forces and/or pressures generated in the reservoir 5110, such as by the user, the reservoir dock 5130 and/or the flow of breathable gas flowing through the reservoir 5110. It is also preferably compliant in the planar direction to be able couple to the lid 5114 and/or the base 5112, and conform to its shape. In one form, the carrier 5117 may be constructed from a nylon material of approximately 2 mm thickness (such as 1 mm, 1.5 mm, 2.5 mm or 3 mm), and a silicone material may be used to overmould onto the carrier 5117 to form the variable portion.

In some arrangements, the variable portion 5116 may couple to the lid 5114 and/or the base 5112, and the base 5112 and/or the lid 5114 may be formed as two separate parts that are able to be assembled with the variable portion 5116 coupled therebetween.

In an alternative arrangement the variable portion 5116 may be located within a wall of the reservoir base 5112 and/or a wall of the reservoir lid 5114, for example integrally by overmoulding or as a separate component connected as a sub-assembly. In such an arrangement the variable portion would not be located between the reservoir base 5112 and the reservoir lid 5114 but within the reservoir base 5112 and/or the reservoir lid 5114. There may be more than one variable portion 5116 to provide more compliance in movement of the reservoir 5110.

5.5.2.5 Water Reservoir Base 5112

According to one arrangement, the reservoir base 5112 comprises a conductive portion 5120 (such as the base conductor plate 5152, e.g., see FIG. 60 configured to thermally couple with a heating element 5240 of the humidifier 5000. The conductive portion 5152 improves efficiency of heat transfer from the heating element 5240 to the volume of liquid in the reservoir 5110. All or a part of the base conductor plate 5152 may be made of a heat conducting material such as aluminium (e.g., approximately 2 mm thick, such as 1 mm, 1.5 mm, 2.5 mm or 3 mm) or another heat conducting material such as metal. In some cases, suitable heat conductivity may be achieved with less conductive materials of suitable thickness.

The reservoir base 5112 may also be configured as a receptacle to retain the given, maximum volume of liquid that the reservoir 5110 is configured to hold. In one form, the base 5112 may comprise further features such as an overfill prevention feature.

In one form, the reservoir base 5112 may further comprise an inner lip 5224 and/or an outer lip 5226, for example as shown in FIG. 52 and FIG. 53. According to one aspect, the inner lip 5224 and/or outer lip 5226 may prevent egress of liquid from the reservoir 5110 through the interface between an intermediate portion 5202 (e.g. the compliant portion 5116) and the base 5112, for example when the intermediate portion 5202 is compressed, or when the intermediate portion 5202 is under vibration.

It should be appreciated that the reservoir base 5112 may be constructed in any number of parts. The reservoir base 5112 may be constructed as a single part made of, for example, aluminium or another heat conducting material such as metal. In another arrangement, the reservoir base 5112 may be constructed in two parts, for example comprising a lower component and an upper component.

According to one arrangement, the reservoir base 5112 comprises a conducting portion (such as the base conductor plate 5152) configured to thermally couple with a heater plate 5120 of the humidifier 5000. The conducting portion improves efficiency of heat transfer from the heater plate 5120 to the volume of liquid in the reservoir 5110. All or a part of the base conductor plate 5152 may be made of a heat conducting material such as aluminium (e.g. approximately 2 mm thick, such as 1 mm, 1.5 mm, 2.5 mm or 3 mm) or another heat conducting metal. In some cases, suitable heat conductivity may be achieved with less conductive materials of suitable thickness.

The reservoir base 5112 may also be configured as a receptacle to retain the given, maximum volume of liquid that the reservoir 5110 is configured to hold. In one form, the base 5112 may comprise further features such as an overfill prevention feature as will be described in further detail below. The reservoir base 5112 may also comprise a base upper body 5146 and a base bottom plate 5148, which together with the base conductor plate 5152 may form a receptacle.

The base upper body 5146 and/or the base bottom plate 5148 may be constructed from a bio-compatible material suitable for retaining the body of liquid, such as a plastic or thermoplastic polymer, for example, ABS or polycarbonate material. The base conductor plate 5152 may comprise of a sealing element 5150, which may be integrated to, and/or sealingly connected to both the base upper body 5146 and the base bottom plate 5148 to prevent egress of water from the water reservoir 5110, particularly from the base 5112. For example, the sealing element 5150 may be overmoulded onto the base conductor plate 5152, and the resulting component may be secured between the base upper body 5146 and the base bottom plate 5148.

In one form as shown in FIG. 11, the base 5112 may comprise a base upper body 5146, a base bottom plate 5148, and a base conductor plate 5152. However, it should be appreciated that the reservoir base 5112 may be constructed in any number of parts. The reservoir base 5112 may be constructed as a single part made of, for example, aluminium or another heat conducting material such as metal. In another arrangement, the reservoir base 5112 may be constructed in two parts, for example comprising a lower component and an upper component. In such an arrangement, the lower component may be constructed from a heat conducted material and perform the roles of the base conductor plate 5152, sealing element 5150 and base bottom plate 5148, and the upper component may be equivalent to the base upper body 5146, and be constructed a polycarbonate material.

In one form, the reservoir base 5114 may further comprise an inner lip 5224 and/or an outer lip 5226, for example as shown in FIGS. 52-53. According to one aspect, the inner lip 5224 and/or outer lip 5226 may prevent egress of liquid from the reservoir 5110 through the interface between an intermediate portion 5202 (e.g. the seal 5204) and the base 5114, for example when the intermediate portion 5202 is compressed, or when the intermediate portion 5202 is under vibration.

5.5.2.6 Reservoir Handles 5154 5156

FIGS. 12-15 show an upper handle 5154 that is located on the reservoir lid 5114, and a lower handle 5156 that is located on the reservoir base 5112. These handles are intended to assist the patient (or user) 1000 to grip and hold the water reservoir 5110. In the shown arrangement, the handles 5154, 5156 are located away from the hinges 5158 such that by holding the reservoir 5110 by the handles 5154 5156 the patient 1000 imparts forces onto the reservoir 5110 compressing the variable portion 5116, which pushes the lid 5114 and the base 5112 towards each other. A compression force may also help maintain the variable portion 5116 in sealing engagement between the reservoir base 5112 and the reservoir lid 5114, such as during transport to/from re-filling the reservoir 5110 with liquid. It is to be understood that the handles 5154 and 5156 may be placed on other components or areas of the water reservoir 5110.

A friction grip 5166 may be provided on a surface of either or both of the handles 5154 5156 as shown in FIG. 13. The friction grip 5166 may be constructed to assist the patient 1000 to hold the reservoir 5110, such as by being made from a higher friction material, made in a higher friction texture and/or made into an easier-to hold shape than the surrounding areas of the reservoir 5110. For example, the friction grip 5166 may be constructed from an elastomeric material such as silicone whereas the water reservoir 5110 may primarily be constructed from a polycarbonate material.

5.5.2.7 Air Flow Path

It is one of the aims of the present technology to force the flow of breathable gas to travel through the reservoir 5110 in a tortuous path between the inlet 5118 and the outlet 5122. This prevents any 'short-circuiting' of the flow of breathable gas, which may lead to inadequate humidity in the flow of breathable gas which is delivered to the patient 1000.

FIG. 16a-18c show an exemplary path of the flow of breathable gas through the reservoir 5110 as it enters through the inlet 5118 and exits through the outlet 5122. The figures are arranged chronologically in three distinct orthogonal views per figure to visually demonstrate the exemplary flow path. In this arrangement the flow of breathable gas received through the inlet 5118 passes through the inlet tube 5124 (FIGS. 16a-16c), into the internal volume of the water reservoir 5110 (FIGS. 17a-17c). The flow of breathable gas then passes through the outlet tube 5126 to exit the water reservoir 5110 at the outlet 5122 (FIGS. 18a-18c) as humidified breathable gas. FIGS. 16a-18c show the reservoir 5110 with the lid 5114 and the base 5112 in exploded view orientation for clarity, and any flow of gas that occurs in the internal volume of the reservoir 5110 is shown in dotted lines. The dotted arrows shown indicate the general direction of the exemplary flow of breathable air, although it is noted that the nature of gas or air flow means that any gas flow path includes swirling (e.g. turbulence) of the gas rather than a straight and direct air flow path.

In some forms of the present technology, the reservoir 5110 may comprise flow elements, or a baffle 5192, configured to increase the length of the tortuous flow path and/or to prevent ingress of water into the inlet tube 5124 and/or the outlet tube 5126. For instance, the reservoir 5110 may comprise a deflector portion 5198 as shown in FIGS. 40a-43, or a deflector portion 5198 or a flow director 5195 FIGS. 46a-46b. In some arrangements, the baffle 5192 may further comprise a locating portion 5196 as will be described in further detail below.

In the arrangement shown in FIGS. 40a-43, the deflector portion 5198 is configured to prevent the flow of breathable gas from entering the outlet tube 5126 immediately after exiting the inlet tube 5124 through the inlet tube outlet 5125 (i.e. short-circuiting). When assembled together as seen in FIG. 40a, the deflector portion 5198 may be located close to the inlet tube inner end 5125, such as by abutting it. In this arrangement, the deflector portion 5198 forms a cover between the inlet tube outlet 5125 and a base of the outlet tube inner end 5127. This cover may be further advantageous in that it forces the flow of breathable gas to travel in a channel created by the cover and the volume of water for improved humidity pickup.

In the arrangement shown in FIGS. 46a-46b, the reservoir 5110 includes a flow director 5195 as well as a deflector portion 5198. The deflector portion 5198 is configured to prevent short-circuiting of the flow of breathable gas, and the flow director 5195 is further configured to direct the flow of breathable gas that exits the inlet tube 5124 in a direction approximately parallel with the volume of liquid in the reservoir 5110. This may ameliorate occurrence of 'spitting', which can occur when the flow of breathable gas exits the inlet tube 5124 in a direction normal to the surface of the volume of liquid.

Figure 21:
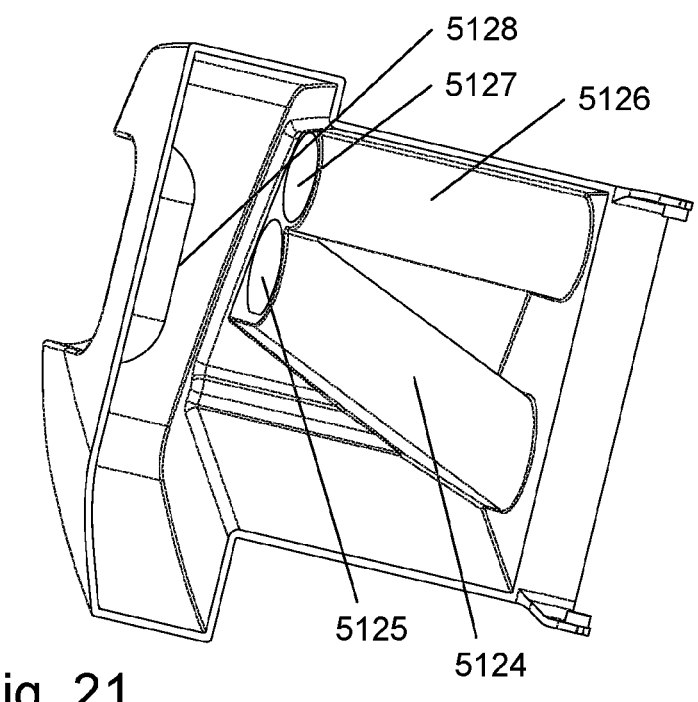
Figure 22:
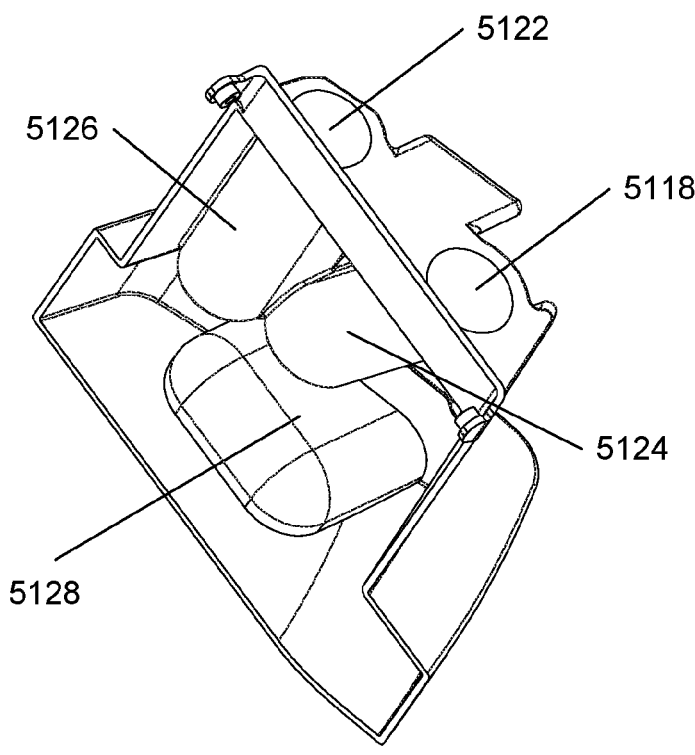
Figure 23:
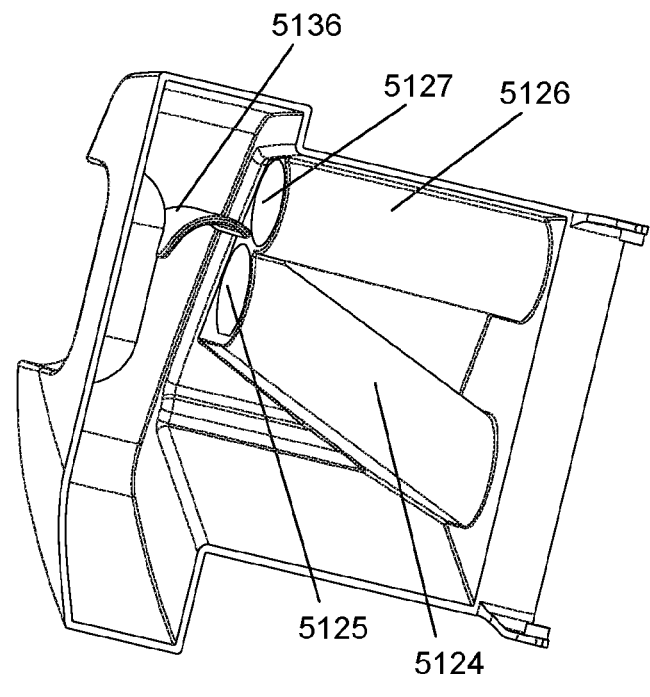
Figure 24:
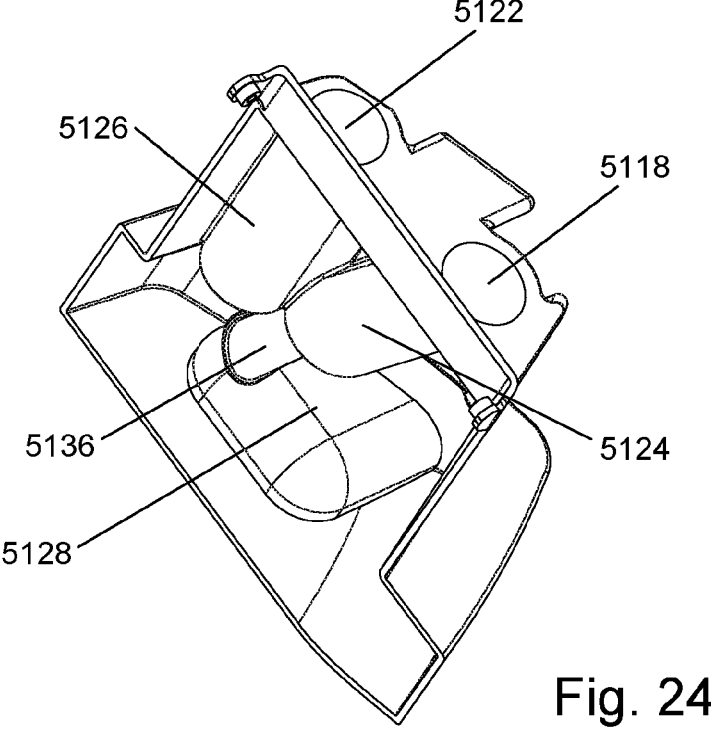
Figure 25:
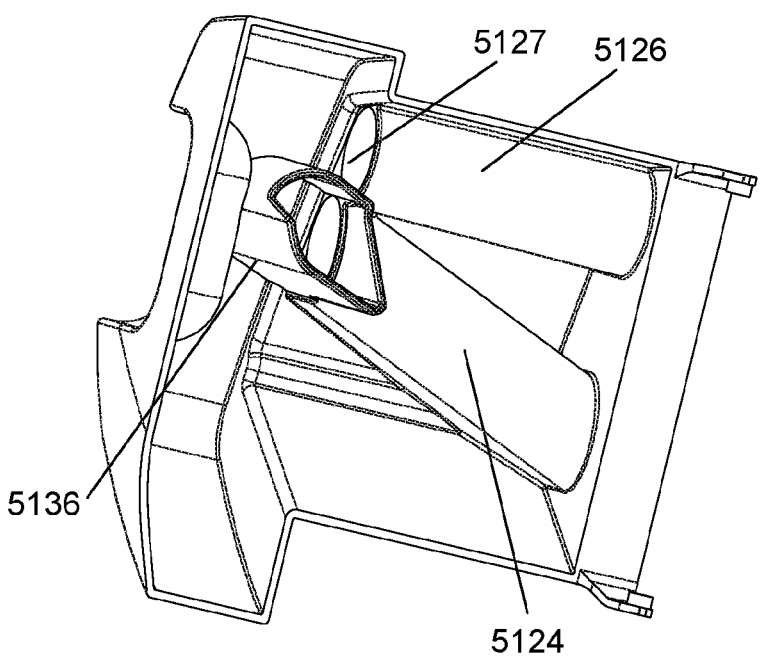
Figure 26:
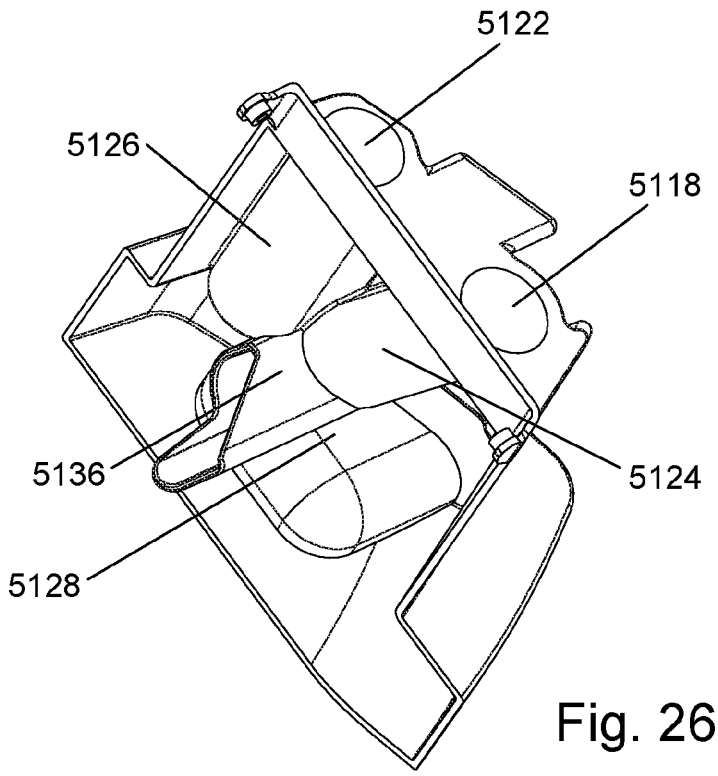

As shown in FIGS. 21-22, the reservoir 5110 may include an end wall 5128 that is near and opposed to an interior end 5125 of the inlet tube 5124. The inner end wall 5128 of the reservoir 5110 directs air exiting the inlet tube 5124 to flow across the water surface before it reaches an interior end 5127 of the outlet tube 5126 and flows out of the outlet 5122 through the outlet tube 5126. FIGS. 23-26 show examples of other arrangements of flow elements, wherein the reservoir 5110 may include a turning vane 5136 which is placed near the interior end 5125 of the inlet tube 5124. The turning vane 5136 may be formed as an extension of the inlet tube 5124 as shown in FIGS. 25-26, or the turning vane 5136 may be a separate component located adjacent to or coupled with the inlet tube 5124. The turning vane may also be profiled as shown in FIGS. 25-26.

The path of the flow of breathable air demonstrated in FIGS. 16a-18c is exemplary only, and is aimed to demonstrate one of many paths that the flow of breathable gas may traverse through, namely that it enters the water reservoir 5110 through the inlet 5118 and exits through the outlet 5122 after experiencing some degree of swirling within the volume of the water reservoir 5110. A person skilled in the art would understand that the particles or molecules that form the flow of breathable air may not follow a single path within the water reservoir 5110 due to a number of factors, including, for example, localised turbulence (eddies) or pressure gradients within the water reservoir 5110. As a result the cumulative path of the flow of breathable air may comprise any number of paths wherein it experiences various degrees of 'swirling' within the water reservoir 5110 prior to exiting via the outlet tube 5126 at the outlet 5122. It is also possible that some small portion of the flow of breathable air may escape the water reservoir 5110 as a leak.

5.5.2.8 Reservoir Inlet/Outlet

As described above, the reservoir inlet 5118 is configured to receive the flow of breathable gas into the reservoir 5110, and the reservoir outlet 5122 is configured to output the humidified flow of breathable gas. The inlet 5118 and/or the outlet 5122 are preferably further configured to prevent egress of liquid from the reservoir 5110 when the reservoir 5110 is displaced and/or rotated from its normal, working orientation. Still further, the inlet 5118 and/or the outlet are preferably configured to prevent short-circuiting of the flow of breathable gas as described above. In one form, the inlet 5118 may be configured to prevent 'spitting', or splashing, of liquid which may be caused by a jet of air impinging on the volume of liquid in the reservoir 5110.

In one arrangement as shown in FIG. 21, the reservoir inlet 5118 includes an inlet tube 5124 to provide a flow path for the inlet flow of breathable gas into the reservoir 5110, and the reservoir outlet 5122 includes an outlet tube 5126 to provide a flow path for the outlet flow of humidified breathable gas from the reservoir 5110.

In one configuration as shown in FIGS. 25-26, it may be advantageous to configure the turning vane 5136 so that the lowest portion of the turning vane 5136 extends below the lowest portion of the outlet tube 5126. This may further prevent ingress of water into the inlet tube 5124 from any 'spitting' of water.

The water reservoir 5110 is preferably configured to provide tilt spillback protection from the water flowing back through the outlet tube 5126 or the inlet tube 5124. Water egress through the inlet tube 5124 may be particularly undesirable as it may introduce water into the PAP device 4000 and damage electronic components (such as an electric motor, a flow sensor or a printed circuit board) from exposure to water.

In one arrangement of the present technology, the reservoir 5110 achieves spillback protection by arranging the inlet tube outlet 5125 so that when the reservoir 5110 is rotated by 90 degrees in any direction from its working, horizontal orientation the given maximum volume of water is able to be stored in the reservoir 5110 without reaching the inlet tube inner end 5125.

Figure 27:
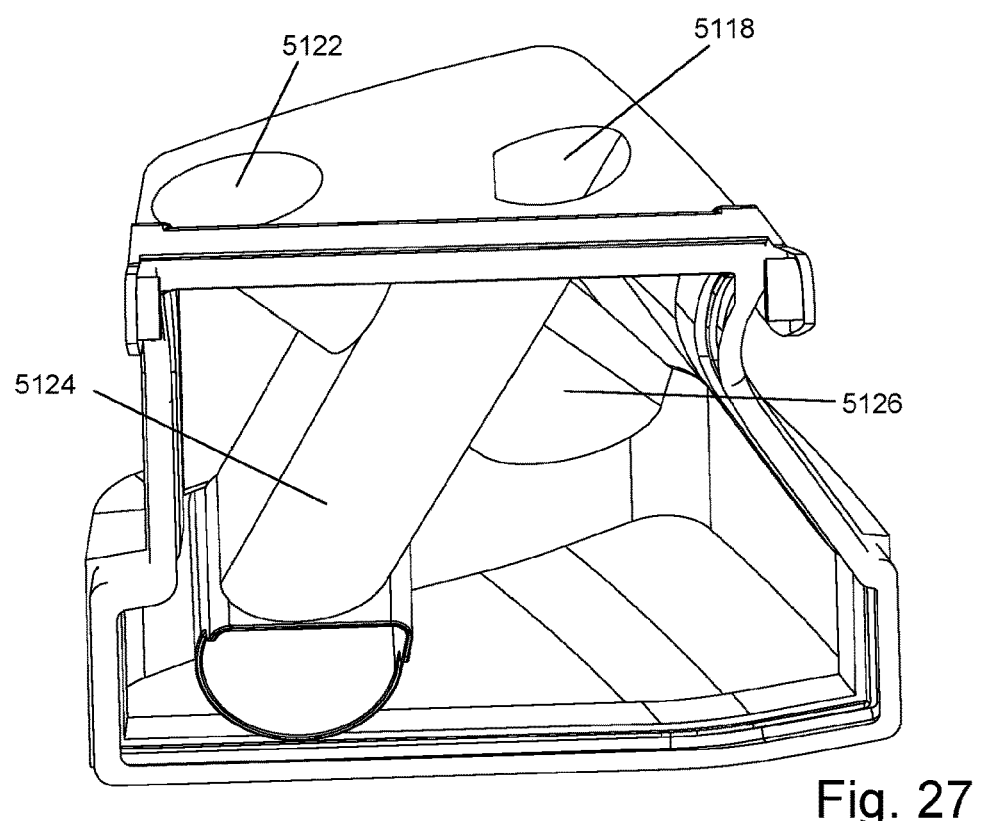
Figure 28:
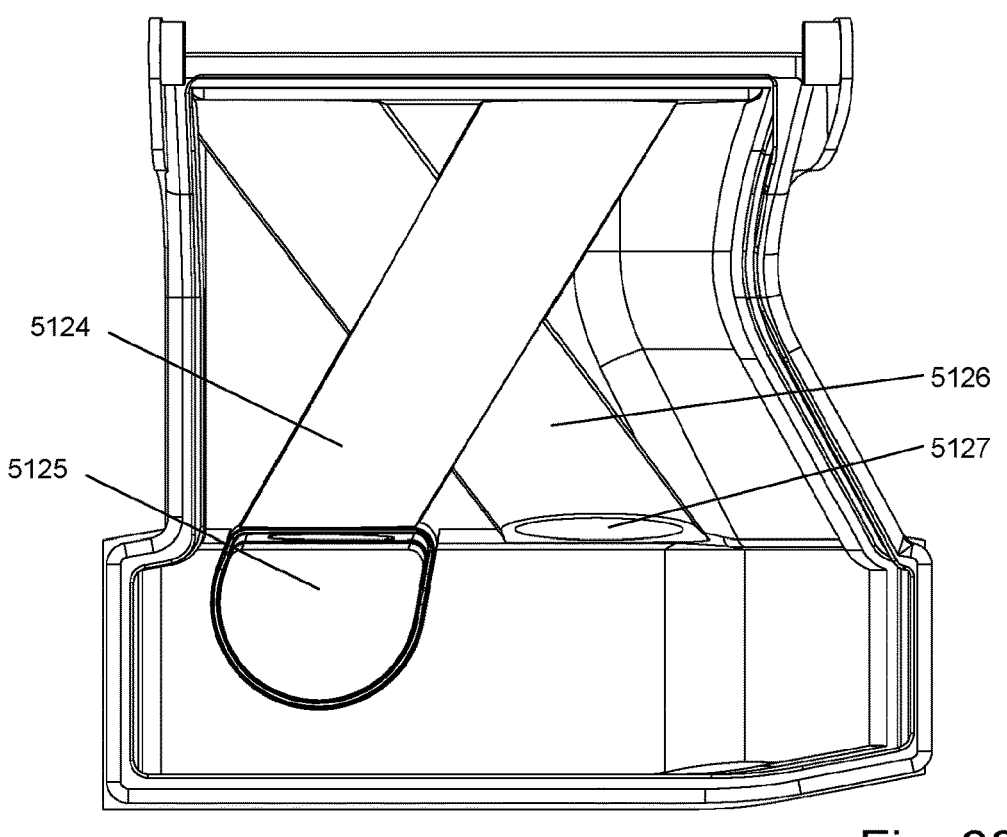

In another arrangement of the reservoir 5110, the axes of inlet tube 5124 and the outlet tube 5126 may intersect when viewed from above as shown in FIGS. 27-28. The inlet tube 5124 and outlet tube 5126 may not be connected to each other as one of the tubes passes below the other tube, such as the inlet tube 5124 passes below the outlet tube 5126.

This configuration may improve the tilt spillback protection by arranging the inlet tube 5124 and the outlet tube 5126 such that when the reservoir 5110 is tilted away from its working orientation, water must reach the higher end of the inlet tube 5124 or the outlet tube 5126 to exit the reservoir 5110. For example, if the reservoir 5110 was tilted such that the water reaches the lower of the interior end 5125 of the inlet tube 5124, the water must still rise higher to reach the exterior end of the inlet tube 5124 to exit the reservoir 5110 as shown in FIG. 28.

Figure 34:
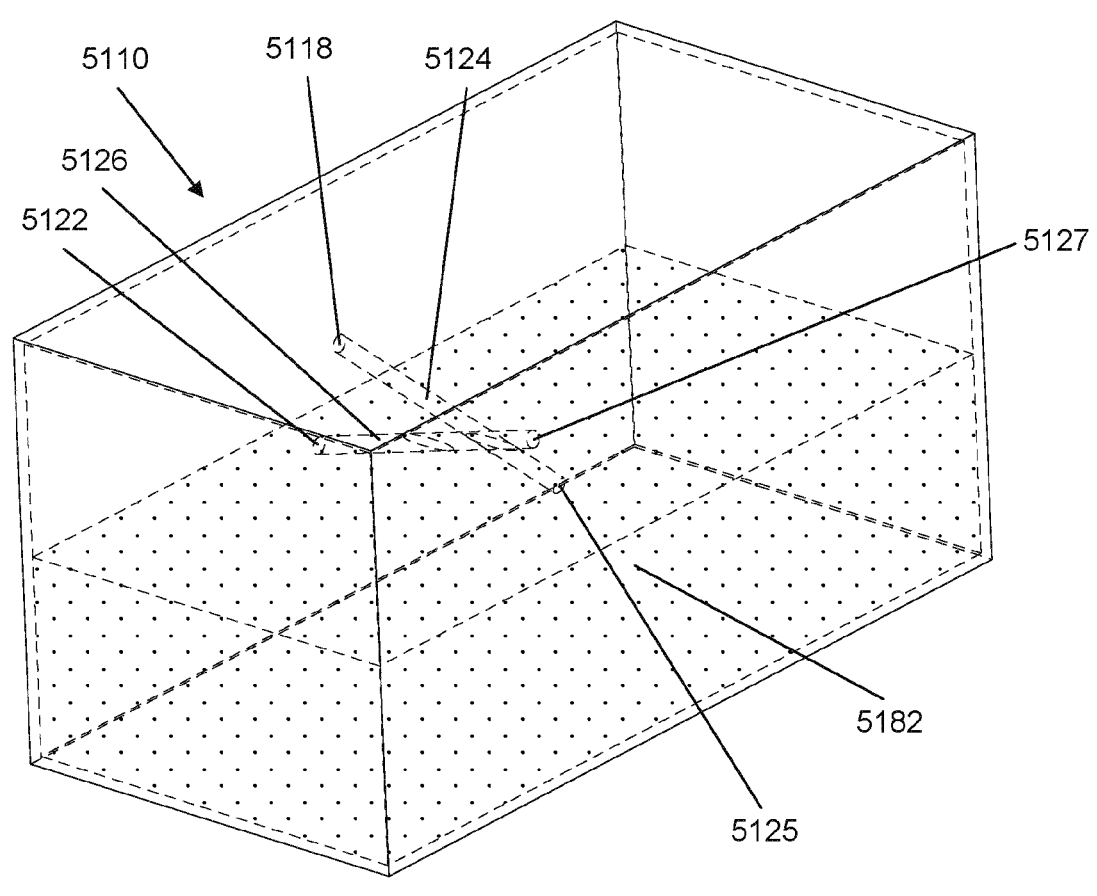
Figure 35:
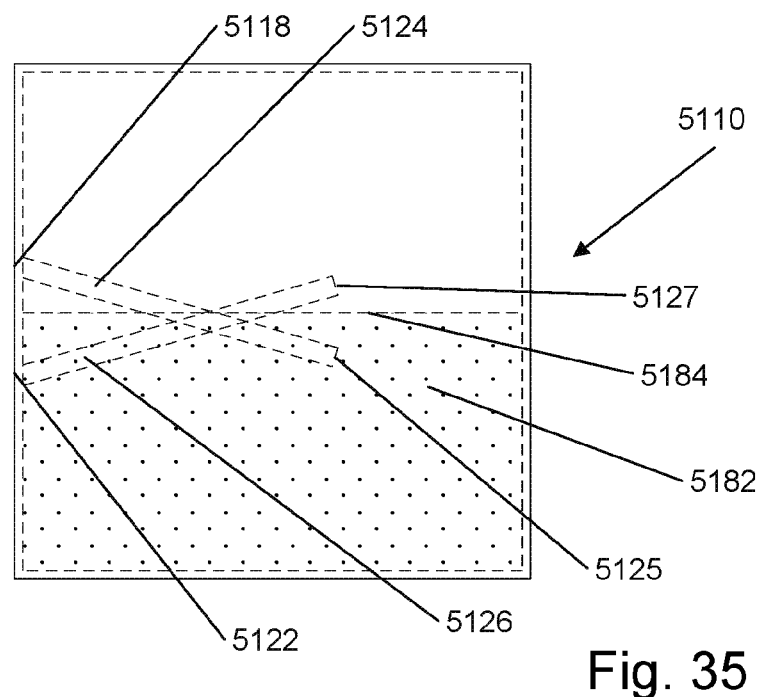
Figure 36:
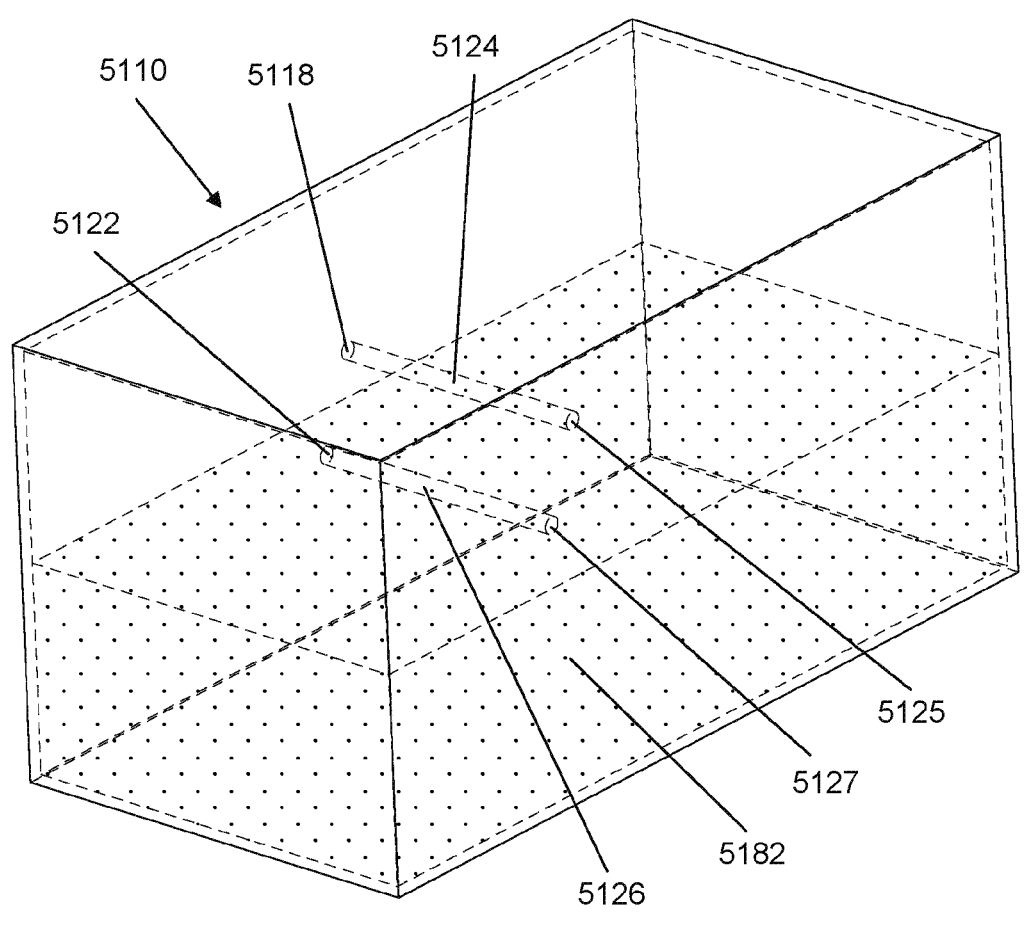
Figure 37:
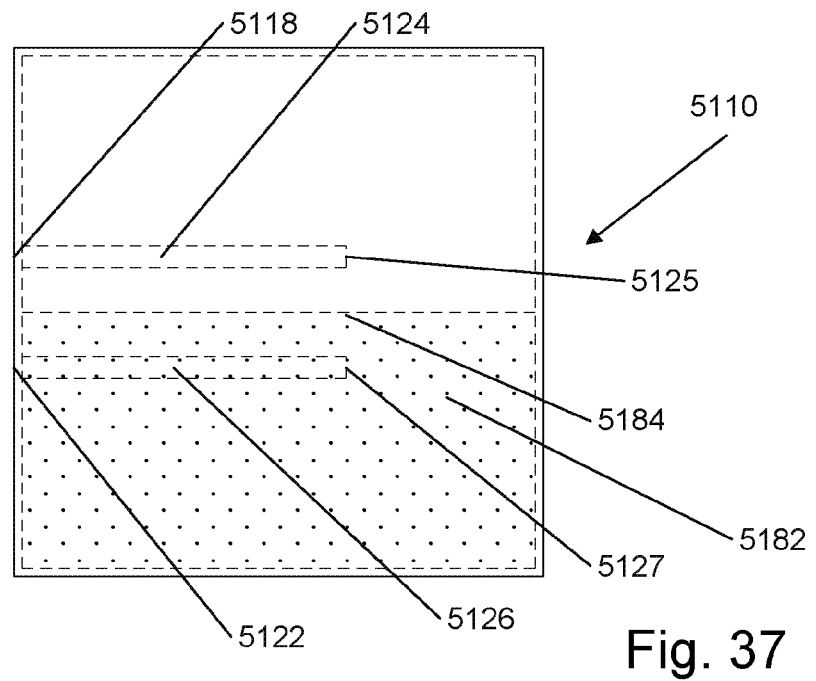

Simplified representations of the effects created by crossed inlet and outlet tubing are shown in FIGS. 34-37, wherein the internal surfaces are shown by dotted lines. These figures show alternate arrangements of a water reservoir 5110, with an inlet 5118 and an outlet 5122 that respectively include an inlet tube 5124 and an outlet tube 5126. FIGS. 34-35 show a configuration wherein the axes of the tubing intersect when viewed from the side (as shown in FIG. 35), and FIGS. 36-37 show an alternate configuration wherein the axes of the tubing are substantially parallel when viewed from the side (as shown in FIG. 37). In FIGS. 34-37, a volume of water 5182 is assumed to fill approximately half of the volume of the reservoir 5110, and the water level 5184 is indicated by the dotted lines extending horizontally.

When the water reservoir 5110 is oriented as shown in FIGS. 34-35, the arrangement of the inlet tube 5124 and the outlet tube 5126 requires the water level 5184 to rise above the higher end of the inlet tube 5124 or the higher end of the outlet tube 5126 if any water 5182 is to exit the water reservoir 5110. On the other hand, in the arrangement shown in FIGS. 35-36 the water level 5184 only needs to rise as high as a lower end of the inlet tube 5124 or the outlet tube 5126 in order to exit the water reservoir 5110.

As the water level 5184 will change as a function of the orientation of the water reservoir 5110, this effect of crossing the inlet tube 5124 and the outlet tube 5126 may be re-created at any orientation as required by re-orienting the inlet tube 5124 and the outlet tube 5126 to suit the shape of the water reservoir 5110. In some forms, the inlet tube 5124 and the outlet tube 5126 may be crossed when viewed from multiple angles orthogonal to each other.

In the forms shown in FIGS. 27-28 and FIGS. 34-37, inlet interior end and the outlet interior end are located within the cavity and the inlet exterior end and the outlet exterior end are located in one of the plurality of walls of the cavity. A first axis (inlet tube axis) is defined by the inlet interior end and the inlet exterior end and a second axis (outlet tube axis) is defined by the outlet interior end and the outlet exterior end. When the reservoir is tilted (for example by approximately 90° to normal working orientation) the first axis is on a first angle such that the inlet interior end and the inlet exterior end are positioned at different heights, such that the predetermined maximum volume of water is below at least one of the inlet interior end or the inlet exterior end to prevent spillback of water through the inlet tube. Furthermore, when the reservoir is tilted (for example by approximately 90° to normal working orientation) the second axis is on a second angle such that the outlet interior end and the outlet exterior end are positioned at different heights, such that the predetermined maximum volume of water is below at least one of the outlet interior end or the outlet exterior end to prevent spillback of water through the outlet tube. This effect may be also created wherein the reservoir is tilted at any other angles, to suit the design and/or tilt conditions of the humidifier 5000 and/or reservoir 5110.

5.5.2.9 Reservoir Arrangement with Removable Inlet/Outlet Tubes

In a yet further example of the current technology, the reservoir 5110 may be configured as shown in FIGS. 40a-41. In this example, the reservoir 5110 comprises a lid portion 5114, an intermediate portion 5202 and a base portion 5112 (base portion not shown in FIGS. 40a-40b for clarity). The lid portion 5114 and the intermediate portion 5202 may be configured to be releasably engaged to each other. They may be further configured to comprise a number of features when engaged to each other, such as an inlet 5118, an outlet 5122, an inlet tube 5124 and an outlet tube 5126, while being releasably engaged to each other. For example, the lid portion 5114 may comprise an inlet 5118, an outlet 5122 and an inlet tube 5124, and the intermediate portion 5202 may comprise an outlet tube 5126 as shown in FIG. 40b.

As shown the intermediate portion 5202 may also comprise a baffle 5192 and at least one support spoke 5194. The support spokes 5194 may be provided for structural support and/or to position the outlet tube 5126 and/or the baffle 5192 on the intermediate portion. The baffle 5192 is arranged to block a direct air path (or short-circuiting as described above) between the inlet tube inner end 5125 and the outlet tube inner end 5127 to encourage movement of the airflow within the reservoir to improve humidity uptake by the airflow within the reservoir 5110. In addition a seal 5204 may be either integrated with the intermediate portion 5202 as shown or may be formed as separate component to the intermediate portion.

An advantage of this arrangement may be improved cleanability of the reservoir 5110 by separating some of the components from the reservoir, such as the inlet tube 5124 and/or the outlet tube 5126. This arrangement may be particularly advantageous in such situations as when at least one of the inlet tube 5124 or the outlet tube 5126 extends into the internal volume of the reservoir 5110, as such features may hinder access the interior of the reservoir 5110. It can be seen in FIGS. 40a-40b that the intermediate portion 5202 is engaged with the lid portion 5114 in its normal working orientation. However, as the intermediate portion 5202 is separable from the lid portion 5114, the inlet tube 5124 and the outlet tube 5126 may be separated to improve access to the interior of the lid portion 5114.

By using two separable portions 5114, 5202 to construct the upper portion of the reservoir and/or configuring the inlet/outlet tubes 5124, 5126 to be releasably engaged to the reservoir 5110, the number of small, difficult-to-access areas may be reduced, which may improve cleanability of the reservoir 5110. Furthermore, the removable inlet tube 5124 and/or the removable outlet tube 5126 may be themselves more easily accessible for cleaning as well.

In another example of the current technology (not shown), the lid portion 5114 and the intermediate portion 5202 may each comprise parts of a feature, wherein they would combine to form a complete feature. For instance, the lid portion

5114 may comprise a part of the inlet tube 5124 and a part of the outlet tube 5126, and the intermediate portion 5202 may comprise another part of the inlet tube 5124 and another part of the outlet tube 5126. Those skilled in the art will understand that the reservoir may be further sub-divided into any number of separable portions, and separable features such as the inlet tube 5124 and/or the outlet tube 5126 may be located in any number of arrangements in relation to the separable portions.

Another advantage of the current arrangement may be to improve spillback performance (prevention of liquid egress through the inlet tube 5124 and/or outlet tube 5126) of the reservoir 5110. Spillback performance may be improved by increase of the internal volume of the reservoir 5110, which may be achieved by introduction of a void above the inlet tube 5124 and/or the outlet tube 5126. Another method of improving spillback performance is to arrange the inlet tube inner end 5125 and/or the outlet tube inner end 5127 proximal to the center of the reservoir 5110. As a reservoir 5110 is typically produced by injection molding, forming an inlet tube 5124 and/or an outlet tube 5126 as a part of the lid 5114 prohibits introduction of a void above the inlet tube 5124 and/or the outlet tube 5126. In such a configuration, a molding tool comprising the internal volume of the lid 5114 would be pinned in place by the inlet tube 5124 and/or the outlet tube 5126 and thus molding would not be possible, or require a complex and costly tooling arrangement. In such a case, the ability to separate the inlet tube 5124 and the outlet tube 5126 may be further advantageous.

It will be understood that the lid portion 5114, the intermediate portion 5202 and the base portion 5112 may be configured in any number of ways. For instance, the relative sizes of the lid portion 5114 and the base portion 5112 may vary, and the lid portion 5114 and/or the base portion 5112 may further comprise multiple materials or components in its construction. One or more of the inlet tube 5124 and the outlet tube 5126 may be removably or releasably coupled to the lid portion 5114 or the base portion 5112, for example as a part of the intermediate portion. The intermediate portion may also be configured to initially engage the lid portion 5114 and/or the base portion 5112, for example by being configured to be inserted into the lid portion 5114 or the base portion 5112.

Another feature of this arrangement is the use of support spokes 5194 in order to provide structural rigidity to the intermediate portion 5202 of the lid 5114. The spokes 5194, by themselves or in combination with the baffle 5192, may provide a handle for disassembly of the lid 5114 from the intermediate portion 5202. This may improve usability of the lid 5114 as the user may grip the baffle 5192 and/or the spokes 5194 to separate the intermediate portion 5202 from the lid portion 5114. It should be understood that a number of other configurations may be possible wherein the support spokes 5194 are arranged alternatively to the exemplary arrangement as shown in FIGS. 42a-43.

In an example of the current technology, the baffle 5192 may comprise a locating portion 5196 and a deflector portion 5198 as seen in FIGS. 42a-43. The locating portion 5196 may be in the form of a cylinder to assist in accurately locating the baffle 5192 in relation to the inlet tube 5124 by fitting around the outside of the vertical portion of the inlet tube 5124. In some forms, the baffle 5192 may further comprise a baffle seal 5197 to seal between the baffle 5192 and the inlet tube 5124, for example as shown in FIG. 47b. The baffle 5192 may also be configured in combination with the spokes 5194 so that at least some portions of the baffle 5192 may act as a spoke 5194 or vice versa.

An exemplary cross-section of the assembled lid 5114 is shown in FIGS. 44*a*-44*b*. The diameter of the inlet tube 5124 or the locating portion 5196 may be varied along its length, for example in a frustro-conical arrangement, so as to progressively engage with each other. The two components 5124, 5196 may also incorporate a complementary retaining mechanism such as a protrusion/slot combination 5205 as shown in FIGS. 44*a*-44*b*.

It is also to be understood that the seal 5204 may be located at an alternative location to the exemplary arrangements shown in FIGS. 40*a*-43. For example, the seal 5204 may be formed as a part of the lid portion 5114, as a part of the reservoir base portion 5112, or as a separate component by itself that is not integrally formed to any of the lid portion 5114, the intermediate portion 5202 and the base 5112. One exemplary method of forming the seal 5204 with the lid portion 5114 or the base 5112 may be by overmoulding or use of a chemical adhesive.

FIG. 45 shows an exploded view of another example of the current technology. In this arrangement, the reservoir 5110 comprises a lid portion 5114, an intermediate portion 5202 and a base portion 5112 (not shown in FIG. 45 for clarity). The intermediate portion 5202 comprises the inlet tube 5124 and the outlet tube 5126 as well as a wall portion 5206 that is configured to be coupled with the lid portion. Alternatively the intermediate portion 5202 may engage the base portion 5112, and may comprise one or both of the inlet tube 5124 and the outlet tube 5126. In some cases, the wall portion 5206 that is configured to couple with the lid portion may connected with one or more of the inlet tube 5124 and the outlet tube 5126.

This configuration may allow removal of the inlet tube 5124 and/or the outlet tube 5126 for improved cleanability of the reservoir 5110. Furthermore, this configuration may improve spillback performance of the reservoir 5110 by increasing the internal volume of the reservoir 5110.

In some cases, the inlet tube 5124 and the outlet tube 5126 may be arranged so that removal of either or both of the tubes 5124, 5126 from the reservoir 5110 does not affect the predetermined maximum volume of water that the reservoir 5110 may retain. Such a configuration may allow cleaning of the tubes 5124, 5126 without removing any water from the reservoir 5110.

FIGS. 54 to 59 show a humidifier tub 5110 (also referred to as a water reservoir) including a separately formed inlet 5118 according to an example of the present technology. As illustrated, the humidifier tub 5110 comprises a base 5112, a lid 5114, and an intermediate portion 5202.

The lid 5114 comprises inlet 5118 including inlet tube 5124 arranged to provide a flow path for the inlet flow of breathable gas into the tub, and the lid 5114 comprises outlet 5122 including outlet tube 5126 arranged to provide a flow path for the outlet flow of humidified breathable gas from the tub.

In the illustrated example, the inlet tube 5124 is provided as a separate and distinct structure from the lid 5114 (e.g., formed (e.g., molded) separately from the lid) and then subsequently attached or otherwise provided to the lid 5114 in an operative position. In an example, the inlet tube 5124 may comprise a similar material to the lid 5114, e.g., polycarbonate. In the illustrated example, the outlet tube 5126 comprises a one-piece construction with the lid 5114, e.g., outlet tube 5126 is formed, e.g., molded, as a part of the lid 5114.

The inlet tube 5124 includes an inlet portion 5131 (tube extension) including inlet end 5133 and an outlet portion 5135 (vertical inlet) including outlet end 5137. When the inlet tube 5124 is attached to the lid 5114, the inlet end 5133 is arranged outside the tub chamber and the outlet end 5137 is arranged inside the tub chamber. In use, the inlet end 5133 is configured to receive a pressurized flow of air from the outlet of the RPT device, and the outlet end 5137 is configured to deliver the pressurized flow of air into the tub chamber for humidification.

The bottom of the tub 5110 (e.g., the conducting portion 5152) includes a bottom surface defining a bottom plane that is substantially horizontal when the tub 5110 is in a normal, working orientation (e.g., see FIG. 57). As illustrated in FIG. 57, the inlet portion 5131 extends transverse to the outlet portion 5135. For example, the outlet portion 5135 extends in a plane that is substantially perpendicular to the bottom plane (e.g., the outlet portion 5135 extends generally vertical), and the inlet portion 5131 extends in a plane that is oriented at an angle to the bottom plane. In an alternative example, the inlet portion 5131 may extend in a plane that is substantially parallel to the bottom plane.

As shown in FIG. 59, the lid 5114 includes an inlet seat 5115 along an exterior of the lid 5114. When the inlet tube 5124 is attached to the lid 5114, the inlet portion 5131 is received in the inlet seat 5115 and the outlet portion 5135 extends into the tub chamber through a chamber opening 5119 in the lid 5114 (see FIG. 58). As shown in FIG. 57, the outlet portion 5135 may interface or otherwise engage with locating portion 5196 provided to the intermediate portion 5202. The inlet tube 5124 may be secured to the top of the lid 5114 in any suitable manner, e.g., snap-fit connection, adhesive.

FIGS. 54 to 57 show the separately formed inlet 5118 secured to the lid 5114 in an operative position. As illustrated, the inlet 5118 also provides a friction grip 5166 to assist the patient in holding the tub in use.

5.5.2.10 Overfill Prevention

In some prior art humidifier water reservoirs, overfilling of the water reservoir 5110 may reduce effectiveness of a spill prevention feature. For example, overfilling may allow the liquid in the reservoir 5110 to reach the inlet 5118 at a lower angle of tilt than if the reservoir 5110 had not been over-filled. As a result, some prior art humidifier water reservoirs have included a water filling indication mark to reduce occurrence of such overfilling, however this may only go some way towards ameliorating this risk.

Another aspect of this technology is the inclusion of one or more overfill protection features configured to prevent filling the reservoir above the maximum volume of water when filling the humidifier reservoir in its open configuration and/or the closed configuration.

In one arrangement as seen in FIGS. 29*a* and 29*b*, an overfill protection feature may include at least one orifice 5138 in the water reservoir 5110 to indicate over-filling. According to this aspect of the technology, when the water reservoir 5110 is being re-filled with the reservoir lid 5114 open, over-filling beyond a predetermined maximum volume of the reservoir 5110 would cause water to spill out from the orifice 5138. This would indicate to the user that the reservoir 5110 is full, as well as preventing such overfilling. Advantageously water would spill out only through the at least one orifice 5138 rather than from all areas of the water reservoir resulting in less overflow spillage for the user to clean up. Thus, the at least one orifice defines an egress path of water when the predetermined maximum volume of water is exceeded. FIG. 29*a* show the water reservoir 5110 in its open configuration, wherein an upper flange of the base 5112 does not span the perimeter of the entire opening, creating an orifice 5138. FIG. 29*b* shows a portion of the base 5112 indicating the at least one orifice 5138. The at least one orifice 5138 may be in the form of one or more apertures, holes, slits or slots, or any other form that allows communication of fluid into and out of the water reservoir 5110. The at least one orifice 5138 may be formed in one or more positions around the upper flange of the base 5112.

In an alternate arrangement, the overfill protection feature may include a sloped profile 5139. As shown in FIGS. 29c and 29d, the reservoir base 5112 may be arranged so that its side profile has a sloped profile 5139 in one or more directions. This arrangement may also indicate over-filling when the reservoir base 5112 is re-filled with liquid or water. In this arrangement, when the reservoir lid 5114 is in its open configuration, water may spill out at the base of the sloped profile 5139 rather than from all areas of the reservoir. Thus, the sloped profile defines an egress path of water when the predetermined maximum volume of water is exceeded. Advantages of the above methods may be that over-filling may become more difficult than has been in the prior art, and presents another advantage that in response to attempted over-filling, spillage may occur at more predictable locations.

Another aspect of this technology is that when the water reservoir 5110 is in its closed position, a seal 5204 sealingly engages the base 5112 and the reservoir lid 5114 and blocks or seals the orifice 5138 or sloped profile 5139 preventing fluid communication into and out of the water reservoir 5110. One arrangement of this feature is shown in FIG. 30, which shows that when the reservoir lid 5114 is closed (lid not shown in this image), the seal 5204 sealingly engages with the base 5112 on the outside of the orifice 5138 and no longer allows communication of liquid or air into and out of the water reservoir 5110 through the orifice 5138. Similarly the seal 5204 would engage with the base 5112 to surround the edges of the sloped profile preventing communication of liquid or air into and out of the water reservoir 5110 through the sloped profile 5139. In some arrangements the seal 5204 may be integrated with the variable portion 5116 as described above. Alternatively the seal 5204 may be a separate seal that may be used in a reservoir with or without a variable portion.

According to another aspect of the present invention, an overfill prevention feature may be configured to prevent overfilling when a user is attempting to fill the reservoir 5110 while in its closed configuration.

In one form (shown in FIG. 48 without the reservoir base 5112), the overfill prevention feature may form one or more air locks to prevent further ingress of liquid into the reservoir 5110 when the predetermined maximum volume of liquid is in the reservoir 5110. In this form, when filling the reservoir 5110 in its closed configuration, the one or more air locks would form an enclosure of gas in the reservoir 5110 that is not displaced by the volume of liquid in the reservoir 5110. In an example shown in FIG. 48, the reservoir 5110 is in an orientation such that the normal to the inlet 5118 and the outlet 5122 are oriented vertically, as a user would orient the reservoir 5110 while filling it with water. The water level 5184 would rise, and reach the level shown on FIG. 48, whereupon the remaining volume of gas in the reservoir 5110 is no longer able to access the inlet tube 5124 or the outlet tube 5126, therefore would no longer be able to escape from the reservoir 5110. The reservoir 5110 would thus not be able to receive any further volume of water into its interior volume.

Preferably, the volume of water in the reservoir 5110 when any further ingress of water into the reservoir 5110 is prevented by formation of the one or more air locks is substantially equal to the predetermined maximum volume of liquid to be retained in the reservoir 5110. In some cases, the reservoir 5110 may allow further filling of the inlet tube 5124 and/or the outlet tube 5126 although further ingress of water into the interior volume is prevented by the air locks. In such cases, the volume of liquid in the reservoir 5110 when the air locks are formed, as well as the volume of the inlet tube 5124 and/or the outlet tube 5126 may be configured so that when added together, they are substantially equal to the predetermined maximum volume of liquid to be retained in the reservoir 5110.

In some cases, for example where the normal to the inlet 5118 and the outlet 5122 may not be parallel, a user may fill the reservoir 5110 in one of a multiple orientations while closed. In such cases, the reservoir 5110 may be configured such that the appropriate air locks are formable at one of, or a plurality of the multiple orientations. The air locks need not be formed solely by occlusion of the inlet tube 5124 and/or the outlet tube 5126. In some forms (not shown), one or more air locks may be formed by occlusion of any cavities or ports which may allow fluid communication between the interior and the exterior of the reservoir 5110. Furthermore, the occlusion need not be performed by the volume of liquid in the reservoir 5110. In some forms, the volume of liquid, as it is increased, may deform or move another component to form a seal (and thus an air lock) in the reservoir.

5.5.2.11 Retaining Clip

The reservoir lid 5114 may include a feature by which the water reservoir 5110 is to be retained in the water reservoir dock 5130 once the two members are engaged with each other. In one arrangement a retaining feature may be a protrusion, or a clip, 5142 on the reservoir lid 5114 as shown in FIGS. 31-32. FIGS. 31-32 show a water reservoir 5110 and the reservoir dock 5130. Here, a protrusion, or a clip, 5142 on the reservoir lid 5114 removably engages with a corresponding dock locking recess 5144 in the water reservoir dock 5130 when the water reservoir 5110 is inserted into the water reservoir dock 5130. This connection secures the water reservoir 5110 relative to the water reservoir dock 5130.

As described above the variable portion 5116 of the reservoir is compressed to enable insertion of the reservoir into the dock 5130. The compression of the variable portion 5116 allows a portion of the reservoir 5110 to slide into the dock 5130 and allows the protrusion or clip 5142 to slide initially under the outer edge surface of the dock 5130 to reach the dock locking recess 5144. The compression force applied to the reservoir for insertion may then be released to allow the protrusion or clip 5142 to engage with the dock locking recess 5144 and securing of the reservoir 5110 within the dock 5130. When the reservoir 5110 is secured within the dock 5130 the variable portion 5116 is no longer in or in a reduced compressed state. Similarly, in order to be able to remove the water reservoir 5110 from the water reservoir dock 5130, the variable portion 5116 must be compressed as to disengage the lid retention protrusion 5142 from the dock locking recess 5144.

The retention protrusion 5142 may be further configured with a taper as shown in FIG. 32. The taper may be directed to increase in height away from the direction of insertion, to increase the amount of interference between the retention protrusion 5142 and the dock 5130 progressively during insertion. It would be clear to those skilled in the art that in an alternative arrangement the lid retention protrusion 5142 may be a recess, and the dock locking recess 5144 may be a corresponding protrusion. Alternatively one of any number of retaining features that are known in the art may be used to achieve the same outcomes as described above.

5.5.2.12 Water Reservoir-to-Humidifier Connection

In one form, the water reservoir 5110 in use receives a flow of air output by the RPT device 4000 at the dock outlet 4132. The water reservoir 5110 is removably coupled with the humidifier 5000, for example configured (as shown in FIGS. 6g-6h) to be insertable into the dock 4130. When the water reservoir 5110 is engaged with the dock 4130, the reservoir inlet 5118 may receive the flow of air output by the RPT device 4000, and direct the flow of air into the water reservoir 5110. Humidity (i.e. water vapour) is added to the flow of air as the air travels through the reservoir 5110, and the humidified flow of air exits the reservoir 5110 through the reservoir outlet tube 5126 and to the reservoir outlet 5122. The reservoir outlet 5122 is connectable to an air circuit 4170 to deliver the flow of humidified air to the patient 1000.

The double-ended arrows in FIG. 6h show the direction of relative motion, i.e. generally horizontal movement, between the humidifier 5000 and the water reservoir 5110 in connection and disconnection with each other in this arrangement. In the arrangement shown in FIGS. 6g-6h, the water reservoir 5110 is connected with the humidifier 5000 by placing the water reservoir 5110 in the dock 4130. In this arrangement, the heights and shapes of the cavity in the dock 4130 and the water reservoir 5110 are such that to engage the water reservoir 5110 with the dock 4130 the compliant portion 5116 is compressed, for example by between about 1 mm and about 5 mm, for example by about 2 mm, about 3 mm or about 4 mm. Thus, the shape of the portion of the water reservoir 5110 that is inserted into the dock 4130 is complementary to the shape of the dock cavity 5160 and the height of the water reservoir 5110 when compliant portion 5116 is compressed is slightly less than the height of the dock cavity 5160 to enable the insertion of the water reservoir 5110 into the dock cavity 5160.

In one form, a compressive force is required to sufficiently compress the compliant portion 5116 and allow relative movement (i.e. sliding) between the water reservoir 5110 and the dock 4130. For example a compression force as measured at the handle recesses 5154, 5156 of between about 10 N and about 30 N, or about 20 N, or some other compression force is required to allow insertion of the water reservoir 5110 into the dock 4130. The vertical gap achieved between the water reservoir 5110 and the cavity of the dock 4130 during insertion (or removal) may be between about 1 mm and about 5 mm, for example about 2 mm, 3 mm or 4 mm, when this compressive force is applied at the handle recesses 5154, 5156 and the water reservoir 5110 is inserted into the dock 4130. The water reservoir 5110 and the dock 4130 may be arranged so that the amount of compression in the compliant portion 5116 is reduced once the water reservoir 5110 is connected with the dock 4130 and the patient 1000 is no longer applying a compressive force. The reduction in compression may be between about 0.5 mm and about 2.5 mm, for example about 1 mm, 1.5 mm or 2 mm.

In the illustrated arrangement (see FIGS. 6a-6b) the reservoir outlet 5122 is connectable to the dock inlet 4134, through which the humidified flow of air travels to the humidifier outlet 5172. The humidifier outlet 5172 is connectable to the air circuit 4170 as indicated in FIG. 12 by the double-ended dotted arrow (see FIG. 12). An advantage of such an arrangement is that the water reservoir 5110 can be removed from the dock 4130 while the air circuit 4170 remains attached to the device outlet 4004. Thus the insertion and removal of the water reservoir 5110 is independent of the connection of the air circuit 4170. A further advantage is that the water reservoir 5110 must be removed from the dock 4130 to fill the water reservoir 5110 with liquid. In this form, neither of the inlet 5118 and the outlet 5122 of the reservoir 5110 are exposed while the reservoir 5110 is inserted in the humidifier 5000 in an operating configuration, while the reservoir 5110 itself remains accessible to the patient 1000, for example to allow easy removal from the humidifier 5000. This arrangement may reduce the likelihood of the user over-filling the water reservoir 5110 over the predetermined, maximum volume of liquid, as the water reservoir 5110 incorporates features to prevent over-filling. Still further, as the user is encouraged to remove the water reservoir 5110 to fill the reservoir 5110 with liquid, the likelihood of spillage of water onto, or into, the humidifier 5000 and/or the RPT device 4000 is reduced.

The compliant portion 5116 may be constructed from an elastomeric material such as silicone, thermoplastic elastomer (TPE), TPE polyester, TPE polyurethane or natural rubber. In choosing the material to be used for the compliant portion 5116 it may be advantageous to choose one that does not experience mechanical relaxation across the range of storage and operational temperatures that the compliant portion 5116 may be exposed to. One example of a material for the compliant portion 5116 which meets these requirements may be silicone.

A reservoir latch 5186 may be provided on the water reservoir 5110, as shown in FIG. 28, so that when the reservoir latch 5186 is engaged, it secures the reservoir lid 5114 and reservoir base 5112 together. The latch 5186 may prevent the reservoir lid 5114 and the reservoir base 5112 from separating and maintain the compliant portion 5116 in sealing engagement between the lid 5114 and the base 5112, for example by compression. In one form, the latch 5186 may be configured to restrict relative movement of the lid 5114 in relation to the base 5112 in one direction only, thus allow further compression of the compliant portion 5116 while preventing separation of the lid 5114 and the base 5112. This may allow insertion of the water reservoir 5110 into the dock 4130, and/or allow the compliant portion 5116 to assist thermal engagement between the reservoir 5110 and the heating element 5240 as described elsewhere in this disclosure.

When in use, the water reservoir 5110 receives the flow of breathable air for example output by the PAP device 4000. In one form, the water reservoir 5110 is removably coupled with the humidifier 5000 as shown in FIGS. 12-15 by inserting the water reservoir into the water reservoir dock 5130, for example by sliding. The inlet 5118 of the water reservoir 5110 is configured to receive the flow of breathable gas that is output by the PAP device 4000, and to direct the flow of breathable gas into the water reservoir 5110. Humidity (i.e. water vapour) is added to the flow of breathable gas as the breathable gas travels through the reservoir 5110, and the humidified flow of breathable gas exits the reservoir 5110 through the outlet tube 5126 and to the reservoir outlet 5122. The reservoir outlet 5122 is connectable to an air circuit 4170 to deliver the flow of humidified breathable gas to the patient 1000.

Figure 15:
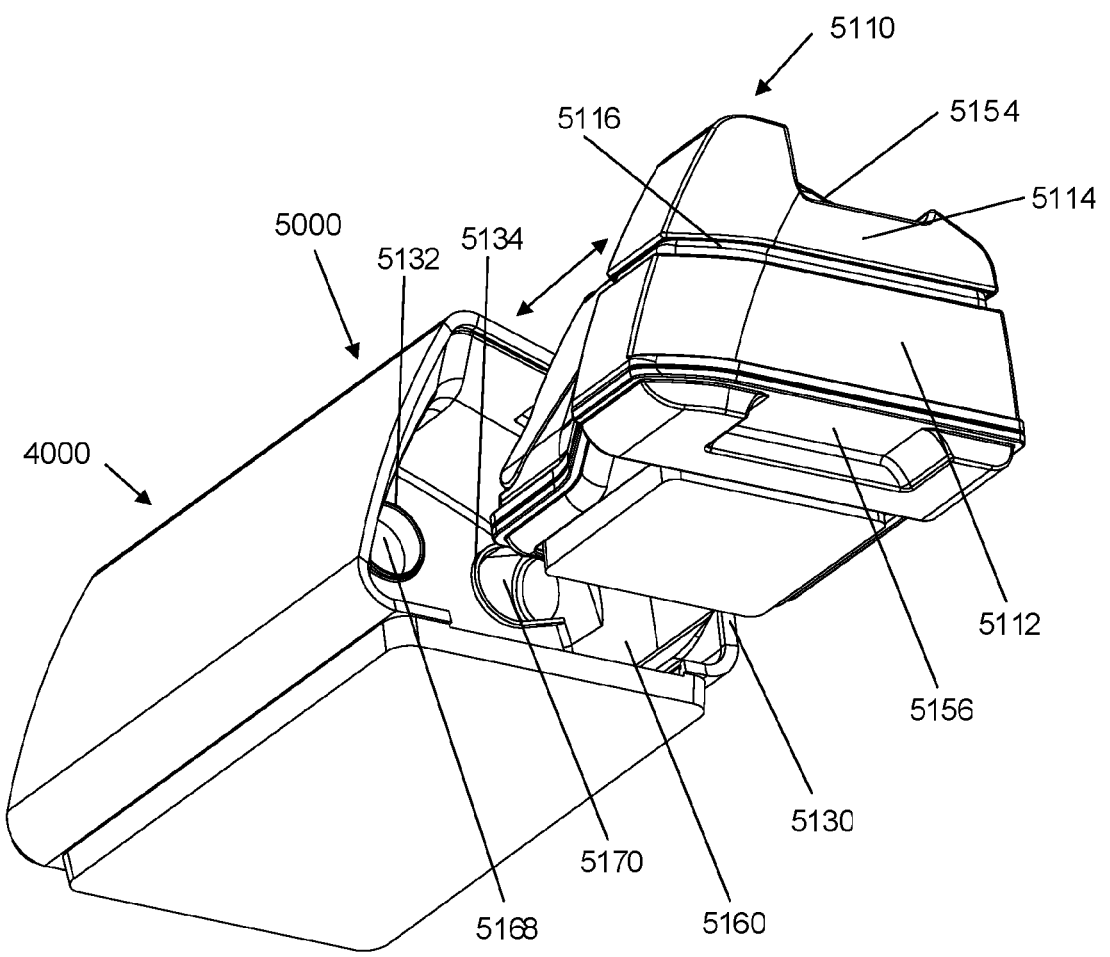
Figure 16B:
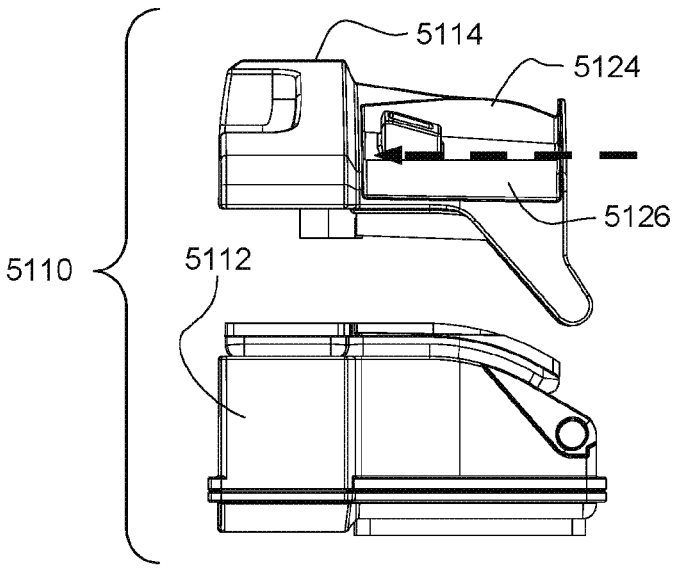
Figure 16A:
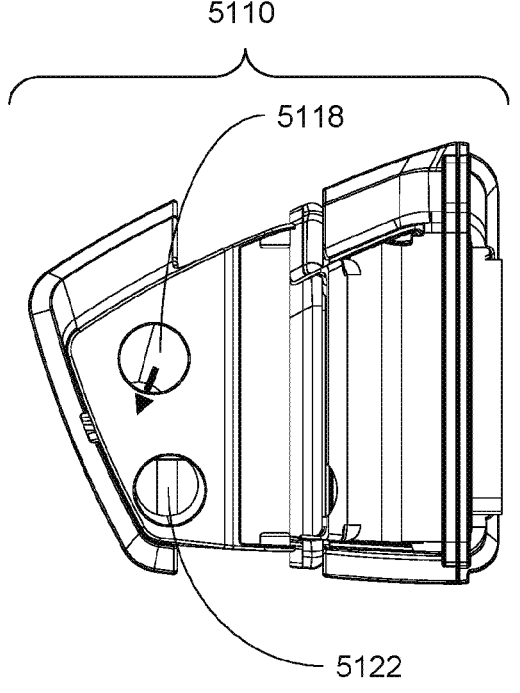
Figure 16C:
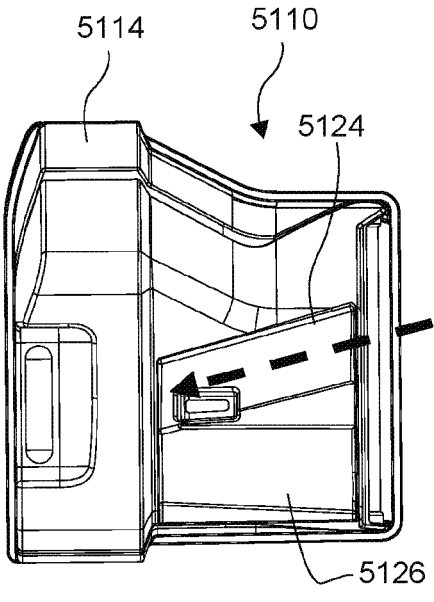
Figure 18B:
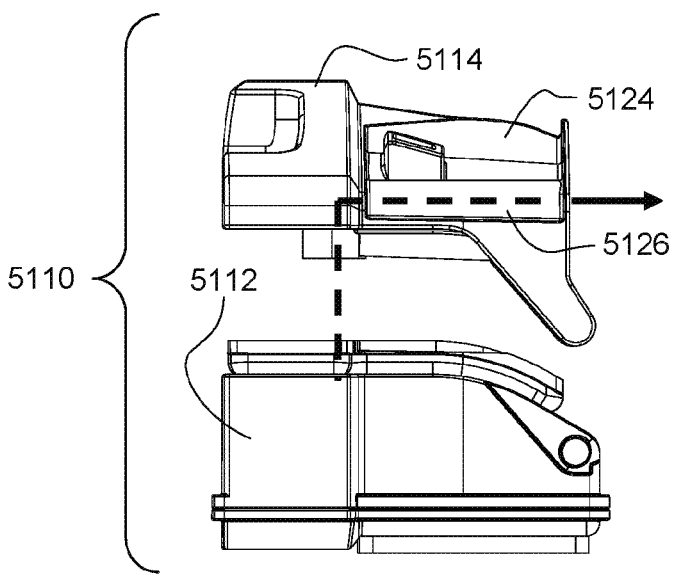
Figure 18A:
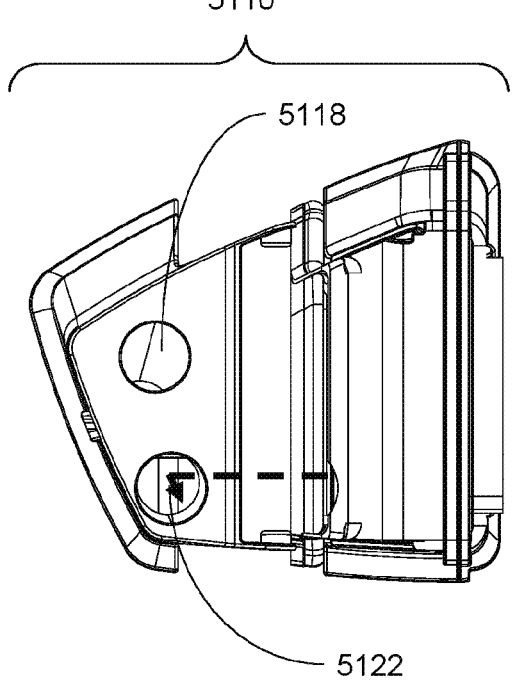
Figure 18C:
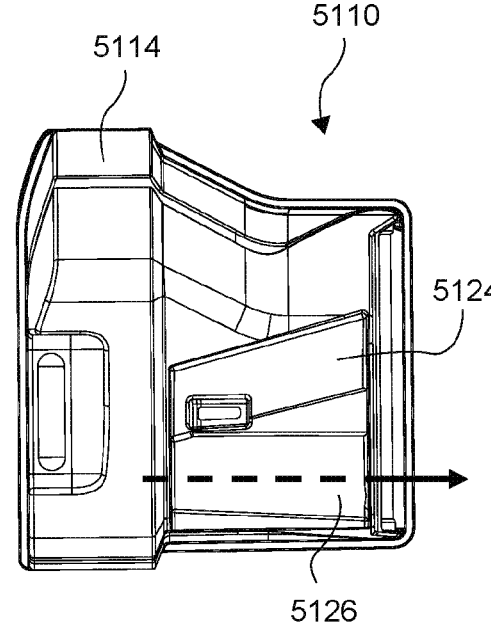

The double-ended arrows in FIG. 13 and FIG. 15 show the direction of relative motion, i.e. generally horizontal movement, between the humidifier 5000 and the water reservoir 5110 in connection and disconnection with each other in this arrangement. However, the water reservoir 5110 may be coupled to the humidifier 5000 by other methods such as insertion in a generally vertical direction, connection by one or more intermediate components (e.g. tubes) or being integrally formed with a humidifier.

In an alternative arrangement, not shown, the water reservoir 5110, may be inserted into the dock cavity 5160 from a vertical direction rather than using a sliding motion. In such an arrangement the dock cavity of the humidifier 5000 may comprise a moveable cover portion, such as a lid or top portion, which is at least partially opened to allow insertion of the water reservoir 5110 and closed following insertion to secure the water reservoir 5110 within the dock cavity 5160.

In the illustrated arrangement (see FIG. 15), the reservoir outlet 5122 is connectable to the reservoir dock gas inlet 5170, through which the humidified flow of breathable air travels to the humidifier outlet 5172. The humidifier outlet 5172 is connectable to the air delivery circuit or air circuit 4170 as indicated in FIG. 12 by the double-ended dotted arrow (see FIG. 12). One advantage of such an arrangement is that the humidifier reservoir 5110 must be removed from the reservoir dock 5130 to fill the humidifier reservoir 5110 with liquid. This arrangement generally prevents access to any openings in the humidifier reservoir 5110 while it is connected to the humidifier 5000, and may reduce the likelihood of the user over-filling the water reservoir 5110 over the given, maximum volume of liquid, as the humidifier reservoir 5110 incorporates features to prevent over-filling as described further below. Still further, as the user is encouraged to remove the water reservoir 5110 to fill the reservoir 5110 with liquid, the likelihood of spillage of water onto, or into, the humidifier 5000 and/or the PAP device 4000 is reduced.

As shown in FIG. 15, first and second dock seals 5132, 5134 may be provided to help seal the connection between the reservoir inlet 5118 and the dock 5130 and the connection between the reservoir outlet 5122 and the dock 5130.

Figure 14:
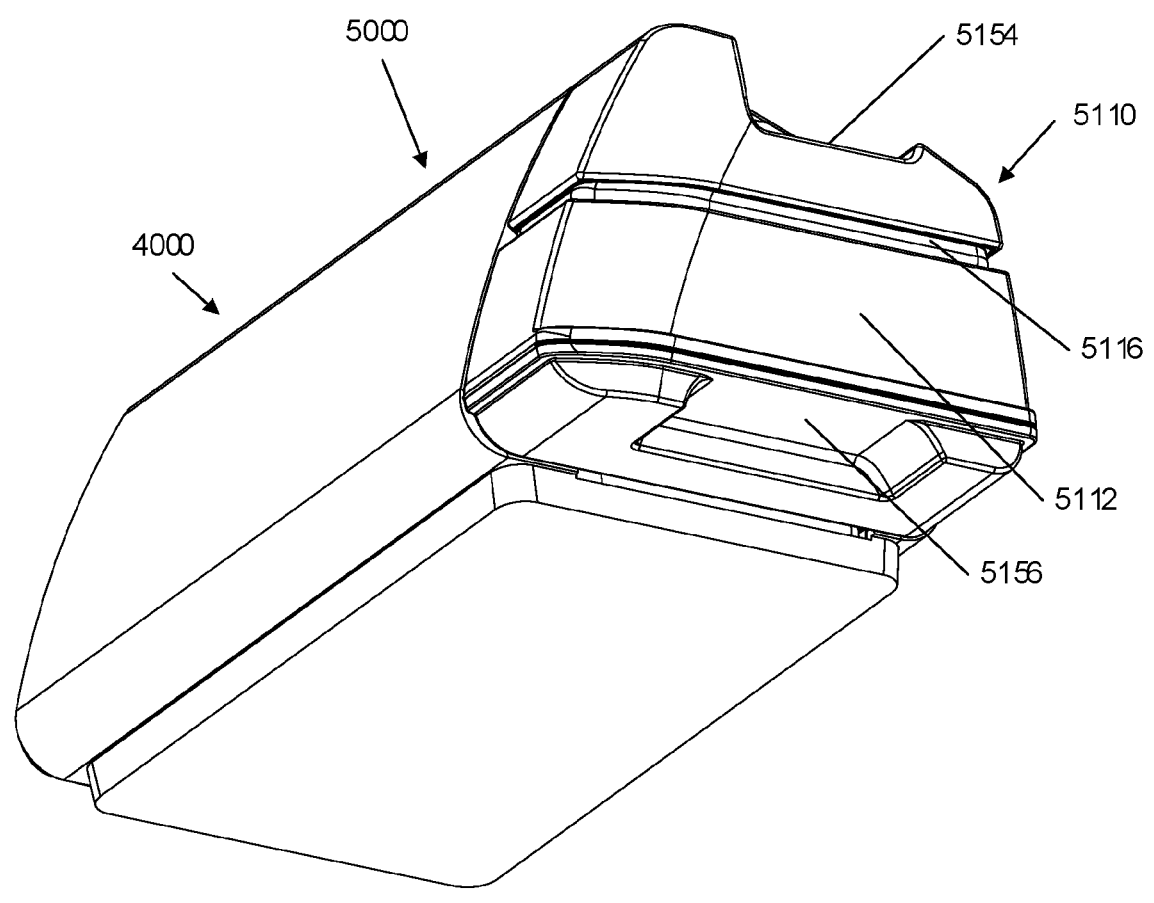

In the arrangement shown in FIGS. 14-15, the water reservoir 5110 is connected with the humidifier 5000 by placing the water reservoir 5110 in the water reservoir dock 5130. In this arrangement, the heights and shapes of the dock internal cavity 5160 and the water reservoir 5110 are such that to engage the water reservoir 5110 with the water reservoir dock 5130 the variable portion 5116 is compressed, for example by between about 1 mm and about 5 mm, for example by about 2 mm, about 3 mm or about 4 mm. Thus, the shape of the portion of the water reservoir 5110 that is inserted into the dock 5130 is complementary to the shape of the dock cavity 5160 and the height of the water reservoir 5110 when variable portion 5116 is compressed is slightly less than the height of the dock cavity 5160 to enable the insertion of the water reservoir 5110 into the dock cavity 5160.

The variable portion 5116 may be constructed with a cross-section shape such as one shown in FIG. 38. A compressive force is required to sufficiently compress the variable portion 5116 and allow relative movement (i.e. sliding) between the water reservoir 5110 and the water reservoir dock 5130. For example a compression force as measured at the handle recesses 5154, 5156 of between about 10 N and about 30 N, or about 20 N, or some other compression force is required to allow insertion of the water reservoir 5110 into the dock cavity 5160. The vertical gap achieved between the water reservoir 5110 and the dock internal cavity 5160 during insertion (or removal) may be between about 1 mm and about 5 mm, for example about 2 mm, 3 mm or 4 mm, when this compressive force is applied at the handle recesses and the water reservoir 5110 is inserted into the reservoir dock 5130. The water reservoir 5110 and the reservoir dock 5130 may be arranged so that the amount of compression in the variable portion 5116 is reduced once the water reservoir 5110 is connected with the reservoir dock 5130 and the patient 1000 is no longer applying a compressive force. The reduction in compression may be between about 0.5 mm and about 2.5 mm, for example about 1 mm, 1.5 mm or 2 mm.

The variable portion 5116 may be constructed from an elastomeric material such as silicone, TPE, TPE polyester, TPE polyurethane or natural rubber. In choosing the material to be used for the variable portion 5116 it may be advantageous to choose one that does not experience mechanical relaxation across the range of storage and operational temperatures that the variable portion 5116 may be exposed to. One example of a material for the variable portion 5116 which meets these requirements may be silicone.

A reservoir latch 5186 may be provided on the water reservoir 5110, as shown in FIG. 28, so that when the reservoir latch 5186 is engaged, it secures the reservoir lid 5114 and reservoir base 5112 together. The latch 5186 may prevent the reservoir lid 5114 and the reservoir base 5112 from separating and maintain the variable portion 5116 in sealing engagement between the lid 5114 and the base 5112, for example by compression. In one form, the latch 5186 may be configured to restrict relative movement of the lid 5114 in relation to the base 5112 in one direction only, thus allow further compression of the variable portion 5116 while preventing separation of the lid 5114 and the base 5112. This may allow insertion of the water reservoir 5110 into the reservoir dock 5130, and/or allow the variable portion 5116 to assist thermal engagement between the reservoir 5110 and the heater plate 5120 as described elsewhere in this disclosure.

5.5.2.12.1 Pre-Compression for Improved Thermal Contact

According to one aspect of this technology, the water reservoir 5110 and the heater plate 5120 of the humidifier are in thermal contact, or thermal engagement, as described above. A degree of thermal contact, for example measured in thermal conductivity or thermal contact resistance, between two components may vary according to a number of parameters.

In the prior art, additional components have been used to improve thermal contact between a water reservoir and a heater plate by increasing the contact pressure therebetween. One example is the use of spring elements, which are used to connect the heater plate to the humidifier body, as described in U.S. Pat. No. 4,203,027, thereby pushing the heater plate towards the water reservoir. Another example is a humidifier with a lid wherein a compressible elastomer seal is provided on the lid, as described in WO2010/031126. In this example, when the lid is in its closed position the seal engages against the water reservoir and pushes it against the heater plate.

In the present technology, pre-compression of the water reservoir 5110, for example in engagement with the water reservoir dock 4130, may be used to help improve thermal contact between the reservoir 5110 and the heating element 5240.

In one arrangement, the water reservoir 5110 may be configured so that in its operating configuration, such as when it is placed in the water reservoir dock 41305130, the compliant portion 5116 is compressed as described above. The reservoir 5110 and the reservoir dock 4130 may be further configured so that a reaction force to the compression of the compliant portion 5116 pushes the base 5112 of the water reservoir 5110 against the heating element 5240 to improve the thermal contact therebetween.

Thus, the compliant portion 5116 may act as a spring that is biased to push the reservoir base 5112 and/or the reservoir lid 5114 in a direction perpendicular to the heating element 5240. As the reservoir 5110 is secured externally, such as confined within the reservoir dock 4130, the compression of the compliant portion 5116 is reacted by a force that encourages improved thermal engagement with the heating element 5240.

The force required for compression of the compliant portion 5116 when the water reservoir 5110 is connected with the humidifier 5000 is preferably in the same direction as the normal to a surface of the conductive portion. The direction may be also preferably in the same direction as the direction of thermal engagement. This force is reacted by the water reservoir dock 4130 at its contacting points and/or surfaces, thereby pushing the base 5112 of the water reservoir 5110 and the heating element 5240 together.

The magnitude of compression force may be between about 5 N and about 15 N when measured at the heating element 5240 when the water reservoir 5110 is placed in the water reservoir dock 4130. However, it should be understood that different configurations of the water reservoir 5110 may require different magnitudes of compression force. The magnitude of this force may be altered by modifying the design of any or all of the compliant portion 5116, the lid 5114, the base 5112, or the reservoir dock 4130. For instance, if the compliant portion 5116 was constructed of a material with higher Young's modulus, it would correspondingly increase the magnitude of the force. It should be noted that FIGS. 19-20 only shows forces and pressures in the vertical direction.

In some cases, the amount of compression of the compliant portion 5116 in the reservoir 5110 may be used to vary a level of thermal engagement between the conductive portion and the heating element 5240.

5.5.2.12.2 Other Examples

FIGS. 60, 61*a*, and 61*b* show a humidifier tub 5110 (water reservoir) including a retention mechanism according to an example of the present technology. In this example, the retention protrusions 5142 for releasably engaging the dock locking recesses 5144 in the dock 5130 are situated on a swingable latch 5400.

In the illustrated example, the latch 5400 is provided as a separate and distinct structure from the tub 5110 and then secured or otherwise provided to the tub 5110 in an operative position, e.g., the latch 5400 comprises a pre-formed structure that is secured to the lid 5114. In an example, the latch 5400 may comprise a plastic or thermoplastic polymer material.

The latch 5400 includes a locking lever 5410 and a support member 5420 to resiliently support the locking lever 5410 on the lid 5114. The locking lever 5410 includes a button end 5412 at one end of the locking lever 5410 and a locking end 5414 at the other end of the locking lever 5410. In the illustrated example, the support member 5420 is in the form of a spring that supports the locking lever 5410 on the lid 5114 and resiliently biases the latch 5400 to an unlocked position.

The locking end 5414 includes the retention protrusions 5142, and the button end 5412 includes a finger grip 5413, e.g., recess, to assist the patient in holding the tub and manipulating the latch 5400. The button end 5412 also includes a detent feature to retain the latch 5400 in a locked position, e.g., button end 5412 includes a bump 5430 adapted to releasably engage within a corresponding depression 5111 in the lid 5114.

FIG. 61*a* shows the latch 5400 in an unlocked position. As illustrated, the detent feature is disengaged which allows the button end 5412 to be lifted and/or biased upwardly into a raised position, which lowers the locking end 5414 downwardly into a depressed position. That is, the button end 5412 of the latch 5400 may be lifted to lower the height of the locking end 5414 and the protrusions 5142 thereof, allowing them to pass into the dock and below the dock locking recesses 5144. Once within the dock, the button end 5412 of the latch 5400 can be depressed into a depressed position to increase the height of the locking end 5414 and the protrusions 5142 thereof, which allows the protrusions 5142 to engage within the dock locking recesses 5144 to releasably lock and retain the tub in an operative position within the dock, i.e., the protrusions 5142 engage behind the forward end forming the recesses 5144. The protrusions 5142 may include a taper to facilitate engagement of the protrusions 5142 into the recesses 5144. FIG. 61*b* shows the latch 5400 in a locked position with the locking end 5414 in a raised position. As shown in FIG. 61*b*, the detent feature captures the latch 5400 in the locked position. It should be appreciated that the position of the spring 5420 can be determined to bias the locking end 5414 into either of the depressed position or the raised position.

FIGS. 62 to 65 show a humidifier tub 5110 including a swingable latch 5400 according to another example of the present technology.

In this example, the locking lever 5410 is pivotally connected to the lid 5114 which allows the latch 5400 to pivot about a pivot axis PA. The button end 5412 includes a "release" area 5412R on one side from the pivot axis PA and a "lock" area 5412L on the other side from the pivot axis PA. This arrangement allows the button end 5412 to be depressed for both releasing and locking the latch 5400. In the illustrated example, the spring 5420 biases the latch 5400 to the released or unlocked position.

In this example, the locking end 5414 includes a single extended retention protrusion 5142 and it will be appreciated that the dock locking recess 5144 in the dock 5130 may be shaped to receive the single protrusion 5142. Alternatively, the locking end 5414 shown in FIGS. 62 to 65 may take the form of the locking end 5414 shown in FIGS. 60, 61*a*, and 61*b* to mate with the dock locking recesses 5144 previously described.

FIG. 64 shows the latch 5400 in an unlocked position. As illustrated, the "release" area 5412R may be depressed which pivots the button end 5412 about the axis PA to lower the height of the protrusion 5142, allowing it to pass into the dock and below the dock locking recess 5144. Once within the dock, the "lock" area 5412L may be depressed which pivots the button end 5412 about the axis PA to increase the height of the protrusion 5142 on the locking end 5414, which allows the protrusion 5142 to engage within the dock locking recess 5144 to releasably lock and retain the tub in an operative position within the dock, i.e., the protrusion 5142 engages behind the forward end forming the recess 5144. FIG. 65 shows the latch 5400 in a locked position. As shown in FIG. 65, similar to the above example, the detent feature captures the latch 5400 in the locked position, e.g., button end 5412 includes a bump 5430 adapted to releasably engage within a corresponding depression 5111 in the lid 5114. It should be appreciated that the spring 5420 can be used to bias the locking end 5414 into either of the depressed position (as shown in FIG. 64) or the raised position.

FIGS. 66 and 67*a* to 67*d* depict another example in which a tongue and key are utilized in the engagement between the tub 5110 and dock 5130.

In this example, one or both sides of the humidifier tub 5110 includes a tongue 5500, e.g., tongue 5500 arranged to protrude laterally outwardly from the lid 5114 of the tub. The tongue 5500 is configured and arranged to pass through a corresponding keyway 5600 formed inside the dock 5130 which guides the tub 5110 into an operative position within the dock 5130.

In the illustrated example, each side wall of the dock 5130 includes a top key rail 5610 and a bottom key rail 5620 that from the keyway 5600 configured to receive a respective tongue 5500 on each side of the tub 5110.

During insertion of the tub 5110 into the dock 5130, the tub 5110 is moved in a generally horizontal direction until each tongue 5500 passes over a respective bottom key rail 5620 and engages a respective stop wall or stop surface 5612 provided by top key rails 5610 (e.g., see FIGS. 67*a* and 67*b*). The tub lid 5114 is then depressed to compress the compliant portion 5116 and allow the tongues 5500 to lower or drop beneath a respective guide wall or guide surface 5614 provided by the top key rails 5610 (e.g., see FIG. 67*c*). Such drop down or vertical movement of the tongues 5500 will allow the tongues 5500 to slide below and past the top key rail 5610. The tub 5110 is slid further in a generally horizontal direction into the dock 5130 until the tub 5110 reaches its operative position. When the tub 5110 reaches its fully seated or operative position, the tongues 5500 are located beyond the respective guide wall or guide surface 5614 provided by the top key rails 5610, which allows the lid 5114 to resiliently return to its undepressed state. This allows the tongues 5500 to raise behind the top key rails 5610 (e.g., see FIG. 67*d*) and allows the lid retention protrusions 5142 to engage respective dock locking recesses 5144. Such tongue and key engagement configuration effectively locks the tub in the operative position and prevents unintended release, e.g., during treatment.

FIGS. 68 to 73 depict another example in which the tapered surfaces of the retention protrusions 5142 on the tub 5110 are replaced with a flat face 5143 configured and arranged to engage an exterior face 5145 of the dock 5130 adjacent the locking recess 5144 during insertion of the tub 5110. This engagement prohibits full insertion of the tub 5110 into the dock 5130 until a user manually depresses the lid 5114 against the base 5112 to compress the compliant portion 5116 and allow the protrusions 5142 and flat face 5143 thereof to lower or drop beneath the exterior face 5145 of the dock 5130, thereby allowing the protrusions 5142 and hence the tub 5110 to pass further into the dock 5130. Once the protrusions 5142 pass beyond the exterior face 5145, the lid 5114 will resiliently return to its undepressed state and the retention protrusions 5142 will raise to engage respective dock locking recesses 5144. FIGS. 70 to 73 show insertion and engagement of the tub 5110 with the dock 5130. In FIG. 70, the flat face 5143 of each protrusion 5142 engages the exterior face 5145 of the dock 5130, which engagement stops the tub 5110 from further insertion into the dock 5130. In FIG. 71, the lid 5114 of the tub 5110 is depressed by the user to drop the level of each protrusion 5142 below the exterior face 5145 of the dock 5130. In FIG. 72, the tub 5110 is slid further into the dock 5130 into an operative position. In FIG. 73, the lid 5114 is released and resiliently returns to its undepressed state, and the retention protrusions 5142 will engage in respective dock locking recesses 5144 to effectively lock the tub 5110 in the operative position and prevent unintended release, e.g., during treatment.

FIGS. 77, 78, 79*a*, and 79*b* depict another example in which a camming slide lock 5400 is utilized to draw the tub

5110 into a fully seated, operative position and releasably lock the tub 5110 in the operative position.

In the illustrated example, the slide lock 5400 includes a slide 5460 slidably supported on the lid 5114 of the tub 5110, a finger 5462 extending from the slide 5460, and a knob or retaining protrusion 5465 on the end of the finger 5462. In use, the slide lock 5400 may be slid laterally between (1) an unlocked position (see FIGS. 77, 78, and 79*a*) to allow insertion/removal of the tub 5110 from dock 5130 and (2) a locked position (see FIG. 79*b*) to releasably lock or retain the tub 5110 to the dock 5130 in an operative position.

In the illustrated example, the roof or top wall of the dock 5130 includes a stop wall or stop surface 5470 and a ramp or cam surface 5475, which are configured to interact with the slide lock 5400 during insertion of the tub 5110.

As the tub 5110 is inserted into the dock 5130, the finger 5462 and retaining protrusion 5465 of the slide lock 5400 extend into the dock 5130 until the retaining protrusion 5465 engages the stop wall or stop surface 5470 extending from the roof of the dock 5130 (see FIG. 79*a*). As shown in FIG. 79*a*, the retaining protrusion 5465 is located beyond the lower edge of the ramp or cam surface 5475, which allows the slide lock 5400 to be laterally slid from the unlocked position (see FIGS. 77, 78, and 79*a*) to the locked position (see FIG. 79*b*) via the slide 5460. As the slide lock 5400 is slid from the unlocked position (see FIGS. 77, 78, and 79*a*) to the locked position (see FIG. 79*b*) via the slide 5460, the retaining protrusion 5465 engages and slides along the ramp or cam surface 5475 extending from the roof of the dock 5130, which pulls or draws the tub 5110 into a fully seated, operative position. When the tub 5110 reaches its fully seated or operative position, the retaining protrusion 5465 engages within a detent 5476 arranged near the end of the ramp or cam surface 5475 which captures the retaining protrusion 5465 to hold the slid lock 5400 in the locked position until disengaged by a user. Such engagement of the retaining protrusion 5465 with the ramp or cam surface 5475 effectively locks the tub 5110 in the operative position and prevents unintended release, e.g., during treatment.

FIGS. 80 to 83 depict another example in which a camming slide lock (e.g., similar to that shown in FIGS. 94 to 96) is combined with a swingable latch (e.g., similar to that shown in FIGS. 60 to 65).

In this example, the retaining mechanism on the lid 5114 of the tub 5110 includes a slide 5460 configured to interact with a locking lever 5410 to releasably lock or retain the tub 5110 to the dock 5130 in an operative position.

The slide 5460 is slidably supported on the lid 5114 of the tub 5110. The underside of the slide 5460 includes a ramp or cam surface 5467. In use, the slide 5460 may be slid laterally between (1) an unlocked position (e.g., see FIGS. 81*a* and 82*a*) to allow insertion/removal of the tub 5110 from dock 5130 and (2) a locked position (e.g., see FIGS. 81*b* and 82*b*) to releasably lock or retain the tub 5110 to the dock 5130 in an operative position.

The locking lever 5410 is pivotally connected to the lid 5114 for pivotal movement about a pivot axis PA. The locking lever 5410 includes a slide engaging end 5412 including a ramp or cam surface 5417 configured to interact with the ramp or cam surface 5467 of the slide 5460. The locking lever 5410 includes a locking end 5414 including the retention protrusions 5142. In the illustrated example, the spring 5420 biases the locking lever 5410 to the locked position.

The slide 5460 is configured to slide along tracks in the lid 5114 while engaging the ramp or cam surface 5417 on the locking lever 5410 to swing the locking lever 5410 up or down (i.e., to raise or lower the retention protrusions 5142). FIGS. 81*a* and 82*a* show the slide 5460 in an unlocked position. As illustrated, the ramp or cam surface 5467 of the slide 5460 engages the ramp or cam surface 5417 on the locking lever 5410 to pivot the locking lever 5410 about the axis PA and lower the height of the protrusions 5142, allowing it to pass into the dock 5130 and below the dock locking recess 5144. Once within the dock 5130, the slide 5460 can be slid to the locked position as shown in FIGS. 81*b* and 82*b*. As illustrated, the ramp or cam surface 5467 of the slide 5460 disengages from the ramp or cam surface 5417 on the locking lever 5410 which allow the locking lever 5410 to pivot and raise the height of the protrusions 5142, allowing the protrusions 5142 to engage within the dock locking recess 5144 to releasably lock and retain the tub in an operative position within the dock. FIG. 83 shows the slide 5460 in a locked position. As shown in FIG. 81*a*, similar to the above examples, a detent feature captures the slide 5460 in an unlocked position, e.g., slide 5460 includes a bump 5430 adapted to releasably engage within a corresponding depression 5111 in the locking lever 5410. It should be appreciated that the spring 5420 can be used to bias the locking lever into either of the locked or unlocked position.

FIGS. 84 to 86 depict another example in which a rotating lever 5700 is deployed through the roof of the dock 5130 to releasably engage a tub retention feature 5142 formed on the lid 5114 of the tub 5110.

In this example, the rotating lever 5700 includes a lever handle 5710 provided to the roof of the dock 5130. One end of the handle 5710 is pivotally connected to the dock 5130 to allow the handle 5710 to pivot about a pivot axis PA between unlocked and locked positions. The opposite end of the handle 5710 includes a retaining knob 5715 that protrudes into the cavity of the dock 5130.

In the illustrated example, the tub retention feature 5142 is in the form of a protrusion including a curved ramp or cam surface 5417 leading to a depression or lever seat 5111.

As the tub 5110 is inserted into the dock 5130, the tub retention feature 5142 moves into the dock 5130 until it is positioned adjacent the retaining knob 5715 rotating lever 5700 (see FIG. 85). As the rotating lever 5700 is rotated from the unlocked position (see FIG. 85) to the locked position (see FIG. 86) via the handle 5710, the retaining knob 5715 engages and slides along the curved ramp or cam surface 5417 of the tub retention feature 5142, which pulls or draws the tub 5110 into a fully seated, operative position. When the tub 5110 reaches its fully seated or operative position, the retaining knob 5715 engages within the lever seat 5111 arranged near the end of the ramp or cam surface 5417 which captures the retaining knob 5715 to hold the rotating lever 5700 in the locked position until disengaged by a user. Such engagement of the retaining knob 5715 with the tub retention feature 5142 effectively locks the tub 5110 in the operative position and prevents unintended release, e.g., during treatment.

FIGS. 87, 88*a*, and 88*b* depict another example in which a release knob 5800 is deployed through the roof of the dock 5130 to releasably engage the lid 5114 of the tub 5110.

In this example, the release knob 5800 includes a knob 5810 and a threaded shaft 5820 that is threadably engaged with the roof of the dock 5130. In use, the release knob 5800 may be rotated between (1) a locked position (e.g., see FIGS. 87 and 88*a*) to releasably lock or retain the tub 5110 to the dock 5130 in an operative position, and (2) an unlocked position (e.g., see FIG. 88*b*) to allow insertion/removal of the tub 5110 from dock 5130.

As shown in FIG. 88*a*, when the release knob 5800 is in the locked position, the free end of the threaded shaft 5820 is sufficiently recessed into the roof of the dock 5130, which allows the lid 5114 to assume an undepressed state and thereby allow the retention protrusions 5142 thereof to engage respective dock locking recesses 5144 to effectively lock the tub 5110 in the operative position. As shown in FIG. 88*b*, when the release knob 5800 is in the unlocked position, the free end of the threaded shaft 5820 protrudes into the cavity of the dock 5130 and beyond the dock locking recesses 5144, which arranges the free end of the threaded shaft 5820 for engagement with the lid 5114 to maintain the lid 5114 in a compressed state, and thereby prevent the retention protrusions 5142 from engaging within respective dock locking recesses 5144 to allow insertion/removal of the tub 5110.

FIGS. 89*a* to 89*d* depict another example in which the release knob 5800 is slidably engaged to the roof of the dock 5130 rather than rotatably engaged as in FIGS. 87, 88*a*, and 88*b*.

In this example, the release knob 5800 includes a knob 5810 and a tub engaging end 5820 arranged within the roof of the dock 5130. In use, the release knob 5800 may be slid between (1) a locked position (e.g., see FIGS. 89*a* and 89*c*) to releasably lock or retain the tub 5110 to the dock 5130 in an operative position, and (2) an unlocked position (e.g., see FIGS. 89*b* and 89*d*) to allow insertion/removal of the tub 5110 from dock 5130.

As shown in FIG. 89*c*, when the release knob 5800 is in the locked position, the tub engaging end 5820 of release knob 5800 is sufficiently recessed into the roof of the dock 5130, which allows the lid 5114 to assume an undepressed or uncompressed state and thereby allow the retention protrusions 5142 thereof to engage a dock locking recess 5144 to effectively lock the tub 5110 in the operative position. As shown in FIG. 89*d*, when the release knob 5800 is in the unlocked position, the tub engaging end 5820 of release knob 5800 protrudes into the cavity of the dock 5130 and beyond the dock locking recess 5144, which arranges the tub engaging end 5820 for engagement with the lid 5114 to maintain the lid 5114 in a depressed or compressed state, and thereby prevent the retention protrusions 5142 from engaging within the dock locking recess 5144 to allow insertion/removal of the tub 5110.

FIGS. 90 and 90*a* to 90*c* depict another example in which a release knob 5800, or rotary wedge, is deployed on the tub 5110 itself to move the tub 5110 between the depressed and undepressed states.

In this example, the release knob 5800 includes a knob 5810 and a tapered shaft 5820 threadably arranged between the lid 5114 and the base 5112 of the tub 5110. In use, the release knob 5800 may be rotated between (1) a locked position (e.g., see FIG. 90*b*) to releasably lock or retain the tub 5110 to the dock 5130 in an operative position, and (2) an unlocked position (e.g., see FIG. 90*c*) to allow insertion/removal of the tub 5110 from dock 5130.

As shown in FIG. 90*b*, when the release knob 5800 is rotated to the locked position, the tapered shaft 5820 protrudes into the tub 5110 and acts as a wedge to expand the lid 5114 and the base 5112 thereby allowing the retention protrusions 5142 on the lid 5114 to raise and engage respective dock locking recesses 5144 to effectively lock the tub 5110 in the operative position. As shown in FIG. 90*c*, when the release knob 5800 is rotated to the unlocked position, the tapered shaft 5820 is withdrawn from the tub 5110 to collapse the lid 5114 and the base 5112 thereby allowing the retention protrusions 5142 on the lid 5114 to lower and release from respective dock locking recesses 5144 to allow insertion/removal of the tub 5110.

FIGS. 91 and 92 depict another example in which the roof of the dock 5130 includes a pivotable locking latch 5400 structured and arranged to releasably engage the lid 5114 of the tub 5110 to hold the tub in a fully seated or operative position. This configuration may be used in place of the retention protrusions and dock locking recesses previously described.

In this example, one end 5410 of the pivotable locking latch 5400 is pivotally coupled to the roof of the dock 5130 and the opposite end includes a retaining protrusion 5142. In use, locking latch 5400 may be rotated between (1) a locked position (e.g., see FIG. 91) to releasably lock or retain the tub 5110 to the dock 5130 in an operative position, and (2) an unlocked position (e.g., see FIG. 92) to allow insertion/removal of the tub 5110 from dock 5130. When the tub 5110 is inserted in the dock 5130, the locking latch 5400 can be rotated to the locked position to allow the latch 5400 to engage within a recess in the lid 5114 configured to receive the latch 5400 and allow the retaining protrusion 5142 thereof to clip down over and behind an edge or catch on the lid 5114 (e.g., with a snap-fit) to effectively lock the tub 5110 in the operative position. The locking latch 5400 can be rotated to the unlocked position to allow the latch 5400 to disengage from the lid 5114 and allow the retaining protrusion 5142 thereof to raise from behind the edge or catch on the lid 5114 to allow insertion/removal of the tub 5110.

FIGS. 93a and 93b depict an example in which the lid 5114 of the tub 5110 includes the pivotable locking latch 5400 structured and arranged to releasably engage the roof of the dock 5130 to hold the tub in a fully seated or operative position.

In this example, one end 5410 of the pivotable locking latch 5400 is pivotally coupled to the lid 5114 of the tub 5110 and the opposite end includes a retaining protrusion 5142. In use, locking latch 5400 may be rotated between (1) a locked position (e.g., see FIG. 93a) to releasably lock or retain the tub 5110 to the dock 5130 in an operative position, and (2) an unlocked position (e.g., see FIG. 93b) to allow insertion/removal of the tub 5110 from dock 5130. When the tub 5110 is inserted in the dock 5130, the locking latch 5400 can be rotated to the locked position to allow the latch 5400 to engage within a recess in the lid 5114 configured to receive the latch 5400 and allow the retaining protrusion 5142 thereof to clip down over and behind an edge or catch on the roof of the dock 5130 (e.g., with a snap-fit) to effectively lock the tub 5110 in the operative position. The locking latch 5400 can be rotated to the unlocked position to allow the retaining protrusion 5142 of the latch 5400 to raise from behind the edge or catch on the dock 5130 to allow insertion/removal of the tub 5110.

5.5.2.13 Conductive Portion 5120

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.5.2.13.1 Thermal Contact/Engagement

According to one aspect of this technology, the water reservoir 5110 and the heater plate 5120 of the humidifier are in thermal contact, or thermal engagement, as described above. A degree of thermal contact, for example measured in thermal conductivity or thermal contact resistance, between two components may vary according to a number of parameters.

In the prior art, additional components have been used to improve thermal contact between a water reservoir and a heater plate by increasing the contact pressure therebetween. One example is the use of spring elements, which are used to connect the heater plate to the humidifier body, as described in U.S. Pat. No. 4,203,027, thereby pushing the heater plate towards the water reservoir. Another example is a humidifier with a lid wherein a compressible elastomer seal is provided on the lid, as described in WO2010/031126. In this example, when the lid is in its closed position the seal engages against the water reservoir and pushes it against the heater plate.

5.5.2.13.1.1 Use of Pressurised Gas for Improved Thermal Contact

According to another aspect, when the water reservoir 5110 is connected with the humidifier 5000, the flow of breathable gas received from the PAP device may pressurise a chamber such as the interior of the reservoir 5110. The pressurisation of the chamber may be used to increase a level of thermal engagement (i.e. thermal contact) between the reservoir 5110 and the heater plate 5120. The reservoir 5110 may be further configured so that by varying the level of pressure in the chamber may vary the level of thermal contact between the reservoir 5110 and the heater plate 5120.

In one form, the variable portion 5116 may be configured to be expandable in the direction of thermal contact, and the reservoir 5110 may be confined by the reservoir dock 5130 in the same direction. In this form, the internal pressure pushes the base 5112 of the water reservoir 5110 against the heater plate 5120 to improve the level of thermal engagement between the heater plate 5120 and the base 5112.

FIG. 20 illustrates this effect by indicating the distributed forces or pressures that are applied to the lid 5114 and the base 5112 by the arrows shown. FIG. 20 shows forces and pressures in the vertical direction only, as in this form the thermal engagement occurs in the vertical direction. The presence of above-atmospheric pressure within the water reservoir 5110 results in forces in the direction of thermal engagement, and is reacted by the water reservoir dock 5130 at its contacting surfaces, thereby pushing the base 5112 of the water reservoir 5110 and the heater plate 5120 towards each other in the direction of thermal engagement. The magnitude of this force may be between about 5 N and about 15 N when measured at the heater plate 5120 at 20 cm $H_2O$ of pressure.

It should be understood that different configurations of the water reservoir 5110 may require different magnitudes of force, which may be achieved by varying the surface area that the pressure acts on, or the effective pressure that acts on the surface. Such changes may be achieved, for example, by a pressure regulating valve.

In another arrangement, substantially the same effects as those described above may be achieved with a non-opening variable portion of a water reservoir 5110. The water reservoir 5110 and the reservoir dock 5130 may be arranged so that elasticity or flexibility is provided by an elastomeric material or a joint that allows freedom of movement (e.g. a sliding connection, or a concertina section of pliable plastic or a flexible portion in the water reservoir) in the direction of the heat transfer. In this configuration the lid 5114 and the base 5112 may be unconstrained relative to each other in the direction of thermal contact. The reservoir 5110 may then be constrained in the direction of the heat transfer in another manner (e.g. by a water reservoir dock or a similar housing) to create a force that reacts to balance the pressure created in the interior of the reservoir 5110 by the pressurized flow of breathable air, wherein some of the reaction force may occur at the heater plate 5120 to improve thermal contact. In such arrangements, another opening to re-fill the water reservoir 5110 may be introduced on the reservoir 5110, such as on the lid 5114, and it may comprise a separate seal.

FIG. 33 shows an example of such an arrangement, including a base 5174, a top 5176, a variable portion 5178 and a re-filling cap 5180. The base, the top and the variable portion may be affixed together in another arrangement, wherein re-filling of the reservoir would be accommodated by the re-filling cap, 5180. The re-filling cap 5180 may be placed such that when the humidifier reservoir 5110 is engaged with the reservoir dock 5130 the re-filling cap 5180 is not accessible. Such an arrangement may preserve the advantage described above, namely that the reservoir 5110 is not able to be re-filled while it is engaged with the reservoir dock 5130. Furthermore, the variable portion 5178 may be replaced by any mechanism known in the art that is able to accommodate a change in vertical length within a reservoir.

In a yet another alternate arrangement, the flow of breathable air may be used to improve the level of thermal contact between the humidifier reservoir 5110 and the heater plate 5120 by pressurisation or inflation of a secondary component. The secondary component may be a chamber, body or surface that acts on the humidifier reservoir 5110, which in turn pushes the water reservoir 5110 and the heater plate 5120 together in the direction of thermal engagement. Similarly, the secondary component may act upon the heater plate 5120 to push the heater plate 5120 and water reservoir 5110 together in the direction of thermal engagement.

The secondary component may be arranged externally to the reservoir 5110 and/or the heater plate 5120. Furthermore, the secondary component may be configured to vary the area in contact with the reservoir 5110 and/or the heater plate 5120, to further profile the change to thermal contact as pressure of the flow of breathable gas changes.

In an alternate arrangement, the water reservoir dock 5130 may include a retaining mechanism (for example, a lid that closes around the water reservoir 5110) to hold the water reservoir 5110 in its intended position. In such an arrangement, a reservoir dock lid may be configured to compress and/or confine the variable portion 5116 in order to improve the level of thermal contact.

The level of thermal contact may also be further improved using a spring loaded or sprung heater plate as is known in the prior art. The heater plate may be constructed with a convex or domed shape towards the humidifier reservoir 5110 so that when the humidifier 5110 is engaged with the reservoir dock 5130 the convex heater plate is flattened, which generates a clamping force pushing the heater plate 5120 to the water reservoir 5110. Similarly, the conductor plate 5152 of the water reservoir 5110 may be domed or convex shaped and be configured to be flattened towards to the heater plate when the water reservoir 5110 is engaged.in the dock cavity 5160 of the humidifier 5000.

Any one of the above means of improving thermal contact may be used independently of each other, or in any combination thereof, including in combination with any prior art means of achieving or improving thermal engagement between the humidifier reservoir and the heater plate.

5.5.2.14 Humidifier Transducer(s) 5270

The humidifier 5000 may comprise one or more humidifier transducers (sensors) 5270 instead of, or in addition to, transducers 4270 described above. Humidifier transducers 5270 may include one or more of an air pressure sensor, an air flow sensor, a temperature sensor or a humidity sensor as shown in FIG. 5*i*. A humidifier transducer 5270 may produce one or more output signals which may be communicated to a controller such as the central controller 4230 or the humidifier controller 5250. In some forms, a humidifier transducer may be located externally to the humidifier 5000 (such as in the air circuit 4170) while communicating the output signal to the controller.

5.5.2.14.1 Pressure Transducer 5212

One or more pressure transducers 5212 may be provided to the humidifier 5000 in addition to, or instead of, a pressure transducer 4272 provided in the RPT device 4000.

5.5.2.14.2 Flow Transducer 5214

One or more flow transducers 5214 may be provided to the humidifier 5000 in addition to, or instead of, a flow transducer 4274 provided in the RPT device 4000.

5.5.2.14.3 Temperature Transducer 5216

The humidifier 5000 may comprise one or more temperature transducers 5216. The one or more temperature transducers 5216 may be configured to measure one or more temperatures such as of the heating element 5240 or of the flow of air downstream of the water reservoir outlet 5122. In some forms, the humidifier 5000 may further comprise a temperature sensor 5216 to detect the temperature of the ambient air.

5.5.2.14.4 Humidity Transducer 5218

In one form, the humidifier 5000 may comprise one or more humidity sensors 5218 to detect a humidity of a gas, such as the ambient air. The humidity sensor 5218 may be placed towards an outlet of the humidifier 5000 in some forms to measure a humidity of the gas delivered from the humidifier 5000. The humidity sensor may be an absolute humidity sensor or a relative humidity sensor.

5.5.2.15 Heating Element 5240

A heating element 5240 may be provided to the humidifier 5000 in some cases to provide a heat input to one or more of the volume of water in the water reservoir 5110 or to the flow of air. The heating element 5240 may comprise a heat generating component 5242 such as an electrically resistive heating track. One suitable example of a heating element 5240 is a layered heating element such as one described in the PCT Patent Application Publication Number WO 2012/171072, the entire document of which is incorporated herewithin by reference.

In some forms, the heating element 5240 may be provided in the chassis 4016 where heat may be provided to the water reservoir 5110 primarily by conduction, for example through a HE cover plate 5241 which may be composed of a conductive material such as a metal (e.g. stainless steel or aluminium).)

The heating element 5240 may be supported by a HE seal 5243, configured to prevent or discourage ingress of any water from the water reservoir 5110 or the dock 4130 into the heating element 5240. In one form, the HE seal 5243 may seal around the periphery of the heating element 5240, and elevate the heating element 5240 from the base of the RPT device 4000. The HE seal 5243 may comprise one or more resilient portions such as the HE cones 5245, configured to provide a compressive force to help engage the heating element 5240 with the conductive portion 5120 of the water reservoir 5110. In one form, the HE seal 5243 and the heating element 5240 may be configured so that when the water reservoir 5110 is inserted into and engaged with the dock 4130, the HE cones 5245 are compressed axially to provide an upward force, thereby pushing the heating element 5240 toward the conductive portion 5120 of the water reservoir 5110 and improving the thermal contact therebetween.

The HE seal 5243 may further comprise one or more HE cable ports 5246 to allow a cable (e.g. for electrical power) to travel therethrough, for example from another portion of the chassis 4016 such as outside of the dock 4130 and near the pneumatic block 4020. The one or more HE cable ports 5246 may sealingly engage around a periphery of the cable travelling therethrough to prevent ingress of water into the heating element 5240. In one form, the HE seal 5243 may be constructed from a resilient material such as silicone, and comprise integrally formed HE cones 5245 and HE cable ports 5246. The HE cable port 5246 may comprise a cavity for the cable to travel therethrough, and may be configured to engage with another cavity for location and/or retention, such as by being shaped as a protrusion to be inserted into a cavity in the chassis 4016.

The humidifier 5000 may comprise a HE base cover 5244. The HE base cover 5244 may be removably coupled to the chassis 4016 (e.g. by screws) to allow access to the heating element 5240, and comprise one or more features configured to support and locate the HE seal 5243. In one form, the HE base cover 5244 may further comprise HE cone slots 52475246 configured to receive HE cones 5245 while allowing a compression thereof 5.5.2.15.1 Humidifier Controller 5250

According to one arrangement of the present technology, a humidifier 5000 may comprise a humidifier controller 5250 as shown in FIG. 5i. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of characteristics (such as temperature, humidity, pressure or flow rate), for example of the flow of air, the water in the reservoir 5110 or the humidifier 5000. The humidifier controller 5250 may also be configured to execute or implement humidifier algorithms or deliver one or more output signals.

As shown in FIG. 5i, the humidifier controller may comprise one or more controllers, such as a central humidifier controller 5251, a heated air circuit controller 5254 configured to control the temperature of a heated air circuit or a heating element controller 5252 configured to control the temperature of a hot plate.

5.6 Glossary

For the purposes of the present technology disclosure, in certain forms of the present technology, one or more of the following definitions may apply. In other forms of the present technology, alternative definitions may apply.

5.6.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g. acoustic) noise may be considered to be the background noise level in the room where a patient is located, other than for example, noise generated by an RPT device or emanating from a mask or patient interface. Ambient noise may be generated by sources outside the room.

Continuous Positive Airway Pressure (CPAP): CPAP treatment will be taken to mean the application of a supply of air to the entrance to the airways at a pressure that is continuously positive with respect to atmosphere, and preferably approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

CDMA: is an abbreviation for Code division multiple access.

GSM: is an abbreviation for Global System for Mobile.

LTE: is an abbreviation for Long Term Evolution.

USB: is an abbreviation for Universal Serial Bus.

5.6.2 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.7 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods, materials (or both) which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified. Additionally, or alternatively, aspects thereof may be conducted concurrently or even synchronously.

It is therefore to be understood that numerous modifications may be made to the illustrative embodiments and that other arrangements may be devised without departing from the spirit and scope of the technology.

The invention claimed is:

1. An apparatus for humidifying a flow of breathable gas, the apparatus comprising:
   a water reservoir including a base and a lid connected to the base, the base and the lid forming a chamber structured to hold a volume of water,
   wherein the base includes a conductor plate constructed from a heat conducting material;
   a water reservoir dock structured and arranged to receive the water reservoir in an operative position,
   wherein the water reservoir dock includes a heater plate, and
   wherein the conductor plate of the base is configured to thermally engage with the heater plate of the water reservoir dock when the water reservoir is in the operative position to allow thermal transfer of heat from the heater plate to the volume of water within the water reservoir; and
   a lock slidably movable between (1) a locked position to releasably lock the water reservoir to the water reservoir dock in the operative position, and (2) an unlocked position to allow insertion of the water reservoir into the water reservoir dock and removal of the water reservoir from the water reservoir dock, the lock configured to interact with a ramp or cam surface during movement into the locked position,
   wherein the lock is provided to the lid of the water reservoir and movable to engage the water reservoir dock in the locked position, the lock being provided as a separate and distinct structure from the lid and then secured or otherwise provided to lid in an operative position, or
   wherein the lock is provided to the water reservoir dock and configured to move to engage the water reservoir in the locked position.

2. The apparatus according to claim 1, wherein the lock is provided to the lid of the water reservoir and movable to engage the water reservoir dock in the locked position, the lock being provided as a separate and distinct structure from the lid and then secured or otherwise provided to the lid in an operative position.

3. The apparatus according to claim 1, wherein the lock is provided to the water reservoir dock and configured to move to engage the water reservoir in the locked position.

* * * * *